US008163532B2

(12) United States Patent
Zelder et al.

(10) Patent No.: US 8,163,532 B2
(45) Date of Patent: Apr. 24, 2012

(54) MICROORGANISMS WITH A REACTIVATION SYSTEM FOR COB(I)ALAMIN-DEPENDENT METHIONINE SYNTHASE

(75) Inventors: Oskar Zelder, Speyer (DE); Hartwig Schröder, Nußloch (DE); Corinna Klopprogge, Mannheim (DE); Andrea Herold, Ketsch (DE); Stefan Haefner, Speyer (DE); R. Rogers Yocum, Lexington, MA (US); Thomas A. Patterson, North Attleboro, MA (US); Mark Williams, Revere, MA (US)

(73) Assignee: Evonik Degussa GmbH, Hanau (DE)

( * ) Notice: Subject to any disclaimer, the term of this patent is extended or adjusted under 35 U.S.C. 154(b) by 0 days.

(21) Appl. No.: 12/472,432

(22) Filed: May 27, 2009

(65) Prior Publication Data

US 2009/0311756 A1 Dec. 17, 2009

(30) Foreign Application Priority Data

May 28, 2008 (EP) .................................... 08157096

(51) Int. Cl.

| | |
|---|---|
| ***C12N 1/20*** | (2006.01) |
| ***C12N 15/00*** | (2006.01) |
| ***C12N 15/74*** | (2006.01) |
| ***C12P 21/06*** | (2006.01) |
| ***C12P 13/12*** | (2006.01) |
| ***C07H 21/04*** | (2006.01) |

(52) U.S. Cl. ............... 435/252.3; 435/252.32; 435/69.1; 435/320.1; 435/440; 435/471; 435/113; 536/23.1; 536/23.2

(58) Field of Classification Search ............... 435/252.3, 435/252.32, 69.1, 320.1, 440, 471, 113; 536/23.1, 536/23.2

See application file for complete search history.

(56) References Cited

U.S. PATENT DOCUMENTS

2009/0053778 A1* 2/2009 Sauer et al. ................... 435/113
2009/0298136 A1* 12/2009 Zelder et al. .................. 435/113

FOREIGN PATENT DOCUMENTS

WO 2007/012078 1/2007
WO 2008/080900 7/2008

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*

Devos et al., Practical limits of function prediction. Proteins: Structure, Function, and Genetics. 2000, vol. 41: 98-107.*

Fleischhacker et al., The ligand trans influence governs conformation in cobalamin-dependent methionine synthase. Biochemistry, 2007, vol. 46(43): 12382-12392.*

Kisselev L., Polypeptide release factors in prokaryotes and eukaryotes: same function, different structure. Structure, 2002, vol. 10: 8-9.*

Seffernick et al., Melamine deaminase and Atrazine chlorohydrolase: 98 percent identical but functionally different. J. Bacteriol.,2001, vol. 183 (8): 2405-2410.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Notification of Transmittal of The International Search Report and The Written Opinion of The International Searching Authority, or the Declaration (Forms PCT/ISA/220, PCT/ISA/210 and PCT/ISA/237) mailed Aug. 26, 2009.

Hall et al., "Interaction of Flavodoxin with Cobalamin-Dependent Methionine Synthase", Biochemistry 200, vol. 39, 2000, No. 35,pp. 10711-10719, XP002540840, ISSN: 0006-2960.

Goulding et al., "Cobalamin-Dependent Methionine Synthase Is a Modular Protein . . . Adenosylmethionine", Biochemistry, American Chemical Society , Easton, PA, US, vol. 35, No. 26, Jul. 1, 1997, pp. 8082-8091, XP009104977, ISSN: 0006-2960.

Ruckert et al., "Genome-wide analysis of the L-methionine . . . complementation", Journal of Biotechnology, Elsevier Science Publishers, Amsterdam, NL, vol. 104, No. 1-3, Sep. 4, 2003, pp. 213-228, XP002329882, ISSN: 0168-1656.

Kromer et al., "Metabolic pathway analysis for rational design of L-methionine . . . glutamicum", Metabolic Engineering, Academic Press, US, vol. 8, No. 4, Jul. 1, 2006, pp. 353-369, XP024946939, ISSN: 1096-7176.

Old et al., Regulation of Methionine Biosynthesis In The Enterobacteriaceae, Progress In Biophysics and Molecular Biology, Pergamon Press, Oxford, GB, vol. 56, No. 3, Jan. 1, 1991, pp. 145-185, XP025215159, ISSN: 0079-6107.

Kumar et al., "Methionine production by fermentation", Biotechnology Advances, Elsevier Publishing, Barking, GB, vol. 23, No. 1, Jan. 1, 2005, pp. 41-61, XP004682516, ISSN: 0734-9750.

* cited by examiner

*Primary Examiner* — Ganapathirama Raghu

(74) *Attorney, Agent, or Firm* — Smith, Gambrell & Russell, LLP

(57) ABSTRACT

The present invention relates to microorganisms and methods for producing methionine by reactivation of the MetH enzyme.

5 Claims, No Drawings

MICROORGANISMS WITH A REACTIVATION SYSTEM FOR COB(I)ALAMIN-DEPENDENT METHIONINE SYNTHASE

CROSS-REFERENCE TO RELATED APPLICATIONS

This application claims the benefit of EP 08157096.2, filed 28 May 2008, which is herein incorporated by reference in its entirety.

REFERENCE TO A SEQUENCE LISTING SUBMITTED VIA EFS-WEB

The content of the ASCII text file of the sequence listing named "20090527_032301_621_seq" which is 350 kb in size was created on 27 May 2009 and electronically submitted via EFS-Web herewith the application is incorporated herein by reference in its entirety.

FIELD OF THE INVENTION

The present invention relates to microorganisms for producing methionine. In particular, the present invention relates to Coryneform bacteria such as *Corynebacterium glutanicum* and bacteria of the genus *Escherichia* such as *Eschericia coli*, which have been genetically modified to produce methionine.

BACKGROUND OF THE INVENTION

Currently, the worldwide annual production of methionine is about 500,000 tons. Methionine is the first limiting amino acid in livestock of poultry and feed and, due to this, mainly applied as feed supplement.

In contrast to other industrial amino acids, methionine is almost exclusively applied as a racemate of D- and L-methionine which is produced by chemical synthesis. Since animals can metabolise both stereo-isomers of methionine, direct feed of the chemically produced racemic mixture is possible (D'Mello and Lewis, Effect of Nutrition Deficiencies in Animals: Amino Acids, Rechgigl (Ed.), CRC Handbook Series in Nutrition and Food, 441-490, 1978).

However, there is still a great interest in replacing the existing chemical production by a biotechnological process producing exclusively L-methionine. This is due to the fact that at lower levels of supplementation L-methionine is a better source of sulfur amino acids than D-methionine (Katz and Baker (1975) Poult. Sci. 545: 1667-74). Moreover, the chemical process uses rather hazardous chemicals and produces substantial waste streams. All these disadvantages of chemical production could be avoided by an efficient biotechnological process.

Fermentative production of fine chemicals such as amino acids, aromatic compounds, vitamins and cofactors is today typically carried out in microorganisms such as *Corynebacterium glutamicum, Escherichia coli, Saccharomyces cerevisiae, Schizzosaccharomycs pombe, Pichia pastoris, Aspergillus niger, Bacillus subtilis, Ashbya gossypii, Kluyveromyces lactis, Kluyveromyces marxianus* or *Gluconobacter oxydans*.

Amino acids such as glutamate are thus produced using fermentation methods. For these purposes, certain microorganisms such as *Escherichia coli* (*E. coli*) and *Corynebacterium glutamicum* (*C. glutamicum*) have proven to be particularly suitable. The production of amino acids by fermentation also has inter alia the advantage that only L-amino acids are produced and that environmentally problematic chemicals such as solvents as they are typically used in chemical synthesis are avoided.

Some attempts in the prior art to produce fine chemicals such as amino acids, lipids, vitamins or carbohydrates in microorganisms such as *E. coli* and *C. glutamicum* have tried to achieve this goal by e.g. increasing the expression of genes involved in the biosynthetic pathways of the respective fine chemicals.

Attempts to increase production of e.g. lysine by upregulating the expression of genes being involved in the biosynthetic pathway of lysine production are e.g. described in WO 02/10209, WO 2006008097, WO2005059093 or in Cremer et al. (*Appl. Environ. Microbiol*, (1991), 57 (6), 1746-1752).

However, there is a continuing interest in identifying further targets in metabolic pathways which can be used to beneficially influence the production of methionine in microorganisms such as *C. glutamicum.*

SUMMARY OF THE INVENTION

In some embodiments, the present invention provides methods for production of L-methionine in microorganisms.

In some embodiments, the present invention provides microorganisms which produce L-methionine.

These embodiments and further embodiments of the invention, as they will become apparent from the ensuing description, are attained by the subject matter of the independent claims.

Some of the preferred embodiments of the invention are set out in the dependent claims.

According to one aspect of the present invention, a method for producing L-methionine in a microorganism is considered which comprises the step of cultivating a microorganism that is derived by genetic modification from a starting organism such that said microorganism has an increased amount and/or activity of a cob(I)alamin-dependent methionine synthase I(MetH) reactivation system compared to said starting organism.

The method may make use of a microorganism that is selected from the group comprising microorganisms of the genus *Enterobacteria, Corynebacterium, Escherichia, Bacillus* and *Streptomyces*. Use of the species *Corynebacterium glutamicum* (*C. glutamicum*) and *Escherichia coli* (*E. coli*) is particularly preferred.

In one of the preferred methods of producing methionine in accordance with the invention, a cob(I)alamin-dependent reactivation system is used which uses:

- at least one electron transfer protein, functional homologues, and/or functional fragments thereof, and/or
- at least one electron transfer reductase, functional homologues, and/or functional fragments thereof.

In these methods, an increase in the amount and/or activity of said cob(I)alamin-dependent reactivation system may be achieved by increasing the amount and/or activity of said at least one electron transfer protein, functional homologues, and/or functional fragments thereof or of said at least one electron transfer protein-reductase, functional homologues, and/or functional fragments thereof. The amount and/or activity of a cob(I)alamin-dependent reactivation system may also be increased by increasing the amount and/or activity of at least said one electron transfer protein, functional homologues, and/or functional fragments thereof as well as said one electron transfer protein-reductase, functional homologues, and/or functional fragments thereof. An increase in the amount and/or activity of any of the aforementioned factors may be judged by as a comparison to a starting microorganism.

In some of the preferred embodiments, the electron transport protein will be selected from the group comprising ferredoxins, flavodoxins, functional homologues, and/or functional fragments thereof. The electron transport protein-reductase will be selected from the group comprising ferredoxin-reductases, flavodoxin-reductases, functional homologues, and/or functional fragments thereof.

In this specification, particular proteins may be referred to by the name of the gene that encodes said protein. For example, "fdxC" may refer to either the gene fdxC or the protein encoded by the gene fdxC.

Typical examples of electron transfer proteins include e.g. the ferredoxins of *C. glutamicum*, namely fdxC (SEQ ID Nos.: 1 and 2), fdxD (SEQ ID Nos.: 3 and 4), fdxA (SEQ ID Nos.: 5 and 6), functional homologues and/or functional fragments thereof. In the case of *E. coli*, electron transport protein include e.g. fldA (SEQ ID Nos.: 7 and 8), fldB (SEQ ID Nos.: 9 and 10), functional homologues, and/or functional fragments thereof.

A typical of example of an electron transfer protein-reductase in the case of e.g. *C. glutamicum* will be fprA1 (SEQ ID Nos.: 11 and 12), fprA2 (SEQ ID Nos.: 13 and 14), fprA3 (SEQ ID Nos.: 15 and 16), fldR1 (SEQ ID Nos.: 17 and 18), functional homologues, and/or functional fragments thereof. In the case of e.g. *E. coli*, a typical example of an electron transfer protein-reductase will be fldR (SEQ ID Nos.: 19 and 20), functional homologues, and/or functional fragments thereof.

An increase in the amount and/or of the activity of the aforementioned electron transfer proteins and/or electron transfer protein-reductases may be achieved by relying either on an increase in the amount and/or activity of factors that are present within the respective microorganism above the endogenous level of these factors or by relying on these proteins being derived from other sources than the microorganism in question.

The above-described embodiments of the methods in accordance with the invention are preferably undertaken by cultivating microorganisms of the genera *Corynebacterium* and *Escherichia*. Cultivating the species *C. glutamicum* and *E. coli* can be particularly preferred. The above-described genetic modifications can be introduced into wild-type strains of e.g. *C. glutamicum* or *E. coli*. In some of the preferred embodiments, genetic alterations will be introduced into e.g. *C. glutamicum* or *E. coli* strains that are already considered to be methionine-producing strains.

In another aspect, the present invention relates to microorganisms which have been derived by genetic modification from a starting microorganism to produce an increased amount and/or activity of a cob(I)alamin-dependent MetH reactivation system.

These microorganisms may be further characterized in that such a cob(I)alamin-dependent metH reactivation system comprises at least one electron transfer protein, functional homologues, and/or functional fragments thereof, and/or at least one electron transfer protein-reductase, functional homologues, and/or functional fragments thereof.

In these microorganisms, an increase in the amount and/or activity of the cob(I)alamin-dependent MetH reactivation system may be achieved by increasing the amount and/or activity of at least one said electron transfer protein, functional homologues, and/or functional fragments thereof or of at least one said electron transfer protein-reductase, functional homologues, and/or functional fragments thereof.

In another preferred embodiment, microorganisms will be modified to show an increase in the amount and/or activity of at least one said electron transfer protein, functional homologues, and/or functional fragments thereof as well as of said electron transfer protein-reductase, functional homologues, and/or functional fragments thereof.

Typically, to evaluate an increase in the amount and/or activity of the aforementioned factors, a comparison is made with respect to a starting microorganism.

A microorganism may be selected from the aforementioned group comprising the genera *Enterobacteria, Corynebacterium, Escherichia, Bacillus*, and *Streptomyceae*. The species *C. glutamicum* and *E. coli* may be particularly preferred again.

As to the electron transfer protein, this may be selected from the group comprising flavodoxin, ferredoxin, functional homologues, and/or functional fragments thereof. For *C. glutamicum*, the aforementioned group comprising fdxC, fdxD, and fdxA as well as their homologues and/or fragments may be considered. In the case of *E. coli*, one may consider fldA and fldB as well as their functional homologues and/or functional fragments.

As far as the electron transport protein reductase is concerned, this may be selected from the group comprising ferredoxin reductases, flavodoxin reductases, functional homologues, and functional fragments thereof. In *C. glutamicum*, one may consider fprA1, fprA2, fprA3, fldR1, functional homologues, and/or functional fragments thereof. In *E. coli*, one may consider fldR, functional homologues, and/or functional fragments thereof. An increase in the amount and/or the activity of the aforementioned factors may be achieved by increasing the amount and/or activity of factors that are endogenously present within the microorganism above the endogenous level or by introducing these factors from other sources.

The present invention further relates to the use of the aforementioned microorganisms for producing methionine. The microorganism can be preferably derived from the genera of *Corynebacterium* and *Escherichia*. The species *C. glutamicum* and *E. coli* are particularly preferred. The genetic alterations can be introduced either in a wild-type strain of e.g. *C. glutamicum* and/or *E. coli* or in a strain that is already considered to be a methionine-producing strain. Similar principles apply to other microorganisms.

DETAILED DESCRIPTION OF THE INVENTION

The present invention relates to a method of producing L-methionine, comprising the step of cultivating a genetically modified microorganism and optionally isolating methionine. The present invention also relates to a genetically modified microorganism which is capable of producing L-methionine.

The present invention is based on the finding that one can increase methionine production in a microorganism not only by increasing the amount and/or activity of cob(I)alamin-dependent MetH, but by increasing the amount and/or activity of a reactivation system for cob(I)alamin-dependent MetH.

In the conventional biosynthesis of methionine, the step of transferring the methyl group from 5-methyltetrahydrofolate to homocysteine by enzymes which are collectively designated as methionine synthases is a rate-limiting step.

Methionine synthases can be grouped into cob(I)alamin-dependent methionine synthases I (the aforementioned MetH, EC 2.1.1.13) and cob(I)alamin-independent methionine synthases II (MetE, EC 2.1.1.14). As regards the cob(I)

alamin-dependent methionine synthase MetH, it has been observed that the cob(I)alamin co-factor bound to MetH becomes oxidized to cob(II)alamine (see e.g. Hall et al. (2000), *Biochemistry,* 39, 10, 711-719).

Surprisingly, it has been found by the inventors that an increased reduction of cob(I)alamin of cob(II)alamine- to cob(I)alamin-bound MetH can lead to increased methionine synthesis in microorganisms.

In *E. coli*, reactivation of cob(I)alamin-dependent MetH is mediated by flavodoxin, which supplies the reducing equivalents for the reductive re-methylation and by NADPH:flavodoxin oxidorexductase (which, for the purposes of the present invention, is also designated as flavodoxin-reductase) supplying the reducing equivalents for recycling flavodoxin. Surprisingly, the inventors have found that such a reactivation system derived from *E. coli* can be used in Coryneform bacteria such as *C. glutamicum* for which reactivation of cob(I) alamin-depending MetH has not been known so far. Further, the inventors have identified a reactivation system that is endogenously present in Coryneform bacteria such as *C. glutamicum.*

Before describing exemplary embodiments of the present invention in detail, the following definitions are provided.

As used in the specification and claims, the singular forms of "a" and "an" also include the respective plurals unless the context clearly dictates otherwise.

The terms "about" and "approximately" in the context of the present invention generally denote a level or interval of accuracy that a person skilled in the art will understand to still ensure the technical effect of the feature in question. As regards numerical values, these terms typically indicate deviation from the indicated numerical value of ±10% and preferably of ±5%.

It is to be understood that the term "comprising" is not limiting. For the purposes of the present invention, the term "consisting of" is considered to be a preferred embodiment of the term "comprising of." If hereinafter a group is defined as comprising at least a certain number of embodiments, this means that it also discloses a group that preferably consists of these embodiments only.

Similarly, if in the context of the present invention a group is defined as comprising "at least one" embodiment, this means that it also discloses a group that preferably consists of the one embodiment that is specifically mentioned.

For the purposes of the present invention, the term "microorganism" refers to prokaryotes and lower eukaryotes.

The microorganisms of the present invention thus comprise microorganisms as they are known in the art to be useful for production of fine chemicals such as amino acids, vitamins, enzyme co-factors, etc. They can be selected from the group comprising the genera *Eneterobacteria, Corynebacterium* and thereof preferably *C. glutamicum, Escherichia* and thereof preferably *E. coli, Klebsiella, Bacillus* and thereof preferably *Bacillus subtilis*, Brevibacterium, actinobacteria, cyanobacteria, proteobacteria, halobacteria, methanococci, mycobacteria, salmonella, shigella, *streptomyceae, Saccharomyces* and thereof preferably *S. cerevisiae, Schizzosaccharomyces* and thereof preferably *S. Pombe, Pichia* and thereof preferably *P. pastoris, Kluyveromyces, Ashbya* and *Aspergillus.*

A preferred embodiment of the invention relates to the use of micoroorganims which are selected from coryneform bacteria such as bacteria of the genus *Corynebacterium*. Particularly preferred are the species *Corynebacterium glutamicum, Corynebacterium acetoglutamicum, Corynebacterium acetoacidophilum, Corynebacterium callunae, Corynebacterium ammoniagenes, Corynebacterium thermoaminogenes, Corynebacterium melassecola* and *Corynebacterium effiziens.*

In preferred embodiments of the invention the host cells may be selected from the group comprising *Corynebacterium glutamicum* ATCC13032, *C. acetoglutamicum* ATCC15806, *C. acetoacidophilum* ATCC13870, *Corynebacterium thermoaminogenes* FERMBP-1539, *Corynebacterium melassecola* ATCC17965, *Corynebacterium effiziens* DSM 44547, *Corynebacterium effiziens* DSM 44549, *Brevibacterium flavum* ATCC14067, *Brevibacterium lactoformentum* ATCC13869, *Brevibacterium divarecatum* ATCC 14020, *Corynebacterium glutamicum* KFCC10065 and *Corynebacterium glutamicum* ATCC21608 as well as strains that are derived thereof by e.g. classical mutagenesis and selection or by directed mutagenesis.

Other particularly preferred strains of *C. glutamicum* may be selected from the group comprising ATCC13058, ATCC 13059, ATCC13060, ATCC21492, ATCC21513, ATCC21526, ATCC21543, ATCC13287, ATCC21851, ATCC21253, ATCC21514, ATCC21516, ATCC21299, ATCC21300, ATCC39684, ATCC21488, ATCC21649, ATCC21650, ATCC19223, ATCC13869, ATCC21157, ATCC21158, ATCC21159, ATCC21355, ATCC31808, ATCC21674, ATCC21562, ATCC21563, ATCC21564, ATCC21565, ATCC21566, ATCC21567, ATCC21568, ATCC21569, ATCC21570, ATCC21571, ATCC21572, ATCC21573, ATCC21579, ATCC19049, ATCC19050, ATCC19051, ATCC19052, ATCC19053, ATCC19054, ATCC19055, ATCC19056, ATCC19057, ATCC19058, ATCC19059, ATCC19060, ATCC19185, ATCC13286, ATCC21515, ATCC21527, ATCC21544, ATCC21492, NRRL B8183, NRRL W8182, B12NRRLB12416, NRRLB12417, NRRLB12418 and NRRLB11476.

The abbreviation KFCC stands for Korean Federation of Culture Collection, ATCC stands for American-Type Strain Culture Collection and the abbreviation DSM stands for Deutsche Sammlung von Mikroorganismen. The abbreviation NRRL stands for ARS cultures collection Northern Regional Research Laboratory, Peorea, Ill., USA.

In the context of the present invention, the term "reactivation system" refers to a combination of enzymatic activities which reduce cob(II)alamin and allow for cob(I)alamin-dependent MetH to begin or resume its enzymatic activity. An increase in the amount and/or activity of a cob(I)alamin-dependent MetH reactivation system in the context of the present invention means that the amount and/or activity of at least one factor of the combination of enzymatic activities forming the aforementioned reactivation system is increased in order to ensure an increased rate and/or level of cob(II) alamin to cob(I)alamin reduction compared to a situation in which the potentially endogenously present reactivation system is not genetically influenced.

As will be pointed out in further detail below, a cob(I) alamin-dependent MetH reactivation system typically consists of at least an electron transport protein which preferably supplies the reducing equivalents for the reductive re-methylation of cob(I)alamin-dependent MetH and at least an electron transport protein reductase which preferably supplies the reducing equivalents for recycling the electron transfer protein.

An electron transport protein in accordance with the present invention may preferably be selected from the group of ferredoxins, flavodoxins, functional fragments, and/or functional homologues thereof.

A person skilled in the art will be aware that the question of whether an electron transfer protein such as a ferredoxin or a flavodoxin can indeed be used to increase the amount and/or activity of a cob(I)alamin-dependent MetH reactivation system will depend on the particular organism. Thus, it will be shown below that the function of an electron transport protein for reactivation of cob(I)alamin-dependent MetH may be fulfilled in *E. coli* by e.g. flavodoxin while the corresponding role may be fulfilled in *C. glutamicum* by ferredoxins.

In accordance with the present invention, the electron transport protein-reductase, which may also be designated as an electron transport protein-oxidoreductase, may be selected from the group of ferredoxin (oxido) reductases. These enzymes may also be designated as NADPH:ferredoxin (oxido) reductases. The electron transport protein-reductases may also be selected from the group comprising flavodoxin (oxido) reductases that, again, may be designated as NADPH: flavodoxin (oxido) reductases. Of course, the electron transport protein-reductases may also be selected from functional homologues and/or functional fragments of the aforementioned reductases.

As for the electron transport protein, a person skilled in the art will understand that the question of whether e.g. an increase in the amount and/or activity of an electron transfer protein-reductase can be used to increase the amount and/or activity of a cob(I)alamin MetH-dependent reactivation system will, to some extent, depend on the specific microorganism. Thus, in *E. coli* this function may be performed by a flavodoxin (oxido) reductase while in *C. glutamicum* the present invention shows this function to be fulfilled by a ferredoxin reductase. Nevertheless, an *E. coli* cob(I)alamin-dependent MetH reactivation system can be established in *C. glutamicum* by e.g. overexpressing *E. coli* flavodoxin and *E. coli* flavodoxin (oxido) reductase while, similarly, a *C. glutamicum* cob(I)alamin-dependent MetH reactivation system can be established in *E. coli* by overexpressing *C. glutamicum* ferredoxin and *C. glutamicum* ferredoxin reductase.

As will be explained in detail by the following description, the present invention is primarily concerned with microorganisms that have been genetically modified in order to display an increased amount and/or activity of certain enzymes.

The terms "genetic modification" and "genetic alteration" as well as their grammatical variations within the meaning of the present invention are intended to mean that a microorganism has been modified by means of gene technology to express an altered amount of one or more proteins which can be naturally present in the respective microorganism, one or more proteins which are not naturally present in the respective microorganism, or one or more proteins with an altered activity in comparison to the proteins of the respective non-modified microorganism. A non-modified microorganism is considered to be a "starting organism", the genetic alteration of which results in a microorganism in accordance with the present invention.

The term "starting organism" therefore can refer to the wild-type of an organism. In the case of *C. glutamicum*, this may e.g. be ATCC13032. However, the term "starting organism" for the purposes of the present invention may also refer to an organism which already carries genetic alterations in comparison to the wild-type organism of the respective species, but which is then further genetically modified in order to yield an organism in accordance with the present invention.

In case of *C. glutamicum*, the starting organism may thus be a wild-type *C. glutamicum* strain such as ATCC13032. However, the starting organism may preferably also be e.g. a *C. glutamicum* strain which has already been engineered for production of methionine.

Such a methionine-producing starting organism can e.g. be derived from a wild type Coryneform bacterium and preferably from a wild type *C. glutamicum* bacterium which contains genetic alterations in at least one of the following genes: $ask^{fbr}$, $hom^{fbr}$ and metH wherein the genetic alterations lead to overexpression of any of these genes, thereby resulting in increased production of methionine relative to methionine produced in the absence of the genetic alterations. In a preferred embodiment, such a methionine producing starter organism will contain genetic alterations simultaneously in $ask^{fbr}$, $hom^{fbr}$ and metH thereby resulting in increased production of methionine relative to methionine produced in the absence of the genetic alterations.

In these starting organisms, the endogenous copies of ask and hom are typically changed to feedback resistant alleles which are no longer subject to feedback inhibition by lysine threonine, methionine or by a combination of these amino acids. This can be either done by mutation and selection or by defined genetic replacements of the genes by with mutated alleles which code for proteins with reduced or diminished feedback inhibition. A *C. glutamicum* strain which includes these genetic alterations is e.g. *C. glutamicum* DSM17322. The person skilled in the art will be aware that alternative genetic alterations to those being described below for generation of *C. glutamcium* DSM17322 can be used to also achieve overexpression of $ask^{fbr}$, $hom^{fbr}$ and metH.

For the purposes of the present invention, $ask^{fbr}$ denotes a feedback resistant aspartate kinase. $Hom^{fbr}$ denotes a feedback resistant homoserine dehydrogenase. MetH denotes a Vitamin B12-dependent methionine synthase.

In another preferred embodiment, a methionine-producing starting organism can be derived from a wild type Coryneform bacterium and preferably from a wild type *C. glutamicum* bacterium which contains genetic alterations in at least one of the following genes: $ask^{fbr}$, $hom^{fbr}$, metH, metA (also referred to as metX), metY (also referred to as metZ), and $hsk^{mutated}$, wherein the genetic alterations lead to overexpression of any of these genes, thereby resulting in increased production of methionine relative to methionine produced in the absence of the genetic alterations. In a preferred embodiment, such a methionine producing starter organism will contain genetic alterations simultaneously in $ask^{fbr}$, $hom^{fbr}$, metH, metA (also referred to as metX), metY (also referred to as metZ), and $hsk^{mutated}$ thereby resulting in increased production of methionine relative to methionine produced in the absence of the genetic alterations.

In these starting organisms, the endogenous copies of ask, hom and hsk are typically replaced by $ask^{fbr}$, $hom^{fbr}$ and $hsk^{mutated}$ as described above for $ask^{fbr}$ and $hom^{fbr}$. A *C. glutamicum* strain which includes these genetic alterations is e.g. *C. glutamicum* M2014. The person skilled in the art will be aware that alternative genetic alterations to those being described below specifically for generation of *C. glutamicum* M2014 can be used to also achieve overexpression of $ask^{fbr}$, $hom^{fbr}$, metH, metA (also referred to as metX), metY (also referred to as metZ), and $hsk^{mutated}$.

For the purposes of the present invention, metA denotes a homoserine succinyltransferase e.g. from *E. coli*. MetY denotes a O-Acetylhomoserine sulfhydrylase. $Hsk^{mutated}$ denotes a homoserine kinase which has been mutated to show reduced enzymatic activity. This may be achieved by exchanging threonine with serine or alanine at a position corresponding to T190 of hsk of *C. glutamicum* ATCC 13032 with Genbank accession no. Cgl1184. Alternatively or additionally one may replace the ATG start codon with a TTG start codon. Such mutations lead to a reduction in enzymatic activity of the resulting hsk protein compared the non-mutated hsk gene.

In another preferred embodiment, a methionine-producing starting organism can be derived from a wild type Coryneform bacterium and preferably from a wild type *C. glutamicum* bacterium which contains genetic alterations in at least one of the following genes: $ask^{fbr}$, $hom^{fbr}$, metH, metA (also referred to as metX), metY (also referred to as metZ), $hsk^{mutated}$ and metF wherein the genetic alterations lead to overexpression of any of these genes, in combination with a genetic alterations in one of the following genes: serA wherein the genetic alterations decrease expression of this gene where the combination results in increased methionine production by the microorganism relative to methionine production in absence of the combination.

In these starting organisms, the endogenous copy of ask, hom, hsk is replaced as described above. A *C. glutamicum* strain which includes these genetic alterations is e.g. *C. glutamicum* OM469. The person skilled in the art will be aware that alternative genetic alterations to those being described below specifically for generation of *C. glutamicum* OM469 can be used to also achieve overexpression of $ask^{fbr}$, $hom^{fbr}$, metH, metA (also referred to as metX), metY (also referred to as metZ), $hsk^{mutated}$ and metF and reduced expression of metQ.

In another preferred embodiment, a methionine-producing starting organism can be derived from a wild type Coryneform bacterium and preferably from a wild type *C. glutamicum* bacterium which contains genetic alterations in at least one of the following genes: $ask^{fbr}$, $hom^{fbr}$, metH, metA (also referred to as metX), metY (also referred to as metZ), $hsk^{mutated}$ and metF wherein the genetic alterations lead to overexpression of any of these genes, in combination with genetic alterations in at least one of the following genes: mcbR and metQ wherein the genetic alterations decrease expression of any of these genes where the combination results in increased methionine production by the microorganism relative to methionine production in absence of the combination. In a preferred embodiment, such a methionine producing starter organism will contain genetic alterations simultaneously in $ask^{fbr}$, $hom^{fbr}$, metH, metA (also referred to as metX), metY (also referred to as metZ), $hsk^{mutated}$ and metF wherein the genetic alterations lead to overexpression of any of these genes, in combination with genetic alterations in mcbR and metQ wherein the genetic alterations decrease expression of any of these genes where the combination results in increased methionine production by the microorganism relative to methionine production in absence of the combination.

In these starting organisms, the endogenous copies of ask, hom and hsk are typically replaced as described above while the endogenous copies of mcbR and metQ are typically functionally disrupted or deleted. A *C. glutamicum* strain which includes these genetic alterations is e.g. *C. glutamicum* OM469. The person skilled in the art will be aware that alternative genetic alterations to those being described below specifically for generation of *C. glutamicum* OM469 can be used to also achieve overexpression of $ask^{fbr}$, $hom^{fbr}$, metH, metA (also referred to as metX), metY (also referred to as metZ), $hsk^{mutated}$ and metF and reduced expression of mcbR and metQ.

For the purposes of the present invention, metF denotes a N5,10-methylene-tetrahydrofolate reductase (EC 1.5.1.20). McbR denotes a TetR-type transcriptional regulator of sulfur metabolism (Genbank accession no: AAP45010). MetQ denotes a D-methionine binding lipoprotein which functions in methionine import.

In a further preferred embodiment, a methionine-producing starting organism can be derived from a wild type Coryneform bacterium and preferably from a wild type *C. glutamicum* bacterium which contains genetic alterations in at least one of the following genes: $ask^{fbr}$, $hom^{fbr}$, metH, metA (also referred to as metX), metY (also referred to as metZ), $hsk^{mutated}$, metF, tkt, tal, zwf and 6pgl wherein the genetic alterations lead to overexpression of any of these genes, in combination with genetic alterations in at least one of the following genes: mcbR, metQ and sda wherein the genetic alterations decrease expression of any of these genes where the combination results in increased methionine production by the microorganism relative to methionine production in absence of the combination. In a preferred embodiment, such a methionine producing starter organism will contain genetic alterations simultaneously in $ask^{fbr}$, $hom^{fbr}$, metH, metA (also referred to as metX), metY (also referred to as metZ), $hsk^{mutated}$, metF, tkt, tal, zwf and 6pgl wherein the genetic alterations lead to overexpression of any of these genes, in combination with genetic alterations in mcbR, metQ and sda wherein the genetic alterations decrease expression of any of these genes where the combination results in increased methionine production by the microorganism relative to methionine production in absence of the combination.

A *C. glutamicum* strain which includes these genetic alterations is e.g. *C. glutamicum* GK1259. The person skilled in the art will be aware that alternative genetic alterations to those being described below specifically for generation of *C. glutamicum* GK1259 can be used to also achieve overexpression of $ask^{fbr}$, $hom^{fbr}$, metH, metA (also referred to as metX), metY (also referred to as metZ), $hsk^{mutated}$, metF, tkt, tal, zwf and 6pgl and reduced expression of mcbR, metQ and sda.

For the purposes of the present invention, tkt denotes transketolase, tal denotes transaldolase, zwf denotes glucose-6-phosphate-dehydrogenase, 6pgl denotes 6-phospho-glucono-lactonase and sda denotes serine deaminase (see Table 1). The person skilled in the art understands that for increasing the amount and/or activity of zwf, one will also increase the amount and/or activity of opca which serves as a structural scaffolding protein of zwf. In GK1259, this is achieved by the use of the $P_{SOD}$ promoter which simultaneously increases transcription of the pentose phosphate operon comprising tkt, tal, zwf and 6pgl.

As has been set out above, the genetically modified microorganisms of the present invention are characterized in that at least the amount and/or activity of a cob(I)alamin MetH reactivation system is increased. To this end, one typically increases the amount and/or activity of an electron transport protein and/or of an electron transport protein reductase. To this end, one may use e.g. ferredoxins, flavodoxins, ferredoxin reductases, flavodoxin reductases, functional homologues, and fragments of the aforementioned factors.

Typically, the amount of these factors is increased in the microorganism in accordance with the present invention compared to the respective starting organism by at least about 2%, at least about 5%, at least about 10%, or at least about 20%. In other preferred embodiments, the amount of these factors are increased by at least 30%, by at least 50%, or by at least 75%. In even more preferred embodiments relating to microorganisms, in which the amount of these factors is increased by at least about a factor of 2, at least about a factor of 5, or at least about a factor of 10.

The methods and microorganisms in accordance with the present invention can be used to produce more methionine compared to a situation where the respective starting organism, which has not been genetically modified as outlined below, is cultivated. The microorganisms and methods of the present invention can also be used to increase the efficiency of methionine synthesis.

The term "efficiency of methionine synthesis" describes the carbon yield of methionine. This efficiency is calculated as a percentage of the energy input which entered the system in the form of a carbon substrate. Throughout the invention this value is given in percent values ((mol methionine)(mol carbon substrate)$^{-1}\times 100$. The term "increased efficiency of methionine synthesis" thus relates to a comparison between the starting organism and the actual Coryneform bacterium in which the amount and/or activity of at least one of the below mentioned enzymes has been increased.

Preferred carbon sources according to the present invention are sugars such as mono-, di- or polysaccharides. For example, sugars selected from the group comprising glucose, fructose, hanose, galactose, ribose, sorbose, lactose, maltose, sucrose, raffinose, starch or cellulose may serve as particularly preferred carbon sources.

The methods and microorganisms in accordance with the invention may also be used to produce more methionine compared to the starting organism.

The methods and microorganisms in accordance with the invention may also be used to produce methionine at a faster rate compared to the starting organism. If, for example, a typical production period is considered, the methods and microorganisms will allow to produce methionine at a faster rate, i.e. the same amount methionine will be produced at an earlier point in time compared to the starting organism. This particularly applies for the logarithmic growth phase.

Methods and microorganisms such as *C. glutamicum* in accordance with the invention allow to produce at least about 3 g methionine/l culture volume if the microorganism is incubated in shake flask incubations. A titer of at least about 4 g methionine/l culture volume, at least about 5 g methionine/l culture volume or at least about 7 g methionine/l culture volume can be preferred if the microorganism is incubated in shake flask incubations. A more preferred value amounts to at least about 10 g methionine/l culture volume and even more preferably to at least about 20 g methionine/l cell mass if the microorganism is incubated in shake flask incubations.

Methods and microorganisms such as *C. glutamicum* in accordance with the invention allow to produce at least about 25 g methionine/l culture volume if the microorganism is incubated in fermentation experiments using a stirred and carbon source fed fermentor. An titer of at least about 30 g methionine/l culture volume, at least about 35 g methionine/l culture volume or at least about 40 g methionine/l culture volume can be preferred if the strain is incubated in fermentation experiments using a stirred and carbon source fed fermentor. A more preferred value amounts to at least about 50 g methionine/l culture volume and even more preferably to at least about 60 g methionine/l cell mass if the microorganism is incubated in fermentation experiments using a stirred and carbon source fed fermentor.

In a preferred embodiment, the methods and microorganisms of the invention (such as *C. glutamicum*) allow to increase the efficiency of methionine synthesis and/or the amount of methionine and/or the titer and/or the rate of methionine synthesis in comparison to the starting organism by at least about 2%, at least about 5%, at least about 10% or at least about 20%. In preferred embodiments the efficiency of methionine synthesis and/or the amount of methionine and/or the titer and/or the rated is increased compared to the starting organism by at least about 30%, at least about 40%, or at least about 50%. Even more preferred is an increase of at least about factor 2, at least about factor 3, at least about factor 5 and at least about factor 10.

The term "standard conditions" refers to the cultivation of a microorganism in a standard medium which is not enriched with respect to a particular compound. The temperature, pH and incubation time can vary, as will be described in more detail below.

The standard culture conditions for microorganisms can be taken from the literature, including textbooks such as "Sambrook & Russell, Molecular Cloning—A Laboratory Manual", Cold Spring Harbor Laboratory Press, 3rd edition (2001).

"Minimal media" are media that contain only the necessities for the growth of wild-type or mutant cells, i.e. inorganic salts, a carbon source and water. In the case of mutant cells, a minimal medium can contain one or more additives of substantially pure chemical compounds to allow growth of mutant cells that are deficient in production of such chemical(s).

In contrast, "enriched media" are designed to fulfill all growth requirements of a specific organism, i.e. in addition to the contents of the minimal media, they contain, e.g. amino acids, growth factors, enzyme co-factors, etc.

As has been set out above, the genetically modified microorganisms of the present invention are characterized in that at least the amount and/or activity of a cob(I)alamin MetH reactivation system is increased. To this end, one typically increases the amount and/or activity of an electron transport protein and/or of an electron transport protein reductase. To this end, one may use e.g. ferredoxins, flavodoxins, ferredoxin reductases, flavodoxin reductases, functional homologues, and fragments of the aforementioned factors.

In a preferred embodiment, the microorganisms and methods in accordance with the invention are characterized in that additionally the amount and/or activity of one or more of the following factors, functional homologous and/or functional fragments thereof is increased compared to a starting organism: metA/X, metZ/Y, metF, metH, thrA, metE, and/or the amount and/or activity of one or more of the following factors functional homologous and/or functional fragments thereof is decreased compared to a starting organism: metK, thrB.

Such microorganisms and methods are particularly useful for the production of methionine.

In a particularly preferred embodiment the amount and/or activity of all of the afore-mentioned factors metA/X, metZ/Y, metF, metH, thrA and metE is increased and the amount and the activity of metK and thrB is decreased.

MetA/X refers to a gene coding for an enzyme catalyzing the transfer of an acetyl or succinyl group from the activated acetyl-coenzyme A or the respective succinyl-coenzyme A to the OH group of homoserine to yield o-acetyl-homoserine or o-succinyl-homoserine (Genbank accession: AF052652)

MetZ/Y refers to a gene coding for an enzyme catalyzing the transfer of sulfide or methyl mercaptane to o-acetyl-homoserine or o-succinyl-homoserine, to yield homocysteine. The enzyme metZ/Y utilizes pyridoxal-phosphate as a cofactor (Genbank accession: AF220150)

MetF relates to a gene coding for an enzyme catalyzing the reduction of methylene tetrahydrofolate to methyl tetrahydrofolate utilizing NADPH or NADH as a cofactor and hydrid donor (EC 1.7.99.5, Genbank accession: AAH68531)

MetH relates to a gene coding for an enzyme catalyzing the methyl transfer from methyl tetrahydrofolate on homocysteine utilizing hydroxycobalamin as a cofactor and SAM as a second cofactor (EC 2.1.1.13, Genbank accession: Cgl1507).

ThrA (Homoserine dehydrogenase) relates to a gene coding for an enzyme catalyzing the reduction of asparto semialdehyde utilizing NADPH or NADH as a cofactor (EC 1.1.1.3, Genbank accession: Cgl1183, AAT03321, AAH68417, AEB13106). The enzyme can be used in a mutated form.

ThrB (Homoserine kinase) relates to a gene coding for an enzyme catalyzing the phosporylation of homoserine to phospho homoserine utilizing ATP as a cofactor (EC 2.7.1.39, Genbank accession: Cgl1183). The enzyme can be used in a mutated form.

MetE relates to a gene coding for an enzyme catalyzing the methyl transfer from methyl tetrahydrofolate on homocysteine utilizing SAM as a cofactor (EC 2.1.1.14, Genbank accession: Cgl1139).

MetK relates to a gene coding for an enzyme catalyzing the transfer of S-adenosyl-residue on methionine utilizing ATP as a cofactor S-adenosylmethionine synthetase (EC 2.5.1.6, Genbank accession: Cgl1603).

These additional modifications can, of course, also be introduced into the above-mentioned starting organisms.

The term "increasing the amount" of at least one protein (such as ferredoxin) compared to a starting organism in the context of the present invention means that a starting microorganism is genetically modified to express a higher amount of e.g. one of the above-mentioned enzymes. It is to be understood that increasing the amount of e.g. one enzyme refers to a situation where the amount of functional enzyme is increased. An enzyme such as ferredoxin in the context of the present invention is considered to be functional if it is capable of catalysing the respective reaction.

There are various options to increase the amount of a protein in microorganisms such as Coryneform bacteria which are well known to the person skilled in the art. These options include increasing the copy number of the nucleic acid sequences which encode the respective protein, increasing transcription and/or translation of such nucleic acid sequences or combinations thereof. These various options will be discussed in more detail below.

The term "increasing the activity" of at least one protein refers to the situation that at least one mutation is introduced into the respective wild-type sequences of the protein which leads to production of more methionine compared to a situation where the same amount of wild-type protein is expressed. This may achieved by e.g. using enzymes which carry specific mutations that allow for an increased activity of the enzyme. Such mutations may e.g. inactivate the regions of the enzymes that are responsible for feedback inhibition. By mutating these positions by e.g. introducing non-conservative point mutations, the enzyme may not provide for feedback regulation any more and thus the activity of the enzyme is not down-regulated if e.g. more product molecules are produced. Furthermore, the activity of an enzyme can be increased by introducing mutations which increase the catalytic turnover of an enzyme. Such mutations may be either introduced into the endogenous copy of the gene encoding for the respective enzyme, or they may be provided by over-expressing a corresponding mutant from the exogenous nucleic acid sequences encoding such an enzyme. Such mutations may comprise point mutations, deletions or insertions. Point mutations may be conservative (replacement of an amino acid with an amino acid of comparable biochemical and physical-chemical properties) or non-conservative (replacement of an amino acid with another which is not comparable in terms of biochemical and physical-chemical properties). Furthermore, the deletions may comprise only two or three amino acids up to complete domains of the respective protein.

Thus, the term "increasing the activity" of at least one enzyme refers to the situation where mutations are introduced into the respective wild-type sequence to reduce negative regulatory mechanisms such as feedback-inhibition and/or to increase catalytic turnover of the enzyme.

An increase of the amount and/or activity of a protein such as an enzyme may thus be achieved by different routes, e.g. by switching off inhibitory regulatory mechanisms at the transcriptional, translational or protein level, and/or by increasing gene expression of a nucleic acid encoding for this protein in comparison with the starting organism, e.g. by inducing the endogenous gene or by introducing nucleic acid sequences coding for the protein.

Of course, the approaches of increasing the amount and/or activity of a protein such as an enzyme can be combined. Thus, it is, for example, possible to replace the endogenous copy of an enzyme of Coryneform bacteria with a mutant that encodes for the feedback-insensitive version thereof. If transcription of this mutated copy is set under the control of a strong promoter, the amount and the activity of the respective enzyme is increased. It is understood that in this case the enzyme must still be capable of catalysing the reaction in which it usually participates.

The nucleic acid sequences encoding for a protein such as an enzyme may be of endogenous or exogenous origin. Thus, one may for example increase the amount of a protein such as ferredoxin by either increasing expression of nucleic acid sequences that naturally occur within the respective starting microorganism by e.g. chromosomal integration of additional nucleic acid sequences, or by using a strong promoter in front of the endogenous gene. Alternatively or additionally, one may also increase the amount of a protein such as ferredoxin by expressing the nucleic acid sequence encoding for a homolog of this enzyme from another organism. Examples for this latter scenario will be put forward below.

Thus, one can e.g. increase the amount of ferredoxin in *C. glutamicum* by over-expressing the respective *C. glutamicum* sequence, either from an autonomously replicating vector or from an additionally inserted chromosomal copy (see below) or one may use the corresponding enzymes from e.g. *Corynebacterium efficiens, C. jeikeium, Brevibacterium linens, B. flavum, B. lactofermentum*, etc., and over-express the enzyme by e.g. use of an autonomously replicable vector.

In some circumstances, it may be preferable to use the endogenous enzymes, as the endogenous coding sequence of e.g. *C. glutamicum* are already optimized with respect to its codon usage for expression in *C. glutamicum.*

If, in the context of the following description, it is stated that the amount and/or activity of a protein such as of a specific enzyme should be decreased in comparison to the starting organism, the above definitions apply mutatis mutandis.

Reduction of the amount and/or activity of a protein such as an enzyme may be achieved by partially or completely deleting the nucleic acid sequences encoding the respective protein, by inhibiting transcription by e.g. introducing weak promoters, by inhibiting translation by amending the codon usage accordingly, by introducing mutations into the nucleic acid sequences encoding the respective proteins which render the proteins non-functional and/or combinations thereof.

In the context of the following description, use will be made of the term "functional homolog". The term "functional homolog" for the purposes of the present invention relates to the fact that a certain enzymatic activity may not only be provided by a specific protein of defined amino acid sequence, but also by proteins of similar sequence from other (un)related organisms.

For example, the activity of ferredoxin can be increased in *C. glutamicum* by expressing nucleic acid sequences which encode for the fdxC of *C. glutamicum* (SEQ ID NO. 1: nucleic acid sequence, SEQ ID NO. 2: amino acid sequence, gene bank accession numbers: 1019087 or Ncgl1057 for the gene, and NP_600330.1 for the protein) or by functional homologs thereof.

Homologues of a protein from other organisms can be easily identified by the skilled person by homology analysis. This can be done by determining similarity, i.e. percent identity between amino acid or nucleic acid sequences for putative homologs and the sequences for the genes or proteins encoded by them (e.g., nucleic acid sequences for fdxC, fdxD, fdxA, fldA, fldB, fprA1, fprA2, fprA3, fldR1, fldR).

Percent identity may be determined, for example, by visual inspection or by using algorithm-based homology.

For example, in order to determine percent identity of two amino acid sequences, the algorithm will align the sequences for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

Various computer programs are known in the art for these purposes. For example, percent identity of two nucleic acid or amino acid sequences can be determined by comparing sequence information using the GAP computer program described by Devereux et al. (1984) Nucl. Acids. Res., 12:387 and available from the University of Wisconsin Genetics Computer Group (UWGCG). Percent identity can also be determined by aligning two nucleic acid or amino acid sequences using the Basic Local Alignment Search Tool (BLAST™) program (as described by Tatusova et al. (1999) FEMS Microbiol. Lett., 174:247.

At the filing date of this patent application, a standard software package providing the BLAST programme can be found on the BLAST website of the NCBI (hypertext transfer protocol://world wide web.ncbi.nlm.nihDOTgov/BLAST/) wherein "hypertext transfer protocol"=http, "world wide web"=www, and wherein "DOT"=".". For example, if one uses any of the aforementioned SEQ IDs, one can either perform a nucleic acid sequence- or amino sequence-based BLAST search and identify closely related homologs of the respective enzymes in e.g. *E. coli, S. cervisiae, Bacillus subtilis*, etc. For example, for nucleic acid sequence alignments using the BLAST™ program, the default settings are as follows: reward for match is 2, penalty for mismatch is −2, open gap and extension gap penalties are 5 and 2 respectively, gap.times.dropoff is 50, expect is 10, word size is 11, and filter is OFF.

Comparable sequence searches and analysis can be performed at the EMBL database (hypertext transfer protocol://world wide web.emblDOTorg) or the Expasy homepage (hypertext transfer protocol://world wide web.expasyDOTorg/) wherein "hypertext transfer protocol"=http, "world wide web"=www, and wherein "DOT"=".". All of the above sequences searches are typically performed with the default parameters as they are pre-installed by the database providers at the filing date of the present application. Homology searches may also routinely be performed using software programmes such as the laser gene software of DNA Star, Inc., Madison, Wis., USA, which uses the CLUSTAL method (Higgins et al. (1989), Comput. Appl. Biosci., 5 (2) 151).

The skilled person understands that two proteins will likely perform the same function (e.g. provide the same enzymatic activity) if they share a certain degree of identity as described above. A typical lower limit on the amino acid level is typically at least about 25% identity. On the nucleic acid level, the lower limit is typically at least 50%.

Preferred identity grades for both type of sequences are at least about 50%, at least about 60% or least about 70%. More preferred identity levels are at least about 80%, at least about 90% or at least about 95%. These identity levels are considered to be significant.

As used herein, the terms "homology" and "homologous" are not limited to designate proteins having a theoretical common genetic ancestor, but includes proteins which may be genetically unrelated that have, none the less, evolved to perform similar functions and/or have similar structures. The requirement that the homologues should be functional means that the homologues herein described encompasse proteins that have substantially the same activity as the reference protein. For proteins to have functional homology, it is not necessarily required that they have significant identity in their amino acid sequences, but, rather, proteins having functional homology are so defined by having similar or identical activities, e.g., enzymatic activities.

Preferably, an enzyme from another organism than e.g. the host Coryneform bacteria will be considered to be a functional homolog if it shows at least significant similarity, i.e. about 50% sequence identity on the amino acid level, and catalyses the same reaction as its counterpart in the Coryneform bacterium. Functional homologues which provide the same enzymatic activity and share a higher degree of identity such as at least about 60%, at least about 70%, at least about 80% or at least about 90% sequence identity on the amino acid level are further preferred functional homolgues.

The person skilled in the art knows that one can also use fragments or mutated versions of the aforementioned enzymes from e.g. Coryneform bacteria and of their functional homologues in other organisms as long as these fragments and mutated versions display the same type of functional activity. Typical functionally active fragments will display N-terminal and/or C-terminal deletions while mutated versions typically comprise deletions, insertions or point mutations.

By way of example, a sequence of *E. coli* will be considered to encode for a functional homolog of *C. glutamicum* ferredoxin fdxC if it displays the above-mentioned identity levels on the amino acid level to SEQ ID NO. 2 and displays the same enzymatic activity. Examples can be taken from Table 1. One can also use fragments or e.g. point mutants of these sequences as long as the resulting proteins still catalyse the same type of reaction as the full-length enzymes.

Increasing the Amount and/or Activity of a Cob(I)Alamin-Dependent MetH Reactivation System in Microorganisms As has been set out above, the present invention is based on the finding that an increase in a cob(I)alamin-dependent MetH reactivation system leads to an improved production of methionine and can be used for improved production of methionine in microorganisms.

It has further been set out above that in some of the preferred embodiments one can achieve an increase in the amount and/or activity of such a cob(I)alamin-dependent MetH reactivation system increasing the amount and/or activity of an electron transport protein and/or an electron transport protein reductase as well as of the functional homologues and/or fragments thereof. It has further been specified that ferredoxins and flavodoxins are typical examples of such electron transfer proteins and that ferredoxin reductases and flavodoxin reductases are typical examples of such electron transport protein reductases.

Increasing the amount and/or activity of a cob(I)alamin-dependent MetH reactivation system will now be discussed with respect to some of these preferred embodiments, namely by overexpressing some of the aforementioned factors in species such as *C. glutamicum* and *E. coli*. A person skilled in the art will nevertheless be aware that these specific examples are not to be construed as limiting. A person skilled in the art will understand how to isolate and identify enzymatic activities participating in cob(I)alamin-dependent MetH reactivation in other organisms than *C. glutamicum* and *E. coli*. A person skilled in the art will, furthermore, understand in light of the present description how to e.g. express ferredoxins, flavodoxins, and their respective reductases, which are described in the present specification in other microorganisms.

As will become clear from the embodiment examples below, microorganisms such as *E. coli* and *C. glutamicum* comprise sequences for ferredoxin, flavodoxin, ferredoxin reductases, and flavodoxin reductases. In such microorganisms, increasing the amount and/or activity of a cob(I)alamin MetH reactivation system may require raising the amount and/or activity of these enzymes above the level of the respective starting organism by e.g. overexpressing endogenous or exogenous nucleic acid sequences encoding for these enzymatic activities.

The present invention thus relates inter alia to a *C. glutamicum* or *E. coli* microorganisms in which the amount and/or activity of the aforementioned factors is increased and the use of such microorganisms to produce methionine. Increasing the amount and/or activity of the aforementioned factors including e.g. ferredoxin, flavodoxin, ferredoxin reductases, and flavodoxin reductases can be achieved by e.g. increasing the copy number of nucleic acid sequences encoding such factors, increasing transcription, and/or translation of sequences encoding such factors, or a combination thereof.

In *C. glutamicum*, only endogenous factors may participate in reactivation of cob(I)alamin-dependent MetH and thus be used for an increase in the amount and/or activity in a corresponding reactivation system. Electron transport proteins comprise fdxC, fdxD, and fdxA.

As far as fdxC is concerned the nucleic acid sequence encoding for this factor is depicted in SEQ ID No. 1, while the amino acid sequence is depicted in SEQ ID No. 2. The gene bank accession number is geneID: 1019087 or Ncgl1057 for the gene NP_600330.1 for the protein).

As far as fdxD is concerned the nucleic acid sequence encoding for this factor is depicted in SEQ ID No. 3, while the amino acid sequence is depicted in SEQ ID No. 4. The gene bank accession number is geneID: 1020899 or NCgl2856 for the gene and NP_602147.1 for the protein).

As far as fdxA is concerned the nucleic acid sequence encoding for this factor is depicted in SEQ ID No. 5, while the amino acid sequence is depicted in SEQ ID No. 6. The gene bank accession number is geneID:1018555 or NCgl0526 for the gene and NP_599787.1 for the protein.

In *C. glutamicum*, an electron transport protein-reductases may be selected from the group fprA1, fprA2, fprA3, and fldR1, all of which have been annotated as ferredoxin reductases.

As far as fprA1 is concerned the nucleic acid sequence encoding for this factor is depicted in SEQ ID No. 11, while the amino acid sequence is depicted in SEQ ID No. 12. The gene bank accession number is geneID:1020760 or NCgl2719 for the gene, and NP_602009.1 for the protein.

As far as fprA2 is concerned the nucleic acid sequence encoding for this factor is depicted in SEQ ID No. 13, while the amino acid sequence is depicted in SEQ ID No. 14. The gene bank accession number is geneID:1020699 or NCgl2658 for the gene, and NP_601949.1 for the protein.

As far as fprA3 is concerned the nucleic acid sequence encoding for this factor is depicted in SEQ ID No. 15, while the amino acid sequence is depicted in SEQ ID No. 16. The gene bank accession number is geneID:1020355 or NCgl2322 for the gene, and protein NP_601606.1 for the protein.

As far as fldR1 is concerned the nucleic acid sequence encoding for this factor is depicted in SEQ ID No. 17, while the amino acid sequence is depicted in SEQ ID No. 18. The gene bank accession number is NCgl2301 or geneID: 1020334 for the gene, and protein NP_601585.1 for the protein.

Further homologues of these factors can be identified by performing the aforementioned homology searches using e.g. the BLAST algorithm.

As far as *E. coli* is concerned the electron transport protein may be selected from the group fldA or fldB. These proteins have been annotated as flavodoxins.

As far as fldA is concerned the nucleic acid sequence encoding for this factor is depicted in SEQ ID No. 7, while the amino acid sequence is depicted in SEQ ID No. 8. The gene bank accession number is g1789262 or EG10318, and Swiss-Prot P23243.

As far as fldB is concerned the nucleic acid sequence encoding for this factor is depicted in SEQ ID No. 9, while the amino acid sequence is depicted in SEQ ID No. 10. The gene bank accession number is g1789262 or EG12697, and Swiss-Prot P41050.

In *E. coli* the electron transport protein reductase may be encoded by fldR, which have been annotated as flavodoxin reductase. This gene has also been given other names, including fpr, flxR, and mvrA. The protein has also been referred to as ferredoxin reductase. As far as this factor is concerned the nucleic acid sequence encoding for this factor is depicted in SEQ ID No. 19, while the amino acid sequence is depicted in SEQ ID No. 20. The gene bank accession number isg1790359 or EG11518, and Swiss-Prot P28861.

To increase the amount and/or activity of a cob(I)alamin-dependent MetH reactivation system in *C. glutamicum*, one may either increase the amount and/or activity of the aforementioned endogenous factors in *C. glutamicum* and thus increase the amount and/or activity of fdxC, fdxD, or fdxA and/or fprA1, fprA2, fprA3, and/or fldR1. Alternatively, one may overexpress exogenous factors such as *E. coli* factors and thus express e.g. fldA and/or fldR. In *C. glutamicum* the combination of overexpressing fdxC and fprA1 optionally in combination with *C. glutamicum* metH may be preferred as well as the overexpression of fldA and fldR optionally in combination with *E. coli* metH, or a combination of the two aforementioned sets.

As far as *E. coli* is concerned one may, again, express the above-described endogenous factors or rely on the exogenous factors being known for e.g. *C. glutamicum*. Overexpression of fldA, fldB, or fldR may be sufficient. However, overexpression of fldA and fldR may be preferred. One may also use e.g. overexpression of fdxC and fprA1.

As far as the present invention is concerned with *C. glutamicum* it considers microorganisms in which the amount and/or activity of ferredoxin or ferredoxin reductase and preferably of ferredoxin and ferredoxin reductase is increased.

Similarly, the invention considers *C. glutamicum* microorganisms in which the corresponding activities from other microorganisms are increased such as flavodoxin and/or flavodoxin reductase from *E. coli.*

As far as *E. coli* is concerned the present invention similarly considers microorganisms in which the amount and/or activity of flavodoxin or flavodoxin reductase and preferably of flavodoxin and flavodoxin reductase is increased. Alternatively, one may use factors that perform comparable functions in *C. glutamicum* such as ferredoxin and ferredoxin reductase.

One may, of course, also increase the amount and/or activity of one endogenous and one exogenous factor, Thus, it may be considered to increase the amount of the endogenous ferredoxin and an *E. coli* flavodoxin reductase in *C. glutamicum*. One may, alternatively, increase the amount and/or activity of an *E. coli* flavodoxin and the endogenous ferredoxin reductase in *C. glutamicum*. In *E. coli* one may, thus, increase the amount and/or activity of exogenous *C. glutamicum* ferredoxin and endogenous flavodoxin reductase or one may increase the amount and/or activity of endogenous flavodoxin and exogenous *C. glutamicum* ferredoxin reductase.

Further embodiments of the present invention will be recognized by a person skilled in the art. The above-mentioned examples have been illustrated with respect to the sequences typically encoding native versions of electron transport proteins and electron transport protein reductases such as e.g. fdxC and fprA1. A person skilled in the art will, however, understand that, regardless of whether the amount and/or activity of an endogenous and/or exogenous factor is to be increased, one can also use functional homologues and/or functional fragments of these factors.

The copy number of nucleic acid sequences encoding the aforementioned factors such as fdxC can be increased in a microorganism and preferably in *C. glutamicum* by e.g. either expressing the sequence from autonomously replicating plasmids or by integrating additional copies of the respective nucleic acid sequences into the genome of the microorganism and preferably of *C. glutamicum.*

In case of autonomously replicable vectors, these can be stably kept within e.g. a Coryneform bacterium. Typical vectors for expressing polypeptides and enzymes such as fdxC in *C. glutamicum* include pCliK, pB and pEKO as described in Bott, M. and Eggeling, L., eds. Handbook of *Corynebacterium glutamicum*. CRC Press LLC, Boca Raton, Fla.; Deb, J. K. et al. (FEMS Microbiol. Lett. (1999), 175 (1), 11-20), Kirchner O. et al. (J. Biotechnol. (2003), 104 (1-3), 287-299), WO2006069711 and in WO2007012078.

In another approach for increasing the copy number of nucleic acid sequences encoding a polypeptide in a Coryneform bacterium, one can integrate additional copies of nucleic acid sequences encoding such polypeptides into the chromosome of *C. glutamicum*. Chromosomal integration can e.g. take place at the locus where the endogenous copy of the respective poly-peptide is localized. Additionally and/or alternatively, chromosomal multiplication of poly-peptide encoding nucleic acid sequences can take place at other loci in the genome of a Coryneform bacterium.

In case of *C. glutamicum*, there are various methods known to the person skilled in the art for increasing the gene copy number by chromosomal integration. One such method makes e.g. use of the vector pK19 sacB and has been described in detail in the publication of Schäfer A, et al. J Bacteriol. 1994 176 (23): 7309-7319. Other vectors for chromosomal integration of polypeptide-encoding nucleic acid sequences include or pCLIK int sacB as described in WO2005059093 and WO2007011845.

Another preferred approach for increasing the amount and/or activity of the aforementioned factors such as fdxC in microorganisms and particularly in *C. glutamicum* is to increase transcription of the coding sequences by use of a strong promoter.

If the activity of an endogenous e.g. ferredoxin is increased by use of a strong promoter, then the term “strong promoter” means that transcription from the newly introduced promoter is stronger than from the naturally occurring endogenous promoter.

However, in a case where e.g. flavodoxin fldA is expressed in *C. glutamicum* which does not know this type of enzyme, a promoter can be used which is known to provide strong expression of endogenous genes of *C. glutamicum.*

Preferred promoters in this context are the promoters $P_{SOD}$ (SEQ ID No. 21), $P_{groES}$ (SEQ ID No. 22), $P_{EFTu}$ (SEQ ID No. 23), phage SP01 promoter $P_{15}$ (SEQ ID No.38), and $\lambda P_R$ (SEQ ID No. 24), also sometimes referred to as lambda$P_R$. In *C. glutamicum* the $\lambda P_R$ promoter can be stronger than the $P_{SOD}$ promoter. The $P_{SOD}$ promoter can be stronger than the $P_{groES}$ promoter, and the $P_{groES}$ promoter can be weaker than the $P_{EFTu}$ promoter or the $P_{15}$ promoter. The $P_{EFTu}$ promoter can be stronger than the $P_{SOD}$ promoter. However the strength of a promoter in any organism is not necessarily an inherent property of the promoter, since promoter strength can vary widely depending on the context in which the promoter is placed by the genetic engineering.

The present invention therefore also relates to a method which comprises culturing the above-described microorganisms and optionally isolating methionine.

Approaches for increasing the amount and/or activity for a protein will be described in detail below. These approaches can, of course, also be applied to factors such as fdxC, fprA1, and fldA.

A preferred embodiment relates to *C. glutamicum* microorganisms which display an increase in the amount and/or activity of one or more ferredoxins such as fdxC, fdxD, or fdxA and of one or more ferredoxin reductases such as fprA1, fprA2, fprA3, and fldR1. The present invention also relates preferably to the use of these *C. glutamicum* organisms in the production of methionine.

A typical *C. glutamicum* strain that can be used as a starting organism will be a wild-type strain such as ATCC13032. However, it can be preferred to use a starting organism which has already been genetically modified to ensure increased methionine production. Such an organism may display the characteristics of DSM17323 and thus display an increased amount and/or activity of $ask^{fbr}$, $hom^{fbr}$ and metH. A preferred starting strain may also have the characteristics of M2014 and display an increased amount and/or activity of $ask^{fbr}$, $hom^{fbr}$, metH, metA, metY, and $hsk^{mutated}$. Other preferred starting organisms may have the characteristics of OM469 and display an increased amount and/or activity of $ask^{fbr}$, $hom^{fbr}$, metH, metA, metY, $hsk^{mutated}$ and metF and display a reduced amount and/or activity of mcbR and metQ. Yet other preferred starting organisms may have the characteristics of GK1259 and display an increased amount and/or activity of $ask^{fbr}$, $hom^{fbr}$, metH, metA, metY, $hsk^{mutated}$, tkt (and optionally g6pdh, zwfa and 6pgl) and metF and display a reduced amount and/or activity of mcbR, metQ and sda or of M2616 and display an increased amount and/or activity of $ask^{fbr}$, $hom^{fbr}$, metH, metA, metY, $hsk^{mutated}$, tkt (and optionally g6pdh, zwfa and 6pgl) and metF and display a reduced amount and/or activity of mcbR and metQ.

As has been stated above, the present invention prefers to not only to introduce the aforementioned genetic alterations into a wild-type organism, but also into starting organisms which have already been optimized with respect to methionine production. One particularly preferred embodiment of the present invention relates to a starting organism in which the amount and/or activity of the cob(I)alamin-dependent MetH is increased by any of the above-described methods such as using the copy number of sequences encoding for cob(I)alamin-dependent MetH.

The following table provides an overview of some of the enzymes which have been discussed above in more detail. The gene bank accession numbers recited refer to the GenBank or other public databases which can be found or accessed at the website hypertext transfer protocol://world wide web.ncbi.nlm.nihDOTgov/, wherein "hypertext transfer protocol"=http, "world wide web"=www, and wherein "DOT"=".". Many homologs of any of the genes or proteins listed in the below table can be found by using the "BLAST" programs found at the same website using a sequences from the table below as the "query", as is well known in the art.

| Enzyme | Gene bank accession number | Organism |
|---|---|---|
| ferredoxin (e.g. fdxC) | NCgl1057, NP 739462, BAC19662, NP 7377770, and others | *C. glutamicum* am others |
| ferredoxin reductase (e.g. fprA1, fprA2) | NCgl2719, Ncgl2658, cgR_2704, Gene ID: 4994420, Gene ID: 1033895, CE2645, NP 739255, NC 004369, and others | *C. glutamicum* am others |
| flavoddoxin (e.g. fldA) | AAC73778, Swiss-Prot P23243, GenBankg1786900, and others | *E. coli* and others |
| flavodoxin reductase (e.g. fldR, fpr, flxR, mvrA, etc.) | AAA23805, Swiss-Prot P28861, GenBank g1790359, and others | *E. coli* and others |
| D-3-phosphoglycerate dehydrogenase (serA) | NCgl1235, CE1379, DIP1104, jk1291, nfa42210, MAP3033c, Mb3020c, MT3074, Rv2996c, ML1692, Tfu_0614, SAV2730, SCO5515, Francci3_3637, Lxx13140, CC3215, Jann_0261, CHY_2698, MMP1588, VNG2424G, RSP_1352, CYB_1383, AGR_L_2264, Atu3706, ZMO1685, tlr0325, NP0272A, Mbur_2385, Moth_0020, Adeh_1262, SMc00641, RHE_CH03454, rrnAC2696, MJ1018, TTE2613, amb3193, AF0813, MK0297, DET0599, CYA_1354, Synpcc7942_1501, syc2486_c, Saro_2680, ELI_01970, MM1753, cbdb_A580, BR1685, MTH970, Mbar_A1431, SPO3355, BruAb1_1670, BAB1_1697, BMEI0349, SYNW0533, Syncc9605_2150, Ava_3759, MA0592, alr1890, Mhun_3063, Syncc9902_0527, RPB_1315, glr2139, RPD_3905, Nwi_2968, RPA4308, SYN_00123, ABC1843, Nham_1119, STH9, bll7401, sll1908, CTC00694, BH1602, GK2247, RPC_4106, SH1200, Pcar_3115, Gmet_2378, SSP1039, BLi02446, BL00647, OB2626, BG10509, Acid345_0115, Dgeo_0710, Pro1436, SAR1801, SAB1582, SAV1724, SA1545, SERP1288, SE1401, SAS1650, MW1666, SAOUHSC_01833, SAUSA300_1670, SACOL1773, mll3875, GSU1198, HH0135, WS1313, Tmden_0875, PMT1431, DR1291, PMT9312_1452, TTC0586, Msp_1145, At1g17745, TTHA0952, PMM1354, At4g34200, RB6248, PMN2A_0926, CJE0970, Cj0891c, Pcar_0417, CMC149C, At3g19480, aq_1905, jhp0984, HP0397, PH1387, PAB0514, TK1966, C31C9.2, PF1394, Cag_1377, TM1401, Afu2g04490, CG6287-PA, rrnAC1762, AGR_pAT_578, PF0319, Atu5399, PAB2374, OB2286, Adeh_1858, BLi03698, BL03435, TK0683, PH0597, Reut_B3530, GK1954, ABC0220, MK0320, DSY0969, BP0155, Bxe_B1896, BB4474, BPP4001, STH3215, OB2844, CAC0015, RPC_3076, rrnAC2056, RPC_1162, AGR_pAT_470, Atu5328, PP3376, PAE3320, Bd1461, Pfl_2987, Rmet_4234, CNA07520, GK2965, MS1743, VV11546, LA1911, mll1021, MS0068, lp_0785, lin0070, VV2851, ebA6869, RPA2975, Tcr_0627, LIC11992, TTE1946, MA1334, LMOf2365_0095, Sde_3388, lmo0078, LmjF03.0030, SH0752, Rmet_4537, orf19.5263, VP2593, BCE1535, RPD_2906, CPE0054, OB2357, bll7965, BAS1325, BA_1955, GBAA1434, BA1434, Reut_B4747, PFL_2717, PA2263, YPTB3189, YP3611, y3301, YPO0914, GOX0218, ACL032C, RSP_3407, VC2481, BT9727_1298, BCZK1299, BMEII0813, BTH_I2298, Reut_B4615, ECA3905, YPTB3910, YP3988, YPO4078, RPB_2550, BruAb2_0769, BRA0453, BAB2_0783, Pfl_2904, plu3605, PAE1038, DSY1673, Sden_3097, NTHI0596, SERP1888, blr4558, Rfer_1867, YER081W, BC1415, Pcar_0629, VF2106, y4096, SPCC4G3.01, SE1879, SAR2389, BB4731, Psyc_0369, TK0551, SCO3478, Csal_1770, XCV1890, Bcep18194_A5027, PM1671, SAOUHSC_02577, SAUSA300_2254, SACOL2296, SAS2196, MW2224, BLi03415, BL02138, Mfla_0724, PSPTO5294, XOO3260, XC_1568, XCC2550, SAB2178, SAV2305, SA2098, PSPPH_4885, | *C. glutamicum* and others |

-continued

| Enzyme | Gene bank accession number | Organism |
|---|---|---|
| | XCV2876, SH2023, Adeh_2960, BURPS1710b_2286, BPSL1577, Pcryo_0410, NE1688, YPTB1320, YP1303, t2980, STY3218, Mbar_A2220, Psyr_4852, HI0465, y2896, YPO1288, STM3062, SPA2933, YIL074C, SERP0516, Bxe_A1982, XAC2724, SC3003, BB1050, Afu5g05500, SSP0606, SG2009, SE0622, XCC1825, SBO_2700, PF0370, SBO_3080, SSO_3065, S3098, SF2898, UTI89_C3299, c3494, ECs3784, Z4251, JW2880, b2913, SRU_0653, SAB0796, SAR0892, Bd2892, ACIAD3302, Saci_1368, SSP1845, Bcep18194_A4216, Psyr_1043, Csal_0273, PPA2251, DVU0339, PFL_5911, SDY_3169, DDB0230052, SAS0800, MW0812, IL2104, PA4626, XC_2364, SAUSA300_0834, SACOL0932, SAV0930, SA0791, Bpro_1736, SMc01622, amb0136, PSPPH_1099, XOO2143, XAC1844, PAB1008, RB6394, LBA0942, MCA1407, PSPTO1215, PH0520, TM0327, SAOUHSC_00866, BG12409, Reut_A2281, ELI_06720, SMc01943, SDY_4350, TTC0431, all8087, GSU1672, Nmul_A0428, BTH_I2885, BURPS1710b_1481, BPSL1250, Ta0779, DSY4020, BLi03716, BL03603, amb0195, RSP_3447, UTI89_C4093, ECs4438, Z4978, PSHAa0666, PFL_1001, SBO_3555, Rru_A2456, Dde_1681, BTH_I1700, Pfl_5387, XF2206, S4182, SF3587, c4372, Reut_C5898, CPS_2082, SSO_3835, VNG0104G, TTHA0786, Pfl_2771, APE1831, SO0862, PD1255, ST1218, Moth_1954, BB1529, Csal_0096, SAV7481, Bxe_A1055, PP5155, UTI89_C3212, CG1236-PA, SSO0905, SAK_1826, gbs1847, SAG1806, blr3173, PA0316, ECA0078, DDB0231445, SMa2137, JW5656, b3553, GOX0065, BURPS1710b_2926, BPSL2459, BMA0513, Rmet_2446, SAOUHSC_00142, SAUSA300_0179, SACOL0162, SAS0152, SAR0178, MW0151, SAV0177, SA0171, BPP2132, RSc1034, PP1261, c3405, Dde_3689, CAC0089, SMc02849, mlr7269, PTO0372, BR2177, RSc3131, Mb0749c, MT0753, Rv0728c, DSY3442, SAB0117, Gmet_2695, Noc_2032, SC3578, BruAb1_2150, BAB1_2178, BMEI1952, BTH_I1402 | |
| methylene tetrahydrofolate reductase (metF) | Cgl2171, EG11585, g1790377 | *C. glutamicum*, *E. coli* and others |
| cob(I)alamin (vitamin B12) dependent methionine synthase I (metH) | Cgl1139, cg1701, CE1637, DIP1259, nfa31930, Rv2124c, Mb2148c, ML1307, SCO1657, Tfu_1825, SAV6667, MT2183, GOX2074, tll1027, syc0184_c, alr0308, slr0212, gll0477, SYNW1238, TTC0253, TTHA0618, PMT0729, Pro0959, PMN2A_0333, PMM0877, WS1234, BH1630, GK0716, BCE4332, ABC1869, BC4250, BCZK4005, BT9727_3995, BA_4925, GBAA4478, BA4478, BAS4156, BLi01192, BL01308, MAP1859c, BruAb1_0184, BMEI1759, BR0188, SMc03112, MCA1545, AGR_C_3907, Atu2155, DR0966, RB9857, ebA3184, VC0390, RPA3702, VV11423, VV2960, VP2717, NE1623, VF0337, LIC20085, LB108, YPTB3653, YPO3722, y0020, YP3084, CV0203, SPA4026, MS1009, SC4067, SO1030, DP2202, STM4188, STY4405, t4115, PP2375, PFL_3662, Z5610, ECs4937, c4976, JW3979, b4019, SF4085, S3645, BB4456, BPP3983, BP3594, bll1418, CPS_1101, Psyr_2464, PSPTO2732, R03D7.1, PSPPH_2620, PBPRA3294, Daro_0046, PA1843, ECA3987, CT1857, CAC0578, ACIAD1045, Psyc_0403, 4548, DDB0230138, BF3039, BF3199, BT0180, 238505, GSU2921, STH2500, XC_2725, XCC1511, XOO2073, TTE1803, RSc0294, XAC1559, BPSL0385, DVU1585, CTC01806, CC2137, TM0268, ZMO1745, FN0163, BG13115, linl786, SAG2048, gbs2004, LMOf2365_1702, lmol678, SE2381, SERP0035, MW0333, SAS0333, SMU.874, SA0345, SAV0357, SACOL0429, SAR0354, SH2637 | |
| O-acetylhomoserine sulfhydrolase | NCgl0625, cg0755, CE0679, DIP0630, jk1694, MAP3457, Mb3372, MT3443, Rv3340, nfa35960, Lxx18930, Tfu_2823, CAC2783, GK0284, BH2603, lmo0595, lin0604, LMOf2365_0624, ABC0432, TTE2151, BT2387, STH2782, str0987, stu0987, BF1406, SH0593, BF1342, lp_2536, L75975, OB3048, BL0933, LIC11852, LA2062, BMAA1890, BPSS0190, SMU.1173, BB1055, PP2528, PA5025, PBPRB1415, GSU1183, | |

-continued

| Enzyme | Gene bank accession number | Organism |
|---|---|---|
| | RPA2763, WS1015, TM0882, VP0629, BruAb1_0807, BMEI1166, BR0793, CPS_2546, XC_1090, XCC3068, plu3517, PMT0875, SYNW0851, Pro0800, CT0604, NE1697, RB8221, bll1235, syc1143_c, ACIAD3382, ebA6307, RSc1562, Daro_2851, DP2506, DR0873, MA2715, PMM0642, PMN2A_0083, IL2014, SPO1431, ECA0820, AGR_C_2311, Atu1251, mlr8465, SMc01809, CV1934, SPBC428.11, PM0738, SO1095, SAR11_1030, PFL_0498, CTC01153, BA_0514, BCE5535, BAS5258, GBAA5656, BA5656, BCZK5104, TTHA0760, TTC0408, BC5406, BT9727_5087, HH0636, YLR303W, ADL031W, CJE1895, spr1095, rrnAC2716, orf19.5645, Cj1727c, VNG2421G, PSPPH_1663, XOO1390, Psyr_1669, PSPTO3810, MCA2488, TDE2200, FN1419, PG0343, Psyc_0792, MS1347, CC3168, Bd3795, MM3085, 389.t00003, NMB1609, SAV3305, NMA1808, GOX1671, APE1226, XAC3602, NGO1149, ZMO0676, SCO4958, lpl0921, lpg0890, lpp0951, EF0290, BPP2532, CBU2025, BP3528, BLi02853, BL02018, BG12291, CG5345-PA, HP0106, ML0275, jhp0098, At3g57050, 107869, HI0086, NTHI0100, SpyM3_0133, SPs0136, spyM18_0170, M6_Spy0192, SE2323, SERP0095, SPy0172, PAB0605, DDB0191318, ST0506, F22B8.6, PTO1102, CPE0176, PD1812, XF0864, SAR0460, SACOL0503, SA0419, Ta0080, PF1266, MW0415, SAS0418, SSO2368, PAE2420, TK1449, 1491, TVN0174, PH1093, VF2267, Saci_0971, VV11364, CMT389C, VV3008 | |
| aspartate kinase (ask) | Cgl0251, NCgl0247, CE0220, DIP0277, jk1998, nfa3180, Mb3736c, MT3812, Rv3709c, ML2323, MAP0311c, Tfu_0043, Francci3_0262, SCO3615, SAV4559, Lxx03450, PPA2148, CHY_1909, MCA0390, cbdb_A1731, TWT708, TW725, Gmet_1880, DET1633, GSU1799, Moth_1304, Tcr_1589, Mfla_0567, HCH_05208, PSPPH_3511, Psyr_3555, PSPTO1843, CV1018, STH1686, NMA1701, Tbd_0969, NMB1498, Pcar_1006, Daro_2515, Csal_0626, Tmden_1650, PA0904, PP4473, Sde_1300, HH0618, NGO0956, ACIAD1252, PFL_4505, ebA637, Noc_0927, WS1729, Pcryo_1639, Psyc_1461, Pfl_4274, LIC12909, LA0693, Rru_A0743, NE2132, RB8926, Cj0582, Nmul_A1941, SYN_02781, TTHA0534, CJE0685, BURPS1710b_2677, BPSL2239, BMA1652, RSc1171, TTC0166, RPA0604, BTH_I1945, Bpro_2860, Rmet_1089, Reut_A1126, RPD_0099, Bxe_A1630, Bcep18194_A5380, aq_1152, RPB_0077, Rfer_1353, RPC_0514, BH3096, BLi02996, BL00324, amb1612, tlr1833, jhp1150, blr0216, Dde_2048, BB1739, BPP2287, BP1913, DVU1913, Nwi_0379, ZMO1653, Jann_3191, HP1229, Saro_3304, Nham_0472, CBU_1051, slr0657, SPO3035, Synpcc7942_1001, BG10350, BruAb1_1850, BAB1_1874, BMEI0189, BT9727_1658, syc0544_d, BR1871, gll1774, BC1748, mll3437, BCE1883, ELI_14545, RSP_1849, BCZK1623, BAS1676, BA_2315, GBAA1811, BA1811, Ava_3642, alr3644, PSHAa0533, AGR_L_1357, Atu4172, lin1198, BH04030, PMT9312_1740, SMc02438, CYA_1747, RHE_CH03758, lmo1235, LMOf2365_1244, PMN2A_1246, CC0843, Pro1808, BQ03060, PMT0073, Syncc9902_0068, GOX0037, CYB_0217 | |
| homoserine dehydrogenase (hom) | Cgl1183, cg1337, NCgl1136, CE1289, DIP1036, jk1352, nfa10490, SAV2918, Mb1326, MT1333, Rv1294, SCO5354, MAP2468c, ML1129, Francci3_3725, Tfu_2424, Lxx06870, PPA1258, Moth_1307, BL1274, CHY_1912, DSY1363, GK2964, CAC0998, BLi03414, BL02137, BC5404, STH2739, BCZK5102, BT9727_5085, Gmet_1629, BCE5533, BB1926, BP2784, CTC02355, BG10460, BPP2479, BAS5256, BA_0512, GBAA5654, BA5654, Synpcc7942_2090, syc2003_c, Adeh_1638, CYA_1100, Pcar_1451, Mfla_1048, Mfla_0904, TW329, TWT439, BH3422, all4120, Daro_2386, gll4295, ebA4952, Ava_0783, Syncc9605_1957, LSL_1519, OB0466, lmo2547, PMT1143, Bpro_2190, SYNW0711, LMOf2365_2520, lin2691, sll0455, CV0996, RSc1327, PMT9312_1062, ABC2942, Bcep18194_A5155, BURPS1710b_2396, BPSL1477, BMA1385, NMA1395, NMB1228, tll0277, Syncc9902_0704, GSU1693, Bxe_A2381, MCA0597, | |

-continued

| Enzyme | Gene bank accession number | Organism |
|---|---|---|
| | NGO0779, CYB_1425, BTH_I2198, BMEI0725, Rmet_1966, Rfer_1912, SMc00293, BruAb1_1275, BAB1_1293, SYN_00890, Reut_A1993, RHE_CH01878, BR1274, aq_1812, TTE2620, ACIAD0264, PFL_1103, stu0469, str0469, Pfl_1027, Psyr_1290, PMN2A_0702, MTH1232, Csal_3010, AGR_C_2919, Atu1588, PSPPH_1360, PP1470, NE2369, PSPTO1480, Tcr_1251, BC1964, Nmul_A1551, Saro_0019, mll0934, WS0450, spr1219, SP1361, Noc_2454, BT9727_1799, BCZK1782, BCE2051, Tbd_0843, PA3736, DET1206, amb3728, Rru_A2410, LIC10571, LA3638, SMU.965, BAS1825, BA_2468, GBAA1968, BA1968, cbdb_A1123, GOX1517, PMM1051, HCH_01779, RB8510, DVU0890, Pro1150, Nham_2309, Tmden_1904, Sde_1209, Psyc_0253, ELI_13775, RSP_0403, L0090, Dde_2731, Pcryo_0279, Nwi_1647, lp_0571, BH10030, SPO1734, Jann_2998, blr4362, RPA2504, EF2422, DP1732, LBA1212, RPD_2495, RPC_2816, CC1383, RPB_2966, CJE0145, Cj0149c, Acid345_1481, ZMO0483, Bpro_5333, SAK_1205, gbs1187, jhp0761, SH1579, SAG1120, HP0822, SE1009, SERP0897, SAOUHSC_01320, SAUSA300_1226, SAB1186, SACOL1362, SAS1268, SAR1338, MW1215, SAV1328, SA1164, HH1750, SSP1438, lp_2535, TTE2152, SAR11_1025, DR1278, PFL_3809, Dgeo_0610, Mhun_2292, DSY3981, PP0664, MA2572, ABC1578, Mbar_A1898, TTHA0489, TTC0115, MM2713, Mbur_1087, BH1737, AF0935, MK1554, MTH417, VNG2650G, Msp_0487, ABC0023, rrnAC2408, TK1627, TM0547, MJ1602, NP0302A, BH1253, MMP1702, BCE2626, LmjF07.0260, BCZK2354, BT9727_2388, BAS2433, BA_3119, GBAA2608, BA2608, BC2548, Acid345_4165, CTC00886, ST1519, Saci_1636, APE1144, SSO0657, PF1104, Adeh_3931, PAB0610, PH1075, Cag_0142, PAE2868, YJR139C, XOO1820, Plut_1983, XAC3038, Adeh_1400, XCV3175, PTO1417, SCO0420, SRU_0482, XC_1253, XCC2855, SO4055, CT2030, SPBC776.03, AO090003000721, TVN0385, ABL080W, AO090009000136, CPS_0456, HI0089, orf19.2951, Sden_0616, UTI89_C4525, Afu3g11640, MS1703, SBO_3960, SSO_4114, STM4101, SC3992, t3517, STY3768, c4893, ECs4869, Z5495, JW3911, b3940, AN2882.2, ECA4251, CMN129C, NTHI0167, plu4755, ECA3891, YPTB0602, YP3723, y3718, YPO0459, PM0113, S3729, SF4018, SPA3944, Mfla_1298, PSHAa2379, PBPRA0262, XOO2242, STM0002, SC0002, SPA0002, t0002, STY0002, c0003, SRU_0691, XCC1800, PD1273, BPEN_115, SDY_3775, VC2684, SDY_0002, SBO_0001, YPTB0106, YP0118, y0303, YPO0116, UTI89_C0002, ECs0002, Z0002, JW0001, b0002, VV3007, VV11365, XC_2389, VP2764, XF2225, SSO_0002, S0002, SF0002 | |
| Serine deaminase (sda, sdaA) | GeneID: 1019614, NCgl1583, EG10930, g178116 | *C. glutamicum*, *E. coli*, and others |
| Homoserine kinase (hsk) | Cgl1184, cg0307, CE0221, DIP0279, jk1997, RHA1_ro04292, nfa3190, Mmcs_4888, MSMEG_6256, MAP0310c, MAV_0394, Mb3735c, MT3811, Rv3708c, Acel_2011, ML2322, PPA0318, Lxx03460, SCO2640, SAV5397, CC3485 | *C. glutamicum* and others |
| D-methionine binding lipoprotein (metQ) | YP_224930, NP_599871, NP_737241, NP_938985, NP_938984, YP_701727, YP_251505, YP_120623, YP_062481, YP_056445, ZP_00121548, NP_696133, YP_034633, YP_034633, YP_081895, ZP_00390696, YP_016928, YP_026579, NP_842863, YP_081895, ZP_00240243, NP_976671 | *C. glutamicum* and others |
| McbR | cg3253, CE2788, DIP2274, jk0101, nfa21280, MSMEG_4517Lxx16190, SCO4454, Bcep18194_A3587, Bamb_0404, Bcen2424_0499, Bcen_2606, Ava_4037, BTH_I2940, RHA1_ro02712, BMA10299_A1735, BMASAVP1_A0031, BMA2807, BURPS1710b_3614 | *C. glutamicum* and others |
| glucose-6-phosphate-dehydrogenase | Cgl1576, BAB98969, NCgl1514, NCgl1514, cg1778, CE1696, DIP1304, jk0994, RHA1_ro07184, nfa35750, MSMEG_3101, Mmcs_2412, MAP1176c, Mb1482c, MT1494, Rv1447c, SAV6313, Acel_1124, SCO1937, MAV_3329, Lxx11590, BL0440, Arth_2094, Tfu_2005, itte weitere angeben | *Corynebacterium glutamicum* and others |
| OPCA protein | Cgl1577, NP_738307.1, NP_939658.1, YP_250777.1, YP_707105.1, YP_119788.1, ZP_01192082.1, NP_335942.1, ZP_01276169.1, NP_215962.1, ZP_01684361.1, YP_887415.1, ZP_01130849.1, YP_062111.1, ZP_00615668.1, YP_953530.1, | *Corynebacterium glutamicum* and others |

-continued

| Enzyme | Gene bank accession number | Organism |
|---|---|---|
| | ZP_00995403.1, YP_882512.1, NP_960109.1, YP_290062.1, YP_831573.1, NP_827488.1, YP_947837.1, NP_822945.1, NP_626203.1, NP_630735.1, CAH10103.1, ZP_00120910.2, NP_695642.1, YP_909493.1, YP_872881.1, YP_923728.1, YP_056265.1, ZP_01648612.1, ZP_01430762.1, ZP_00569428.1, YP_714762.1, YP_480751.1, NP_301492.1, YP_642845.1, ZP_00767699.1 | |
| transaldolase | Cgl1575, cg1776, CE1695, DIP1303, jk0993, Mmcs_2413, MSMEG_3102, MAP1177c, RHA1_ro07185, MAV_3328, Mb1483c, Rv1448c, MT1495, nfa35740, ML0582, Arth_2096, Lxx11610, SAV1767, Tfu_2003, SCO1936, Francci3_1648 | *Corynebacterium glutamicum* and others |
| lactonase6-phosphogluconolactonase | Cgl1578, NCgl1516, NCgl1516, cg1780, CE1698, DIP1306, Mmcs_2410, MSMEG_3099, Mb1480c, MT1492, Rv1445c, MAV_3331, RHA1_ro07182, nfa35770, MAP1174c, ML0579, jk0996, Tfu_2007, FRAAL4578, SAV6311, SCO1939, SCC22.21, TW464 | *Corynebacterium glutamicum* and others |
| transketolase | Cgl1574, YP_225858, cg1774, CE1694, DIP1302, jk0992, nfa35730, RHA1_ro07186, MSMEG_3103, MAP1178c, ML0583, MAV_3327, Mb1484c, MT1496, Rv1449c, Mmcs_2414, Tfu_2002, Arth_2097, Lxx11620, SAV1766, SCO1935, Acel_1127 | *Corynebacterium glutamicum* and others |

The above accession numbers are the official accession numbers of Genbank or are synonyms for accession numbers which have cross-references at Genbank. These numbers can be searched and found at hypertext transfer protocol://world wide web.ncbi.nlm.nihDOTgov/, wherein "hypertext transfer protocol"=http, "world wide web"=www, and wherein "DOT"=".".

A general overview is given below how to increase and decrease the amount and/or activity of polypeptides and genes in *C. glutamicum* and *E. coli*. Nevertheless, the person skilled in the art will be aware of other technologies and approaches for either identifying new homologs of the enzymes of Table 1 by performing appropriate database searches and/or altering the expression of these enzymes in organisms other than Coryneform bacteria or bacteria of the genus *Escherichia.*

Increasing or Introducing the Amount and/or Activity

With respect to increasing the amount, two basic scenarios can be differentiated. In the first scenario, the amount of the enzyme is increased by expression of an exogenous version of the respective protein. In the other scenario, expression of the endogenous protein is increased by influencing the activity of e.g. the promoter and/or enhancers element and/or other regulatory activities that regulate the activities of the respective proteins either on a transcriptional, translational or post-translational level.

Thus, the increase of the activity and the amount of a protein may be achieved via different routes, e.g. by switching off inhibitory regulatory mechanisms at the transcriptional, translational, and protein level or by increase of gene expression of a nucleic acid coding for these proteins in comparison with the starting organism, e.g. by inducing endogenous ferredoxin by a strong promoter and/or by introducing nucleic acids encoding for ferredoxin.

In one embodiment, the increase of the amount and/or activity of the enzymes of Table 1 is achieved by introducing nucleic acids encoding the enzymes of Table 1 into microorganism such as *C. glutamicum* and *E. coli.*

In principle, any protein of different organisms with an enzymatic activity of the proteins listed in Table 1 can be used. With genomic nucleic acid sequences of such enzymes from eukaryotic sources containing introns, already processed nucleic acid sequences like the corresponding cDNAs are to be used in the case as the host organism is not capable or cannot be made capable of splicing the corresponding mRNAs. All nucleic acids mentioned in the description can be, e.g., an RNA, DNA or cDNA sequence.

According to the present invention, increasing or introducing the amount of a protein typically comprises the following steps:

a) production of a vector comprising the following nucleic acid sequences, preferably DNA sequences, in 5'-3'-orientation:
  - a promoter sequence functional in an organism of the invention
  - operatively linked thereto a DNA sequence coding for a protein of e.g. Table 1, functional homologues, functional fragments or functional mutated versions thereof
  - optionally, a termination sequence functional in the organisms of the invention b) transfer of the vector from step a) to an organisms of the invention such as *C. glutamicum* and, optionally, integration into the respective genomes.

As set out above, functional fragments relate to fragments of nucleic acid sequences coding for enzymes of e.g. Table 1, the expression of which still leads to proteins having the enzymatic activity substantially similar to that of the respective full length protein.

The above-mentioned method can be used for increasing the expression of DNA sequences coding for enzymes of e.g. Table 1 or functional fragments thereof. The use of such vectors comprising regulatory sequences, like promoter and termination sequences are, is known to the person skilled in the art. Furthermore, the person skilled in the art knows how a vector from step a) can be transferred to organisms such as *C. glutamicum* or *E. coli* and which properties a vector must have to be able to be integrated into their genomes.

If the enzyme content in an organism such as *C. glutamicum* is increased by transferring a nucleic acid coding for an enzyme from another organism, like e.g. *E. coli*, it is advisable to transfer the amino acid sequence encoded by the nucleic acid sequence e.g. from *E. coli* by back-translation of the polypeptide sequence according to the genetic code into a nucleic acid sequence comprising mainly those codons, which are used more often due to the organism-specific codon usage. The codon usage can be determined by means of computer evaluations of other known genes of the relevant organisms.

According to the present invention, an increase of the gene expression of a nucleic acid encoding an enzyme of Table 1 is also understood to be the manipulation of the expression of the endogenous respective endogenous enzymes of an organism, in particular of *C. glutamicum*. This can be achieved, e.g., by altering the promoter DNA sequence for genes encoding these enzymes. Such an alteration, which causes an altered, preferably increased, expression rate of these enzymes can be achieved by replacement with strong promoters and by deletion and/or insertion of DNA sequences.

An alteration of the promoter sequence of endogenous genes usually causes an alteration of the expressed amount of the gene and therefore also an alteration of the activity detectable in the cell or in the organism.

Furthermore, an altered and increased expression, respectively, of an endogenous gene can be achieved by a regulatory protein, which does not occur or has been deleted in the transformed organism, and which interacts with the promoter of these genes. Such a regulator can be a chimeric protein consisting of a DNA binding domain and a transcription activator domain, as e.g. described in WO 96/06166.

A further possibility for increasing the activity and the content of endogenous genes is to up-regulate transcription factors involved in the transcription of the endogenous genes, e.g. by means of overexpression. The measures for overexpression of transcription factors are known to the person skilled in the art.

The expression of endogenous enzymes such as those of Table 1 can e.g. be regulated via the expression of aptamers specifically binding to the promoter sequences of the genes. Depending on the aptamer binding to stimulating or repressing promoter regions, the amount of the enzymes of Table 1 can e.g. be increased.

Furthermore, an alteration of the activity of endogenous genes can be achieved by targeted mutagenesis of the endogenous gene copies.

An alteration of the endogenous genes coding for the enzymes of e.g. Table 1 can also be achieved by influencing the post-translational modifications of the enzymes. This can happen e.g. by regulating the activity of enzymes like kinases or phosphatases involved in the post-translational modification of the enzymes by means of corresponding measures like overexpression or gene silencing.

In another embodiment, an enzyme may be improved in efficiency, or its allosteric control region destroyed such that feedback inhibition of production of the compound is prevented. Similarly, a degradative enzyme may be deleted or modified by substitution, deletion, or addition such that its degradative activity is lessened for the desired enzyme of Table 1 without impairing the viability of the cell. In each case, the overall yield, rate of production or amount of methionine be increased.

These aforementioned strategies for increasing or introducing the amount and/or activity of the enzymes of Table 1 are not meant to be limiting; variations on these strategies will be readily apparent to one of ordinary skill in the art.

Reducing the Amount and/or Activity of Enzymes

It has been set out above that it may be preferred to use a starting organism which has already been engineered for methionine production. In *C. glutamicum* one may, for example, downregulate the activity of metQ for obtaining a suitable starting organism.

For reducing the amount and/or activity of enzymes, various strategies are available.

The expression of endogenous enzymes such as those of Table 1 can e.g. be regulated via the expression of aptamers specifically binding to the promoter sequences of the genes. Depending on the aptamer binding to stimulating or repressing promoter regions, the amount and thus, in this case, the activity of the enzymes of Table 1 can e.g. be reduced.

Aptamers can also be designed in a way as to specifically bind to the enzymes themselves and to reduce the activity of the enzymes by e.g. binding to the catalytic center of the respective enzymes. The expression of aptamers is usually achieved by vector-based overexpression (see above) and is, as well as the design and the selection of aptamers, well known to the person skilled in the art (Famulok et al., (1999) *Curr Top Microbiol Immunol.,* 243, 123-36).

Furthermore, a decrease of the amount and the activity of the endogenous enzymes of Table 1 can be achieved by means of various experimental measures, which are well known to the person skilled in the art. These measures are usually summarized under the term "gene silencing". For example, the expression of an endogenous gene can be silenced by transferring an above-mentioned vector, which has a DNA sequence coding for the enzyme or parts thereof in antisense order, to organisms such as *C. glutamicum*. This is based on the fact that the transcription of such a vector in the cell leads to an RNA, which can hybridize with the mRNA transcribed by the endogenous gene and therefore prevents its translation.

In principle, the antisense strategy can be coupled with a ribozyme method. Ribozymes are catalytically active RNA sequences, which, if coupled to the antisense sequences, cleave the target sequences catalytically (Tanner et al., (1999) *FEMS Microbiol Rev.* 23 (3), 257-75). This can enhance the efficiency of an antisense strategy.

To create a homologous recombinant microorganism, a vector is prepared which contains at least a portion of gene coding for an enzyme of Table 1 into which a deletion, addition or substitution has been introduced to thereby alter, e.g., functionally disrupt, the endogenous gene.

In one embodiment, the vector is designed such that, upon homologous recombination, the endogenous gene is functionally disrupted (i.e., no longer encodes a functional protein). Alternatively, the vector can be designed such that, upon homologous recombination, the endogenous gene is mutated or otherwise altered but still encodes functional protein, e.g., the upstream regulatory region can be altered to thereby alter the expression of the endogenous enzymes of Table 1. This approach can have the advantage that expression of an enzyme is not completely abolished, but reduced to the required minimum level. The skilled person knows which vectors can be used to replace or delete endogenous sequences. A specific description for disrupting chromosomal sequences in *C. glutamicum* is provided below.

Furthermore, gene repression is possible by reducing the amount of transcription factors. Factors inhibiting the target protein itself can also be introduced into a cell. The protein-binding factors may e.g. be the above-mentioned aptamers (Famulok et al., (1999) *Curr Top Microbiol Immunol.* 243, 123-36).

As further protein-binding factors, the expression of which can cause a reduction of the amount and/or the activity of the enzymes of table 1, enzyme-specific antibodies may be considered. The production of recombinant enzyme-specific antibodies such as single chain antibodies is known in the art. The expression of antibodies is also known from the literature (Fiedler et al., (1997) *Immunotechnology* 3, 205-216; Maynard and Georgiou (2000) *Annu. Rev. Biomed.* Eng. 2, 339-76).

The mentioned techniques are well known to the person skilled in the art. Therefore, the skilled also knows the typical size that a nucleic acid constructs used for e.g. antisense methods must have and which complementarity, homology or identity, the respective nucleic acid sequences must have. The terms complementarity, homology, and identity are known to the person skilled in the art.

The term complementarity describes the capability of a nucleic acid molecule to hybridize with another nucleic acid molecule due to hydrogen bonds between two complementary bases. The person skilled in the art knows that two nucleic acid molecules do not have to display a complementarity of 100% in order to be able to hybridize with each other. A nucleic acid sequence, which is to hybridize with another nucleic acid sequence, is preferably at least 30%, at least 40%, at least 50%, at least 60%, preferably at least 70%, particularly preferred at least 80%, also particularly preferred at least 90%, in particular preferred at least 95% and most preferably at least 98 or 100%, respectively, complementary with said other nucleic acid sequence.

The hybridization of an antisense sequence with an endogenous mRNA sequence typically occurs in vivo under cellular conditions or in vitro. According to the present invention, hybridization is carried out in vivo or in vitro under conditions that are stringent enough to ensure a specific hybridization.

Stringent in vitro hybridization conditions are known to the person skilled in the art and can be taken from the literature (see e.g. Sambrook et al., Molecular Cloning, Cold Spring Harbor Press (2001)). The term "specific hybridization" refers to the case wherein a molecule preferentially binds to a certain nucleic acid sequence under stringent conditions, if this nucleic acid sequence is part of a complex mixture of e.g. DNA or RNA molecules.

The term "stringent conditions" therefore refers to conditions, under which a nucleic acid sequence preferentially binds to a target sequence, but not, or at least to a significantly reduced extent, to other sequences.

Stringent conditions are dependent on the circumstances. Longer sequences specifically hybridize at higher temperatures. In general, stringent conditions are chosen in such a way that the hybridization temperature lies about 5° C. below the melting point (Tm) of the specific sequence with a defined ionic strength and a defined pH value. Tm is the temperature (with a defined pH value, a defined ionic strength and a defined nucleic acid concentration), at which 50% of the molecules, which are complementary to a target sequence, hybridize with said target sequence. Typically, stringent conditions comprise salt concentrations between 0.01 and 1.0 M sodium ions (or ions of another salt) and a pH value between 7.0 and 8.3. The temperature is at least 30° C. for short molecules (e.g. for such molecules comprising between 10 and 50 nucleic acids). In addition, stringent conditions can comprise the addition of destabilizing agents like e.g. form amide. Typical hybridization and washing buffers are of the following composition.

| | |
|---|---|
| Pre-hybridization solution: | 0.5% SDS |
| | 5x SSC |
| | 50 mM $NaPO_4$, pH 6.8 |
| | 0.1% Na-pyrophosphate |
| | 5x Denhardt's reagent |
| | 100 µg/salmon sperm |
| Hybridization solution: | Pre-hybridization solution |
| | $1 \times 10^6$ cpm/ml probe (5-10 min 95° C.) |
| 20x SSC: | 3 M NaCl |
| | 0.3 M sodium citrate |
| | ad pH 7 with HCl |
| 50x Denhardt's reagent: | 5 g Ficoll |
| | 5 g polyvinylpyrrolidone |
| | 5 g Bovine Serum Albumin |
| | ad 500 ml A. dest. |

-continued

A typical procedure for the hybridization is as follows:

| | | | |
|---|---|---|---|
| Optional: | wash Blot 30 min in 1x SSC/0.1% SDS at 65° C. | | |
| Pre-hybridization: | at least 2 h at 50-55° C. | | |
| Hybridization: | over night at 55-60° C. | | |
| Washing: | 05 min | 2x SSC/0.1% SDS | |
| | Hybridization temperature | | |
| | 30 min | 2x SSC/0.1% SDS | |
| | Hybridization temperature | | |
| | 30 min | 1x SSC/0.1% SDS | |
| | Hybridization temperature | | |
| | 45 min | 0.2x SSC/0.1% SDS | 65° C. |
| | 5 min | 0.1x SSC | room temperature |

For antisense purposes complementarity over sequence lengths of 100 nucleic acids, 80 nucleic acids, 60 nucleic acids, 40 nucleic acids and 20 nucleic acids may suffice. Longer nucleic acid lengths will certainly also suffice. A combined application of the above-mentioned methods is also conceivable.

If, according to the present invention, DNA sequences are used, which are operatively linked in 5'-3'-orientation to a promoter active in the organism, vectors can, in general, be constructed, which, after the transfer to the organism's cells, allow the overexpression of the coding sequence or cause the suppression or competition and blockage of endogenous nucleic acid sequences and the proteins expressed there from, respectively.

The activity of a particular enzyme may also be reduced by over-expressing a non-functional mutant thereof in the organism. Thus, a non-functional mutant which is not able to catalyze the reaction in question, but that is able to bind e.g. the substrate or co-factor, can, by way of over-expression outcompete the endogenous enzyme and therefore inhibit the reaction. Further methods in order to reduce the amount and/or activity of an enzyme in a host cell are well known to the person skilled in the art.

According to the present invention, non-functional enzymes have essentially the same nucleic acid sequences and amino acid sequences, respectively, as functional enzymes and functionally fragments thereof, but have, at some positions, point mutations, insertions or deletions of nucleic acids or amino acids, which have the effect that the non-functional enzyme are not, or only to a very limited extent, capable of catalyzing the respective reaction. These non-functional enzymes may not be intermixed with enzymes that still are capable of catalyzing the respective reaction, but which are not feedback regulated anymore. According to the present invention, the term "non-functional enzyme" does not comprise such proteins having no substantial sequence homology to the respective functional enzymes at the amino acid level and nucleic acid level, respectively. Proteins unable to catalyse the respective reactions and having no substantial sequence homology with the respective enzyme are therefore, by definition, not meant by the term "non-functional enzyme" of the present invention. Non-functional enzymes are, within the scope of the present invention, also referred to as inactivated or inactive enzymes.

Therefore, non-functional enzymes of e.g. Table 1 according to the present invention bearing the above-mentioned point mutations, insertions, and/or deletions are characterized by an substantial sequence homology to the wild type enzymes of e.g. Table 1 according to the present invention or functionally equivalent parts thereof. For determining a substantial sequence homology, the above described identity grades are to applied.

Vectors and Host Cells

One aspect of the invention pertains to vectors, preferably expression vectors, containing nucleic acid sequences as mentioned above. As used herein, the term "vector" refers to a nucleic acid molecule capable of transporting another nucleic acid to which it has been linked.

One type of vector is a "plasmid", which refers to a circular double stranded DNA loop into which additional DNA segments can be ligated. Another type of vector is a viral vector, wherein additional DNA segments can be ligated into the viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked.

Such vectors are referred to herein as "expression vectors".

In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention may comprise a modified nucleic acid as mentioned above in a form suitable for expression of the respective nucleic acid in a host cell, which means that the recombinant expression vectors include one or more regulatory sequences, selected on the basis of the host cells to be used for expression, which is operatively linked to the nucleic acid sequence to be expressed.

Within a recombinant expression vector, "operably linked" is intended to mean that the nucleic acid sequence of interest is linked to the regulatory sequence (s) in a manner which allows for expression of the nucleic acid sequence (e.g., in an in vitro transcription/translation system or in a host cell when the vector is introduced into the host cell). The term "regulatory sequence" is intended to include promoters, repressor binding sites, activator binding sites, enhancers and other expression control elements (e.g., terminators, polyadenylation signals, or other elements of mRNA secondary structure). Such regulatory sequences are described, for example, in Goeddel; Gene Expression Technology: Methods in Enzymology 185, Academic Press, San Diego, Calif. (1990). Regulatory sequences include those which direct constitutive expression of a nucleic acid sequence in many types of host cell and those which direct expression of the nucleic acid sequence only in certain host cells. Preferred regulatory sequences are, for example, promoters such as cos-, tac-, trp-, tet-, trp-, tet-, lpp-, lac-, lpp-lac-, lacIq-, T7-, T5-, T3-, gal-, trc-, ara-, SP6-, arny, SP02, phage lambda$P_R$, phage lambda$P_L$, phage SP01 $P_{15}$, phage SP01 $P_{26}$, pSOD, EFTu, EFTs, GroEL, MetZ (last 5 from *C. glutamicum*), which are used preferably in bacteria. Additional regulatory sequences are, for example, promoters from yeasts and fungi, such as ADC1, MFa, AC, P-60, CYC1, GAPDH, TEF, rp28, ADH, ENO2, promoters from plants such as CaMV/35S, SSU, OCS, lib4, usp, STLS1, B33, nos or ubiquitin- or phaseolin-promoters. It is also possible to use artificial promoters. It will be appreciated by one of ordinary skill in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by the above-mentioned modified nucleic acid sequences.

Expression of proteins in prokaryotes is most often carried out with vectors containing constitutive or inducible promoters directing the expression of either fusion or non-fusion proteins.

Fusion vectors add a number of amino acids to a protein encoded therein, usually to the amino terminus of the recombinant protein but also to the C-terminus or fused within suitable regions in the proteins. Such fusion vectors typically serve four purposes: 1) to increase expression of recombinant protein; 2) to increase the solubility of the recombinant protein; and 3) to aid in the purification of the recombinant protein by acting as a ligand in affinity purification 4) to provide a "tag" for later detection of the protein. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) Gene 67: 31-40), pMAL (New England Biolabs, Beverly, Mass.) and pRIT5 (Pharmacia, Piscataway, N.J.) which fuse glutathione S-transferase (GST), maltose E binding protein, or protein A, respectively.

Examples of suitable inducible non-fusion *E. coli* expression vectors include pTrc (Amann et al., (1988) Gene 69: 301-315), pLG338, pACYC184, pBR322, pUC18, pUC19, pKC30, pRep4, pHS1, pHS2, pPLc236, pMBL24, pLG200, pUR290, pIN-III113-B1, egtl1, pBdC1, and pET 11d (Studier et al., Gene Expression Technology: Methods in Enzymology 185, Academic Press, San Diego, Calif. (1990) 60-89; and Pouwels et al., eds. (1985) Cloning Vectors. Elsevier: New York IBSN 0 444 904018). Target gene expression from the pTrc vector relies on host RNA polymerase transcription from a hybrid trp-lac fusion promoter. Target gene expression from the pET 11d vector relies on transcription from a T7 gnlO-lac fusion promoter mediated by a coexpressed viral RNA polymerase (T7gnl). This viral polymerase is supplied by host strains BL21 (DE3) or HMS174 (DE3) from a resident X prophage harboring a T7gnl gene under the transcriptional control of the lacUV 5 promoter. For transformation of other varieties of bacteria, appropriate vectors may be selected. For example, the plasmids pIJ101, pIJ364, pIJ702 and pIJ361 are known to be useful in transforming *Streptomyces*, while plasmidspUB110, pC194 or pBD214 are suited for transformation of *Bacillus* species. Several plasmids of use in the transfer of genetic information into *Corynebacterium* include pHM1519, pBL1, pSA77 or pAJ667 (Pouwels et al., eds. (1985) Cloning Vectors. Elsevier: New York IBSN 0 444 904018).

Examples of suitable *C. glutamicum* and *E. coli* shuttle vectors are e.g. pClik5aMCS (WO2005059093) or can be found in Eikmanns et al (*Gene.* (1991) 102, 93-8).

Examples for suitable vectors to manipulate *Corynebacteria* can be found in the Handbook of *Corynebacterium* (edited by Eggeling and Bott, ISBN 0-8493-1821-1, 2005). One can find a list of *E. coli-C. glutamicum* shuttle vectors (table 23.1), a list of *E. coli-C. glutamicum* shuttle expression vectors (table 23.2), a list of vectors which can be used for the integration of DNA into the *C. glutamicum* chromosome (table 23.3), a list of expression vectors for integration into the *C. glutamicum* chromosome (table 23.4.) as well as a list of vectors for site-specific integration into the *C. glutamicum* chromosome (table 23.6).

In another embodiment, the protein expression vector is a yeast expression vector. Examples of vectors for expression in yeast *S. cerevisiae* include pYepSecl (Baldari, et al., (1987) *Embo J.* 6: 229-234), 2i, pAG-1, Yep6, Yep13, pEMBLYe23, pMFa (Kurjan and Herskowitz, (1982) *Cell* 30: 933-943), pJRY88 (Schultz et al., (1987) *Gene* 54: 113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) in: Applied Molecular Genetics of Fungi, J. F. Peberdy, et al., eds., p. 1-28, Cambridge University Press: Cambridge, and Pouwels et al., eds. (1985) Cloning Vectors. Elsevier: New York (IBSN 0 444 904018).

For the purposes of the present invention, an operative link is understood to be the sequential arrangement of promoter, coding sequence, terminator and, optionally, further regulatory elements in such a way that each of the regulatory elements can fulfill its function, according to its determination, when expressing the coding sequence.

For other suitable expression systems for both prokaryotic and eukaryotic cells see chapters 16 and 17 of Sambrook, J. et al. Molecular Cloning: A Laboratory Manual. 3rd ed., Cold Spring Harbor Laboratory, Cold Spring Harbor Laboratory Press, Cold Spring Harbor, N.Y., 2003.

Vector DNA can be introduced into prokaryotic via conventional transformation or transfection techniques. As used herein, the terms "transformation" and "transfection", "conjugation" and "transduction" are intended to refer to a variety of art-recognized techniques for introducing foreign nucleic acid (e.g., linear DNA or RNA (e.g., a linearized vector or a gene construct alone without a vector) or nucleic acid in the form of a vector (e.g., a plasmid, phage, phasmid, phagemid, transposon or other DNA into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (Molecular Cloning: A Laboratory Manual. 3rd ed., Cold Spring Harbor Laboratory, Cold Spring Harbor Laboratory Press, Cold Spring Harbor, N.Y., 2003), and other laboratory manuals.

In order to identify and select these integrants, a gene that encodes a selectable marker (e.g., resistance to antibiotics) is generally introduced into the host cells along with the gene of interest. Preferred selectable markers include those which confer resistance to drugs, such as, but not limited to, G418, hygromycin, kanamycine, tetracycline, neomycineampicillin (and other pencillins), cephalosporins, fluoroquinones, naladixic a id, chloramphenicol, spectinomyin, erytythromycin, streptomycin and methotrexate. Other selectable markers include wild type genes that can complement mutated versions of the equivalent gene in a host or starting strain. For example, an essential gene for growth on a minimal medium can be mutated or deleted from the genome of a *C. glutamicum* starting or host strain of the invention as described herein above to create a serine auxotroph. Then, a vector containing a wild type or other functional copy of this gene can be used to select for transformants or integrants. Nucleic acid encoding a selectable marker can be introduced into a host cell on the same vector as that encoding the above-mentioned modified nucleic acid sequences or can be introduced on a separate vector. Cells stably transfected with the introduced nucleic acid can be identified by drug selection (e.g., cells that have incorporated the selectable marker gene will survive, while the other cells die).

When plasmids without an origin of replication and two different marker genes are used (e.g. pClik int sacB), it is also possible to generate marker-free strains which have part of the insert inserted into the genome. This is achieved by two consecutive events of homologous recombination (see also Becker et al., Applied and Environmental Microbilogy, 71 (12), p. 8587-8596). The sequence of plasmid pClik int sacB can be found in WO2005059093; SEQ ID 24; the plasmid is called pCIS in this document.

In another embodiment, recombinant microorganisms can be produced which contain selected systems which allow for regulated expression of the introduced gene. For example, inclusion of one of the above-mentioned nucleic acid sequences on a vector placing it under control of the lac operon permits expression of the gene only in the presence of IPTG. Such regulatory systems are well known in the art.

Another aspect of the invention pertains to organisms or host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Growth of *E. coli* and *C. glutamicum*—Media and Culture Conditions

The person skilled in the art is familiar with the cultivation of common microorganisms such as *C. glutamicum* and *E. coli*. Thus, a general teaching will be given below as to the cultivation of *C. glutamicum*. Corresponding information may be retrieved from standard textbooks for cultivation of *E. coli*.

*E. coli* strains are routinely grown in MB and LB broth, respectively (Follettie et al. (1993) *J. Bacteriol.* 175, 4096-4103). Minimal Several minimal media for bacteria, including *E. coli* and *C. glutamicum* are well known in the art. Minimal media for *E. coli* include, but are not limited to, E medium, M9medium and modified MCGC (Yoshihama et al. (1985) *J. Bacteriol.* 162, 591-507), respectively. Glucose may be added at a final concentration of between about 0.2% and 1%. Antibiotics may be added in the following amounts (micrograms per millilitre): ampicillin, 5 to 1000; kanamycin, 25; nalidixic acid, 25; chloramphenicol, 5 to 120, spectinomycin 50 to 100, tetracyline 5 to 120. Amino acids, vitamins, and other supplements may be added, for example, in the following amounts: methionine, 9.3 mM; arginine, 9.3 mM; histidine, 9.3 mM; thiamine, 0.05 mM. *E. coli* cells are routinely grown at 18 to 37 44° C., respectively, depending on the particular experiment or procedure being performed.

Genetically modified *Corynebacteria* are typically cultured in synthetic or natural growth media. A number of different growth media for *Corynebacteria* are both well-known and readily available (Lieb et al. (1989) *Appl. Microbiol. Biotechnol.*, 32: 205-210; von der Osten et al. (1998) *Biotechnology Letters*, 11: 11-16; Patent DE 4,120,867; Liebl (1992) "The Genus *Corynebacterium*, in: The Procaryotes, Volume II, Balows, A. et al., eds. Springer-Verlag). Instructions can also be found in the Handbook of *Corynebacterium* (edited by Eggeling and Bott, ISBN 0-8493-1821-1, 2005).

These media consist of one or more carbon sources, nitrogen sources, inorganic salts, vitamins and trace elements. Preferred carbon sources are sugars, such as mono-, di-, or polysaccharides. For example, glucose, fructose, mannose, galactose, ribose, sorbose, ribose, lactose, maltose, sucrose, glycerol, raffinose, starch or cellulose serve as very good carbon sources.

It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates, urea, amino acids or complex nitrogen sources like corn steep liquor, soy bean flour, soy bean protein, yeast extract, meat extract and others.

The overproduction of methionine is possible using different sulfur sources. Sulfates, thiosulfates, sulfites and also more reduced sulfur sources like $H_2S$ and sulfides and derivatives can be used. Also organic sulfur sources like methyl mercaptan, thioglycolates, thiocyanates, and thiourea, sulfur containing amino acids like cysteine and other sulfur containing compounds can be used to achieve efficient methionine production. Formate may also be possible as a supplement as are other C1 sources such as methanol or formaldehyde.

Inorganic salt compounds which may be included in the media include the chloride-, phosphorous- or sulfate-salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include cyanocobalamin (or other form of vitamin B12), biotin, riboflavin, thiamine, folic acid, nicotinic acid, pantothenate and pyrridoxin. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook "Applied Microbiol. Physiology, A Practical Approach (Eds. P. M. Rhodes, P. F. Stanbury, IRL Press (1997) pp. 53-73, ISBN 0 19 963577 3). It is also possible to select growth media from commercial suppliers, like standard 1 (Merck) or BHI (grain heart infusion, DIFCO) or others.

All medium components should be sterilized, either by heat (20 minutes at 1.5 bar and 121 C) or by sterile filtration. The components can either be sterilized together or, if necessary, separately.

All media components may be present at the beginning of growth, or they can optionally be added continuously or batch wise. Culture conditions are defined separately for each experiment.

The temperature should be is usually in a range between 15° C. and 45° C., but the range may be higher, up to 105° C. for thermophilic organisms. The temperature can be kept constant or can be altered during the experiment. The pH of the medium may be in the range of 5 to 8.5, preferably around 7.0, and can be maintained by the addition of buffers to the media. An exemplary buffer for this purpose is a potassium phosphate buffer. Synthetic buffers such as MOPS, HEPES, ACES and others can alternatively or simultaneously be used. It is also possible to maintain a constant culture pH through the addition of an acid or base, such as acetic acid, sulfuric acid, phosphoric acid, NaOH, KOH or $NH_4OH$ during growth. If complex medium components such as yeast extract are utilized, the necessity for additional buffers may be reduced, due to the fact that many complex compounds have high buffer capacities. If a fermentor is utilized for culturing the microorganisms, the pH can also be controlled using gaseous ammonia.

The incubation time is usually in a range from several hours to several days. This time is selected in order to permit the maximal amount of product to accumulate in the broth. The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 ml or 250 shake flasks are used, filled with about 10% (by volume) of the required growth medium. The flasks should be shaken on a rotary shaker (amplitude about 25 mm) using a speed-range of about 100-300 'rpm. Evaporation losses can be diminished by the maintenance of a humid atmosphere; alternatively, a mathematical correction for evaporation losses should be performed.

If genetically modified clones are tested, an unmodified control clone or a control clone containing the basic plasmid without any insert should also be tested. The medium is inoculated to an OD600 of 0.5-1.5 using cells grown on agar plates, such as CM plates (10 g/1 glucose, 2.5 g/1 NaCl, 2 g/1 urea, 10 g/1 polypeptone, 5 g/1 yeast extract, 5 g/1 meat extract, 22 g/1 $(NH_4)_2SO_4$, 2 g/1 urea, 10 g/1 polypeptone, 5 g/1 yeast extract, 5 g/1 meat extract, 22 g/1 agar, pH about 6.8 to 7.2 with 2M NaOH) that had been incubated at 30° C. Inoculation of the media is accomplished by either introduction of a saline suspension of *C. glutamicum* cells from CM plates or addition of a liquid preculture of this bacterium.

General Methods

Protocols for general methods can be found in Handbook on *Corynebacterium glutamicum*, (2005) eds.: L. Eggeling, M. Bott., Boca Raton, CRC Press, at Martin et al. (*Biotechnology* (1987) 5, 137-146), Guerrero et al. (*Gene* (1994), 138, 35-41), Tsuchiya und Morinaga (*Biotechnology* (1988), 6, 428-430), Eikmanns et al. (Gene (1991), 102, 93-98), EP 0 472 869, U.S. Pat. No. 4,601,893, Schwarzer and Pühler (*Biotechnology* (1991), 9, 84-87, Reinscheid et al. (*Applied and Environmental Microbiology* (1994), 60, 126-132), LaBarre et al. (*Journal of Bacteriology* (1993), 175, 1001-1007), WO 96/15246, Malumbres et al. (*Gene* (1993), 134, 15-24), in JP-A-10-229891, at Jensen und Hammer (*Biotechnology and Bioengineering* (1998), 58, 191-195), Makrides (*Microbiological Reviews* (1996), 60, 512-538) and in well known textbooks of genetic and molecular biology.

Strains, Media and Plasmids

Strains can be taken e.g. for example, but not limited to, from the following list:

*Corynebacterium glutamicum* ATCC 13032,
*Corynebacterium acetoglutamicum* ATCC 15806,
*Corynebacterium acetoacidophilum* ATCC 13870,
*Corynebacterium thermoaminogenes* FERM BP-1539,
*Corynebacterium melassecola* ATCC 17965,
*Brevibacterium flavum* ATCC 14067,
*Brevibacterium lactofermentum* ATCC 13869, and
*Brevibacterium divaricatum* ATCC 14020 or strains which have been derived therefrom such as

*Corynebacterium glutamicum* KFCC10065, DSM 17322 or

*Corynebacterium glutamicum* ATCC21608

*Corynebacterium efficiens* DSMZ44547, 44548, 44549

Recombinant DNA Technology

Protocols can be found in: Sambrook, J., Fritsch, E. F., and Maniatis, T., in Molecular Cloning: A Laboratory Manual, 3rd edition (2001) Cold Spring Harbor Laboratory Press, NY, Vol. 1, 2, 3, and Handbook on *Corynebacterium glutamicum* (2005) eds. L. Eggeling, M. Bott., Boca Raton, CRC Press.

Quantification of Amino Acids and Methionine Intermediates.

The analysis is done by HPLC (Agilent 1100, Agilent, Waldbronn, Germany) with a guard cartridge and a Synergi 4 μm column (MAX-RP 80 Å, 150*4.6 mm) (Phenomenex, Aschaffenburg, Germany). Prior to injection the analytes are derivatized using o-phthaldialdehyde (OPA) and mercaptoethanol as reducing agent (2-MCE). Additionally sulfhydryl groups are blocked with iodoacetic acid. Separation is carried out at a flow rate of 1 ml/min using 40 mM $NaH_2PO_4$ (eluent A, pH=7.8, adjusted with NaOH) as polar and a methanol water mixture (100/1) as non-polar phase (eluent B). The following gradient is applied: Start 0% B; 39 min 39% B; 70 min 64% B; 100% B for 3.5 min; 2 min 0% B for equilibration. Derivatization at room temperature is automated as described below. Initially 0.5 μl of 0.5% 2-MCE in bicine (0.5M, pH 8.5) are mixed with 0.5 μl cell extract. Subsequently 1.5 μl of 50 mg/ml iodoacetic acid in bicine (0.5M, pH 8.5) are added, followed by addition of 2.5 μl bicine buffer (0.5M, pH 8.5). Derivatization is done by adding 0.5 μl of 10 mg/ml OPA reagent dissolved in 1/45/54 v/v/v of 2-MCE/MeOH/bicine (0.5M, pH 8.5). Finally the mixture is diluted with 32 μl $H_2O$. Between each of the above pipetting steps there is a waiting time of 1 min. A total volume of 37.5 μl is then injected onto the column. Note, that the analytical results can be significantly improved, if the auto sampler needle is periodically cleaned during (e.g. within waiting time) and after sample preparation. Detection is performed by a fluorescence detector (340 nm excitation, emission 450 nm, Agilent, Waldbronn, Germany). For quantification α-amino butyric acid (ABA) or D,L-norvaline is used as internal standard Definition of Recombination Protocol In the following it will be described how a strain of *C. glutamicum* with increased efficiency of methionine production can be constructed implementing the findings of the above predictions. Before the construction of the strain is described, a definition of a recombination event/protocol is given that will be used in the following.

"Campbell in," as used herein, refers to a transformant of an original host cell in which an entire circular double stranded DNA molecule (for example a plasmid being based on pCLIK int sacB has integrated into a chromosome by a single homologous recombination event (a cross-in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point. The name comes from Professor Alan Campbell, who first proposed this kind of recombination. "Campbell out," as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above).

A "Campbell out" cell or strain is usually, but not necessarily, obtained by a counter-selection against a gene that is contained in a portion (the portion that is desired to be jettisoned) of the "Campbelled in" DNA sequence, for example the *Bacillus subtilis* sacB gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

For practicality, in *C. glutamicum*, typical first and second homologous DNA sequence are at least about 200 base pairs in length, and can be up to several thousand base pairs in length, however, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs. The "Campbell In and -Out-method" is described in WO2007012078

EXAMPLES

The following experiments demonstrate how overexpression of ferredoxins, ferredoxin reductases, flavodoxins and flavodoxin reductases in micororganisms such as *C.*

*glutamicum* and *E. coli* allow for reactivation of MetH and improved methionine production. These examples are however in no way meant to limit the invention in any way.

In the examples given below, methods well known in the art were used to construct plasmids and *E. coli* strains and to construct *C. glutamicum* strains containing replicating plasmids and/or various chromosomal insertions, deletions, and substitutions using the "Campbelling in" and Campbelling out" procedure (see above) A suffix of "–X", where X is a number, attached to a strain name designates one or more isolates from a particular strain construction, and which are either identical or similar to each other. For example, OM403-4 and OM403-8 are both ΔmcbR derivatives of M2014 (see below), originating from the same construction experiment.

Unless otherwise specified, all tests for methionine prototrophy and auxotrophy, and all selections for methionine prototrophy, were conducted on agar petri plates containing chemically defined medium named "methionine free medium" or "MF", with or without methionine added at a final concentration of 100 mg/l. The recipe for MF is given below. All stock solutions are made sterile by autoclaving for 20 minutes or by filtering through a Nalgene 0.2 micron filter unit.

A prototrophic strain of *E. coli* or *C. glutamicum* will grow well on MF medium without added methionine. An auxotrophic strain of *E. coli* or *C. glutamicum* will grow well only on MF that has sufficient methionine added, usually about 5 to 100 mg/l.

Methionine Free Medium to give a total of about 1 liter:
20 g Agar
785 ml distilled water
autoclave, and while mixture is still hot, add and mix:
100 ml of 100 g/l Difco™ Methionine Assay Medium, filter sterilized
100 ml of 10× Spizizen's salts
6 ml of 50% Glucose, autoclaved
5 ml of 400 mM L-threonine, filter sterilized
5 ml of 10 g/l L-cysteine HCl, filter sterilized
4 ml of "4B" solution
5 ml 2% $CaCl_2$ dihydrate, autoclaved
Pour 25 ml into each 100 mm Petri plate 4B Solution to give a total of 100 ml:
25 mg thiamine HCl (vitamin $B_1$)
5 mg cyanocobalamin (vitamin $B_{12}$)
2.5 ml of 1 mg/ml biotin dissolved in 50 mM potassium phosphate, pH 7.0
125 mg pyrridoxin HCl (vitamin B6)
distilled water to 100 ml, filter sterilize 10× Spizizen's Salts:

to give a total of about 1 liter:
20 g Ammonium sulfate
174 g Potassium phosphate dibasic (trihydrate)
60 g Potassium phosphate monobasic (anhydrous)
10 g Sodium citrate
2 g Magnesium sulfate (heptahydrate)
distilled water to 1 liter
1 ml Micronutrient solution***
after autoclaving, add 3.5 ml of filter sterilized 4 g/l $FeCl_3$.6H20

***Micronutrient Solution:

to give a total of 1 liter:
0.15 g $Na_2MoO_4.2H_2O$
2.5 g $H_3BO_3$
0.7 g $CuSO_4.5H_2O$
1.6 g $MnCl_2.4H_2O$
0.3 g $ZnSO_4.7H_2O$
distilled water to 1 liter, filter sterilize Brain Heart Infusion Medium (BHI), also Called "Rich Medium" for Growth of *C. Glutamicum:*

37.5 g Bacto™ Brain Heart Infusion (Becton, Dickinson and Company, Sparks, Md.)
15 g Agar
distilled water to 1 liter
autoclave, cool to 60° C., add antibiotic as necessary (for example 2.5 ml of 10 mg/ml kanamycin sulfate, filter sterilized)
Pour 25 ml into each 100 mm Petri plate.

Unless otherwise specified, routine transformation of *C. glutamicum* was accomplished by electroporation using a Bio Rad electroporator (model 1652076 Gene Pulser together with a model 1652098 Pulse Controller) as recommended by the manufacturer and selection for antibiotic resistant transformants of *C. glutamicum* on BHI (Brain Heart Infusion) medium (see below) supplemented with the appropriate antibiotic, for example, 25 mg/1 kanamycin sulfate.

Unless otherwise specified, all tests for methionine production described herein use a "standard shake flask" protocol with a molasses medium. The molasses medium contains 2 mM threonine added and the flasks are shaken for about 48 hours at 30° C.

Shake Flask Experiments and HPLC Assay

Shake flasks experiments, with the standard Molasses Medium, were performed with strains in duplicate or quadruplicate. Molasses Medium contained in one liter of medium: 40 g glucose; 60 g molasses; 20 g $(NH_4)_2SO_4$; 0.4 g $MgSO_4*7H_2O$; 0.6 g $KH_2PO_4$; 10 g yeast extract (DIFCO); 5 ml of 400 mM threonine; 2 mg $FeSO_4.7H_2O$; 2 mg of $MnSO_4.H_2O$; and 50 g $CaCO_3$ (Riedel-de Haen), with the volume made up with $ddH_2O$. The pH was adjusted to 7.8 with 20% $NH_4OH$. 20 ml of continuously stirred medium (in order to keep $CaCO_3$ suspended) was added to 250 ml baffled Bellco shake flasks and the flasks were autoclaved for 20 min. Subsequent to autoclaving, 4 ml of "4B solution" was added per liter of the base medium (or 80 μl/flask). The "4B solution" contained per liter: 0.25 g of thiamine hydrochloride (vitamin B1), 50 mg of cyanocobalamin (vitamin B12), 25 mg biotin, 1.25 g pyrridoxin hydrochloride (vitamin B6) and was buffered with 12.5 mM $KPO_4$, pH 7.0 to dissolve the biotin, and was filter sterilized. Cultures were grown in baffled flasks covered with Bioshield paper secured by rubber bands for about 48 hours at about 28° C. or 30° C. and at 200 or 300 rpm in a New Brunswick Scientific floor shaker. Samples were typically taken at about 24 hours and/or about 48 hours. Cells were removed by centrifugation followed by dilution of the supernatant with an equal volume of 60% acetonitrile or 60% ethanol and then membrane filtration of the solution mixture using Centricon 0.45 μm spin columns. The filtrates were assayed using HPLC for the concentrations of methionine, glycine plus homoserine, O-acetylhomoserine, threonine, isoleucine, lysine, and other indicated amino acids.

For the HPLC assay, filtered supernatants were diluted 1:100 with 0.45 μm filtered 1 mM $Na_2EDTA$ and 1 μl of the solution was derivatized with OPA reagent (AGILENT) in Borate buffer (80 mM $NaBO_3$, 2.5 mM EDTA, pH 10.2) and injected onto a 200×4.1 mm Hypersil 5μ AA-ODS column run on an Agilent 1100 series HPLC equipped with a G1321A fluorescence detector (AGILENT). The excitation wavelength was 338 nm and the monitored emission wavelength was 425 nm. Amino acid standard solutions were chromatographed and used to determine the retention times and standard peak areas for the various amino acids. Chem Station, the accompanying software package provided by Agilent, was used for instrument control, data acquisition and data manipulation. The hardware was an HP Pentium 4 computer that supports Microsoft Windows NT 4.0 updated with a Microsoft Service Pack (SP6a).

Experiment 1

Generation of the M2014 Strain

*C. glutamicum* strain ATCC 13032 was transformed with DNA A (also referred to as pH273) (SEQ ID NO: 25) and "Campbelled in" to yield a "Campbell in" strain. The "Campbell in" strain was then "Campbelled out" to yield a "Campbell out" strain, M440, which contains a gene encoding a feedback resistant homoserine dehydrogenase enzyme (hom-$^{fbr}$). The resultant homoserine dehydrogenase protein included an amino acid change where S393 was changed to F393 (referred to as Hsdh S393F).

The strain M440 was subsequently transformed with DNA B (also referred to as pH373) (SEQ ID NO: 26) to yield a "Campbell in" strain. The "Campbell in" strain were then "Campbelled out" to yield a "Campbell out" strain, M603, which contains a gene encoding a feedback resistant aspartate kinase enzyme (Ask$^{fbr}$) (encoded by lysC). In the resulting aspartate kinase protein, T311 was changed to I311 (referred to as LysC T311I).

It was found that the strain M603 produced about 17.4 mM lysine, while the ATCC13032 strain produced no measurable amount of lysine. Additionally, the M603 strain produced about 0.5 mM homoserine, compared to no measurable amount produced by the ATCC13032 strain, as summarized in Table 2.

TABLE 2

Amounts of homoserine, O-acetylhomoserine, methionine and lysine produced by strains ATCC13032 and M603

| Strain | Homoserine (mM) | O-acetyl homoserine (mM) | Methionine (mM) | Lysine (mM) |
|---|---|---|---|---|
| ATCC13032 | 0.0 | 0.4 | 0.0 | 0.0 |
| M603 | 0.5 | 0.7 | 0.0 | 17.4 |

The strain M603 was transformed with DNA C (also referred to as pH304) (SEQ ID NO:27) to yield a "Campbell in" strain, which was then "Campbelled out" to yield a "Campbell out" strain, M690. The M690 strain contained a PgroES promoter upstream of the metH gene (referred to as $P_{497}$ metH). The sequence of the $P_{497}$ promoter is depicted in SEQ ID NO: 22. The M690 strain produced about 77.2 mM lysine and about 41.6 mM homoserine, as shown below in Table 3.

TABLE 3

Amounts of homoserine, O-acetyl homoserine, methionine and lysine produced by the strains M603 and M690

| Strain | Homoserine (mM) | O-acetyl homoserine (mM) | Methionine (mM) | Lysine (mM) |
|---|---|---|---|---|
| M603 | 0.5 | 0.7 | 0.0 | 17.4 |
| M690 | 41.6 | 0.0 | 0.0 | 77.2 |

The M690 strain was subsequently mutagenized as follows: an overnight culture of M603, grown in BHI medium (BECTON DICKINSON), was washed in 50 mM citrate buffer pH 5.5, treated for 20 min at 30° C. with N-methyl-N-nitrosoguanidine (10 mg/ml in 50 mM citrate pH 5.5). After treatment, the cells were again washed in 50 mM citrate buffer pH 5.5 and plated on a medium containing the following ingredients: (all mentioned amounts are calculated for 500 ml medium) 10 g $(NH_4)_2SO_4$; 0.5 g $KH_2PO_4$; 0.5 g $K_2HPO_4$; 0.125 g $MgSO_4.7H_2O$; 21 g MOPS; 50 mg $CaCl_2$; 15 mg protocatechuic acid; 0.5 mg biotin; 1 mg thiamine; and 5 g/l D,L-ethionine (SIGMA CHEMICALS, CATALOG #E5139), adjusted to pH 7.0 with KOH. In addition the medium contained 0.5 ml of a trace metal solution composed of: 10 g/l $FeSO_4.7H_2O$; 1 g/l $MnSO_4*H_2O$; 0.1 g/l $ZnSO_4*7H_2O$; 0.02 g/l $CuSO_4$; and 0.002 g/l $NiCl_2*6H_2O$; all dissolved in 0.1 M HCl. The final medium was sterilized by filtration and to the medium, 40 mls of sterile 50% glucose solution (40 ml) and sterile agar to a final concentration of 1.5% were added. The final agar containing medium was poured to agar plates and was labeled as minimal-ethionine medium. The mutagenized strains were spread on the plates (minimal-ethionine) and incubated for 3-7 days at 30° C. Clones that grew on the medium were isolated and restreaked on the same minimal-ethionine medium. Several clones were selected for methionine production analysis.

Methionine production was analyzed as follows. Strains were grown on CM-agar medium for two days at 30° C., which contained: 10 g/l D-glucose, 2.5 g/l NaCl; 2 g/l urea; 10 g/l Bacto Peptone (DIFCO); 5 g/l Yeast Extract (DIFCO); 5 g/l Beef Extract (DIFCO); 22 g/l Agar (DIFCO); and which was autoclaved for 20 min at about 121° C.

After the strains were grown, cells were scraped off and resuspended in 0.15 M NaCl. For the main culture, a suspension of scraped cells was added at a starting OD of 600 nm to about 1.5 to 10 ml of Medium II (see below) together with 0.5 g solid and autoclaved $CaCO_3$ (RIEDEL DE HAEN) and the cells were incubated in a 100 ml shake flask without baffles for 72 h on a orbital shaking platform at about 200 rpm at 30° C. Medium II contained: 40 g/l sucrose; 60 g/l total sugar from molasses (calculated for the sugar content); 10 g/l $(NH_4)_2SO_4$; 0.4 g/l $MgSO_4*7H_2O$; 0.6 g/l $KH_2PO_4$; 0.3 mg/l thiamine*HCl; 1 mg/l biotin; 2 mg/l $FeSO_4$; and 2 mg/l $MnSO_4$. The medium was adjusted to pH 7.8 with $NH_4OH$ and autoclaved at about 121° C. for about 20 min). After autoclaving and cooling, vitamin $B_{12}$ (cyanocobalamine) (SIGMA CHEMICALS) was added from a filter sterile stock solution (200 μg/ml) to a final concentration of 100 μg/l.

Samples were taken from the medium and assayed for amino acid content. Amino acids produced, including methionine, were determined using the Agilent amino acid method on an Agilent 1100 Series LC System HPLC. (AGILENT). A pre-column derivatization of the sample with ortho-pthalaldehyde allowed the quantification of produced amino acids after separation on a Hypersil AA-column (AGILENT).

Clones that showed a methionine titer that was at least twice that in M690 were isolated. One such clone, used in further experiments, was named M1197 and was deposited on May 18, 2005, at the DSMZ strain collection as strain number DSM 17322. Amino acid production by this strain was compared to that by the strain M690, as summarized below in Table 4.

TABLE 4

Amounts of homoserine, O-acetylhomoserine, methionine and lysine produced by strains M690 and M1197

| Strain | Homoserine (mM) | O-acetyl-homoserine (mM) | Methionine (mM) | Lysine (mM) |
|---|---|---|---|---|
| M690 | 41.6 | 0.0 | 0.0 | 77.2 |
| M1179 | 26.4 | 1.9 | 0.7 | 79.2 |

The strain M1197 was transformed with DNA F (also referred to as pH399, SEQ ID NO: 28) to yield a "Campbell in" strain, which was subsequently "Campbelled out" to yield strain M1494. This strain contains a mutation in the gene for the homoserine kinase, which results in an amino acid change in the resulting homoserine kinase enzyme from T190 to A190 (referred to as HskT190A). Amino acid production by the strain M1494 was compared to the production by strain M1197, as summarized below in Table 5.

TABLE 5

Amounts of homoserine, O-acetylhomoserine, methionine and lysine produced by strains M1197 and M1494

| Strain | Homoserine (mM) | O-acetyl-homoserine (mM) | Methionine (mM) | Lysine (mM) |
|---|---|---|---|---|
| M1197 | 26.4 | 1.9 | 0.7 | 79.2 |
| M1494 | 18.3 | 0.2 | 2.5 | 50.1 |

The strain M1494 was transformed with DNA D (also referred to as pH484, SEQ ID NO:29) to yield a "Campbell in" strain, which was subsequently "Campbelled out" to yield the M1990 strain. The M1990 strain overexpresses a metY allele using both a groES-promoter and an EFTU (elongation factor Tu)-promoter (referred to as $P_{497}$ $P_{1284}$ metY). The sequence of $P_{497}P_{1284}$ promoter is set forth in SEQ ID NO:30 Amino acid production by the strain M1494 was compared to the production by strain M1990, as summarized below in Table 6.

TABLE 6

Amounts of homoserine, O-acetylhomoserine, methionine and lysine produced by strains M1494 and M1990

| Strain | Homoserine (mM) | O-acetyl-homoserine (mM) | Methionine (mM) | Lysine (mM) |
|---|---|---|---|---|
| M1494 | 18.3 | 0.2 | 2.5 | 50.1 |
| M1990 | 18.2 | 0.3 | 5.6 | 48.9 |

The strain M1990 was transformed with DNA E (also referred to as pH 491, SEQ ID NO: 31) to yield a "Campbell in" strain, which was then "Campbelled out" to yield a "Campbell out" strain M2014. The M2014 strain overexpresses a metA allele using a superoxide dismutase promoter (referred to as $P_{3119}$ metA). The sequence of $P_{3119}$ promoter is set forth in SEQ ID NO: 21. Amino acid production by the strain M2014 was compared to the production by strain M1990, as summarized below in Table 7

TABLE 7

Amounts of homoserine, O-acetylhomoserine, methionine and lysine produced by strains M1494 and M1990

| Strain | Homoserine (mM) | O-acetyl-homoserine (mM) | Methionine (mM) | Lysine (mM) |
|---|---|---|---|---|
| M1990 | 18.2 | 0.3 | 5.6 | 48.9 |
| M2014 | 12.3 | 1.2 | 5.7 | 49.2 |

Experiment 2

Deletion of mcbR from M2014

Plasmid pH429 containing an RXA00655 deletion, (SEQ ID NO:32) was used to introduce the mcbR deletion into *C. glutamicum* via integration and excision (see WO 2004/050694 A1).

Plasmid pH429 was transformed into the M2014 strain with selection for kanamycin resistance (Campbell in). Using sacB counter-selection, kanamycin-sensitive derivatives of the transformed strain were isolated which presumably had lost the integrated plasmid by excision (Campbell out). The transformed strain produced kanamycin-sensitive derivatives that made small colonies and larger colonies. Colonies of both sizes were screened by PCR to detect the presence of mcbR deletion. None of the larger colonies contained the deletion, whereas 60-70% of the smaller colonies contained the expected mcbR deletion.

When an original isolate was streaked for single colonies on BHI plates, a mixture of tiny and small colonies appeared. When the tiny colonies were restreaked on BHI, once again a mixture of tiny and small colonies appeared. When the small colonies were restreaked on BHI, the colony size was usually small and uniform. Two small single colony isolates, called OM403-4 and OM403-8, were selected for further study.

Shake flask experiments (Table 8) showed that OM403-8 produced at least twice the amount of methionine as the parent M2014. This strain also produced less than one-fifth the amount of lysine as M2014, suggesting a diversion of the carbon flux from aspartate semialdehyde towards homoserine. A third striking difference was a greater than 10-fold increase in the accumulation of isoleucine by OM403 relative to M2014. Cultures were grown for 48 hours in standard molasses medium.

TABLE 8

Amino acid production by isolates of the OM403 strain in shake flask cultures inoculated with freshly grown cells.

| Strain | Colony size | Deletion ΔmcbR | Met (g/l) | Lys (g/l) | Hse + Gly (g/l) | Ile (g/l) |
|---|---|---|---|---|---|---|
| M2014 | Large | none | 0.2 | 2.4 | 0.3 | 0.04 |
| | | | 0.2 | 2.5 | 0.3 | 0.03 |
| | | | 0.2 | 2.4 | 0.3 | 0.03 |
| | | | 0.4 | 3.1 | 0.4 | 0.03 |
| OM403-8 | Small | ΔRXA0655 | 1.0 | 0.3 | 0.8 | 0.8 |
| | | | 1.0 | 0.3 | 0.8 | 0.8 |
| | | | 0.9 | 0.3 | 0.8 | 0.8 |
| | | | 1.0 | 0.3 | 0.8 | 0.6 |

Also as shown in Table 9, there was a greater than 15-fold decrease in the accumulation of O-acetylhomoserine by OM403 relative to M2014. The most likely explanation for this result is that most of the O-acetylhomoserine that accumulates in M2014 is being converted to methionine, homocysteine, and isoleucine in OM403. Cultures were grown for 48 hours in standard molasses medium.

TABLE 9

| Amino acid production by two isolates of OM403 in shake flask cultures inoculated with freshly grown cells. | | | | |
|---|---|---|---|---|
| Strain | Deletion ΔmcbR | Met (g/l) | OAc-Hse (g/l) | Ile (g/l) |
| M2014 | None | 0.4 | 3.4 | 0.1 |
| | | 0.4 | 3.2 | 0.1 |
| OM403-4 | ΔRXA0655 | 1.7 | 0.2 | 0.3 |
| | | 1.5 | 0.1 | 0.3 |
| OM403-8 | ΔRXA0655 | 2.2 | <0.05 | 0.6 |
| | | 2.5 | <0.05 | 0.6 |

Experiment 3

Methionine Synthase is a Limiting Step in Methionine Synthesis

*C. glutamicum* strain OM403-8, which has been engineered to produce methionine, was transformed with a replicating plasmid, pH447 (SEQ ID No.: 33), which overexpresses the $metE_{Cg}$ gene to give strain OM419, or with pH170 (SEQ ID No.: 34), which overexpresses $metH_{Cg}$, to give strain OM418. The two strains and their parent, transformed with the empty vector pCLIK, were tested for methionine production using our standard shake flask protocol, and the results are shown in Table 10 below.

TABLE 10

Methionine production by transformants of OM403 that overexpress $metE_{Cg}$ or $metH_{Cg}$ in shake flask cultures.

| Strain | Plasmid | Gene expression cassette on plasmid | [met] (g/l) |
|---|---|---|---|
| OM403-8 | pCLIK | none | 1.5 |
| " | " | " | 2.0 |
| " | " | " | 1.7 |
| " | " | " | 1.8 |
| OM403-8 average | " | " | 1.8 |
| OM418-1 | pH170 | $MetH_{Cg}$ | 2.2 |
| OM418-2 | " | " | 2.0 |
| OM418-3 | " | " | 2.2 |
| OM418-4 | " | " | 2.3 |
| OM418 average | " | " | 2.2 |
| OM419-1 | PH447 | $MetE_{Cg}$ | 1.9 |
| OM419-2 | " | " | 1.8 |
| OM419-3 | " | " | 2.4 |
| OM419-4 | " | " | 2.1 |
| OM419 average | " | " | 2.1 |

The increases in methionine synthase in OM418 and OM419 both result in an increase in methionine titer, demonstrating that methionine synthase is a limiting step in OM403-8.

However, the extent of the increase in methionine titer from OM418 is somewhat less than predicted based on the at least 5-fold increase in concentration of $MetH_{Cg}$ in OM418 that was estimated from a Coomassie Blue stained protein gel.

Experiment 4

*E. coli* MetH does not Function by Itself in *C. glutamicum*

*C. glutamicum* strain OM246C was constructed from strain M2014 by first deleting a portion of metE, using plasmid pH469 (SEQ ID No.: 35), and then next by deleting a portion of metH, using plasmid pH300 (SEQ ID No.: 36). As expected, OM246C is a methionine auxotroph.

When transformed either with a replicating plasmid containing $P_{497}$ $metE_{Cg}$ (pH447, SEQ ID No.: 33), or $P_{497}$ $metH_{Cg}$ (pH170, SEQ ID No.: 34) the resulting transformants are methionine prototrophs, as expected. The latter transformant depends on cyanocobalamin in the medium, while the first does not.

However, when OM246C is transformed with an integrating plasmid containing $P_{15}$ $metH_{Ec}$ (pOM232, SEQ ID No.: 37) designed to integrate at $bioAD_{Cg}$, the resulting transformant, named OM292, is still an auxotroph in the presence of cyanocobalamin, even though the $MetH_{Ec}$ protein can be seen on a Coomassie Blue stained protein gel. $P_{15}$ (SEQ ID No.: 38) is a strong constitutive promoter derived from *Bacillus subtilis* phage SPO1. However, when an *E. coli* metE, metH mutant, RY714B (for RY714B see Experiment 5), is transformed with pOM232 (which replicates as an episomal plasmid in *E. coli*), the resulting transformant is a prototroph demonstrating that the $metH_{Ec}$ gene on pOM232 is functional. The surprising discovery from this example is that $MetH_{Ec}$ is not necessarily functional by itself in *C. glutamicum.*

Experiment 5

*C. Glutamicum* MetH does not Function by Itself in *E. Coli*

*E. coli* strain RY714B was constructed from strain YMC9 (ATCC 33927) by installing a $metE_{Ec}$::Tn10 allele and deleting a portion of $metH_{Ec}$. As expected, RY714B is a methionine auxotroph.

When RY714B is transformed with a replicating plasmid containing $P_{497}$ $metE_{Cg}$ (pH447, SEQ ID No.: 33), the transformant becomes a methionine prototroph, but when RY714B is transformed with $P_{497}$ $metH_{Cg}$ (pH170, SEQ ID No.: 34), or pOM240 (SEQ ID No.: 39), which expresses $metH_{Cg}$ from the $P_{15}$ promoter, the resulting transformants are still methionine auxotrophs, even in the presence of cyanocobalamin, and even though the $MetH_{Cg}$ protein can be seen on a Coomassie Blue stained protein gel. However, as a positive control, when RY714B is transformed with a plasmid that replicates in *E. coli* by the pSC101 origin of replication and carries $P_{15}$ $metH_{Ec}$ (pOM232, SEQ ID No.: 37), the resulting transformant is a prototroph in the presence of cyanocobalamin. The surprising discovery from this example is that $MetH_{Cg}$ is not necessarily functional by itself in *E. coli.*

Experiment 6

*E. coli*Flavodoxin can Reactivate *E. coli* MetH in *C. glutamicum*

*C. glutamicum* strain OM292 (see Experiment 4) is a derivative of OM246C that is deleted for $metE_{Cg}$ and $metH_{Cg}$, but contains an integrated $metH_{Ec}$. Nonetheless, OM292 is a methionine auxotroph.

OM292 was transformed with integrating plasmid pOM324 (SEQ ID No.: 40) by the Campbelling in and out procedure, which inserts a $P15fldA_{Ec}$ cassette at the $crtEb_{Cg}$ locus.

The resulting strain, named OM182, is a methionine prototroph, demonstrating that *E. coli* flavodoxin ($FldA_{Ec}$) is sufficient to reactivate $MetH_{Ec}$ in *C. glutamicum.* Since OM182 lacks *E. coli* flavodoxin reductase ($FldR_{Ec}$), it seems reasonable to assume that *C. glutamicum* contains a reductase that can function to recycle (re-reduce) *E. coli* flavodoxin.

Experiment 7

Reconstitution of the *E. Coli* MetH Reactivation System in *C. Glutamicum*

*C. glutamicum* strain OM182, from the previous Experiment 6, was transformed with pOM154 (SEQ ID No.: 41) using the "Campbelling in" and Campbelling out" procedure. Plasmid pOM154 is designed to integrate a $P_{15}$fldR$_{Ec}$ cassette at the marR$_{Cg}$ locus. The resulting strain, named OM190, contains cassettes expressing metH$_{Ec}$, fldA$_{Ec}$, and fldR$_{Ec}$. Strain OM190 and its predecessor strain, M2014, which uses the native MetH$_{Cg}$ reactivation system, were tested for methionine production with molasses medium in our standard shake flask protocol (see Table 11 below).

TABLE 11

Methionine production by strains derived from OM246C, containing $P_{15}$ metH$_{Ec}$ integrated at bioAD and grown in shake flasks in molasses medium for 48 hours.

| Strain | MetH system | $OD_{600}$ | [Met] g/l |
|---|---|---|---|
| M2014 | $P_{497}$ metH$_{Cg}$ | 51 | 1.5 |
| " | " | 49 | 1.5 |
| OM246C/pCLIK-1 | none | 62 | 0.02 |
| OM246C/pCLIK-2 | " | 51 | 0.03 |
| OM190-1 | $P_{15}$ metH$_{Ec}$, $P_{15}$ fldA$_{Ec}$, $P_{15}$ fldR$_{Ec}$ | 47 | 1.1 |
| OM190-2 | $P_{15}$ metH$_{Ec}$, $P_{15}$ fldA$_{Ec}$, $P_{15}$ fldR$_{Ec}$ | 45 | 1.0 |
| OM190-3 | $P_{15}$ metH$_{Ec}$, $P_{15}$ fldA$_{Ec}$, $P_{15}$ fldR$_{Ec}$ | 46 | 1.2 |
| OM190-4 | $P_{15}$ metH$_{Ec}$, $P_{15}$ fldA$_{Ec}$, $P_{15}$ fldR$_{Ec}$ | 43 | 0.9 |
| OM190-7 | $P_{15}$ metH$_{Ec}$, $P_{15}$ fldA$_{Ec}$, $P_{15}$ fldR$_{Ec}$ | 50 | 1.1 |
| OM190-8 | $P_{15}$ metH$_{Ec}$, $P_{15}$ fldA$_{Ec}$, $P_{15}$ fldR$_{Ec}$ | 50 | 1.4 |

The OM190 isolates produced much more methionine than grandparent OM246C (transformed with an empty vector) and almost as much methionine as the control strain M2014, showing that the *E. coli* MetH$_{Ec}$ system could function almost as well as the native *C. glutamicum* system when reconstituted in *C. glutamicum*. The copy number of the *E. coli* MetH$_{Ec}$ expression cassette can be increased to increase the level and hence activity of *E. coli* MetH$_{Ec}$ Experiment 8

*C. Glutamicum* FprA1 has a Function Important for Methionine Biosynthesis

*C. glutamicum* contains a divergently transcribed operon that encodes many, if not all of the genes involved in reduction of sulfate to sulfide for cysteine and methionine biosynthesis. The left hand side of the operon as conventionally drawn probably contains only one gene, fprA1$_{Cg}$, which encodes a protein annotated as a ferredoxin protein reductase that has been assumed to function in sulfate reduction. A plasmid named pOM413 (SEQ ID No: 42) was constructed to replace the regulated native divergent promoter of this operon with a different divergent promoter that would not be regulated in *C. glutamicum*. pOM413 contains the *E. coli* phage λ $P_{RM}/P_R$ divergent promoter replacing the native sulfate reduction region divergent promoters, with the relatively weak $P_{RM}$ promoter driving expression of the fprA1$_{Cg}$ gene and the relatively strong λ $P_R$ promoter driving expression of the multi-gene portion of the sulfate reduction operon.

Strain M2014 was transformed with pOM413, selecting for kanamycin resistance. Following sacB counter-selection, kanamycin sensitive derivatives were isolated from transformants derived from each plasmid. These were analyzed by PCR to determine the promoter structures of the sulfate reduction region. Approximately 50% of the pOM413-derived isolates contained the $P_{RM}/P_R$ divergent promoter region, suggesting no bias had occurred during excision of the plasmid. Isolates containing the $P_{RM}/P_R$ divergent promoter region were named OM404.

Colonies of OM404 are not noticeably different in size from those of the M2014 parent strain, and there have been no indications that OM404 grows more slowly than M2014. Six isolates of OM404 were tested for amino acid production using our standard shake flask protocol. The results (Table 12) show that all the isolates of OM404 produced less than one-half the methionine titer that M2014 produces.

TABLE 12

Methionine production by isolates of OM404 in shake flask cultures.

| Strain | | Sulfate regulon promoter | [met] (g/l) |
|---|---|---|---|
| M2014 | | native | 0.78 |
| OM404 | -1 | λ $P_{RM}/P_R$ | 0.32 |
| | -2 | | 0.27 |
| | -3 | | 0.26 |
| | -4 | | 0.26 |
| | -5 | | 0.29 |
| | -6 | | 0.27 |
| | -7 | | 0.38 |

Introduction of the constitutive divergent promoter clearly had a negative effect on methionine production, but it was not clear whether one transcript or the other or both was responsible for the effect.

One explanation for these results could be that one has impaired the sulfate reduction pathway by replacing the native promoters and has thus limited methionine production.

To independently assess the sulfate reduction activity of the strains, a technique used to estimate relative sulfide production was employed. Strips of filter paper are soaked in a 5 mM solution of Ellman's reagent (DTNB) buffered with 0.1 M potassium phosphate, pH 7.2, and subsequently dried. One such dried strip is suspended in the air space above the liquid of each shake flask culture of the strain to be tested for 48 hours. Hydrogen sulfide produced by the growing culture reduces the DTNB, producing a yellow color, the intensity of which is roughly proportional to the amount of $H_2S$ generated, up to a limit. Thus, the intensity of the color produced can be used to obtain a rough estimate of the relative sulfate reduction activity of various strains. Strains M2014, OM403 (M2014 ΔmcbR), and OM404 were tested using this method. The results are shown below in Table 13.

TABLE 13

Ellman's reagent test for sulfate reduction activity of M2014 and derivatives.

| Strain | mcbR locus | Sulfate regulon promoter | Relative estimated color intensity |
|---|---|---|---|
| M2014 | native | native | +/− |
| OM403-4-2 | ΔmcbR | native | +++ |
| OM403-8-2 | ΔmcbR | native | +++ |
| OM404-1 | native | λ $P_{RM}/P_R$ | ++ |
| OM404-2 | native | λ $P_{RM}/P_R$ | ++ |

The results (Table 13) indicate that OM403 has the greatest sulfate reduction activity and M2014 has the least. Strains OM404 demonstrate intermediate levels of activity, with OM404 having greater activity than M2014. Thus, the results are somewhat paradoxical: sulfate reduction is clearly up in OM404, but methionine production is down, compared to OM2014. This is a surprising result, since in the literature it is reported that deletion of the fprA1$_{Cg}$ gene (named fpr2 in this reference) gives a phenotype similar to wild type, in other words no auxotrophy and similar growth rates on sulfate as the sole sulfur source. (Ruckert et al. (2005) BMC Genomics, 6, 121).

One explanation for these results may be that the expression of fprA1$_{Cg}$ from the λ $P_{RM}$ promoter is weaker than from the native promoter, and that fprA1$_{Cg}$ is involved in an aspect of methionine synthesis separate from sulfate reduction, even though it might also still function in an aspect of sulfate reduction.

It was hypothesized that FprA1$_{Cg}$ may be a reductase for recycling the redox component of MetH$_{Cg}$ reactivation. Even though being annotated as a ferredoxin reductase, FprA1$_{Cg}$ may thus be the functional equivalent of FldR$_{Ec}$ for reactivation of MetH$_{Ec}$.

pOM413 was also used to integrate the divergent λ $P_{RM}$/$P_R$ promoter into strain OM403-4 to give strains named OM406. Like the case for OM404, OM406 isolates produced less methionine than their parent using the standard shake flask protocol, as shown below in Table 14.

TABLE 14

Methionine production by two isolates of OM406

| Strain | Parent | Sulfate operon promoter | $OD_{600}$ | [met] (g/l) |
|---|---|---|---|---|
| OM403-4 | M2014 | native | 29 | 0.9 |
| OM406-6 | OM403-4 | λ $P_{RM}$/$P_R$ | 32 | 0.5 |
| OM403-4 | M2014 | native | 39 | 0.8 |
| " | " | " | 36 | 0.9 |
| OM406-7 | OM403-4 | λ $P_{RM}$/$P_R$ | 35 | 0.5 |
| " | " | " | 20 | 0.4 |

In addition, on Coomassie Blue stained protein gels, a band of the predicted size for FprA1$_{Cg}$ is visible from extracts of OM403-4, but not from OM406 isolates. These data support the hypothesis that FprA1$_{Cg}$ is important for methionine synthesis is further supported.

A high level of FprA1$_{Cg}$ was then reintroduced into OM406-6 as follows:

A plasmid was constructed that replicates in *C. glutamicum* and contains a cassette for expressing fprA1$_{Cg}$ at a high level from the λ$P_R$ promoter. This plasmid is named pOM429 (SEQ ID No: 43). Isolates of OM406-6 transformed with pOM429 are named OM454.

In shake flask cultures, OM454 isolates produced much more methionine than parent OM406 (see Table 15 below), almost as much as grandparent OM403-4.

TABLE 15

Methionine production by OM454

| Strain | parent | [Met] (g/l) |
|---|---|---|
| OM403-4 | M2014 | 3.6 |
| " | " | 3.6 |
| OM406-6 | OM403-4 | 1.4 |
| " | " | 1.2 |
| OM454-1 | OM406-6 | 3.2 |
| OM454-2 | " | 3.2 |

In addition, whole cell extracts of OM454 run on SDS PAGE protein gels stained with Coomassie Blue showed a prominent band at the expected size for FprA1$_{Cg}$, showing that high level FprA1$_{Cg}$ synthesis had been reinstated by pOM429 in OM454. Thus, the combination of strong λ $P_R$ driving expression of fprA1$_{Cg}$ and λ $P_R$ driving expression of the multigene branch of the sulfate reduction operon (OM454) gives higher methionine production than an isogenic strain that produces a much lower level of FprA1$_{Cg}$ (OM406). This result further showed that FprA1$_{Cg}$ is important for methionine production at a step in addition to, or instead of, sulfate reduction. Thus there is yet further support for the hypothesis that FprA1$_{Cg}$ functions in the reactivation of MetH$_{Cg}$.

Experiment 9

Ferredoxin may Function in Reactivation of MetH in *C. glutamicum*

Examination of a region of the *Brevibacterium linens* genome for genes that encode enzymes involved in sulfate reduction led to the finding of an operon (SEQ ID No.: 44) that contained genes similar to those of the sulfate reduction operon of *C. glutamicum* (Ruckert et al., vide supra).

However, the details of the structure of the *B. linens* operon are different from those of the related *C. glutamicum* sulfate reduction operon. In particular, the *B. linens* sulfate reduction operon is unidirectional, and the *B. linens* fprA1$_{B1}$ gene (FprA1$_{B1}$ is a close homolog of FprA1$_{Cg}$) is transcribed together with the other sulfate reduction genes. In addition, a gene annotated as "ferredoxin" is present in this *B. linens* sulfate reduction operon just upstream from the fprA1$_{B1}$ gene (Ruckert et al., vide supra).

In the *C. glutamicum* genome, the closest homologs to ferredoxin from the *B. linens* sulfate reduction operon are two genes annotated as encoding "ferredoxin 3". These two genes have been named herein as fdxC and fdxD. In the *C. glutamicum* genome, neither fdxC$_{Cg}$ nor fdxD$_{Cg}$ are located in or near the sulfate reduction operon or near any other gene known to be involved with methionine biosynthesis.

Nonetheless, it was hypothesized that some microorganisms, including but not limited to *C. glutamicum* may use FdxC and/or FdxD or close homologs thereof in the reactivation of MetH.

A plasmid named pOM327 (SEQ ID No.: 45) was constructed that replicates in *E. coli* using the pACYC177 origin of replication and contains an ampicillin resistance gene, an expression cassette that expresses, under non-inducing conditions, a non-lethal level of FprA1$_{Cg}$ from a tetracycline regulated promoter that is called Ptet, and the $P_{497}$ metH$_{Cg}$ cassette subcloned from plasmid pH170. Plasmid pOM327 also contains a copy of a gene named tetR that encodes a repressor of the Ptet promoter, but which allows a low level leaky expression from Ptet in the absence of inducer.

Then the fdxC$_{Cg}$ gene was cloned by complementation in *E. coli* using a *C. glutamicum* genomic DNA plasmid library. The plasmid library consisted of nominally 8 kilobase (kb) inserts of *C. glutamicum* ATCC 13032 genomic DNA fragments, from a partial (incomplete) Sau 3A1 digest, ligated into the BamHI site of pCLIK, which is a plasmid vector that replicates in both *E. coli* and *C. glutamicum*. About 100 ng of library DNA was transformed into RY714B/pOM327, and methionine prototrophs were selected for on methione free medium. Two distinct clones from the library were isolated from the selection, and both contained the fdxC$_{Cg}$ gene. A fragment of about 1744 bases, that contains the fdxC$_{Cg}$ gene, the dap$C_{Cg}$ gene, and some flanking DNA, was subcloned into the Sma I site of either plasmid pH170 (SEQ ID No.: 34), which is a replicating plasmid that contains a $P_{497}$ met$H_{Cg}$ cassette, or plasmid pH382 (SEQ ID No.: 46), which is a replicating plasmid that contains, in addition to a $P_{497}$ met$H_{Cg}$ cassette, cassettes that express met$Y_{Cg}$ and met$X_{Cg}$. An isolate that was derived from pH382 and contains one copy of the fdx$C_{Cg}$ subclone in the "forward" orientation (transcribed in the same direction as $P_{497}$ met$H_{Cg}$) was named pOM160 (SEQ ID No.: 47). An isolate that was derived from pH170 and contains two copies of the fdx$C_{Cg}$ subclone, both in the "forward" orientation (transcribed in the same direction as $P_{497}$ met$H_{Cg}$) was named pOM161 (SEQ ID No.: 48).

When the plasmids pOM327 and pOM160 or pOM327 and pOM161 were transformed into naive RY714B, the transformants were methionine prototrophs. The prototrophy was cyanocobalmin dependent. When pOM160 or poM161 was transformed into RY714B without pOM327, and the transformation mix was plated directly on methionine free plates, no transformants grew.

Therefore, the prototrophy from pOM160 and pOM161 were conferred by fprA$1_{Cg}$ and the fdx$C_{Cg}$ gene, the dap$C_{Cg}$ gene, or the combination of the two latter.

Since the dapC gene has been established to encode a well known enzyme involved in lysine biosynthesis, namely N-succinyl diaminopimelate amino transferase, it is highly unlikely that Dap$C_{Cg}$ participates directly in methionine synthesis or MetH reactivation. Nonetheless, it can be shown that dapC is not necessary for Met$H_{Cg}$ activation by deleting the majority of the dapC gene(s) from pOM160 and pOM161. This is accomplished by noting that the dap$C_{Cg}$ gene contains two Sal I sites, performing a partial Sal I digest of each plasmid, isolating fragments of the appropriate size (12,702 bp from pOM160 and 9811 bp from pOM161), ligating, after cutting with Mfe I, which cuts once in the dapC gene between the two Sal I sites, transforming RY714B, and screening for plasmids that have deleted the 810 bp Sal I fragment that is internal to dapC. The resulting plasmids are then tested for complementation of methionine auxotrophy in RY714B.

Experiment 10

Generalization of the Invention to Other MetH Reactivation Systems

The method and materials disclosed in the above experiments can be used to identify, test, or confirm components of cob(I)alamin-dependent MetH reactivation systems from organisms other than *C. glutamicum* or *E. coli*, such as species from the genera *Corynebacterium, Escherichia, Brevibacterium, Salmonella, Klebsiella*, etc. The met$H_{Cg}$ coding sequence in pOM327 can be replaced by a DNA or cDNA sequence encoding a close homolog of MetH, using PCR, mutagenic PCR primers, and techniques well known in the art, to give a plasmid named pHYP1. The resulting plasmid pHYP1 is then tested for ability to confer methionine prototrophy after transformation into RY714B. If pHYP1 is unable to confer prototrophy, then one or more components of the MetH reactivation system may be missing. An appropriate genomic DNA library (or cDNA or DNA expression library) is constructed in an appropriate vector (for example pCLIK) that is compatible with the pOM327 derivative pHYP1 using a pool of DNA fragments or cDNA fragments from the organism (or a close relative thereof) from which the metH gene was isolated. If appropriate or necessary, the library vector's cloning site will be adjacent to, and just downstream from, a promoter (for example $P_{497}$) that functions at a moderate level in *E. coli*. The library is then transformed into RY714B/pHYP1, and methionine prototrophs are selected directly on MF medium, or indirectly after pooling transformants from rich plates containing the appropriate antibiotic and then selecting or screening on MF medium. Library isolates that confer prototrophy will contain a gene or genes that encode the desired reactivation factor. The gene that encodes the reactivation protein can be identified by subcloning experiments.

Similarly, the coding sequence of the fprA$1_{Cg}$ gene of pOM327 or pHYP1 can be replaced by a DNA or cDNA sequence containing the coding sequence for a gene suspected of encoding a component of a MetH reactivation system, for example, a close homolog of FprA$1_{Cg}$ or of Fld$R_{Ec}$, to give pHYP2, and RY714B/pHYP2 can be used to select or screen for genes that encode a reactivation factor from a library.

After a reactivation factor that functions together with a particular MetH has been identified or confirmed as described above, then one or more components of the reactivation system can be overexpressed in the homologous host organism or reconstituted in a heterologous host organism and tested for improved methionine production. Using such an approach one may for example overexpress fdxC and fprA1 in *C. glutamicum.*

Experiment 11

Close Homologs of FdxC

The amino acid sequence of Fdx$C_{cg}$ (SEQ ID No.: 1) was used as the query in a BLASTp search of the non-redundant (nr) amino acid GenBank sequence database (all translated coding sequences) of NCBI on Jan. 18, 2006. The web page address is hypertext transfer protocol://world wide web.ncbi.nlm.nihDOTgov/BLAST/, wherein "hypertext transfer protocol"=http, "world wide web"=www, and "DOT"=".".

The default parameters supplied by the web site were used. As expected, the first entry in the output result table is the query itself, Fdx$C_{Cg}$. The next few entries are close homologs from *Corynebacterium* species closely related to *C. glutamicum*. Many other close homologs of Fdx$C_{Cg}$ can be found in this table. The fifth entry in the table is the amino acid sequence of a second gene annotated as "ferredoxin 3" from the NCBI GenBank annotated genome of *C. glutamicum* ATCC 13032. This gene encoding this close homolog has been named fdx$D_{Cg}$, to differentiate it from fdx$C_{Cg}$.

FdxD can be cloned using methods well known in the art. For example, it can be cloned together with upstream and down stream flanking DNA sequences using PCR. Examples of useful primers are RY842 (5'-pGATAGGTCGCAGCGGTGATCTGTT-3') (SEQ ID No.: 49) and RY841 (5'-pAGTGGATCCTCGCACTCTTGGTGGTGATTTGGTCAATGAT-3') (SEQ ID No.: 50), where "5'-p" means a phosphate residue at the 5' end of the synthetic primer. Pfu polymerase (Invitrogen, Carlsbad, Calif., U.S.) was used as recommended by the manufacturer for with genomic DNA from *C. glutamicum* ATCC 13032 as the template. Primer annealing was done at 54° C. for the first four cycles and then at 58° C. for an additional 25 cycles, and elongation was done at 72° C. for one minute. The resulting PCR product was purified by agarose gel electrophoresis and cloned into the Sma I site of plasmid pH382 or pH170 to give plasmids pOM352 and pOM350 (SEQ ID NO.: 51 and 60), respectively. Testing for reactivation function can be done as described above.

Alternatively, the coding region of fdxD without any upstream flanking DNA sequence and some or no downstream flanking sequence can be cloned by PCR for installation into an expression vector such as pOM324 (SEQ ID No.: 40), substituting the fdxD$_{Cg}$ coding region for the fldA$_{Ec}$ coding region. Examples of useful primers for this approach are RY843 (5'-pTTATTCTAGAAGGAGGAGAAAACAT-GACCTACACAATCGCCCAGCCCT) (SEQ ID No.: 52) and RY847 (5'-pCCATCACTATGAGGATCCAGGAA-CAACTATTGGTACGAG) (SEQ ID No.: 53).

As above, Pfu polymerase was used as recommended by the manufacturer for a total of 29 cycles with genomic DNA from *C. glutamicum* ATCC 13032 as the template. Primer annealing was done at 54° C. for the first four cycles, and elongation was done at 72° C. for one minute, and then the annealing temperature was raised to 58° C. for the next 25 cycles, while leaving the other cycling parameters unchanged. The resulting desired PCR DNA product was purified from other reactants using Qiagen spin columns designed for the purpose. Next, the PCR product was cleaved with Xba I and Bam HI to produce sticky ends and ligated into the Xba I to Bam H1 backbone of either pOM322 or pOM324 to give plasmids pOM355 (SEQ ID No.: 54) and pOM356 (SEQ ID No.: 55), respectively. The resulting plasmids can then used to test for reactivation function as described above. The ability of FdxD or FdxA to function with reductases other than FprA1 (such as FprA2, FprA3, FldR1, etc.) to reactivate MetH$_{Cg}$ can also be tested as described above for FdxC and FprA1.

The following examples describe the preparation of some useful starting organisms Experiment 12

Decreasing MetQ Expression

In order to decrease the import of methionine in OM403-8, the promoter and 5' portion of the metQ gene were deleted. The metQ gene encodes a subunit of a methionine import complex that is required for the complex to function. This was accomplished using the standard Campbelling in and Campbelling out technique with plasmid pH449 (SEQ ID NO: 56). OM403-8 and OM456-2 were assayed for methionine production in shake flask assays. The results (Table 16) show that OM456-2 produced more methionine than OM403-8. Cultures were grown for 48 hours in standard molasses medium.

TABLE 16

Shake flask assays of OM456-2

| Strain | vector | [Met] (g/l) | [Lys] (g/l) | [Gly/Hse] (g/l) | [OAcHS] (g/l) | [Ile] (g/l) |
|---|---|---|---|---|---|---|
| OM403-8 | none | 4.0 | 0.8 | 2.2 | 0.4 | 1.9 |
|  |  | 3.9 | 0.6 | 2.2 | 0.4 | 1.9 |
| OM456-2 | none | 4.2 | 0.4 | 2.3 | 0.4 | 2.3 |
|  |  | 4.3 | 0.5 | 2.4 | 0.4 | 2.3 |

Experiment 13

Construction of OM469

A strain referred to as OM469 was constructed which included both deletion of metQ and overexpression of metF by replacing the metF promoter with the phage $\lambda P_R$ promoter in OM456-2. This was accomplished using the standard Campbelling in and Campbelling out technique with plasmid pOM427 (SEQ ID No.: 57). Four isolates of OM469 were assayed for methionine production in shake flask culture assays where they all produced more methionine than OM456-2, as shown in Table 17. Cultures were grown for 48 hours in standard molasses medium containing 2 mM threonine.

TABLE 17

Shake flask assays of OM469, a derivative of OM456-2 containing the phage lambda P$_R$ promoter in place of the metF promoter.

| Strain |  | metF promoter | MetQ | [Met] (g/l) | [Lys] (g/l) | [Gly/Hse] (g/l) | [OAcHS] (g/l) | [Ile] (g/l) |
|---|---|---|---|---|---|---|---|---|
| OM428-2 |  | $\lambda P_R$ | Native | 4.5 | 0.5 | 2.6 | 0.4 | 2.6 |
|  |  |  |  | 4.6 | 0.4 | 2.6 | 0.3 | 2.5 |
| OM456-2 |  | native | ΔmetQ | 4.2 | 0.4 | 2.4 | 0.3 | 2.5 |
|  |  |  |  | 4.2 | 0.5 | 2.4 | 0.3 | 2.5 |
| OM469 | -1 | $\lambda P_R$ | ΔmetQ | 5.0 | 0.5 | 2.7 | 0.4 | 3.1 |
|  | -2 |  |  | 4.9 | 0.5 | 2.7 | 0.4 | 2.8 |
|  | -3 |  |  | 4.8 | 0.4 | 2.6 | 0.4 | 2.7 |
|  | -4 |  |  | 4.7 | 0.5 | 2.6 | 0.4 | 2.8 |

Experiment 14

Construction of M 2543

The strain OM469-2 was transformed by electroporation with the plasmid pCLIK5A PSOD TKT as depicted in SEQ ID No.: 58. This was accomplished using the standard Campbelling in and Campbelling out technique.

Isolates of OM 469 PSOD TKT which are labelled M2543 were assayed for methionine production in shake flask culture assays, where they produced more methionine than OM469-2. The results of strain M2543 are shown in Table 18.

TABLE 18

| Shake flask assays of OM469 and M2543 | | | | | | | | |
|---|---|---|---|---|---|---|---|---|
| Strain | plas-mid | met genes on plasmid | [Met] (mm | [Lys] (mm) | [Gly] (mm) | [Hse] (mm) | [AHs] (mm) | [Ile] (mm) |
| OM469-2 | | None | 14 | 3.4 | 16 | 1.7 | 0.3 | 11.8 |
| M2543# | | None | 20.4 | 1.9 | 21.8 | 0.8 | <0.1 | 12.4 |

Experiment 15

Construction of GK1259

In order to decrease production of serine deaminase (Sda), a portion of the sda gene was deleted. This was accomplished using the standard Campbelling in and Campbelling out technique with plasmid pH626 int SacB delta sdaA (SEQ ID No. 59). To this end, strain M2543 was transformed by electroporation with the plasmid pH626 int SacB delta sdaA. The resulting strain was named GK1259.

Using the components described in this invention (namely genes that encode MetH, a flavodoxin or ferredoxin, and a flavodoxin or ferredoxin reductase) a package designed to activate or reactivate a MetH enzyme can be assembled in any methionine production strain containing a MetH enzyme, for example in the methionine production strains described above, such as OM469-2, GK1259, or M2543. For example, any of these example strains, which overproduce $MetH_{Cg}$ and FprA1, can be transformed with pOM160 or pOM161, which overproduces FdxC. Alternatively, for example, any of these example strains can be sequentially transformed with pOM232, pOM324, and pOM154, selecting appropriate "Campbell outs" at each step to give a strain that uses the $MetH_{Ec}$ enzyme and reactivation system. Of course these examples are not intended to be limiting. Anyone skilled in the art can learn from the examples given here to identify and clone genes for other MetH enzymes and the factors that reactivate them.

What is claimed is:

1. An isolated microorganism of the genus *Corynebacterium:* wherein said microorganism is obtained by genetic modification from a starting microorganism such that said microorganism has an increased amount or activity of a cob(I)alamin-dependent methionine synthase I (MetH) reactivation system compared to said starting microorganism, wherein said cob(I)alamin dependent MetH reactivation system comprises at least:

(a) one electron transport protein selected from the group comprising fdxC having SEQ ID NO:2 and functional homologues thereof providing the same enzymatic activity and having at least 95% sequence identity to SEQ ID NO:2, fdxD having SEQ ID NO:4 and functional homologues thereof providing the same enzymatic activity and having at least 95% sequence identity to SEQ ID NO:4, fdxA having SEQ ID NO:6 and functional homologues thereof providing the same enzymatic activity and having at least 95% sequence identity to SEQ ID NO:6; and (b) one electron transfer protein-reductase selected from the group comprising fprA1 having SEQ ID NO:12 and functional homologues thereof providing the same enzymatic activity and having at least 95% sequence identity to SEQ ID NO:12, fprA2 having SEQ ID NO:14 and functional homologues thereof providing the same enzymatic activity and having at least 95% sequence identity to SEQ ID NO:14, fprA3 having SEQ ID NO:16 and functional homologues thereof providing the same enzymatic activity and having at least 95% sequence identity to SEQ ID NO:16, fldR1 having SEQ ID NO:18 and functional homologues thereof providing the same enzymatic activity and having at least 95% sequence identity to SEQ ID NO:18;

and wherein the amount, activity, or both, of at least said electron transfer protein or of at least said electron transfer protein-reductase is increased compared to said starting microorganism.

2. The microorganism according to claim 1, wherein said at least one electron transport protein, said at least one electron transfer protein-reductase, or both are endogenously present in said microorganism, or obtained from another organism.

3. The microorganism according to claim 1, wherein said microorganism is selected from the group comprising the species *Corynebacterium glutamicum, Corynebacterium acetoglutamicum, Corynebacterium acetoacidophilum, Corynebacterium thermoaminogenes, Corynebacterium jeiekium, Corynebacterium melassecola* and *Corynebacterium effiziens.*

4. The microorganism according to claim 1, wherein the amount or activity of at least fdxC having SEQ ID NO:2 and functional homologues thereof providing the same enzymatic activity and having at least 95% sequence identity to SEQ ID NO:2 and of at least fprA1 having SEQ ID NO:12 and functional homologues thereof providing the same enzymatic activity and having at least 95% sequence identity to SEQ ID NO:12 is/are increased in *C. glutamicum* compared to said starting microorganism.

5. A method of producing methionine in a microorganism which comprises cultivating the microorganism according to claim 1 under conditions whereby the microorganism produces the methionine.

* * * * *

SEQUENCE LISTING

```
<160> NUMBER OF SEQ ID NOS: 60

<210> SEQ ID NO 1
<211> LENGTH: 318
<212> TYPE: DNA
<213> ORGANISM: Corynebacterium glutamicum

<400> SEQUENCE: 1

atgacataca caatcgcaca gccctgcgtt gacgtcttgg atcgtgcctg cgttgaagaa      60

tgcccagtag attgcatcta cgaaggtaag cgcatgctgt acatccaccc ggatgagtgc     120

gttgactgtg gtgcatgtga gcctgcttgc ccagttgagg caatcttcta cgaggacgat     180

gtcccagacg aatggcttga ctacaacgat gccaacgctg cattcttcga tgatctgggc     240

tccccaggtg gtgcggctaa gcttggacca caagattttg atcacccaat gatcgctgcg     300

ctgccgcctc aggcataa                                                   318


<210> SEQ ID NO 2
<211> LENGTH: 105
<212> TYPE: PRT
<213> ORGANISM: Corynebacterium glutamicum

<400> SEQUENCE: 2

Met Thr Tyr Thr Ile Ala Gln Pro Cys Val Asp Val Leu Asp Arg Ala
1               5                   10                  15

Cys Val Glu Glu Cys Pro Val Asp Cys Ile Tyr Glu Gly Lys Arg Met
            20                  25                  30

Leu Tyr Ile His Pro Asp Glu Cys Val Asp Cys Gly Ala Cys Glu Pro
        35                  40                  45

Ala Cys Pro Val Glu Ala Ile Phe Tyr Glu Asp Asp Val Pro Asp Glu
    50                  55                  60

Trp Leu Asp Tyr Asn Asp Ala Asn Ala Ala Phe Phe Asp Asp Leu Gly
65                  70                  75                  80

Ser Pro Gly Gly Ala Ala Lys Leu Gly Pro Gln Asp Phe Asp His Pro
                85                  90                  95

Met Ile Ala Ala Leu Pro Pro Gln Ala
            100                 105
```

<210> SEQ ID NO 3
<211> LENGTH: 324
<212> TYPE: DNA
<213> ORGANISM: Corynebacterium glutamicum

<400> SEQUENCE: 3
atgacctaca caatcgccca gccctgcgtt gatgtcctgg atcgagcctg cgtcgaggaa 60
tgtcccgtgg actgcatcta cgagggcaaa cggatgctct acatccaccc cgatgagtgc 120
gtcgactgcg gtgcctgcga gcccgtctgc ccggttgaag ccatcttcta cgaagatgat 180
gttccccacg aatggtggga ctacaccggc gctaacgccg cctttttcga cgacctcggt 240
tcgccaggcg gtgccgccag cctgggtccg caggacttcg acgcccagct cgtcgcggtg 300
ctgccgccac agaaccagaa ctag 324

<210> SEQ ID NO 4
<211> LENGTH: 107
<212> TYPE: PRT
<213> ORGANISM: Corynebacterium glutamicum

<400> SEQUENCE: 4

Met Thr Tyr Thr Ile Ala Gln Pro Cys Val Asp Val Leu Asp Arg Ala
1 5 10 15

Cys Val Glu Glu Cys Pro Val Asp Cys Ile Tyr Glu Gly Lys Arg Met
20 25 30

Leu Tyr Ile His Pro Asp Glu Cys Val Asp Cys Gly Ala Cys Glu Pro
35 40 45

Val Cys Pro Val Glu Ala Ile Phe Tyr Glu Asp Asp Val Pro His Glu
50 55 60

Trp Trp Asp Tyr Thr Gly Ala Asn Ala Ala Phe Phe Asp Asp Leu Gly
65 70 75 80

Ser Pro Gly Gly Ala Ala Ser Leu Gly Pro Gln Asp Phe Asp Ala Gln
85 90 95

Leu Val Ala Val Leu Pro Pro Gln Asn Gln Asn
100 105

<210> SEQ ID NO 5
<211> LENGTH: 321
<212> TYPE: DNA
<213> ORGANISM: Corynebacterium glutamicum

<400> SEQUENCE: 5
atgtctacta ttcatttcat tgatcatgct ggcaaaaccc gcaccatcga ggcgactgtt 60
ggtgattcag taatggagac cgcagtccga aacggagtgc ctggaattgt tgctgaatgc 120
ggcggttcct tatcgtgtgc aacctgccat gtgtttgttg accctgcaca gtatgatgcg 180
cttcccccaa tggaggagat ggaagatgaa atgctgtggg gtgctgccgt ggaccgtgag 240
gattgctccc gtttgtcttg ccaaatcaag gtcaccgaag gcatggatct ttcgttgacc 300
acgccagaaa cgcaagtgtg a 321

<210> SEQ ID NO 6
<211> LENGTH: 106
<212> TYPE: PRT
<213> ORGANISM: Corynebacterium glutamicum

<400> SEQUENCE: 6

Met Ser Thr Ile His Phe Ile Asp His Ala Gly Lys Thr Arg Thr Ile
1 5 10 15

Glu Ala Thr Val Gly Asp Ser Val Met Glu Thr Ala Val Arg Asn Gly

-continued

```
            20                  25                  30

Val Pro Gly Ile Val Ala Glu Cys Gly Gly Ser Leu Ser Cys Ala Thr
        35                  40                  45

Cys His Val Phe Val Asp Pro Ala Gln Tyr Asp Ala Leu Pro Pro Met
    50                  55                  60

Glu Glu Met Glu Asp Glu Met Leu Trp Gly Ala Ala Val Asp Arg Glu
65                  70                  75                  80

Asp Cys Ser Arg Leu Ser Cys Gln Ile Lys Val Thr Glu Gly Met Asp
                85                  90                  95

Leu Ser Leu Thr Thr Pro Glu Thr Gln Val
            100                 105


<210> SEQ ID NO 7
<211> LENGTH: 531
<212> TYPE: DNA
<213> ORGANISM: Escherichia coli

<400> SEQUENCE: 7

atggctatca ctggcatctt tttcggcagc gacaccggta ataccgaaaa tatcgcaaaa     60

atgattcaaa aacagcttgg taaagacgtt gccgatgtcc atgacattgc aaaaagcagc    120

aaagaagatc tggaagctta tgacattctg ctgctgggca tcccaacctg gtattacggc    180

gaagcgcagt gtgactggga tgacttcttc ccgactctcg aagagattga tttcaacggc    240

aaactggttg cgctgtttgg ttgtggtgac caggaagatt acgccgaata tttctgcgac    300

gcattgggca ccatccgcga catcattgaa ccgcgcggtg caaccatcgt tggtcactgg    360

ccaactgcgg gctatcattt cgaagcatca aaaggtctgg cagatgacga ccactttgtc    420

ggtctggcta tcgacgaaga ccgtcagccg gaactgaccg ctgaacgtgt agaaaaatgg    480

gttaaacaga tttctgaaga gttgcatctc gacgaaattc tcaatgcctg a             531


<210> SEQ ID NO 8
<211> LENGTH: 176
<212> TYPE: PRT
<213> ORGANISM: Escherichia coli

<400> SEQUENCE: 8

Met Ala Ile Thr Gly Ile Phe Phe Gly Ser Asp Thr Gly Asn Thr Glu
1               5                   10                  15

Asn Ile Ala Lys Met Ile Gln Lys Gln Leu Gly Lys Asp Val Ala Asp
            20                  25                  30

Val His Asp Ile Ala Lys Ser Ser Lys Glu Asp Leu Glu Ala Tyr Asp
        35                  40                  45

Ile Leu Leu Leu Gly Ile Pro Thr Trp Tyr Tyr Gly Glu Ala Gln Cys
    50                  55                  60

Asp Trp Asp Asp Phe Phe Pro Thr Leu Glu Glu Ile Asp Phe Asn Gly
65                  70                  75                  80

Lys Leu Val Ala Leu Phe Gly Cys Gly Asp Gln Glu Asp Tyr Ala Glu
                85                  90                  95

Tyr Phe Cys Asp Ala Leu Gly Thr Ile Arg Asp Ile Ile Glu Pro Arg
            100                 105                 110

Gly Ala Thr Ile Val Gly His Trp Pro Thr Ala Gly Tyr His Phe Glu
        115                 120                 125

Ala Ser Lys Gly Leu Ala Asp Asp Asp His Phe Val Gly Leu Ala Ile
    130                 135                 140

Asp Glu Asp Arg Gln Pro Glu Leu Thr Ala Glu Arg Val Glu Lys Trp
145                 150                 155                 160
```

-continued

Val Lys Gln Ile Ser Glu Glu Leu His Leu Asp Glu Ile Leu Asn Ala
165 170 175

<210> SEQ ID NO 9
<211> LENGTH: 522
<212> TYPE: DNA
<213> ORGANISM: Escherichia coli

<400> SEQUENCE: 9
atgaatatgg gtcttttta cggttccagc acctgttaca ccgaaatggc ggcagaaaaa 60
atccgcgata ttatcggccc agaactggtg accttacata acctcaagga cgactccccg 120
aaattaatgg agcagtacga tgtgctcatt ctgggtatcc cgacctggga ttttggtgaa 180
atccaggaag actgggaagc cgtctgggat cagctcgacg acctgaacct tgaaggtaaa 240
attgttgcgc tgtatgggct tggcgatcaa ctgggatacg gcgagtggtt cctcgatgcg 300
ctcggtatgc tgcatgacaa actctcgacc aaaggcgtga agttcgtcgg ctactggcca 360
acggaaggat atgaatttac cagcccgaaa ccggtgattg ctgacgggca actgttcgtg 420
ggtctggcgc tggatgaaac taaccagtat gaccttagcg acgagcgtat tcagagctgg 480
tgcgagcaaa tcctcaacga aatggcagag cattacgcct ga 522

<210> SEQ ID NO 10
<211> LENGTH: 173
<212> TYPE: PRT
<213> ORGANISM: Escherichia coli

<400> SEQUENCE: 10

Met Asn Met Gly Leu Phe Tyr Gly Ser Ser Thr Cys Tyr Thr Glu Met
1 5 10 15

Ala Ala Glu Lys Ile Arg Asp Ile Ile Gly Pro Glu Leu Val Thr Leu
20 25 30

His Asn Leu Lys Asp Asp Ser Pro Lys Leu Met Glu Gln Tyr Asp Val
35 40 45

Leu Ile Leu Gly Ile Pro Thr Trp Asp Phe Gly Glu Ile Gln Glu Asp
50 55 60

Trp Glu Ala Val Trp Asp Gln Leu Asp Asp Leu Asn Leu Glu Gly Lys
65 70 75 80

Ile Val Ala Leu Tyr Gly Leu Gly Asp Gln Leu Gly Tyr Gly Glu Trp
85 90 95

Phe Leu Asp Ala Leu Gly Met Leu His Asp Lys Leu Ser Thr Lys Gly
100 105 110

Val Lys Phe Val Gly Tyr Trp Pro Thr Glu Gly Tyr Glu Phe Thr Ser
115 120 125

Pro Lys Pro Val Ile Ala Asp Gly Gln Leu Phe Val Gly Leu Ala Leu
130 135 140

Asp Glu Thr Asn Gln Tyr Asp Leu Ser Asp Glu Arg Ile Gln Ser Trp
145 150 155 160

Cys Glu Gln Ile Leu Asn Glu Met Ala Glu His Tyr Ala
165 170

<210> SEQ ID NO 11
<211> LENGTH: 1374
<212> TYPE: DNA
<213> ORGANISM: Corynebacterium glutamicum

<400> SEQUENCE: 11
atgacaactc ccctgcgcgt agccgtcatc ggagctggcc ctgctggcat ttacgcatcc 60

```
gacctcctca tccgcaatga agagcgcgaa gtgttcgttg accttttcga gcaaatgcct    120

gcaccgttcg gactcatccg ttacggcgtt gctccagacc acccacgcat caagggcatc    180

gttaagtccc tgcacaacgt gttggacaag ccacgcctgc gcctgctcgg taacattgaa    240

atcggcaaag acatcaccgt cgaagaactc cgcgactact acgatgcagt cgtgttctcc    300

accggcgcag ttgcagaccg cgacctcaac atccccggaa ttgaagcaga aggctccttc    360

ggtgccggcg agttcgttgg cttctacgac ggcaacccac gcttcgagcg ctcctgggat    420

ctgtctgcac agtccgtcgc tgttatcggc gttggtaacg tcggcctcga cgtagcccgc    480

atcctggcta agacaggcga cgagctcaaa gtcaccgaaa tttccgacaa cgtctacgac    540

tccctcaaag aaaacaaggc cactgaagtg cacgttttcg gacgtcgtgg cccagcacag    600

gtcaagttca ccccacagga actcaaagaa ctcgaccact cccccaccat caacgtggtt    660

gttgatccag aagacatcga ctacgacggc gcctctgaag aagcccgccg cgcatccaag    720

tcccaggacc tggtctgcca gatcctggaa cagtacgcaa tccgcgagcc aaaggacgct    780

ccgcacaccc tgcagatcca cctctttgaa aacccagttg aggttcttca aaaggacggc    840

aaggttgttg gcctgcgcac cgaacgcacc tcacttgatg gcaacggcgg cgtaaacgga    900

accggcgaat tcaaggactg gccagtccag gctgtctacc gcgcagtcgg ctacaagtcc    960

gaccccatcg acggcgtccc attcgatgag aacaagcacg tcatccctaa tgacggcgga   1020

catgtcctca ccgctccagg cgcagaacca gtaccaggcc tctatgcaac cggctggatc   1080

aagcgtggac caatcggtct aatcggcaac accaagtccg acgccaagga aaccaccgac   1140

atcctcatca aggatgccgt cgccggtgta cttgaagctc caaagcacca gggcgaagaa   1200

gccatcatcg agcttctcga ttcccgcaac atcccattca ccacctggga aggctggtac   1260

aaactcgacg cagcagagcg cgcactcggt gaagccgaag gccgcgagcg caagaagatt   1320

gttgattggg aagaaatggt ccgccaggcc cgcgaagctc cagcaattgt ctaa         1374
```

<210> SEQ ID NO 12
<211> LENGTH: 457
<212> TYPE: PRT
<213> ORGANISM: Corynebacterium glutamicum

<400> SEQUENCE: 12

```
Met Thr Thr Pro Leu Arg Val Ala Val Ile Gly Ala Gly Pro Ala Gly
1               5                   10                  15

Ile Tyr Ala Ser Asp Leu Leu Ile Arg Asn Glu Glu Arg Glu Val Phe
            20                  25                  30

Val Asp Leu Phe Glu Gln Met Pro Ala Pro Phe Gly Leu Ile Arg Tyr
        35                  40                  45

Gly Val Ala Pro Asp His Pro Arg Ile Lys Gly Ile Val Lys Ser Leu
    50                  55                  60

His Asn Val Leu Asp Lys Pro Arg Leu Arg Leu Leu Gly Asn Ile Glu
65                  70                  75                  80

Ile Gly Lys Asp Ile Thr Val Glu Glu Leu Arg Asp Tyr Tyr Asp Ala
                85                  90                  95

Val Val Phe Ser Thr Gly Ala Val Ala Asp Arg Asp Leu Asn Ile Pro
            100                 105                 110

Gly Ile Glu Ala Glu Gly Ser Phe Gly Ala Gly Glu Phe Val Gly Phe
        115                 120                 125

Tyr Asp Gly Asn Pro Arg Phe Glu Arg Ser Trp Asp Leu Ser Ala Gln
    130                 135                 140
```

```
Ser Val Ala Val Ile Gly Val Gly Asn Val Gly Leu Asp Val Ala Arg
145                 150                 155                 160

Ile Leu Ala Lys Thr Gly Asp Glu Leu Lys Val Thr Glu Ile Ser Asp
                165                 170                 175

Asn Val Tyr Asp Ser Leu Lys Glu Asn Lys Ala Thr Glu Val His Val
            180                 185                 190

Phe Gly Arg Arg Gly Pro Ala Gln Val Lys Phe Thr Pro Gln Glu Leu
        195                 200                 205

Lys Glu Leu Asp His Ser Pro Thr Ile Asn Val Val Val Asp Pro Glu
    210                 215                 220

Asp Ile Asp Tyr Asp Gly Ala Ser Glu Glu Ala Arg Arg Ala Ser Lys
225                 230                 235                 240

Ser Gln Asp Leu Val Cys Gln Ile Leu Glu Gln Tyr Ala Ile Arg Glu
                245                 250                 255

Pro Lys Asp Ala Pro His Thr Leu Gln Ile His Leu Phe Glu Asn Pro
            260                 265                 270

Val Glu Val Leu Gln Lys Asp Gly Lys Val Val Gly Leu Arg Thr Glu
        275                 280                 285

Arg Thr Ser Leu Asp Gly Asn Gly Gly Val Asn Gly Thr Gly Glu Phe
    290                 295                 300

Lys Asp Trp Pro Val Gln Ala Val Tyr Arg Ala Val Gly Tyr Lys Ser
305                 310                 315                 320

Asp Pro Ile Asp Gly Val Pro Phe Asp Glu Asn Lys His Val Ile Pro
                325                 330                 335

Asn Asp Gly Gly His Val Leu Thr Ala Pro Gly Ala Glu Pro Val Pro
            340                 345                 350

Gly Leu Tyr Ala Thr Gly Trp Ile Lys Arg Gly Pro Ile Gly Leu Ile
        355                 360                 365

Gly Asn Thr Lys Ser Asp Ala Lys Glu Thr Thr Asp Ile Leu Ile Lys
    370                 375                 380

Asp Ala Val Ala Gly Val Leu Glu Ala Pro Lys His Gln Gly Glu Glu
385                 390                 395                 400

Ala Ile Ile Glu Leu Leu Asp Ser Arg Asn Ile Pro Phe Thr Thr Trp
                405                 410                 415

Glu Gly Trp Tyr Lys Leu Asp Ala Ala Glu Arg Ala Leu Gly Glu Ala
            420                 425                 430

Glu Gly Arg Glu Arg Lys Lys Ile Val Asp Trp Glu Glu Met Val Arg
        435                 440                 445

Gln Ala Arg Glu Ala Pro Ala Ile Val
    450                 455


<210> SEQ ID NO 13
<211> LENGTH: 1368
<212> TYPE: DNA
<213> ORGANISM: Corynebacterium glutamicum

<400> SEQUENCE: 13

atgtctcgcc ctttgcgtgt tgccgttgtc ggtgcaggtc cagcaggaat ctacgcgtct      60

gatttgttga tgaaatccga cacggacgtg cagattgatc tttttgaacg tatgccagcg     120

cctttcggtt tgatccgtta tggtgttgcg cctgatcacc ctcgcatcaa gggcatcgtg     180

aagtccctgc acaatgtgat ggacaaggag cagctgcgtt tcttgggcaa cattgaggtc     240

ggcaaggaca tcactgttga ggagttgcgt gagttttatg acgcgatcgt gttctccact     300

ggcgctactg gcgaccagga tcttcgggtt ccaggttctg atctggaagg ttcgtggggc     360
```

-continued gctggcgagt tcgttggttt ctatgatggc aacccgaact ttgaacgcaa ctgggatctt 420
tctgctgaga aggtagcggt tgttggtgtc ggtaacgtgg cgttggacgt tgctcgtatt 480
ttggcgaaga ctggcgatga gctgctagtt actgaaatcc ctgacaatgt ctatgagagc 540
ttggctaaga atcaggctaa ggaagtgcac gtttttggtc gtcgtggacc tgctcaggcg 600
aagttcactc cgttggagct gaaggaactt gaccattccg acaccatcga ggtgatcgtg 660
aaccctgagg acattgatta cgatgcagct tcggagcagg ctcgtcgtga ttccaagtct 720
caggacctcg tgtgccagac tttggaaagc tacgcgatgc gcgatcctaa gggcgctcct 780
cacaagctgt tcattcactt ctttgagtcc ccagtggaga tcctcggtga ggacggcaag 840
gttgttggcc tcaagactga gcgtactcag ctggacggca acggtggcgt gactggcacc 900
ggcgagttca agacctggga tatgcagtca gtttaccgcg cggtaggtta ccgttctgat 960
gcgatcgagg gtgttccttt tgacgatgag cgcgcggttg tccccaacga cggcggccac 1020
atcatcgatc ctgaggtcgg ctcccccatc actggcctgt acgccactgg ctggatcaag 1080
cgtggcccaa ttggactgat cggcaacacc aagtccgacg ccaaggaaac cactgagatg 1140
ctgcttgctg atcacgctgc tggttctttg cctgcgcctg caaagcctga gttggagtcc 1200
atcattgagt tcctcgatga gcgcaaggtt gcgttcacca catgggatgg ctggcacctg 1260
ctggatgctg cggagcgcgc gctgggtgag cctgagggcc gcgagcgcaa gaagatcgtt 1320
gagtggaatg acatggtgcg ccatgctcgt ccagaatacg acatctaa 1368

<210> SEQ ID NO 14
<211> LENGTH: 455
<212> TYPE: PRT
<213> ORGANISM: Corynebacterium glutamicum

<400> SEQUENCE: 14

Met Ser Arg Pro Leu Arg Val Ala Val Val Gly Ala Gly Pro Ala Gly
1 5 10 15

Ile Tyr Ala Ser Asp Leu Leu Met Lys Ser Asp Thr Asp Val Gln Ile
20 25 30

Asp Leu Phe Glu Arg Met Pro Ala Pro Phe Gly Leu Ile Arg Tyr Gly
35 40 45

Val Ala Pro Asp His Pro Arg Ile Lys Gly Ile Val Lys Ser Leu His
50 55 60

Asn Val Met Asp Lys Glu Gln Leu Arg Phe Leu Gly Asn Ile Glu Val
65 70 75 80

Gly Lys Asp Ile Thr Val Glu Glu Leu Arg Glu Phe Tyr Asp Ala Ile
85 90 95

Val Phe Ser Thr Gly Ala Thr Gly Asp Gln Asp Leu Arg Val Pro Gly
100 105 110

Ser Asp Leu Glu Gly Ser Trp Gly Ala Gly Glu Phe Val Gly Phe Tyr
115 120 125

Asp Gly Asn Pro Asn Phe Glu Arg Asn Trp Asp Leu Ser Ala Glu Lys
130 135 140

Val Ala Val Val Gly Val Gly Asn Val Ala Leu Asp Val Ala Arg Ile
145 150 155 160

Leu Ala Lys Thr Gly Asp Glu Leu Leu Val Thr Glu Ile Pro Asp Asn
165 170 175

Val Tyr Glu Ser Leu Ala Lys Asn Gln Ala Lys Glu Val His Val Phe
180 185 190

Gly Arg Arg Gly Pro Ala Gln Ala Lys Phe Thr Pro Leu Glu Leu Lys
195 200 205

-continued

```
Glu Leu Asp His Ser Asp Thr Ile Glu Val Ile Val Asn Pro Glu Asp
    210                 215                 220

Ile Asp Tyr Asp Ala Ala Ser Glu Gln Ala Arg Arg Asp Ser Lys Ser
225                 230                 235                 240

Gln Asp Leu Val Cys Gln Thr Leu Glu Ser Tyr Ala Met Arg Asp Pro
                245                 250                 255

Lys Gly Ala Pro His Lys Leu Phe Ile His Phe Phe Glu Ser Pro Val
            260                 265                 270

Glu Ile Leu Gly Glu Asp Gly Lys Val Val Gly Leu Lys Thr Glu Arg
        275                 280                 285

Thr Gln Leu Asp Gly Asn Gly Gly Val Thr Gly Thr Gly Glu Phe Lys
    290                 295                 300

Thr Trp Asp Met Gln Ser Val Tyr Arg Ala Val Gly Tyr Arg Ser Asp
305                 310                 315                 320

Ala Ile Glu Gly Val Pro Phe Asp Asp Glu Arg Ala Val Val Pro Asn
                325                 330                 335

Asp Gly Gly His Ile Ile Asp Pro Glu Val Gly Ser Pro Ile Thr Gly
            340                 345                 350

Leu Tyr Ala Thr Gly Trp Ile Lys Arg Gly Pro Ile Gly Leu Ile Gly
        355                 360                 365

Asn Thr Lys Ser Asp Ala Lys Glu Thr Thr Glu Met Leu Leu Ala Asp
    370                 375                 380

His Ala Ala Gly Ser Leu Pro Ala Pro Ala Lys Pro Glu Leu Glu Ser
385                 390                 395                 400

Ile Ile Glu Phe Leu Asp Glu Arg Lys Val Ala Phe Thr Thr Trp Asp
                405                 410                 415

Gly Trp His Leu Leu Asp Ala Ala Glu Arg Ala Leu Gly Glu Pro Glu
            420                 425                 430

Gly Arg Glu Arg Lys Lys Ile Val Glu Trp Asn Asp Met Val Arg His
        435                 440                 445

Ala Arg Pro Glu Tyr Asp Ile
    450                 455
```

<210> SEQ ID NO 15
<211> LENGTH: 1539
<212> TYPE: DNA
<213> ORGANISM: Corynebacterium glutamicum

<400> SEQUENCE: 15

```
atgactcacc aagttgcact tgcctttgaa gacggcatca cccgattcat cgactgcgaa      60

gatgaccaaa ctgttgcaga tgccgcctac caggcacgca tcaacattcc tttcgactgc     120

cgcgacggcg cctgcggaac ctgcaaagcg ttctgcgaat ccggcgactt tgacgaaggc     180

gactacatcg acgacgccct gtccgaagat gaagcagccg acggctactg cctgccttgc     240

cagatgaccc caaagaccga cctcatcttg cagatcgcca ccacctccgt gctggcaaag     300

accggcgcat ccactttcga tggcgagttg aaggagatca atcacttctc tgattccacc     360

atcggcattg agatcgaact ggaaaaccgc caagatttgg cgttcctccc tggtcaatac     420

atgaacatcc aggttccagg cagcgaccag actcgttcct actctttctc ctgcgctcaa     480

gattccggca acgtgcagtt cctgatcaag gtaaccccag gtggactcat gaccacctat     540

ctcaccgatc acgcgaaggt cggcgacaag ctcaccttga ccggcccgat gggttccttc     600

ttcctgcgtg aacctgtccg cccgatcctg ctgctcgccg gcggaactgg acttgcaccg     660

atcttggcta ttttggaaaa gctttcccgc gatgagcttc tcgacgtccc aatccgcctg     720
```

```
gtttacggcg cgaacttcac ccacgatctg gtggaattgg atcgacttga tgccttcaag    780

gacaagttcg acttcgatta catcaccgtg ctttccgaca aggacaccga gcatccacgc    840

aagggctacg tcccagcaca cctgaccggc gaatatgagc cagatgagga cactgatgtg    900

tacctctgcg gccctcctcc aatggtcgag gccgtgcgcc aattcctggg caccctggag    960

catcctccgc tggactttta ttacgagaag ttcacttccg ccgctgcccc tgctgctggt   1020

aagccagaga tcaccgtgga gaccagcgaa gttgcagagg atttcaacct ggtcgaggtg   1080

tccactccag gcatgtcttc cggcgaggtg cactcttctg caacccagct gcaggcccgc   1140

atggctctgg agctcggcgc gctggagctt gcgatcaaca aactcggcga gcgcgacatc   1200

gagcgattcc gcaacttggc cgacatcgcg aactccttca tcgacggcga taagtttatc   1260

gacgcggtga agttcaccga ggccaacgcc gatttccacg agttcctctt ccgccgcgca   1320

aacaacgagg cgctgcttgc ggcgtaccag aacctccagg ttgttcaaga aatgaacgca   1380

acccttccag gcgccgagtg gattgatccg gcaattgcca ccgagcactt ggcgcttgtc   1440

gacgccgtct cccagaatga tctcgagacc gcgagaacaa tcattcgtga acacgcggag   1500

cacggcattg acactatggt taaggccctc gagaaatga                          1539
```

<210> SEQ ID NO 16
<211> LENGTH: 512
<212> TYPE: PRT
<213> ORGANISM: Corynebacterium glutamicum

<400> SEQUENCE: 16

```
Met Thr His Gln Val Ala Leu Ala Phe Glu Asp Gly Ile Thr Arg Phe
1               5                   10                  15

Ile Asp Cys Glu Asp Asp Gln Thr Val Ala Asp Ala Ala Tyr Gln Ala
            20                  25                  30

Arg Ile Asn Ile Pro Phe Asp Cys Arg Asp Gly Ala Cys Gly Thr Cys
        35                  40                  45

Lys Ala Phe Cys Glu Ser Gly Asp Phe Asp Glu Gly Asp Tyr Ile Asp
    50                  55                  60

Asp Ala Leu Ser Glu Asp Glu Ala Ala Asp Gly Tyr Cys Leu Pro Cys
65                  70                  75                  80

Gln Met Thr Pro Lys Thr Asp Leu Ile Leu Gln Ile Ala Thr Thr Ser
                85                  90                  95

Val Leu Ala Lys Thr Gly Ala Ser Thr Phe Asp Gly Glu Leu Lys Glu
            100                 105                 110

Ile Asn His Phe Ser Asp Ser Thr Ile Gly Ile Glu Ile Glu Leu Glu
        115                 120                 125

Asn Arg Gln Asp Leu Ala Phe Leu Pro Gly Gln Tyr Met Asn Ile Gln
    130                 135                 140

Val Pro Gly Ser Asp Gln Thr Arg Ser Tyr Ser Phe Ser Cys Ala Gln
145                 150                 155                 160

Asp Ser Gly Asn Val Gln Phe Leu Ile Lys Val Thr Pro Gly Gly Leu
                165                 170                 175

Met Thr Thr Tyr Leu Thr Asp His Ala Lys Val Gly Asp Lys Leu Thr
            180                 185                 190

Leu Thr Gly Pro Met Gly Ser Phe Phe Leu Arg Glu Pro Val Arg Pro
        195                 200                 205

Ile Leu Leu Leu Ala Gly Gly Thr Gly Leu Ala Pro Ile Leu Ala Ile
    210                 215                 220

Leu Glu Lys Leu Ser Arg Asp Glu Leu Leu Asp Val Pro Ile Arg Leu
```

-continued

```
225                 230                 235                 240

Val Tyr Gly Ala Asn Phe Thr His Asp Leu Val Glu Leu Asp Arg Leu
                245                 250                 255

Asp Ala Phe Lys Asp Lys Phe Asp Phe Asp Tyr Ile Thr Val Leu Ser
            260                 265                 270

Asp Lys Asp Thr Glu His Pro Arg Lys Gly Tyr Val Pro Ala His Leu
        275                 280                 285

Thr Gly Glu Tyr Glu Pro Asp Glu Asp Thr Asp Val Tyr Leu Cys Gly
    290                 295                 300

Pro Pro Pro Met Val Glu Ala Val Arg Gln Phe Leu Gly Thr Leu Glu
305                 310                 315                 320

His Pro Pro Leu Asp Phe Tyr Tyr Glu Lys Phe Thr Ser Ala Ala Ala
                325                 330                 335

Pro Ala Ala Gly Lys Pro Glu Ile Thr Val Glu Thr Ser Glu Val Ala
            340                 345                 350

Glu Asp Phe Asn Leu Val Glu Val Ser Thr Pro Gly Met Ser Ser Gly
        355                 360                 365

Glu Val His Ser Ser Ala Thr Gln Leu Gln Ala Arg Met Ala Leu Glu
    370                 375                 380

Leu Gly Ala Leu Glu Leu Ala Ile Asn Lys Leu Gly Glu Arg Asp Ile
385                 390                 395                 400

Glu Arg Phe Arg Asn Leu Ala Asp Ile Ala Asn Ser Phe Ile Asp Gly
                405                 410                 415

Asp Lys Phe Ile Asp Ala Val Lys Phe Thr Glu Ala Asn Ala Asp Phe
            420                 425                 430

His Glu Phe Leu Phe Arg Arg Ala Asn Asn Glu Ala Leu Leu Ala Ala
        435                 440                 445

Tyr Gln Asn Leu Gln Val Val Gln Glu Met Asn Ala Thr Leu Pro Gly
    450                 455                 460

Ala Glu Trp Ile Asp Pro Ala Ile Ala Thr Glu His Leu Ala Leu Val
465                 470                 475                 480

Asp Ala Val Ser Gln Asn Asp Leu Glu Thr Ala Arg Thr Ile Ile Arg
                485                 490                 495

Glu His Ala Glu His Gly Ile Asp Thr Met Val Lys Ala Leu Glu Lys
            500                 505                 510
```

<210> SEQ ID NO 17
<211> LENGTH: 978
<212> TYPE: DNA
<213> ORGANISM: Corynebacterium glutamicum

<400> SEQUENCE: 17

```
atgaactcgc aatggcaaga tgcacatgtt gtttccagcg aaatcatcgc tgcagacatt      60

cggcgaatag aactatcccc gaaatttgcg attccagtaa aacccggcga acatctcaag     120

atcatggtgc ccctaaaaac tggacaggaa aagagatcgt actccatcgt tgacgctcgt     180

cacgacggtt cgactctcgc cctgagcgta ctcaaaacca gaaactcccg tggaggatct     240

gagttcatgc atacgcttcg agctggagac acagttactg tctccaggcc gtctcaggat     300

tttcctctcc gcgtgggtgc gcctgagtat gtacttgttg ccggcggaat tggaatcaca     360

gcgatccgtt caatggcatc tttattaaag aaattgggag cgaactaccg catccatttc     420

gcagcacgca gccttgatgc catggcttac aaagatgagc tcgtggcaga acacggcgac     480

aagctgcacc tgcatctaga ttctgaaggc accaccatcg atgtcccagc attgatcgaa     540

accttaaacc cccacactga gctttatatg tgcggcccca tccgcttgat ggatgccatc     600
```

-continued

```
cggcgcgcat ggaacacccg cggacttgac cccaccaatc tgcgtttcga aacgtttgga    660

aacagtggat ggttctcccc agaggttttc cacatccaag taccagagct ggggcttcac    720

gccacagtca acaaggatga aagcatgctg gaggctttgc aaaaggctgg ggcgaatatg    780

atgtttgatt gtcgaaaagg cgaatgtggt ttgtgccagg ttcgcgttct agaagtcgat    840

ggccaggttg atcaccgcga tgtgttcttc tctgatcgtc aaaaagaatc cgacgcaaag    900

gcatgcgcct gcgtgtctcg agtagtctcc tccccttcct cgtccccaac ctcgaccatt    960

acggtcgccc tctcctaa                                                  978
```

<210> SEQ ID NO 18
<211> LENGTH: 325
<212> TYPE: PRT
<213> ORGANISM: Corynebacterium glutamicum

<400> SEQUENCE: 18

```
Met Asn Ser Gln Trp Gln Asp Ala His Val Val Ser Ser Glu Ile Ile
1               5                   10                  15

Ala Ala Asp Ile Arg Arg Ile Glu Leu Ser Pro Lys Phe Ala Ile Pro
            20                  25                  30

Val Lys Pro Gly Glu His Leu Lys Ile Met Val Pro Leu Lys Thr Gly
        35                  40                  45

Gln Glu Lys Arg Ser Tyr Ser Ile Val Asp Ala Arg His Asp Gly Ser
    50                  55                  60

Thr Leu Ala Leu Ser Val Leu Lys Thr Arg Asn Ser Arg Gly Gly Ser
65                  70                  75                  80

Glu Phe Met His Thr Leu Arg Ala Gly Asp Thr Val Thr Val Ser Arg
                85                  90                  95

Pro Ser Gln Asp Phe Pro Leu Arg Val Gly Ala Pro Glu Tyr Val Leu
            100                 105                 110

Val Ala Gly Gly Ile Gly Ile Thr Ala Ile Arg Ser Met Ala Ser Leu
        115                 120                 125

Leu Lys Lys Leu Gly Ala Asn Tyr Arg Ile His Phe Ala Ala Arg Ser
    130                 135                 140

Leu Asp Ala Met Ala Tyr Lys Asp Glu Leu Val Ala Glu His Gly Asp
145                 150                 155                 160

Lys Leu His Leu His Leu Asp Ser Glu Gly Thr Thr Ile Asp Val Pro
                165                 170                 175

Ala Leu Ile Glu Thr Leu Asn Pro His Thr Glu Leu Tyr Met Cys Gly
            180                 185                 190

Pro Ile Arg Leu Met Asp Ala Ile Arg Arg Ala Trp Asn Thr Arg Gly
        195                 200                 205

Leu Asp Pro Thr Asn Leu Arg Phe Glu Thr Phe Gly Asn Ser Gly Trp
    210                 215                 220

Phe Ser Pro Glu Val Phe His Ile Gln Val Pro Glu Leu Gly Leu His
225                 230                 235                 240

Ala Thr Val Asn Lys Asp Glu Ser Met Leu Glu Ala Leu Gln Lys Ala
                245                 250                 255

Gly Ala Asn Met Met Phe Asp Cys Arg Lys Gly Glu Cys Gly Leu Cys
            260                 265                 270

Gln Val Arg Val Leu Glu Val Asp Gly Gln Val Asp His Arg Asp Val
        275                 280                 285

Phe Phe Ser Asp Arg Gln Lys Glu Ser Asp Ala Lys Ala Cys Ala Cys
    290                 295                 300
```

```
Val Ser Arg Val Val Ser Ser Pro Ser Ser Ser Pro Thr Ser Thr Ile
305                 310                 315                 320

Thr Val Ala Leu Ser
                325


<210> SEQ ID NO 19
<211> LENGTH: 747
<212> TYPE: DNA
<213> ORGANISM: Escherichia coli

<400> SEQUENCE: 19

atggctgatt gggtaacagg caaagtcact aaagtgcaga actggaccga cgccctgttt      60

agtctcaccg ttcacgcccc cgtgcttccg tttaccgccg ggcaatttac caagcttggc     120

cttgaaatcg acggcgaacg cgtccagcgc gcctactcct atgtaaactc gcccgataat     180

cccgatctgg agttttacct ggtcaccgtc cccgatggca aattaagccc acgactggcg     240

gcactgaaac caggcgatga agtgcaggtg gttagcgaag cggcaggatt ctttgtgctc     300

gatgaagtgc cgcactgcga aacgctatgg atgctggcaa ccggtacagc gattggccct     360

tatttatcga ttctgcaact aggtaaagat ttagatcgct tcaaaaatct ggtcctggtg     420

cacgccgcac gttatgccgc cgacttaagc tatttgccac tgatgcagga actggaaaaa     480

cgctacgaag gaaaactgcg cattcagacg gtggtcagtc gggaaacggc agcggggtcg     540

ctcaccggac ggataccggc attaattgaa agtggggaac tggaaagcac gattggcctg     600

ccgatgaata aagaaaccag ccatgtgatg ctgtgcggca atccacagat ggtgcgcgat     660

acacaacagt tgctgaaaga gacccggcag atgacgaaac atttacgtcg ccgaccgggc     720

catatgacag cggagcatta ctggtaa                                         747


<210> SEQ ID NO 20
<211> LENGTH: 248
<212> TYPE: PRT
<213> ORGANISM: Escherichia coli

<400> SEQUENCE: 20

Met Ala Asp Trp Val Thr Gly Lys Val Thr Lys Val Gln Asn Trp Thr
1               5                   10                  15

Asp Ala Leu Phe Ser Leu Thr Val His Ala Pro Val Leu Pro Phe Thr
            20                  25                  30

Ala Gly Gln Phe Thr Lys Leu Gly Leu Glu Ile Asp Gly Glu Arg Val
        35                  40                  45

Gln Arg Ala Tyr Ser Tyr Val Asn Ser Pro Asp Asn Pro Asp Leu Glu
    50                  55                  60

Phe Tyr Leu Val Thr Val Pro Asp Gly Lys Leu Ser Pro Arg Leu Ala
65                  70                  75                  80

Ala Leu Lys Pro Gly Asp Glu Val Gln Val Val Ser Glu Ala Ala Gly
                85                  90                  95

Phe Phe Val Leu Asp Glu Val Pro His Cys Glu Thr Leu Trp Met Leu
            100                 105                 110

Ala Thr Gly Thr Ala Ile Gly Pro Tyr Leu Ser Ile Leu Gln Leu Gly
        115                 120                 125

Lys Asp Leu Asp Arg Phe Lys Asn Leu Val Leu Val His Ala Ala Arg
    130                 135                 140

Tyr Ala Ala Asp Leu Ser Tyr Leu Pro Leu Met Gln Glu Leu Glu Lys
145                 150                 155                 160

Arg Tyr Glu Gly Lys Leu Arg Ile Gln Thr Val Val Ser Arg Glu Thr
                165                 170                 175
```

```
Ala Ala Gly Ser Leu Thr Gly Arg Ile Pro Ala Leu Ile Glu Ser Gly
            180                 185                 190

Glu Leu Glu Ser Thr Ile Gly Leu Pro Met Asn Lys Glu Thr Ser His
        195                 200                 205

Val Met Leu Cys Gly Asn Pro Gln Met Val Arg Asp Thr Gln Gln Leu
    210                 215                 220

Leu Lys Glu Thr Arg Gln Met Thr Lys His Leu Arg Arg Arg Pro Gly
225                 230                 235                 240

His Met Thr Ala Glu His Tyr Trp
                245
```

```
<210> SEQ ID NO 21
<211> LENGTH: 192
<212> TYPE: DNA
<213> ORGANISM: artificial
<220> FEATURE:
<223> OTHER INFORMATION: Promoter PSOD

<400> SEQUENCE: 21

gagctgccaa ttattccggg cttgtgaccc gctacccgat aaataggtcg gctgaaaaat      60

ttcgttgcaa tatcaacaaa aaggcctatc attgggaggt gtcgcaccaa gtacttttgc     120

gaagcgccat ctgacggatt ttcaaaagat gtatatgctc ggtgcggaaa cctacgaaag     180

gattttttac cc                                                         192


<210> SEQ ID NO 22
<211> LENGTH: 184
<212> TYPE: DNA
<213> ORGANISM: artificial
<220> FEATURE:
<223> OTHER INFORMATION: Promoter PgroES

<400> SEQUENCE: 22

ggtcgagcgg cttaaagttt ggctgccatg tgaattttta gcaccctcaa cagttgagtg      60

ctggcactct cgggggtaga gtgccaaata ggttgtttga cacacagttg ttcacccgcg     120

acgacggctg tgctggaaac ccacaaccgg cacacacaaa atttttctca tggagggatt     180

catc                                                                  184


<210> SEQ ID NO 23
<211> LENGTH: 199
<212> TYPE: DNA
<213> ORGANISM: artificial
<220> FEATURE:
<223> OTHER INFORMATION: Promoter PEFTU

<400> SEQUENCE: 23

ggccgttacc ctgcgaatgt ccacagggta gctggtagtt tgaaaatcaa cgccgttgcc      60

cttaggattc agtaactggc acattttgta atgcgctaga tctgtgtgct cagtcttcca     120

ggctgcttat cacagtgaaa gcaaaaccaa ttcgtggctg cgaaagtcgt agccaccacg     180

aagtccagga ggacataca                                                  199


<210> SEQ ID NO 24
<211> LENGTH: 114
<212> TYPE: DNA
<213> ORGANISM: artificial
<220> FEATURE:
<223> OTHER INFORMATION: Promoter lambdaPR

<400> SEQUENCE: 24
```

```
gtcgactcat acgttaaatc tatcaccgca agggataaat atctaacacc gtgcgtgttg     60

actattttac ctctggcggt gataatggtt gcatgtacta aggaggatta atta          114


<210> SEQ ID NO 25
<211> LENGTH: 7070
<212> TYPE: DNA
<213> ORGANISM: artificial
<220> FEATURE:
<223> OTHER INFORMATION: Plasmid pH273

<400> SEQUENCE: 25

tcgagaggcc tgacgtcggg cccggtacca cgcgtcatat gactagttgg agaatcatga     60

cctcagcatc tgccccaagc tttaaccccg gcaagggtcc cggctcagca gtcggaattg    120

ccctttttagg attcggaaca gtcggcactg aggtgatgcg tctgatgacc gagtacggtg    180

atgaacttgc gcaccgcatt ggtggcccac tggaggttcg tggcattgct gtttctgata    240

tctcaaagcc acgtgaaggc gttgcacctg agctgctcac tgaggacgct tttgcactca    300

tcgagcgcga ggatgttgac atcgtcgttg aggttatcgg cggcattgag tacccacgtg    360

aggtagttct cgcagctctg aaggccggca agtctgttgt taccgccaat aaggctcttg    420

ttgcagctca ctctgctgag cttgctgatg cagcggaagc cgcaaacgtt gacctgtact    480

tcgaggctgc tgttgcaggc gcaattccag tggttggccc actgcgtcgc tccctggctg    540

gcgatcagat ccagtctgtg atgggcatcg ttaacggcac caccaacttc atcttggacg    600

ccatggattc caccggcgct gactatgcag attctttggc tgaggcaact cgtttgggtt    660

acgccgaagc tgatccaact gcagacgtcg aaggccatga cgccgcatcc aaggctgcaa    720

ttttggcatc catcgctttc cacacccgtg ttaccgcgga tgatgtgtac tgcgaaggta    780

tcagcaacat cagcgctgcc gacattgagg cagcacagca ggcaggccac accatcaagt    840

tgttggccat ctgtgagaag ttcaccaaca aggaaggaaa gtcggctatt tctgctcgcg    900

tgcacccgac tctattacct gtgtcccacc cactggcgtc ggtaaacaag tcctttaatg    960

caatctttgt tgaagcagaa gcagctggtc gcctgatgtt ctacggaaac ggtgcaggtg   1020

gcgcgccaac cgcgtctgct gtgcttggcg acgtcgttgg tgccgcacga aacaaggtgc   1080

acggtggccg tgctccaggt gagtccacct acgctaacct gccgatcgct gatttcggtg   1140

agaccaccac tcgttaccac ctcgacatgg atgtggaaga tcgcgtgggg gttttggctg   1200

aattggctag cctgttctct gagcaaggaa tcttcctgcg tacaatccga caggaagagc   1260

gcgatgatga tgcacgtctg atcgtggtca cccactctgc gctggaatct gatctttccc   1320

gcaccgttga actgctgaag gctaagcctg ttgttaaggc aatcaacagt gtgatccgcc   1380

tcgaaaggga ctaattttac tgacatggca attgaactga acgtcggtcg taaggttacc   1440

gtcacggtac ctggatcttc tgcaaacctc ggacctggct ttgacacttt aggtttggca   1500

ctgtcggtat acgacactgt cgaagtggaa attattccat ctggcttgga agtggaagtt   1560

tttggcgaag gccaaggcga agtccctctt gatggctccc acctggtggt taaagctatt   1620

cgtgctggcc tgaaggcagc tgacgctgaa gttcctggat tgcgagtggt gtgccacaac   1680

aacattccgc agtctcgtgg tcttggctcc tctgctgcag cggcggttgc tggtgttgct   1740

gcagctaatg gtttggcgga tttcccgctg actcaagagc agattgttca gttgtcctct   1800

gcctttgaag gccacccaga taatgctgcg gcttctgtgc tgggtggagc agtggtgtcg   1860

tggacaaatc tgtctatcga cggcaagagc cagccacagt atgctgctgt accacttgag   1920

gtgcaggaca atattcgtgc gactgcgctg gttcctaatt tccacgcatc caccgaagct   1980
```

-continued

```
gtgcgccgag tccttcccac tgaagtcact cacatcgatg cgcgatttaa cgtgtcccgc   2040
gttgcagtga tgatcgttgc gttgcagcag cgtcctgatt tgctgtggga gggtactcgt   2100
gaccgtctgc accagcctta tcgtgcagaa gtgttgccta ttacctctga gtgggtaaac   2160
cgcctgcgca accgtggcta cgcggcatac ctttccggtg ccggcccaac cgccatggtg   2220
ctgtccactg agccaattcc agacaaggtt ttggaagatg ctcgtgagtc tggcattaag   2280
gtgcttgagc ttgaggttgc gggaccagtc aaggttgaag ttaaccaacc ttaggcccaa   2340
caaggaaggc cccccttcgaa tcaagaaggg ggccttatta gtgcagcaat tattcgctga   2400
acacgtgaac cttacaggtg cccggcgcgt tgagtggttt gagttccagc tggatgcggt   2460
tgttttcacc gaggctttct tggatgaatc cggcgtggat ggcgcagacg aaggctgatg   2520
ggcgtttgtc gttgaccaca aatgggcagc tgtgtagagc gagggagttt gcttcttcgg   2580
tttcggtggg gtcaaagccc atttcgcgga ggcggttaat gagcggggag agggcttcgt   2640
cgagttcttc ggcttcggcg tggttaatgc ccatgacgtg tgcccactgg gttccgatgg   2700
aaagtgcttt ggcgcggagg tcggggttgt gcattgcgtc atcgtcgaca tcgccgagca   2760
tgttggccat gagttcgatc agggtgatgt attctttggc gacagcgcgg ttgtcgggga   2820
cgcgtgtttg gaagatgagg gaggggcggg atcctctaga cccgggattt aaatcgctag   2880
cgggctgcta aaggaagcgg aacacgtaga aagccagtcc gcagaaacgg tgctgacccc   2940
ggatgaatgt cagctactgg gctatctgga caagggaaaa cgcaagcgca aagagaaagc   3000
aggtagcttg cagtgggctt acatggcgat agctagactg ggcggtttta tggacagcaa   3060
gcgaaccgga attgccagct ggggcgccct ctggtaaggt tgggaagccc tgcaaagtaa   3120
actggatggc tttcttgccg ccaaggatct gatggcgcag gggatcaaga tctgatcaag   3180
agacaggatg aggatcgttt cgcatgattg aacaagatgg attgcacgca ggttctccgg   3240
ccgcttgggt ggagaggcta ttcggctatg actgggcaca acagacaatc ggctgctctg   3300
atgccgccgt gttccggctg tcagcgcagg ggcgcccggt tctttttgtc aagaccgacc   3360
tgtccggtgc cctgaatgaa ctgcaggacg aggcagcgcg gctatcgtgg ctggccacga   3420
cgggcgttcc ttgcgcagct gtgctcgacg ttgtcactga agcgggaagg gactggctgc   3480
tattgggcga agtgccgggg caggatctcc tgtcatctca ccttgctcct gccgagaaag   3540
tatccatcat ggctgatgca atgcggcggc tgcatacgct tgatccggct acctgcccat   3600
tcgaccacca agcgaaacat cgcatcgagc gagcacgtac tcggatggaa gccggtcttg   3660
tcgatcagga tgatctggac gaagagcatc aggggctcgc gccagccgaa ctgttcgcca   3720
ggctcaaggc gcgcatgccc gacggcgagg atctcgtcgt gacccatggc gatgcctgct   3780
tgccgaatat catggtggaa aatggccgct tttctggatt catcgactgt ggccggctgg   3840
gtgtggcgga ccgctatcag gacatagcgt tggctacccg tgatattgct gaagagcttg   3900
gcggcgaatg ggctgaccgc ttcctcgtgc tttacggtat cgccgctccc gattcgcagc   3960
gcatcgcctt ctatcgcctt cttgacgagt tcttctgagc gggactctgg ggttcgaaat   4020
gaccgaccaa gcgacgccca acctgccatc acgagatttc gattccaccg ccgccttcta   4080
tgaaaggttg ggcttcggaa tcgttttccg ggacgccggc tggatgatcc tccagcgcgg   4140
ggatctcatg ctggagttct tcgcccacgc tagcggcgcg ccggccggcc cggtgtgaaa   4200
taccgcacag atgcgtaagg agaaaatacc gcatcaggcg ctcttccgct tcctcgctca   4260
ctgactcgct gcgctcggtc gttcggctgc ggcgagcggt atcagctcac tcaaaggcgg   4320
taatacggtt atccacagaa tcaggggata acgcaggaaa gaacatgtga gcaaaaggcc   4380
```

-continued

```
agcaaaaggc caggaaccgt aaaaaggccg cgttgctggc gtttttccat aggctccgcc   4440
cccctgacga gcatcacaaa aatcgacgct caagtcagag gtggcgaaac ccgacaggac   4500
tataaagata ccaggcgttt ccccctggaa gctccctcgt gcgctctcct gttccgaccc   4560
tgccgcttac cggatacctg tccgcctttc tcccttcggg aagcgtggcg ctttctcata   4620
gctcacgctg taggtatctc agttcggtgt aggtcgttcg ctccaagctg ggctgtgtgc   4680
acgaaccccc cgttcagccc gaccgctgcg ccttatccgg taactatcgt cttgagtcca   4740
acccggtaag acacgactta tcgccactgg cagcagccac tggtaacagg attagcagag   4800
cgaggtatgt aggcggtgct acagagttct tgaagtggtg gcctaactac ggctacacta   4860
gaaggacagt atttggtatc tgcgctctgc tgaagccagt taccttcgga aaaagagttg   4920
gtagctcttg atccggcaaa caaaccaccg ctggtagcgg tggttttttt gtttgcaagc   4980
agcagattac gcgcagaaaa aaaggatctc aagaagatcc tttgatcttt tctacggggt   5040
ctgacgctca gtggaacgaa aactcacgtt aagggatttt ggtcatgaga ttatcaaaaa   5100
ggatcttcac ctagatcctt ttaaaggccg gccgcggccg ccatcggcat tttcttttgc   5160
gtttttattt gttaactgtt aattgtcctt gttcaaggat gctgtctttg acaacagatg   5220
ttttcttgcc tttgatgttc agcaggaagc tcggcgcaaa cgttgattgt ttgtctgcgt   5280
agaatcctct gtttgtcata tagcttgtaa tcacgacatt gtttcctttc gcttgaggta   5340
cagcgaagtg tgagtaagta aaggttacat cgttaggatc aagatccatt tttaacacaa   5400
ggccagtttt gttcagcggc ttgtatgggc cagttaaaga attagaaaca taaccaagca   5460
tgtaaatatc gttagacgta atgccgtcaa tcgtcatttt tgatccgcgg gagtcagtga   5520
acaggtacca tttgccgttc attttaaaga cgttcgcgcg ttcaatttca tctgttactg   5580
tgttagatgc aatcagcggt ttcatcactt ttttcagtgt gtaatcatcg tttagctcaa   5640
tcataccgag agcgccgttt gctaactcag ccgtgcgttt tttatcgctt tgcagaagtt   5700
tttgactttc ttgacggaag aatgatgtgc ttttgccata gtatgctttg ttaaataaag   5760
attcttcgcc ttggtagcca tcttcagttc cagtgtttgc ttcaaatact aagtatttgt   5820
ggcctttatc ttctacgtag tgaggatctc tcagcgtatg gttgtcgcct gagctgtagt   5880
tgccttcatc gatgaactgc tgtacatttt gatacgtttt tccgtcaccg tcaaagattg   5940
atttataatc ctctacaccg ttgatgttca aagagctgtc tgatgctgat acgttaactt   6000
gtgcagttgt cagtgtttgt ttgccgtaat gtttaccgga gaaatcagtg tagaataaac   6060
ggatttttcc gtcagatgta aatgtggctg aacctgacca ttcttgtgtt tggtctttta   6120
ggatagaatc atttgcatcg aatttgtcgc tgtctttaaa gacgcggcca gcgtttttcc   6180
agctgtcaat agaagtttcg ccgacttttt gatagaacat gtaaatcgat gtgtcatccg   6240
catttttagg atctccggct aatgcaaaga cgatgtggta gccgtgatag tttgcgacag   6300
tgccgtcagc gttttgtaat ggccagctgt cccaaacgtc caggcctttt gcagaagaga   6360
tatttttaat tgtggacgaa tcaaattcag aaacttgata tttttcattt ttttgctgtt   6420
cagggatttg cagcatatca tggcgtgtaa tatgggaaat gccgtatgtt tccttatatg   6480
gcttttggtt cgtttctttc gcaaacgctt gagttgcgcc tcctgccagc agtgcggtag   6540
taaaggttaa tactgttgct tgttttgcaa actttttgat gttcatcgtt catgtctcct   6600
tttttatgta ctgtgttagc ggtctgcttc ttccagccct cctgtttgaa gatggcaagt   6660
tagttacgca caataaaaaa agacctaaaa tatgtaaggg gtgacgccaa agtatacact   6720
ttgcccttta cacattttag gtcttgcctg ctttatcagt aacaaacccg cgcgatttac   6780
```

```
ttttcgacct cattctatta gactctcgtt tggattgcaa ctggtctatt ttcctctttt   6840

gtttgataga aaatcataaa aggatttgca gactacgggc ctaaagaact aaaaaatcta   6900

tctgtttctt ttcattctct gtattttta tagtttctgt tgcatgggca taaagttgcc   6960

tttttaatca caattcagaa aatatcataa tatctcattt cactaaataa tagtgaacgg   7020

caggtatatg tgatgggtta aaaaggatcg gcggccgctc gatttaaatc             7070
```

<210> SEQ ID NO 26
<211> LENGTH: 7070
<212> TYPE: DNA
<213> ORGANISM: artificial
<220> FEATURE:
<223> OTHER INFORMATION: Plasmid pH373

<400> SEQUENCE: 26

```
tcgagaggcc tgacgtcggg cccggtacca cgcgtcatat gactagttgg agaatcatga     60

cctcagcatc tgccccaagc tttaaccccg gcaagggtcc cggctcagca gtcggaattg    120

ccctttttagg attcggaaca gtcggcactg aggtgatgcg tctgatgacc gagtacggtg    180

atgaacttgc gcaccgcatt ggtggcccac tggaggttcg tggcattgct gtttctgata    240

tctcaaagcc acgtgaaggc gttgcacctg agctgctcac tgaggacgct tttgcactca    300

tcgagcgcga ggatgttgac atcgtcgttg aggttatcgg cggcattgag tacccacgtg    360

aggtagttct cgcagctctg aaggccggca agtctgttgt taccgccaat aaggctcttg    420

ttgcagctca ctctgctgag cttgctgatg cagcggaagc cgcaaacgtt gacctgtact    480

tcgaggctgc tgttgcaggc gcaattccag tggttggccc actgcgtcgc tccctggctg    540

gcgatcagat ccagtctgtg atgggcatcg ttaacggcac caccaacttc atcttggacg    600

ccatggattc caccggcgct gactatgcag attctttggc tgaggcaact cgtttgggtt    660

acgccgaagc tgatccaact gcagacgtcg aaggccatga cgccgcatcc aaggctgcaa    720

ttttggcatc catcgctttc cacacccgtg ttaccgcgga tgatgtgtac tgcgaaggta    780

tcagcaacat cagcgctgcc gacattgagg cagcacagca ggcaggccac accatcaagt    840

tgttggccat ctgtgagaag ttcaccaaca aggaaggaaa gtcggctatt tctgctcgcg    900

tgcacccgac tctattacct gtgtcccacc cactggcgtc ggtaaacaag tcctttaatg    960

caatctttgt tgaagcagaa gcagctggtc gcctgatgtt ctacggaaac ggtgcaggtg   1020

gcgcgccaac cgcgtctgct gtgcttggcg acgtcgttgg tgccgcacga aacaaggtgc   1080

acggtggccg tgctccaggt gagtccacct acgctaacct gccgatcgct gatttcggtg   1140

agaccaccac tcgttaccac ctcgacatgg atgtggaaga tcgcgtgggg gttttggctg   1200

aattggctag cctgttctct gagcaaggaa tcttcctgcg tacaatccga caggaagagc   1260

gcgatgatga tgcacgtctg atcgtggtca cccactctgc gctggaatct gatctttccc   1320

gcaccgttga actgctgaag gctaagcctg ttgttaaggc aatcaacagt gtgatccgcc   1380

tcgaaaggga ctaattttac tgacatggca attgaactga acgtcggtcg taaggttacc   1440

gtcacggtac ctggatcttc tgcaaacctc ggacctggct ttgacacttt aggtttggca   1500

ctgtcggtat acgacactgt cgaagtggaa attattccat ctggcttgga agtggaagtt   1560

tttggcgaag gccaaggcga agtccctctt gatggctccc acctggtggt taaagctatt   1620

cgtgctggcc tgaaggcagc tgacgctgaa gttcctggat tgcgagtggt gtgccacaac   1680

aacattccgc agtctcgtgg tcttggctcc tctgctgcag cggcggttgc tggtgttgct   1740

gcagctaatg gtttggcgga tttcccgctg actcaagagc agattgttca gttgtcctct   1800
```

-continued

```
gcctttgaag gccacccaga taatgctgcg gcttctgtgc tgggtggagc agtggtgtcg   1860
tggacaaatc tgtctatcga cggcaagagc cagccacagt atgctgctgt accacttgag   1920
gtgcaggaca atattcgtgc gactgcgctg gttcctaatt tccacgcatc caccgaagct   1980
gtgcgccgag tccttcccac tgaagtcact cacatcgatg cgcgatttaa cgtgtcccgc   2040
gttgcagtga tgatcgttgc gttgcagcag cgtcctgatt tgctgtggga gggtactcgt   2100
gaccgtctgc accagcctta tcgtgcagaa gtgttgccta ttacctctga gtgggtaaac   2160
cgcctgcgca accgtggcta cgcggcatac ctttccggtg ccggcccaac cgccatggtg   2220
ctgtccactg agccaattcc agacaaggtt ttggaagatg ctcgtgagtc tggcattaag   2280
gtgcttgagc ttgaggttgc gggaccagtc aaggttgaag ttaaccaacc ttaggcccaa   2340
caaggaaggc cccttcgaa tcaagaaggg ggccttatta gtgcagcaat tattcgctga   2400
acacgtgaac cttacaggtg cccggcgcgt tgagtggttt gagttccagc tggatgcggt   2460
tgttttcacc gaggctttct tggatgaatc cggcgtggat ggcgcagacg aaggctgatg   2520
ggcgtttgtc gttgaccaca aatgggcagc tgtgtagagc gagggagttt gcttcttcgg   2580
tttcggtggg gtcaaagccc atttcgcgga ggcggttaat gagcggggag agggcttcgt   2640
cgagttcttc ggcttcggcg tggttaatgc ccatgacgtg tgcccactgg gttccgatgg   2700
aaagtgcttt ggcgcggagg tcggggttgt gcattgcgtc atcgtcgaca tcgccgagca   2760
tgttggccat gagttcgatc agggtgatgt attctttggc gacagcgcgg ttgtcgggga   2820
cgcgtgtttg gaagatgagg gaggggcggg atcctctaga cccgggattt aaatcgctag   2880
cgggctgcta aaggaagcgg aacacgtaga aagccagtcc gcagaaacgg tgctgacccc   2940
ggatgaatgt cagctactgg gctatctgga caagggaaaa cgcaagcgca aagagaaagc   3000
aggtagcttg cagtgggctt acatggcgat agctagactg ggcggtttta tggacagcaa   3060
gcgaaccgga attgccagct ggggcgccct ctggtaaggt tgggaagccc tgcaaagtaa   3120
actggatggc tttcttgccg ccaaggatct gatggcgcag gggatcaaga tctgatcaag   3180
agacaggatg aggatcgttt cgcatgattg aacaagatgg attgcacgca ggttctccgg   3240
ccgcttgggt ggagaggcta ttcggctatg actgggcaca acagacaatc ggctgctctg   3300
atgccgccgt gttccggctg tcagcgcagg ggcgcccggt tctttttgtc aagaccgacc   3360
tgtccggtgc cctgaatgaa ctgcaggacg aggcagcgcg gctatcgtgg ctggccacga   3420
cgggcgttcc ttgcgcagct gtgctcgacg ttgtcactga agcgggaagg gactggctgc   3480
tattgggcga agtgccgggg caggatctcc tgtcatctca ccttgctcct gccgagaaag   3540
tatccatcat ggctgatgca atgcggcggc tgcatacgct tgatccggct acctgcccat   3600
tcgaccacca agcgaaacat cgcatcgagc gagcacgtac tcggatggaa gccggtcttg   3660
tcgatcagga tgatctggac gaagagcatc aggggctcgc gccagccgaa ctgttcgcca   3720
ggctcaaggc gcgcatgccc gacggcgagg atctcgtcgt gacccatggc gatgcctgct   3780
tgccgaatat catggtggaa aatggccgct tttctggatt catcgactgt ggccggctgg   3840
gtgtggcgga ccgctatcag gacatagcgt tggctacccg tgatattgct gaagagcttg   3900
gcggcgaatg ggctgaccgc ttcctcgtgc tttacggtat cgccgctccc gattcgcagc   3960
gcatcgcctt ctatcgcctt cttgacgagt tcttctgagc gggactctgg ggttcgaaat   4020
gaccgaccaa gcgacgccca acctgccatc acgagatttc gattccaccg ccgccttcta   4080
tgaaaggttg ggcttcggaa tcgttttccg ggacgccggc tggatgatcc tccagcgcgg   4140
ggatctcatg ctggagttct tcgcccacgc tagcggcgcg ccggccggcc cggtgtgaaa   4200
```

-continued

```
taccgcacag atgcgtaagg agaaaatacc gcatcaggcg ctcttccgct tcctcgctca   4260

ctgactcgct gcgctcggtc gttcggctgc ggcgagcggt atcagctcac tcaaaggcgg   4320

taatacggtt atccacagaa tcaggggata acgcaggaaa gaacatgtga gcaaaaggcc   4380

agcaaaaggc caggaaccgt aaaaaggccg cgttgctggc gtttttccat aggctccgcc   4440

cccctgacga gcatcacaaa aatcgacgct caagtcagag gtggcgaaac ccgacaggac   4500

tataaagata ccaggcgttt ccccctggaa gctccctcgt gcgctctcct gttccgaccc   4560

tgccgcttac cggatacctg tccgcctttc tcccttcggg aagcgtggcg ctttctcata   4620

gctcacgctg taggtatctc agttcggtgt aggtcgttcg ctccaagctg ggctgtgtgc   4680

acgaaccccc cgttcagccc gaccgctgcg ccttatccgg taactatcgt cttgagtcca   4740

acccggtaag acacgactta tcgccactgg cagcagccac tggtaacagg attagcagag   4800

cgaggtatgt aggcggtgct acagagttct tgaagtggtg gcctaactac ggctacacta   4860

gaaggacagt atttggtatc tgcgctctgc tgaagccagt taccttcgga aaaagagttg   4920

gtagctcttg atccggcaaa caaaccaccg ctggtagcgg tggttttttt gtttgcaagc   4980

agcagattac gcgcagaaaa aaaggatctc aagaagatcc tttgatcttt tctacggggt   5040

ctgacgctca gtggaacgaa aactcacgtt aagggatttt ggtcatgaga ttatcaaaaa   5100

ggatcttcac ctagatcctt ttaaaggccg gccgcggccg ccatcggcat tttcttttgc   5160

gtttttattt gttaactgtt aattgtcctt gttcaaggat gctgtctttg acaacagatg   5220

ttttcttgcc tttgatgttc agcaggaagc tcggcgcaaa cgttgattgt ttgtctgcgt   5280

agaatcctct gtttgtcata tagcttgtaa tcacgacatt gtttcctttc gcttgaggta   5340

cagcgaagtg tgagtaagta aaggttacat cgttaggatc aagatccatt tttaacacaa   5400

ggccagtttt gttcagcggc ttgtatgggc cagttaaaga attagaaaca taaccaagca   5460

tgtaaatatc gttagacgta atgccgtcaa tcgtcatttt tgatccgcgg gagtcagtga   5520

acaggtacca tttgccgttc attttaaaga cgttcgcgcg ttcaatttca tctgttactg   5580

tgttagatgc aatcagcggt ttcatcactt ttttcagtgt gtaatcatcg tttagctcaa   5640

tcataccgag agcgccgttt gctaactcag ccgtgcgttt tttatcgctt tgcagaagtt   5700

tttgactttc ttgacggaag aatgatgtgc ttttgccata gtatgctttg ttaaataaag   5760

attcttcgcc ttggtagcca tcttcagttc cagtgtttgc ttcaaatact aagtatttgt   5820

ggcctttatc ttctacgtag tgaggatctc tcagcgtatg gttgtcgcct gagctgtagt   5880

tgccttcatc gatgaactgc tgtacatttt gatacgtttt tccgtcaccg tcaaagattg   5940

atttataatc ctctacaccg ttgatgttca aagagctgtc tgatgctgat acgttaactt   6000

gtgcagttgt cagtgtttgt ttgccgtaat gtttaccgga gaaatcagtg tagaataaac   6060

ggatttttcc gtcagatgta aatgtggctg aacctgacca ttcttgtgtt tggtctttta   6120

ggatagaatc atttgcatcg aatttgtcgc tgtctttaaa gacgcggcca gcgtttttcc   6180

agctgtcaat agaagtttcg ccgacttttt gatagaacat gtaaatcgat gtgtcatccg   6240

catttttagg atctccggct aatgcaaaga cgatgtggta gccgtgatag tttgcgacag   6300

tgccgtcagc gttttgtaat ggccagctgt cccaaacgtc caggcctttt gcagaagaga   6360

tatttttaat tgtggacgaa tcaaattcag aaacttgata tttttcattt ttttgctgtt   6420

cagggatttg cagcatatca tggcgtgtaa tatgggaaat gccgtatgtt tccttatatg   6480

gcttttggtt cgtttctttc gcaaacgctt gagttgcgcc tcctgccagc agtgcggtag   6540

taaaggttaa tactgttgct tgttttgcaa actttttgat gttcatcgtt catgtctcct   6600
```

-continued

```
tttttatgta ctgtgttagc ggtctgcttc ttccagccct cctgtttgaa gatggcaagt   6660

tagttacgca caataaaaaa agacctaaaa tatgtaaggg gtgacgccaa agtatacact   6720

ttgcccttta cacattttag gtcttgcctg ctttatcagt aacaaacccg cgcgatttac   6780

ttttcgacct cattctatta gactctcgtt tggattgcaa ctggtctatt ttcctctttt   6840

gtttgataga aaatcataaa aggatttgca gactacgggc ctaaagaact aaaaaatcta   6900

tctgtttctt ttcattctct gtatttttta tagtttctgt tgcatgggca taaagttgcc   6960

tttttaatca caattcagaa aatatcataa tatctcattt cactaaataa tagtgaacgg   7020

caggtatatg tgatgggtta aaaaggatcg gcggccgctc gatttaaatc              7070
```

<210> SEQ ID NO 27
<211> LENGTH: 8766
<212> TYPE: DNA
<213> ORGANISM: artificial
<220> FEATURE:
<223> OTHER INFORMATION: Plasmid pH304

<400> SEQUENCE: 27

```
tcgagaggcc tgacgtcggg cccggtacca cgcgtcatat gactagttcg gacctaggga     60

tatcgtcgac atcgatgctc ttctgcgtta attaacaatt gggatctctc aactaatgca    120

gcgatgcgtt ctttccagaa tgctttcatg acagggatgc tgtcttgatc aggcaggcgt    180

ctgtgctgga tgccgaagct ggatttattg tcgcctttgg aggtgaagtt gacgctcact    240

cgagaatcat cggccaacca tttggcattg aatgttctag gttcggaggc ggaggttttc    300

tcaattagtg cgggatcgag ccactgcgcc cgcaggtcat cgtctccgaa gagcttccac    360

actttttcga ccggcaggtt aagggttttg gaggcattgg ccgcgaaccc atcgctggtc    420

atcccgggtt tgcgcatgcc acgttcgtat tcataaccaa tcgcgatgcc ttgagcccac    480

cagccactga catcaaagtt gtccacgatg tgctttgcga tgtgggtgtg agtccaagag    540

gtggctttta cgtcgtcaag caattttagc cactcttccc acggctttcc ggtgccgttg    600

aggatagctt caggggacat gcctggtgtt gagccttgcg gagtggagtc agtcatgcga    660

ccgagactag tggcgctttg ggtaccgggc ccccccctcga ggtcgagcgg cttaaagttt    720

ggctgccatg tgaatttta gcaccctcaa cagttgagtg ctggcactct cgggggtaga    780

gtgccaaata ggttgtttga cacacagttg ttcacccgcg acgacggctg tgctggaaac    840

ccacaaccgg cacacacaaa atttttctca tggagggatt catcatgtcg acttcagtta    900

cttcaccagc ccacaacaac gcacattcct ccgaattttt ggatgcgttg gcaaaccatg    960

tgttgatcgg cgacggcgcc atgggcaccc agctccaagg ctttgacctg gacgtggaaa   1020

aggatttcct tgatctggag gggtgtaatg agattctcaa cgacacccgc cctgatgtgt   1080

tgaggcagat tcaccgcgcc tactttgagg cgggagctga cttggttgag accaatactt   1140

ttggttgcaa cctgccgaac ttggcggatt atgacatcgc tgatcgttgc cgtgagcttg   1200

cctacaaggg cactgcagtg gctagggaag tggctgatga gatggggccg ggccgaaacg   1260

gcatgcggcg tttcgtggtt ggttccctgg gacctggaac gaagcttcca tcgctgggcc   1320

atgcaccgta tgcagatttg cgtgggcact acaaggaagc agcgcttggc atcatcgacg   1380

gtggtggcga tgccttttg attgagactg ctcaggactt gcttcaggtc aaggctgcgg   1440

ttcacggcgt tcaagatgcc atggctgaac ttgatacatt cttgcccatt atttgccacg   1500

tcaccgtaga gaccaccggc accatgctca tgggttctga gatcggtgcc gcgttgacag   1560

cgctgcagcc actgggtatc gacatgattg gtctgaactg cgccaccggc ccagatgaga   1620
```

-continued tgagcgagca cctgcgttac ctgtccaagc acgccgatat tcctgtgtcg gtgatgccta 1680
acgcaggtct tcctgtcctg ggtaaaaacg gtgcagaata cccacttgag gctgaggatt 1740
tggcgcaggc gctggctgga ttcgtctccg aatatggcct gtccatggtg ggtggttgtt 1800
gtggcaccac acctgagcac atccgtgcgg tccgcgatgc ggtggttggt gttccagagc 1860
aggaaacctc cacactgacc aagatccctg caggccctgt tgagcaggcc tcccgcgagg 1920
tggagaaaga ggactccgtc gcgtcgctgt acacctcggt gccattgtcc caggaaaccg 1980
gcatttccat gatcggtgag cgcaccaact ccaacggttc caaggcattc cgtgaggcaa 2040
tgctgtctgg cgattgggaa aagtgtgtgg atattgccaa gcagcaaacc cgcgatggtg 2100
cacacatgct ggatctttgt gtggattacg tgggacgaga cggcaccgcc gatatggcga 2160
ccttggcagc acttcttgct accagctcca ctttgccaat catgattgac tccaccgagc 2220
cagaggttat tcgcacaggc cttgagcact tgggtggacg aagcatcgtt aactccgtca 2280
actttgaaga cggcgatggc cctgagtccc gctaccagcg catcatgaaa ctggtaaagc 2340
agcacggtgc ggccgtggtt gcgctgacca ttgatgagga aggccaggca cgtaccgctg 2400
agcacaaggt gcgcattgct aaacgactga ttgacgatat caccggcagc tacggcctgg 2460
atatcaaaga catcgttgtg gactgcctga ccttcccgat ctctactggc caggaagaaa 2520
ccaggcgaga tggcattgaa accatcgaag ccatccgcga gctgaagaag ctctacccag 2580
aaatccacac caccctgggt ctgtccaata tttccttcgg cctgaaccct gctgcacgcc 2640
aggttcttaa ctctgtgttc ctcaatgagt gcattgaggc tggtctggac tctgcgattg 2700
cgcacagctc caagattttg ccgatgaacc gcattgatga tcgccagcgc gaagtggcgt 2760
tggatatggt ctatgatcgc cgcaccgagg attacgatcc gctgcaggaa ttcatgcagc 2820
tgtttgaggg cgtttctgct gccgatgcca aggatgctcg cgctgaacag ctggccgcta 2880
tgcctttgtt tgagcgtttg gcacagcgca tcatcgacgg cgataagaat ggccttgagg 2940
atgatctgga agcaggcatg aaggagaagt ctcctattgc gatcatcaac gaggaccttc 3000
tcaacggcat gaagaccgtg ggtgagctgt ttggttccgg acagatgcag ctgccattcg 3060
tgctgcaatc ggcagaaacc atgaaaactg cggtggccta tttggaaccg ttcatggaag 3120
aggaagcaga agctaccgga tctgcgcagg cagagggcaa gggcaaaatc gtcgtggcca 3180
ccgtcaaggg tgacgtgcac gatatcggca agaacttggt ggacatcatt ttgtccaaca 3240
acggttacga cgtggtgaac ttgggcatca agcagccact gtccgccatg ttggaagcag 3300
cggaagaaca caaagcagac gtcatcggca tgtcgggact tcttgtgaag tccaccgtgg 3360
tgatgaagga aaaccttgag gagatgaaca acgccggcgc atccaattac ccagtcattt 3420
tgggtggcgc tgcgctgacg cgtacctacg tggaaaacga tctcaacgag gtgtacaccg 3480
gtgaggtgta ctacgcccgt gatgctttcg agggcctgcg cctgatggat gaggtgatgg 3540
cagaaaagcg tggtgaagga cttgatccca actcaccaga agctattgag caggcgaaga 3600
agaaggcgga acgtaaggct cgtaatgagc gttcccgcaa gattgccgcg gagcgtaaag 3660
ctaatgcggc tcccgtgatt gttccggagc gttctgatgt ctccaccgat actccaaccg 3720
cggcaccacc gttctgggga acccgcattg tcaagggtct gcccttggcg gagttcttgg 3780
gcaaccttga tgagcgcgcc ttgttcatgg ggcagtgggg tctgaaatcc acccgcggca 3840
acgagggtcc aagctatgag gatttggtgg aaactgaagg ccgaccacgc ctgcgctact 3900
ggctggatcg cctgaagtct gagggcattt tggaccacgt ggccttggtg tatggctact 3960
tcccagcggt cgcggaaggc gatgacgtgg tgatcttgga atccccggat ccacacgcag 4020

-continued

```
ccgaacgcat gcgctttagc ttcccacgcc agcagcgcgg caggttcttg tgcatcgcgg   4080
atttcattcg cccacgcgag caagctgtca aggacggcca agtggacgtc atgccattcc   4140
agctggtcac catgggtaat cctattgctg atttcgccaa cgagttgttc gcagccaatg   4200
aataccgcga gtacttggaa gttcacggca tcggcgtgca gctcaccgaa gcattggccg   4260
agtactggca ctcccgagtg cgcagcgaac tcaagctgaa cgacggtgga tctgtcgctg   4320
attttgatcc agaagacaag accaagttct tcgacctgga ttaccgcggc gcccgcttct   4380
cctttggtta cggttcttgc cctgatctgg aagaccgcgc aaagctggtg gaattgctcg   4440
agccaggccg tatcggcgtg gagttgtccg aggaactcca gctgcaccca gagcagtcca   4500
cagacgcgtt tgtgctctac cacccagagg caaagtactt taacgtctaa tctagacccg   4560
ggatttaaat cgctagcggg ctgctaaagg aagcggaaca cgtagaaagc cagtccgcag   4620
aaacggtgct gaccccggat gaatgtcagc tactgggcta tctggacaag ggaaaacgca   4680
agcgcaaaga gaaagcaggt agcttgcagt gggcttacat ggcgatagct agactgggcg   4740
gttttatgga cagcaagcga accggaattg ccagctgggg cgccctctgg taaggttggg   4800
aagccctgca aagtaaactg gatggctttc ttgccgccaa ggatctgatg gcgcagggga   4860
tcaagatctg atcaagagac aggatgagga tcgtttcgca tgattgaaca agatggattg   4920
cacgcaggtt ctccggccgc ttgggtggag aggctattcg gctatgactg ggcacaacag   4980
acaatcggct gctctgatgc cgccgtgttc cggctgtcag cgcaggggcg cccggttctt   5040
tttgtcaaga ccgacctgtc cggtgccctg aatgaactgc aggacgaggc agcgcggcta   5100
tcgtggctgg ccacgacggg cgttccttgc gcagctgtgc tcgacgttgt cactgaagcg   5160
ggaagggact ggctgctatt gggcgaagtg ccggggcagg atctcctgtc atctcacctt   5220
gctcctgccg agaaagtatc catcatggct gatgcaatgc ggcggctgca tacgcttgat   5280
ccggctacct gcccattcga ccaccaagcg aaacatcgca tcgagcgagc acgtactcgg   5340
atggaagccg gtcttgtcga tcaggatgat ctggacgaag agcatcaggg gctcgcgcca   5400
gccgaactgt tcgccaggct caaggcgcgc atgcccgacg gcgaggatct cgtcgtgacc   5460
catggcgatg cctgcttgcc gaatatcatg gtggaaaatg gccgcttttc tggattcatc   5520
gactgtggcc ggctgggtgt ggcggaccgc tatcaggaca tagcgttggc tacccgtgat   5580
attgctgaag agcttggcgg cgaatgggct gaccgcttcc tcgtgcttta cggtatcgcc   5640
gctcccgatt cgcagcgcat cgccttctat cgccttcttg acgagttctt ctgagcggga   5700
ctctggggtt cgaaatgacc gaccaagcga cgcccaacct gccatcacga gatttcgatt   5760
ccaccgccgc cttctatgaa aggttgggct tcggaatcgt tttccgggac gccggctgga   5820
tgatcctcca gcgcggggat ctcatgctgg agttcttcgc ccacgctagc ggcgcgccgg   5880
ccggcccggt gtgaaatacc gcacagatgc gtaaggagaa aataccgcat caggcgctct   5940
tccgcttcct cgctcactga ctcgctgcgc tcggtcgttc ggctgcggcg agcggtatca   6000
gctcactcaa aggcggtaat acggttatcc acagaatcag gggataacgc aggaaagaac   6060
atgtgagcaa aaggccagca aaaggccagg aaccgtaaaa aggccgcgtt gctggcgttt   6120
ttccataggc tccgcccccc tgacgagcat cacaaaaatc gacgctcaag tcagaggtgg   6180
cgaaacccga caggactata aagataccag gcgtttcccc ctggaagctc cctcgtgcgc   6240
tctcctgttc cgaccctgcc gcttaccgga tacctgtccg cctttctccc ttcgggaagc   6300
gtggcgcttt ctcatagctc acgctgtagg tatctcagtt cggtgtaggt cgttcgctcc   6360
aagctgggct gtgtgcacga accccccgtt cagcccgacc gctgcgcctt atccggtaac   6420
```

-continued

```
tatcgtcttg agtccaaccc ggtaagacac gacttatcgc cactggcagc agccactggt   6480
aacaggatta gcagagcgag gtatgtaggc ggtgctacag agttcttgaa gtggtggcct   6540
aactacggct acactagaag gacagtattt ggtatctgcg ctctgctgaa gccagttacc   6600
ttcggaaaaa gagttggtag ctcttgatcc ggcaaacaaa ccaccgctgg tagcggtggt   6660
tttttgttt gcaagcagca gattacgcgc agaaaaaaag gatctcaaga agatcctttg   6720
atcttttcta cggggtctga cgctcagtgg aacgaaaact cacgttaagg gattttggtc   6780
atgagattat caaaaaggat cttcacctag atccttttaa aggccggccg cggccgccat   6840
cggcattttc ttttgcgttt ttatttgtta actgttaatt gtccttgttc aaggatgctg   6900
tctttgacaa cagatgtttt cttgcctttg atgttcagca ggaagctcgg cgcaaacgtt   6960
gattgtttgt ctgcgtagaa tcctctgttt gtcatatagc ttgtaatcac gacattgttt   7020
cctttcgctt gaggtacagc gaagtgtgag taagtaaagg ttacatcgtt aggatcaaga   7080
tccattttta acacaaggcc agttttgttc agcggcttgt atgggccagt taaagaatta   7140
gaaacataac caagcatgta aatatcgtta gacgtaatgc cgtcaatcgt catttttgat   7200
ccgcgggagt cagtgaacag gtaccatttg ccgttcattt taaagacgtt cgcgcgttca   7260
atttcatctg ttactgtgtt agatgcaatc agcggtttca tcactttttt cagtgtgtaa   7320
tcatcgttta gctcaatcat accgagagcg ccgtttgcta actcagccgt gcgtttttta   7380
tcgctttgca gaagtttttg actttcttga cggaagaatg atgtgctttt gccatagtat   7440
gctttgttaa ataaagattc ttcgccttgg tagccatctt cagttccagt gtttgcttca   7500
aatactaagt atttgtggcc tttatcttct acgtagtgag gatctctcag cgtatggttg   7560
tcgcctgagc tgtagttgcc ttcatcgatg aactgctgta cattttgata cgtttttccg   7620
tcaccgtcaa agattgattt ataatcctct acaccgttga tgttcaaaga gctgtctgat   7680
gctgatacgt taacttgtgc agttgtcagt gtttgtttgc cgtaatgttt accggagaaa   7740
tcagtgtaga ataaacggat tttccgtca gatgtaaatg tggctgaacc tgaccattct   7800
tgtgtttggt cttttaggat agaatcattt gcatcgaatt tgtcgctgtc tttaaagacg   7860
cggccagcgt tttccagct gtcaatagaa gtttcgccga ctttttgata gaacatgtaa   7920
atcgatgtgt catccgcatt tttaggatct ccggctaatg caaagacgat gtggtagccg   7980
tgatagtttg cgacagtgcc gtcagcgttt tgtaatggcc agctgtccca aacgtccagg   8040
ccttttgcag aagagatatt tttaattgtg gacgaatcaa attcagaaac ttgatatttt   8100
tcattttttt gctgttcagg gatttgcagc atatcatggc gtgtaatatg ggaaatgccg   8160
tatgtttcct tatatggctt ttggttcgtt tctttcgcaa acgcttgagt tgcgcctcct   8220
gccagcagtg cggtagtaaa ggttaatact gttgcttgtt ttgcaaactt tttgatgttc   8280
atcgttcatg tctccttttt tatgtactgt gttagcggtc tgcttcttcc agccctcctg   8340
tttgaagatg gcaagttagt tacgcacaat aaaaaaagac ctaaaatatg taaggggtga   8400
cgccaaagta tacactttgc cctttacaca ttttaggtct tgcctgcttt atcagtaaca   8460
aacccgcgcg atttactttt cgacctcatt ctattagact ctcgtttgga ttgcaactgg   8520
tctattttcc tcttttgttt gatagaaaat cataaaagga tttgcagact acgggcctaa   8580
agaactaaaa aatctatctg tttcttttca ttctctgtat tttttatagt ttctgttgca   8640
tgggcataaa gttgcctttt taatcacaat tcagaaaata tcataatatc tcatttcact   8700
aaataatagt gaacggcagg tatatgtgat gggttaaaaa ggatcggcgg ccgctcgatt   8760
taaatc                                                              8766
```

<210> SEQ ID NO 28
<211> LENGTH: 7070
<212> TYPE: DNA
<213> ORGANISM: artificial
<220> FEATURE:
<223> OTHER INFORMATION: Plasmid pH399

<400> SEQUENCE: 28
tcgagaggcc tgacgtcggg cccggtacca cgcgtcatat gactagttgg agaatcatga 60
cctcagcatc tgccccaagc tttaaccccg gcaagggtcc cggctcagca gtcggaattg 120 ccctttttagg attcggaaca gtcggcactg aggtgatgcg tctgatgacc gagtacggtg 180
atgaacttgc gcaccgcatt ggtggcccac tggaggttcg tggcattgct gtttctgata 240
tctcaaagcc acgtgaaggc gttgcacctg agctgctcac tgaggacgct tttgcactca 300
tcgagcgcga ggatgttgac atcgtcgttg aggttatcgg cggcattgag tacccacgtg 360
aggtagttct cgcagctctg aaggccggca agtctgttgt taccgccaat aaggctcttg 420
ttgcagctca ctctgctgag cttgctgatg cagcggaagc cgcaaacgtt gacctgtact 480
tcgaggctgc tgttgcaggc gcaattccag tggttggccc actgcgtcgc tccctggctg 540
gcgatcagat ccagtctgtg atgggcatcg ttaacggcac caccaacttc atcttggacg 600
ccatggattc caccggcgct gactatgcag attctttggc tgaggcaact cgtttgggtt 660
acgccgaagc tgatccaact gcagacgtcg aaggccatga cgccgcatcc aaggctgcaa 720
ttttggcatc catcgctttc cacacccgtg ttaccgcgga tgatgtgtac tgcgaaggta 780
tcagcaacat cagcgctgcc gacattgagg cagcacagca ggcaggccac accatcaagt 840
tgttggccat ctgtgagaag ttcaccaaca aggaaggaaa gtcggctatt tctgctcgcg 900
tgcacccgac tctattacct gtgtcccacc cactggcgtc ggtaaacaag tcctttaatg 960
caatctttgt tgaagcagaa gcagctggtc gcctgatgtt ctacggaaac ggtgcaggtg 1020
gcgcgccaac cgcgtctgct gtgcttggcg acgtcgttgg tgccgcacga aacaaggtgc 1080
acggtggccg tgctccaggt gagtccacct acgctaacct gccgatcgct gatttcggtg 1140
agaccaccac tcgttaccac ctcgacatgg atgtggaaga tcgcgtgggg gttttggctg 1200
aattggctag cctgttctct gagcaaggaa tcttcctgcg tacaatccga caggaagagc 1260
gcgatgatga tgcacgtctg atcgtggtca cccactctgc gctggaatct gatctttccc 1320
gcaccgttga actgctgaag gctaagcctg ttgttaaggc aatcaacagt gtgatccgcc 1380
tcgaaaggga ctaattttac tgacatggca attgaactga acgtcggtcg taaggttacc 1440
gtcacggtac ctggatcttc tgcaaacctc ggacctggct ttgacacttt aggtttggca 1500
ctgtcggtat acgacactgt cgaagtggaa attattccat ctggcttgga agtggaagtt 1560
tttggcgaag gccaaggcga agtccctctt gatggctccc acctggtggt taaagctatt 1620
cgtgctggcc tgaaggcagc tgacgctgaa gttcctggat tgcgagtggt gtgccacaac 1680
aacattccgc agtctcgtgg tcttggctcc gctgctgcag cggcggttgc tggtgttgct 1740
gcagctaatg gtttggcgga tttcccgctg actcaagagc agattgttca gttgtcctct 1800
gcctttgaag gccacccaga taatgctgcg gcttctgtgc tgggtggagc agtggtgtcg 1860
tggacaaatc tgtctatcga cggcaagagc cagccacagt atgctgctgt accacttgag 1920
gtgcaggaca atattcgtgc gactgcgctg gttcctaatt tccacgcatc caccgaagct 1980
gtgcgccgag tccttcccac tgaagtcact cacatcgatg cgcgatttaa cgtgtcccgc 2040
gttgcagtga tgatcgttgc gttgcagcag cgtcctgatt tgctgtggga gggtactcgt 2100

-continued

```
gaccgtctgc accagcctta tcgtgcagaa gtgttgccta ttacctctga gtgggtaaac   2160
cgcctgcgca accgtggcta cgcggcatac ctttccggtg ccggcccaac cgccatggtg   2220
ctgtccactg agccaattcc agacaaggtt ttggaagatg ctcgtgagtc tggcattaag   2280
gtgcttgagc ttgaggttgc gggaccagtc aaggttgaag ttaaccaacc ttaggcccaa   2340
caaggaaggc cccttcgaa tcaagaaggg ggccttatta gtgcagcaat tattcgctga    2400
acacgtgaac cttacaggtg cccggcgcgt tgagtggttt gagttccagc tggatgcggt   2460
tgttttcacc gaggctttct tggatgaatc cggcgtggat ggcgcagacg aaggctgatg   2520
ggcgtttgtc gttgaccaca aatgggcagc tgtgtagagc gagggagttt gcttcttcgg   2580
tttcggtggg gtcaaagccc atttcgcgga ggcggttaat gagcggggag agggcttcgt   2640
cgagttcttc ggcttcggcg tggttaatgc ccatgacgtg tgcccactgg gttccgatgg   2700
aaagtgcttt ggcgcggagg tcggggttgt gcattgcgtc atcgtcgaca tcgccgagca   2760
tgttggccat gagttcgatc agggtgatgt attctttggc gacagcgcgg ttgtcgggga   2820
cgcgtgtttg gaagatgagg gaggggcggg atcctctaga cccgggattt aaatcgctag   2880
cgggctgcta aaggaagcgg aacacgtaga aagccagtcc gcagaaacgg tgctgacccc   2940
ggatgaatgt cagctactgg gctatctgga caagggaaaa cgcaagcgca aagagaaagc   3000
aggtagcttg cagtgggctt acatggcgat agctagactg ggcggtttta tggacagcaa   3060
gcgaaccgga attgccagct ggggcgccct ctggtaaggt tgggaagccc tgcaaagtaa   3120
actggatggc tttcttgccg ccaaggatct gatggcgcag gggatcaaga tctgatcaag   3180
agacaggatg aggatcgttt cgcatgattg aacaagatgg attgcacgca ggttctccgg   3240
ccgcttgggt ggagaggcta ttcggctatg actgggcaca acagacaatc ggctgctctg   3300
atgccgccgt gttccggctg tcagcgcagg ggcgcccggt tctttttgtc aagaccgacc   3360
tgtccggtgc cctgaatgaa ctgcaggacg aggcagcgcg gctatcgtgg ctggccacga   3420
cgggcgttcc ttgcgcagct gtgctcgacg ttgtcactga agcgggaagg gactggctgc   3480
tattgggcga agtgccgggg caggatctcc tgtcatctca ccttgctcct gccgagaaag   3540
tatccatcat ggctgatgca atgcggcggc tgcatacgct tgatccggct acctgcccat   3600
tcgaccacca agcgaaacat cgcatcgagc gagcacgtac tcggatggaa gccggtcttg   3660
tcgatcagga tgatctggac gaagagcatc aggggctcgc gccagccgaa ctgttcgcca   3720
ggctcaaggc gcgcatgccc gacggcgagg atctcgtcgt gacccatggc gatgcctgct   3780
tgccgaatat catggtggaa aatggccgct tttctggatt catcgactgt ggccggctgg   3840
gtgtggcgga ccgctatcag gacatagcgt tggctacccg tgatattgct gaagagcttg   3900
gcggcgaatg ggctgaccgc ttcctcgtgc tttacggtat cgccgctccc gattcgcagc   3960
gcatcgcctt ctatcgcctt cttgacgagt tcttctgagc gggactctgg ggttcgaaat   4020
gaccgaccaa gcgacgccca acctgccatc acgagatttc gattccaccg ccgccttcta   4080
tgaaaggttg ggcttcggaa tcgttttccg ggacgccggc tggatgatcc tccagcgcgg   4140
ggatctcatg ctggagttct tcgcccacgc tagcggcgcg ccggccggcc cggtgtgaaa   4200
taccgcacag atgcgtaagg agaaaatacc gcatcaggcg ctcttccgct tcctcgctca   4260
ctgactcgct gcgctcggtc gttcggctgc ggcgagcggt atcagctcac tcaaaggcgg   4320
taatacggtt atccacagaa tcaggggata acgcaggaaa gaacatgtga gcaaaaggcc   4380
agcaaaaggc caggaaccgt aaaaaggccg cgttgctggc gtttttccat aggctccgcc   4440
cccctgacga gcatcacaaa aatcgacgct caagtcagag gtggcgaaac ccgacaggac   4500
```

```
tataaagata ccaggcgttt ccccctggaa gctccctcgt gcgctctcct gttccgaccc   4560
tgccgcttac cggatacctg tccgcctttc tcccttcggg aagcgtggcg ctttctcata   4620
gctcacgctg taggtatctc agttcggtgt aggtcgttcg ctccaagctg ggctgtgtgc   4680
acgaaccccc cgttcagccc gaccgctgcg ccttatccgg taactatcgt cttgagtcca   4740
acccggtaag acacgactta tcgccactgg cagcagccac tggtaacagg attagcagag   4800
cgaggtatgt aggcggtgct acagagttct tgaagtggtg gcctaactac ggctacacta   4860
gaaggacagt atttggtatc tgcgctctgc tgaagccagt taccttcgga aaaagagttg   4920
gtagctcttg atccggcaaa caaaccaccg ctggtagcgg tggttttttt gtttgcaagc   4980
agcagattac gcgcagaaaa aaaggatctc aagaagatcc tttgatcttt tctacggggt   5040
ctgacgctca gtggaacgaa aactcacgtt aagggatttt ggtcatgaga ttatcaaaaa   5100
ggatcttcac ctagatcctt ttaaaggccg gccgcggccg ccatcggcat ttttcttttgc   5160
gtttttattt gttaactgtt aattgtcctt gttcaaggat gctgtctttg acaacagatg   5220
ttttcttgcc tttgatgttc agcaggaagc tcggcgcaaa cgttgattgt ttgtctgcgt   5280
agaatcctct gtttgtcata tagcttgtaa tcacgacatt gtttcctttc gcttgaggta   5340
cagcgaagtg tgagtaagta aaggttacat cgttaggatc aagatccatt tttaacacaa   5400
ggccagtttt gttcagcggc ttgtatgggc cagttaaaga attagaaaca taaccaagca   5460
tgtaaatatc gttagacgta atgccgtcaa tcgtcatttt tgatccgcgg gagtcagtga   5520
acaggtacca tttgccgttc attttaaaga cgttcgcgcg ttcaatttca tctgttactg   5580
tgttagatgc aatcagcggt ttcatcactt ttttcagtgt gtaatcatcg tttagctcaa   5640
tcataccgag agcgccgttt gctaactcag ccgtgcgttt tttatcgctt tgcagaagtt   5700
tttgactttc ttgacggaag aatgatgtgc ttttgccata gtatgctttg ttaaataaag   5760
attcttcgcc ttggtagcca tcttcagttc cagtgtttgc ttcaaatact aagtatttgt   5820
ggcctttatc ttctacgtag tgaggatctc tcagcgtatg gttgtcgcct gagctgtagt   5880
tgccttcatc gatgaactgc tgtacatttt gatacgtttt tccgtcaccg tcaaagattg   5940
atttataatc ctctacaccg ttgatgttca aagagctgtc tgatgctgat acgttaactt   6000
gtgcagttgt cagtgtttgt ttgccgtaat gtttaccgga gaaatcagtg tagaataaac   6060
ggatttttcc gtcagatgta aatgtggctg aacctgacca ttcttgtgtt tggtctttta   6120
ggatagaatc atttgcatcg aatttgtcgc tgtctttaaa gacgcggcca gcgtttttcc   6180
agctgtcaat agaagtttcg ccgacttttt gatagaacat gtaaatcgat gtgtcatccg   6240
catttttagg atctccggct aatgcaaaga cgatgtggta gccgtgatag tttgcgacag   6300
tgccgtcagc gttttgtaat ggccagctgt cccaaacgtc caggcctttt gcagaagaga   6360
tatttttaat tgtggacgaa tcaaattcag aaacttgata tttttcattt ttttgctgtt   6420
cagggatttg cagcatatca tggcgtgtaa tatgggaaat gccgtatgtt tccttatatg   6480
gcttttggtt cgtttctttc gcaaacgctt gagttgcgcc tcctgccagc agtgcggtag   6540
taaaggttaa tactgttgct tgttttgcaa actttttgat gttcatcgtt catgtctcct   6600
tttttatgta ctgtgttagc ggtctgcttc ttccagccct cctgtttgaa gatggcaagt   6660
tagttacgca caataaaaaa agacctaaaa tatgtaaggg gtgacgccaa agtatacact   6720
ttgcccttta cacattttag gtcttgcctg ctttatcagt aacaaacccg cgcgatttac   6780
ttttcgacct cattctatta gactctcgtt tggattgcaa ctggtctatt ttcctctttt   6840
gtttgataga aaatcataaa aggatttgca gactacgggc ctaaagaact aaaaaatcta   6900
```

tctgtttctt ttcattctct gtatttttta tagtttctgt tgcatgggca taaagttgcc 6960
tttttaatca caattcagaa aatatcataa tatctcattt cactaaataa tagtgaacgg 7020
caggtatatg tgatgggtta aaaaggatcg gcggccgctc gatttaaatc 7070

<210> SEQ ID NO 29
<211> LENGTH: 6625
<212> TYPE: DNA
<213> ORGANISM: artificial
<220> FEATURE:
<223> OTHER INFORMATION: Plasmid pH484

<400> SEQUENCE: 29
tcgagaggcc tgacgtcggg cccggtaccg ttgctcgctg atctttcggc ttaacaactt 60
tgtattcaat cagtcgggca tagaaagaaa acgcaatgat ataggaacca actgccgcca 120
aaaccagcca cacagagttg attgtttcgc cacgggagaa agcgattgct ccccaaccca 180
ccgccgcgat aaccccaaag acaaggagac caacgcgggc ggtcggtgac attttagggg 240
acttcttcac gcctactgga aggtcagtag cgttgctgta caccaaatca tcgtcattga 300
tgttgtcagt ctgttttatg gtcacgatct ttactgtttt ctcttcgggt cgtttcaaag 360
ccactatgcg tagaaacagc gggcagaaac agcgggcaga aactgtgtgc agaaatgcat 420
gcagaaaaag gaaagttcgg ccagatgggt gtttctgtat gccgatgatc ggatctttga 480
cagctgggta tgcgacaaat caccgagagt tgttaattct taacaatgga aaagtaacat 540
tgagagatga tttataccat cctgcaccat ttagagtggg gctagtcata cccccataac 600
cctagctgta cgcaatcgat ttcaaatcag ttggaaaaag tcaagaaaat tacccgagac 660
atatgcggct taaagtttgg ctgccatgtg aatttttagc accctcaaca gttgagtgct 720
ggcactctcg agggtagagt gccaaatagg ttgtttgaca cacagttgtt cacccgcgac 780
gacggctgtg ctggaaaccc acaaccggca cacacaaaat ttttctcatg gccgttaccc 840
tgcgaatgtc cacagggtag ctggtagttt gaaaatcaac gccgttgccc ttaggattca 900
gtaactggca cattttgtaa tgcgctagat ctgtgtgctc agtcttccag gctgcttatc 960
acagtgaaag caaaaccaat tcgtggctgc gaaagtcgta gccaccacga agtccaggag 1020
gacatacaat gccaaagtac gacaattcca atgctgacca gtggggcttt gaaacccgct 1080
ccattcacgc aggccagtca gtagacgcac agaccagcgc acgaaacctt ccgatctacc 1140
aatccaccgc tttcgtgttc gactccgctg agcacgccaa gcagcgtttc gcacttgagg 1200
atctaggccc tgtttactcc cgcctcacca acccaaccgt tgaggctttg gaaaaccgca 1260
tcgcttccct cgaaggtggc gtccacgctg tagcgttctc ctccggacag gccgcaacca 1320
ccaacgccat tttgaacctg gcaggagcgg gcgaccacat cgtcacctcc ccacgcctct 1380
acggtggcac cgagactcta ttccttatca ctcttaaccg cctgggtatc gatgtttcct 1440
tcgtggaaaa ccccgacgac cctgagtcct ggcaggcagc cgttcagcca aacaccaaag 1500
cattcttcgg cgagactttc gccaacccac aggcagacgt cctggatatt cctgcggtgg 1560
ctgaagttgc gcaccgcaac agcgttccac tgatcatcga caacaccatc gctaccgcag 1620
cgctcgtgcg cccgctcgag ctcggcgcag acgttgtcgt cgcttccctc accaagttct 1680
acaccggcaa cggctccgga ctgggcggcg tgcttatcga cggcggaaag ttcgattgga 1740
ctgtcgaaaa ggatggaaag ccagtattcc cctacttcgt cactccagat gctgcttacc 1800
acggattgaa gtacgcagac cttggtgcac cagccttcgg cctcaaggtt cgcgttggcc 1860
ttctacgcga caccggctcc accctctccg cattcaacgc atgggctgca gtccagggca 1920

-continued

```
tcgacaccct ttccctgcgc ctggagcgcc acaacgaaaa cgccatcaag gttgcagaat   1980
tcctcaacaa ccacgagaag gtggaaaagg ttaacttcgc aggcctgaag gattcccctt   2040
ggtacgcaac caaggaaaag cttggcctga agtacaccgg ctccgttctc accttcgaga   2100
tcaagggcgg caaggatgag gcttgggcat ttatcgacgc cctgaagcta cactccaacc   2160
ttgcaaacat cggcgatgtt cgctccctcg ttgttcaccc agcaaccacc acccattcac   2220
agtccgacga agctggcctg gcacgcgcgg gcgttaccca gtccaccgtc cgcctgtccg   2280
ttggcatcga gaccattgat gatatcatcg ctgacctcga aggcggcttt gctgcaatct   2340
agcactagtt cggacctagg gatatcgtcg acatcgatgc tcttctgcgt taattaacaa   2400
ttgggatcct ctagacccgg gatttaaatc gctagcgggc tgctaaagga agcggaacac   2460
gtagaaagcc agtccgcaga aacggtgctg accccggatg aatgtcagct actgggctat   2520
ctggacaagg gaaaacgcaa gcgcaaagag aaagcaggta gcttgcagtg ggcttacatg   2580
gcgatagcta gactgggcgg ttttatggac agcaagcgaa ccggaattgc cagctggggc   2640
gccctctggt aaggttggga agccctgcaa agtaaactgg atggctttct tgccgccaag   2700
gatctgatgg cgcaggggat caagatctga tcaagagaca ggatgaggat cgtttcgcat   2760
gattgaacaa gatggattgc acgcaggttc tccggccgct tgggtggaga ggctattcgg   2820
ctatgactgg gcacaacaga caatcggctg ctctgatgcc gccgtgttcc ggctgtcagc   2880
gcaggggcgc ccggttcttt ttgtcaagac cgacctgtcc ggtgccctga atgaactgca   2940
ggacgaggca gcgcggctat cgtggctggc cacgacgggc gttccttgcg cagctgtgct   3000
cgacgttgtc actgaagcgg gaagggactg gctgctattg ggcgaagtgc cggggcagga   3060
tctcctgtca tctcaccttg ctcctgccga gaaagtatcc atcatggctg atgcaatgcg   3120
gcggctgcat acgcttgatc cggctacctg cccattcgac caccaagcga aacatcgcat   3180
cgagcgagca cgtactcgga tggaagccgg tcttgtcgat caggatgatc tggacgaaga   3240
gcatcagggg ctcgcgccag ccgaactgtt cgccaggctc aaggcgcgca tgcccgacgg   3300
cgaggatctc gtcgtgaccc atggcgatgc ctgcttgccg aatatcatgg tggaaaatgg   3360
ccgcttttct ggattcatcg actgtggccg gctgggtgtg gcggaccgct atcaggacat   3420
agcgttggct acccgtgata ttgctgaaga gcttggcggc gaatgggctg accgcttcct   3480
cgtgctttac ggtatcgccg ctcccgattc gcagcgcatc gccttctatc gccttcttga   3540
cgagttcttc tgagcgggac tctggggttc gaaatgaccg accaagcgac gcccaacctg   3600
ccatcacgag atttcgattc caccgccgcc ttctatgaaa ggttgggctt cggaatcgtt   3660
ttccgggacg ccggctggat gatcctccag cgcggggatc tcatgctgga gttcttcgcc   3720
cacgctagcg gcgcgccggc cggcccggtg tgaaataccg cacagatgcg taaggagaaa   3780
ataccgcatc aggcgctctt ccgcttcctc gctcactgac tcgctgcgct cggtcgttcg   3840
gctgcggcga gcggtatcag ctcactcaaa ggcggtaata cggttatcca cagaatcagg   3900
ggataacgca ggaaagaaca tgtgagcaaa aggccagcaa aaggccagga accgtaaaaa   3960
ggccgcgttg ctggcgtttt tccataggct ccgcccccct gacgagcatc acaaaaatcg   4020
acgctcaagt cagaggtggc gaaacccgac aggactataa agataccagg cgtttccccc   4080
tggaagctcc ctcgtgcgct ctcctgttcc gaccctgccg cttaccggat acctgtccgc   4140
ctttctccct tcgggaagcg tggcgctttc tcatagctca cgctgtaggt atctcagttc   4200
ggtgtaggtc gttcgctcca agctgggctg tgtgcacgaa ccccccgttc agcccgaccg   4260
ctgcgcctta tccggtaact atcgtcttga gtccaacccg gtaagacacg acttatcgcc   4320
```

```
actggcagca gccactggta acaggattag cagagcgagg tatgtaggcg gtgctacaga   4380

gttcttgaag tggtggccta actacggcta cactagaagg acagtatttg gtatctgcgc   4440

tctgctgaag ccagttacct tcggaaaaag agttggtagc tcttgatccg gcaaacaaac   4500

caccgctggt agcggtggtt tttttgtttg caagcagcag attacgcgca gaaaaaaagg   4560

atctcaagaa gatcctttga tcttttctac ggggtctgac gctcagtgga acgaaaactc   4620

acgttaaggg attttggtca tgagattatc aaaaaggatc ttcacctaga tccttttaaa   4680

ggccggccgc ggccgccatc ggcattttct tttgcgtttt tatttgttaa ctgttaattg   4740

tccttgttca aggatgctgt ctttgacaac agatgttttc ttgcctttga tgttcagcag   4800

gaagctcggc gcaaacgttg attgtttgtc tgcgtagaat cctctgtttg tcatatagct   4860

tgtaatcacg acattgtttc ctttcgcttg aggtacagcg aagtgtgagt aagtaaaggt   4920

tacatcgtta ggatcaagat ccatttttaa cacaaggcca gttttgttca gcggcttgta   4980

tgggccagtt aaagaattag aaacataacc aagcatgtaa atatcgttag acgtaatgcc   5040

gtcaatcgtc atttttgatc cgcgggagtc agtgaacagg taccatttgc cgttcatttt   5100

aaagacgttc gcgcgttcaa tttcatctgt tactgtgtta gatgcaatca gcggtttcat   5160

cactttttc agtgtgtaat catcgtttag ctcaatcata ccgagagcgc cgtttgctaa   5220

ctcagccgtg cgttttttat cgctttgcag aagtttttga ctttcttgac ggaagaatga   5280

tgtgcttttg ccatagtatg ctttgttaaa taaagattct tcgccttggt agccatcttc   5340

agttccagtg tttgcttcaa atactaagta tttgtggcct ttatcttcta cgtagtgagg   5400

atctctcagc gtatggttgt cgcctgagct gtagttgcct tcatcgatga actgctgtac   5460

attttgatac gtttttccgt caccgtcaaa gattgattta taatcctcta caccgttgat   5520

gttcaaagag ctgtctgatg ctgatacgtt aacttgtgca gttgtcagtg tttgtttgcc   5580

gtaatgttta ccggagaaat cagtgtagaa taaacggatt tttccgtcag atgtaaatgt   5640

ggctgaacct gaccattctt gtgtttggtc ttttaggata gaatcatttg catcgaattt   5700

gtcgctgtct ttaaagacgc ggccagcgtt tttccagctg tcaatagaag tttcgccgac   5760

tttttgatag aacatgtaaa tcgatgtgtc atccgcattt ttaggatctc cggctaatgc   5820

aaagacgatg tggtagccgt gatagtttgc gacagtgccg tcagcgtttt gtaatggcca   5880

gctgtcccaa acgtccaggc cttttgcaga agagatattt ttaattgtgg acgaatcaaa   5940

ttcagaaact tgatattttt catttttttg ctgttcaggg atttgcagca tatcatggcg   6000

tgtaatatgg gaaatgccgt atgtttcctt atatggcttt tggttcgttt ctttcgcaaa   6060

cgcttgagtt gcgcctcctg ccagcagtgc ggtagtaaag gttaatactg ttgcttgttt   6120

tgcaaacttt ttgatgttca tcgttcatgt ctcctttttt atgtactgtg ttagcggtct   6180

gcttcttcca gccctcctgt ttgaagatgg caagttagtt acgcacaata aaaaaagacc   6240

taaaatatgt aaggggtgac gccaaagtat acactttgcc ctttacacat tttaggtctt   6300

gcctgcttta tcagtaacaa acccgcgcga tttacttttc gacctcattc tattagactc   6360

tcgtttggat tgcaactggt ctattttcct cttttgtttg atagaaaatc ataaaaggat   6420

ttgcagacta cgggcctaaa gaactaaaaa atctatctgt ttcttttcat tctctgtatt   6480

ttttatagtt tctgttgcat gggcataaag ttgccttttt aatcacaatt cagaaaatat   6540

cataatatct catttcacta aataatagtg aacggcaggt atatgtgatg ggttaaaaag   6600

gatcggcggc cgctcgattt aaatc                                         6625
```

<210> SEQ ID NO 30

<211> LENGTH: 363
<212> TYPE: DNA
<213> ORGANISM: artificial
<220> FEATURE:
<223> OTHER INFORMATION: Promoter P497 P1284 = PgrESPEFTu

<400> SEQUENCE: 30

```
cggcttaaag tttggctgcc atgtgaattt ttagcaccct caacagttga gtgctggcac     60

tctcgagggt agagtgccaa ataggttgtt tgacacacag ttgttcaccc gcgacgacgg    120

ctgtgctgga aacccacaac cggcacacac aaaatttttc tcatggccgt taccctgcga    180

atgtccacag ggtagctggt agtttgaaaa tcaacgccgt tgcccttagg attcagtaac    240

tggcacattt tgtaatgcgc tagatctgtg tgctcagtct tccaggctgc ttatcacagt    300

gaaagcaaaa ccaattcgtg gctgcgaaag tcgtagccac cacgaagtcc aggaggacat    360

aca                                                                  363
```

<210> SEQ ID NO 31
<211> LENGTH: 6350
<212> TYPE: DNA
<213> ORGANISM: artificial
<220> FEATURE:
<223> OTHER INFORMATION: Plasmid: pH491

<400> SEQUENCE: 31

```
tcgagctcgg cgcagacgtt gtcgtcgctt ccctcaccaa gttctacacc ggcaacggct     60

ccggactggg cggcgtgctt atcgacggcg gaaagttcga ttggactgtc gaaaaggatg    120

gaaagccagt attcccctac ttcgtcactc cagatgctgc ttaccacgga ttgaagtacg    180

cagaccttgg tgcaccagcc ttcggcctca aggttcgcgt tggccttcta cgcgacaccg    240

gctccaccct ctccgcattc aacgcatggg ctgcagtcca gggcatcgac acccctttccc    300

tgcgcctgga gcgccacaac gaaaacgcca tcaaggttgc agaattcctc aacaaccacg    360

agaaggtgga aaaggttaac ttcgcaggcc tgaaggattc cccttggtac gcaaccaagg    420

aaaagcttgg cctgaagtac accggctccg ttctcacctt cgagatcaag ggcggcaagg    480

atgaggcttg ggcatttatc gacgccctga agctacactc caaccttgca aacatcggcg    540

atgttcgctc cctcgttgtt cacccagcaa ccaccaccca ttcacagtcc gacgaagctg    600

gcctggcacg cgcgggcgtt acccagtcca ccgtccgcct gtccgttggc atcgagacca    660

ttgatgatat catcgctgac ctcgaaggcg gctttgctgc aatctagcac tagttcggac    720

ctagggatat cgtcgagagc tgccaattat tccgggcttg tgacccgcta cccgataaat    780

aggtcggctg aaaaatttcg ttgcaatatc aacaaaaagg cctatcattg ggaggtgtcg    840

caccaagtac ttttgcgaag cgccatctga cggattttca aaagatgtat atgctcggtg    900

cggaaaccta cgaaaggatt ttttacccat gcccaccctc gcgccttcag gtcaacttga    960

aatccaagcg atcggtgatg tctccaccga agccggagca atcattacaa acgctgaaat   1020

cgcctatcac cgctggggtg aataccgcgt agataaagaa ggacgcagca atgtcgttct   1080

catcgaacac gccctcactg gagattccaa cgcagccgat tggtgggctg acttgctcgg   1140

tcccggcaaa gccatcaaca ctgatattta ctgcgtgatc tgtaccaacg tcatcggtgg   1200

ttgcaacggt tccaccggac ctggctccat gcatccagat ggaaatttct ggggtaatcg   1260

cttccccgcc acgtccattc gtgatcaggt aaacgccgaa aaacaattcc tcgacgcact   1320

cggcatcacc acggtcgccg cagtacttgg tggttccatg ggtggtgccc gcaccctaga   1380

gtgggccgca atgtacccag aaactgttgg cgcagctgct gttcttgcag tttctgcacg   1440
```

cgccagcgcc tggcaaatcg gcattcaatc cgcccaaatt aaggcgattg aaaacgacca 1500
ccactggcac gaaggcaact actacgaatc cggctgcaac ccagccaccg gactcggcgc 1560
cgcccgacgc atcgcccacc tcacctaccg tggcgaacta gaaatcgacg aacgcttcgg 1620
caccaaagcc caaaagaacg aaaacccact cggtccctac cgcaagcccg accagcgctt 1680
cgccgtggaa tcctacttgg actaccaagc agacaagcta gtacagcgtt tcgacgccgg 1740
ctcctacgtc ttgctcaccg acgccctcaa ccgccacgac attggtcgcg accgcggagg 1800
cctcaacaag gcactcgaat ccatcaaagt tccagtcctt gtcgcaggcg tagataccga 1860
tattttgtac ccctaccacc agcaagaaca cctctccaga aacctgggaa atctactggc 1920
aatggcaaaa atcgtatccc ctgtcggcca cgatgctttc ctcaccgaaa gccgccaaat 1980
ggatcgcatc gtgaggaact tcttcagcct catctcccca gacgaagaca acccttcgac 2040
ctacatcgag ttctacatct aacatatgac tagttcggac ctagggatat cgtcgacatc 2100
gatgctcttc tgcgttaatt aacaattggg atcctctaga cccgggattt aaatcgctag 2160
cgggctgcta aaggaagcgg aacacgtaga aagccagtcc gcagaaacgg tgctgacccc 2220
ggatgaatgt cagctactgg gctatctgga caagggaaaa cgcaagcgca aagagaaagc 2280
aggtagcttg cagtgggctt acatggcgat agctagactg ggcggtttta tggacagcaa 2340
gcgaaccgga attgccagct ggggcgccct ctggtaaggt tgggaagccc tgcaaagtaa 2400
actggatggc tttcttgccg ccaaggatct gatggcgcag gggatcaaga tctgatcaag 2460
agacaggatg aggatcgttt cgcatgattg aacaagatgg attgcacgca ggttctccgg 2520
ccgcttgggt ggagaggcta ttcggctatg actgggcaca acagacaatc ggctgctctg 2580
atgccgccgt gttccggctg tcagcgcagg ggcgcccggt tctttttgtc aagaccgacc 2640
tgtccggtgc cctgaatgaa ctgcaggacg aggcagcgcg gctatcgtgg ctggccacga 2700
cgggcgttcc ttgcgcagct gtgctcgacg ttgtcactga agcgggaagg gactggctgc 2760
tattgggcga agtgccgggg caggatctcc tgtcatctca ccttgctcct gccgagaaag 2820
tatccatcat ggctgatgca atgcggcggc tgcatacgct tgatccggct acctgcccat 2880
tcgaccacca agcgaaacat cgcatcgagc gagcacgtac tcggatggaa gccggtcttg 2940
tcgatcagga tgatctggac gaagagcatc aggggctcgc gccagccgaa ctgttcgcca 3000
ggctcaaggc gcgcatgccc gacggcgagg atctcgtcgt gacccatggc gatgcctgct 3060
tgccgaatat catggtggaa aatggccgct tttctggatt catcgactgt ggccggctgg 3120
gtgtggcgga ccgctatcag gacatagcgt tggctacccg tgatattgct gaagagcttg 3180
gcggcgaatg ggctgaccgc ttcctcgtgc tttacggtat cgccgctccc gattcgcagc 3240
gcatcgcctt ctatcgcctt cttgacgagt tcttctgagc gggactctgg ggttcgaaat 3300
gaccgaccaa gcgacgccca acctgccatc acgagatttc gattccaccg ccgccttcta 3360
tgaaaggttg ggcttcggaa tcgttttccg ggacgccggc tggatgatcc tccagcgcgg 3420
ggatctcatg ctggagttct tcgcccacgc tagcggcgcg ccggccggcc cggtgtgaaa 3480
taccgcacag atgcgtaagg agaaaatacc gcatcaggcg ctcttccgct tcctcgctca 3540
ctgactcgct gcgctcggtc gttcggctgc ggcgagcggt atcagctcac tcaaaggcgg 3600
taatacggtt atccacagaa tcaggggata acgcaggaaa gaacatgtga gcaaaaggcc 3660
agcaaaaggc caggaaccgt aaaaaggccg cgttgctggc gtttttccat aggctccgcc 3720
cccctgacga gcatcacaaa aatcgacgct caagtcagag gtggcgaaac ccgacaggac 3780
tataaagata ccaggcgttt ccccctggaa gctccctcgt gcgctctcct gttccgaccc 3840

-continued

```
tgccgcttac cggatacctg tccgcctttc tcccttcggg aagcgtggcg ctttctcata   3900
gctcacgctg taggtatctc agttcggtgt aggtcgttcg ctccaagctg ggctgtgtgc   3960
acgaaccccc cgttcagccc gaccgctgcg ccttatccgg taactatcgt cttgagtcca   4020
acccggtaag acacgactta tcgccactgg cagcagccac tggtaacagg attagcagag   4080
cgaggtatgt aggcggtgct acagagttct tgaagtggtg gcctaactac ggctacacta   4140
gaaggacagt atttggtatc tgcgctctgc tgaagccagt taccttcgga aaaagagttg   4200
gtagctcttg atccggcaaa caaaccaccg ctggtagcgg tggttttttt gtttgcaagc   4260
agcagattac gcgcagaaaa aaaggatctc aagaagatcc tttgatcttt tctacggggt   4320
ctgacgctca gtggaacgaa aactcacgtt aagggatttt ggtcatgaga ttatcaaaaa   4380
ggatcttcac ctagatcctt ttaaaggccg gccgcggccg ccatcggcat tttcttttgc   4440
gtttttattt gttaactgtt aattgtcctt gttcaaggat gctgtctttg acaacagatg   4500
ttttcttgcc tttgatgttc agcaggaagc tcggcgcaaa cgttgattgt ttgtctgcgt   4560
agaatcctct gtttgtcata tagcttgtaa tcacgacatt gtttcctttc gcttgaggta   4620
cagcgaagtg tgagtaagta aaggttacat cgttaggatc aagatccatt tttaacacaa   4680
ggccagtttt gttcagcggc ttgtatgggc cagttaaaga attagaaaca taaccaagca   4740
tgtaaatatc gttagacgta atgccgtcaa tcgtcatttt tgatccgcgg gagtcagtga   4800
acaggtacca tttgccgttc attttaaaga cgttcgcgcg ttcaatttca tctgttactg   4860
tgttagatgc aatcagcggt ttcatcactt ttttcagtgt gtaatcatcg tttagctcaa   4920
tcataccgag agcgccgttt gctaactcag ccgtgcgttt tttatcgctt tgcagaagtt   4980
tttgactttc ttgacggaag aatgatgtgc ttttgccata gtatgctttg ttaaataaag   5040
attcttcgcc ttggtagcca tcttcagttc cagtgtttgc ttcaaatact aagtatttgt   5100
ggcctttatc ttctacgtag tgaggatctc tcagcgtatg gttgtcgcct gagctgtagt   5160
tgccttcatc gatgaactgc tgtacatttt gatacgtttt tccgtcaccg tcaaagattg   5220
atttataatc ctctacaccg ttgatgttca aagagctgtc tgatgctgat acgttaactt   5280
gtgcagttgt cagtgtttgt ttgccgtaat gtttaccgga gaaatcagtg tagaataaac   5340
ggatttttcc gtcagatgta aatgtggctg aacctgacca ttcttgtgtt tggtctttta   5400
ggatagaatc atttgcatcg aatttgtcgc tgtctttaaa gacgcggcca gcgtttttcc   5460
agctgtcaat agaagtttcg ccgacttttt gatagaacat gtaaatcgat gtgtcatccg   5520
catttttagg atctccggct aatgcaaaga cgatgtggta gccgtgatag tttgcgacag   5580
tgccgtcagc gttttgtaat ggccagctgt cccaaacgtc caggcctttt gcagaagaga   5640
tatttttaat tgtggacgaa tcaaattcag aaacttgata tttttcattt ttttgctgtt   5700
cagggatttg cagcatatca tggcgtgtaa tatgggaaat gccgtatgtt tccttatatg   5760
gcttttggtt cgtttctttc gcaaacgctt gagttgcgcc tcctgccagc agtgcggtag   5820
taaaggttaa tactgttgct tgttttgcaa actttttgat gttcatcgtt catgtctcct   5880
tttttatgta ctgtgttagc ggtctgcttc ttccagccct cctgtttgaa gatggcaagt   5940
tagttacgca caataaaaaa agacctaaaa tatgtaaggg gtgacgccaa agtatacact   6000
ttgcccttta cacattttag gtcttgcctg ctttatcagt aacaaacccg cgcgatttac   6060
ttttcgacct cattctatta gactctcgtt tggattgcaa ctggtctatt ttcctctttt   6120
gtttgataga aaatcataaa aggatttgca gactacgggc ctaaagaact aaaaaatcta   6180
tctgtttctt ttcattctct gtatttttta tagtttctgt tgcatgggca taaagttgcc   6240
```

-continued tttttaatca caattcagaa aatatcataa tatctcattt cactaaataa tagtgaacgg 6300
caggtatatg tgatgggtta aaaaggatcg gcggccgctc gatttaaatc 6350

<210> SEQ ID NO 32
<211> LENGTH: 5477
<212> TYPE: DNA
<213> ORGANISM: artificial
<220> FEATURE:
<223> OTHER INFORMATION: Plasmid: pH429

<400> SEQUENCE: 32
tcgagctctc caatctccac tgaggtactt aatccttccg gggaattcgg gcgcttaaat 60
cgagaaatta ggccatcacc ttttaataac aatacaatga ataattggaa taggtcgaca 120
cctttggagc ggagccggtt aaaattggca gcattcaccg aaagaaaagg agaaccacat 180
gcttgcccta ggttggatta catggatcat tattggtggt ctagctggtt ggattgcctc 240
caagattaaa ggcactgatg ctcagcaagg aattttgctg aacatagtcg tcggtattat 300
cggtggtttg ttaggcggct ggctgcttgg aatcttcgga gtggatgttg ccggtggcgg 360
cttgatcttc agcttcatca catgtctgat tggtgctgtc attttgctga cgatcgtgca 420
gttcttcact cggaagaagt aatctgcttt aaatccgtag ggcctgttga tatttcgata 480
tcaacaggcc ttttggtcat tttggggtgg aaaaagcgct agacttgcct gtggattaaa 540
actatacgaa ccggtttgtc tatattggtg ttagacagtt cgtcgtatct tgaaacagac 600
caacccgaaa ggacgtggcc gaacgtggct gctagctaat ccttgatggt ggacttgctg 660
gatctcgatt ggtccacaac atcagtcctc ttgagacggc tcgcgatttg gctcggcagt 720
tgttgtcggc tccacctgcg gactactcaa tttagtttct tcattttccg aaggggtatc 780
ttcgttgggg gaggcgtcga taagcccctt ctttttagct ttaacctcag cgcgacgctg 840
ctttaagcgc tgcatggcgg cgcggttcat ttcacgttgc gtttcgcgcc tcttgttcgc 900
gatttctttg cgggcctgtt ttgcttcgtt gatttcggca gtacgggttt tggtgagttc 960
cacgtttgtt gcgtgaagcg ttgaggcgtt ccatggggtg agaatcatca gggcgcggtt 1020
tttgcgtcgt gtccacagga agatgcgctt ttctttttgt tttgcgcggt agatgtcgcg 1080
ctgctctagg tggtgcactt tgaaatcgtc ggtaagtggg tatttgcgtt ccaaaatgac 1140
catcatgatg attgtttgga ggagcgtcca caggttgttg ctgacgcgtc atatgactag 1200
ttcggaccta gggatatcgt cgacatcgat gctcttctgc gttaattaac aattgggatc 1260
ctctagaccc gggatttaaa tcgctagcgg gctgctaaag gaagcggaac acgtagaaag 1320
ccagtccgca gaaacggtgc tgaccccgga tgaatgtcag ctactgggct atctggacaa 1380
gggaaaacgc aagcgcaaag agaaagcagg tagcttgcag tgggcttaca tggcgatagc 1440
tagactgggc ggttttatgg acagcaagcg aaccggaatt gccagctggg gcgccctctg 1500
gtaaggttgg gaagccctgc aaagtaaact ggatggcttt cttgccgcca aggatctgat 1560
ggcgcagggg atcaagatct gatcaagaga caggatgagg atcgtttcgc atgattgaac 1620
aagatggatt gcacgcaggt tctccggccg cttgggtgga gaggctattc ggctatgact 1680
gggcacaaca gacaatcggc tgctctgatg ccgccgtgtt ccggctgtca gcgcaggggc 1740
gcccggttct ttttgtcaag accgacctgt ccggtgccct gaatgaactg caggacgagg 1800
cagcgcggct atcgtggctg gccacgacgg gcgttccttg cgcagctgtg ctcgacgttg 1860
tcactgaagc gggaagggac tggctgctat tgggcgaagt gccggggcag gatctcctgt 1920
catctcacct tgctcctgcc gagaaagtat ccatcatggc tgatgcaatg cggcggctgc 1980

-continued

```
atacgcttga tccggctacc tgcccattcg accaccaagc gaaacatcgc atcgagcgag   2040
cacgtactcg gatggaagcc ggtcttgtcg atcaggatga tctggacgaa gagcatcagg   2100
ggctcgcgcc agccgaactg ttcgccaggc tcaaggcgcg catgcccgac ggcgaggatc   2160
tcgtcgtgac ccatggcgat gcctgcttgc cgaatatcat ggtggaaaat ggccgctttt   2220
ctggattcat cgactgtggc cggctgggtg tggcggaccg ctatcaggac atagcgttgg   2280
ctacccgtga tattgctgaa gagcttggcg gcgaatgggc tgaccgcttc ctcgtgcttt   2340
acggtatcgc cgctcccgat tcgcagcgca tcgccttcta tcgccttctt gacgagttct   2400
tctgagcggg actctggggt tcgaaatgac cgaccaagcg acgcccaacc tgccatcacg   2460
agatttcgat tccaccgccg ccttctatga aaggttgggc ttcggaatcg ttttccggga   2520
cgccggctgg atgatcctcc agcgcgggga tctcatgctg gagttcttcg cccacgctag   2580
cggcgcgccg gccggcccgg tgtgaaatac cgcacagatg cgtaaggaga aaataccgca   2640
tcaggcgctc ttccgcttcc tcgctcactg actcgctgcg ctcggtcgtt cggctgcggc   2700
gagcggtatc agctcactca aaggcggtaa tacggttatc cacagaatca ggggataacg   2760
caggaaagaa catgtgagca aaaggccagc aaaaggccag gaaccgtaaa aaggccgcgt   2820
tgctggcgtt tttccatagg ctccgccccc ctgacgagca tcacaaaaat cgacgctcaa   2880
gtcagaggtg gcgaaacccg acaggactat aaagatacca ggcgtttccc cctggaagct   2940
ccctcgtgcg ctctcctgtt ccgaccctgc cgcttaccgg atacctgtcc gcctttctcc   3000
cttcgggaag cgtggcgctt tctcatagct cacgctgtag gtatctcagt tcggtgtagg   3060
tcgttcgctc caagctgggc tgtgtgcacg aaccccccgt tcagcccgac cgctgcgcct   3120
tatccggtaa ctatcgtctt gagtccaacc cggtaagaca cgacttatcg ccactggcag   3180
cagccactgg taacaggatt agcagagcga ggtatgtagg cggtgctaca gagttcttga   3240
agtggtggcc taactacggc tacactagaa ggacagtatt tggtatctgc gctctgctga   3300
agccagttac cttcggaaaa agagttggta gctcttgatc cggcaaacaa accaccgctg   3360
gtagcggtgg tttttttgtt tgcaagcagc agattacgcg cagaaaaaaa ggatctcaag   3420
aagatccttt gatcttttct acggggtctg acgctcagtg gaacgaaaac tcacgttaag   3480
ggattttggt catgagatta tcaaaaagga tcttcaccta gatcctttta aaggccggcc   3540
gcggccgcca tcggcatttt cttttgcgtt tttatttgtt aactgttaat tgtccttgtt   3600
caaggatgct gtctttgaca acagatgttt tcttgccttt gatgttcagc aggaagctcg   3660
gcgcaaacgt tgattgtttg tctgcgtaga atcctctgtt tgtcatatag cttgtaatca   3720
cgacattgtt tcctttcgct tgaggtacag cgaagtgtga gtaagtaaag gttacatcgt   3780
taggatcaag atccattttt aacacaaggc cagttttgtt cagcggcttg tatgggccag   3840
ttaaagaatt agaaacataa ccaagcatgt aaatatcgtt agacgtaatg ccgtcaatcg   3900
tcatttttga tccgcgggag tcagtgaaca ggtaccattt gccgttcatt ttaaagacgt   3960
tcgcgcgttc aatttcatct gttactgtgt tagatgcaat cagcggtttc atcacttttt   4020
tcagtgtgta atcatcgttt agctcaatca taccgagagc gccgtttgct aactcagccg   4080
tgcgtttttt atcgctttgc agaagttttt gactttcttg acggaagaat gatgtgcttt   4140
tgccatagta tgctttgtta aataaagatt cttcgccttg gtagccatct tcagttccag   4200
tgtttgcttc aaatactaag tatttgtggc ctttatcttc tacgtagtga ggatctctca   4260
gcgtatggtt gtcgcctgag ctgtagttgc cttcatcgat gaactgctgt acattttgat   4320
acgtttttcc gtcaccgtca aagattgatt tataatcctc tacaccgttg atgttcaaag   4380
```

-continued agctgtctga tgctgatacg ttaacttgtg cagttgtcag tgtttgtttg ccgtaatgtt 4440
taccggagaa atcagtgtag aataaacgga tttttccgtc agatgtaaat gtggctgaac 4500
ctgaccattc ttgtgtttgg tcttttagga tagaatcatt tgcatcgaat ttgtcgctgt 4560
ctttaaagac gcggccagcg tttttccagc tgtcaataga agtttcgccg actttttgat 4620
agaacatgta aatcgatgtg tcatccgcat tttaggatc tccggctaat gcaaagacga 4680
tgtggtagcc gtgatagttt gcgacagtgc cgtcagcgtt ttgtaatggc cagctgtccc 4740
aaacgtccag gccttttgca gaagagatat ttttaattgt ggacgaatca aattcagaaa 4800
cttgatattt ttcatttttt tgctgttcag ggatttgcag catatcatgg cgtgtaatat 4860
gggaaatgcc gtatgtttcc ttatatggct tttggttcgt ttctttcgca aacgcttgag 4920
ttgcgcctcc tgccagcagt gcggtagtaa aggttaatac tgttgcttgt tttgcaaact 4980
ttttgatgtt catcgttcat gtctcctttt ttatgtactg tgttagcggt ctgcttcttc 5040
cagccctcct gtttgaagat ggcaagttag ttacgcacaa taaaaaaaga cctaaaatat 5100
gtaaggggtg acgccaaagt atacactttg ccctttacac attttaggtc ttgcctgctt 5160
tatcagtaac aaacccgcgc gatttacttt tcgacctcat tctattagac tctcgtttgg 5220
attgcaactg gtctattttc ctcttttgtt tgatagaaaa tcataaaagg atttgcagac 5280
tacgggccta aagaactaaa aaatctatct gtttcttttc attctctgta tttttatag 5340 tttctgttgc atgggcataa agttgccttt ttaatcacaa ttcagaaaat atcataaatat 5400 ctcatttcac taaataatag tgaacggcag gtatatgtga tgggttaaaa aggatcggcg 5460
gccgctcgat ttaaatc 5477

<210> SEQ ID NO 33
<211> LENGTH: 7534
<212> TYPE: DNA
<213> ORGANISM: artificial
<220> FEATURE:
<223> OTHER INFORMATION: Plasmid: pH447

<400> SEQUENCE: 33
tcgatttaaa tctcgagagg cctgacgtcg ggcccggtac cacgcgtcat atgactagtt 60
cggacctagg gatatcgtcg accggcttaa agtttggctg ccatgtgaat tttagcacc 120 ctcaacagtt gagtgctggc actctcgggg gtagagtgcc aaataggttg tttgacacac 180
agttgttcac ccgcgacgac ggctgtgctg gaaacccaca accggcacac acaaaatttt 240
tctcatggag ggattcatca tgacttccaa cttttcttcc actgtcgctg gtcttcctcg 300
catcggagcg aagcgtgaac tgaagttcgc gctcgaaggc tactggaatg gatcaattga 360
aggtcgcgaa cttgcgcaga ccgcccgcca attggtcaac actgcatcgg attctttgtc 420
tggattggat tccgttccgt ttgcaggacg ttcctactac gacgcaatgc tcgataccgc 480
cgctattttg ggtgtgctgc cggagcgttt tgatgacatc gctgatcatg aaaacgatgg 540
tctcccactg tggattgacc gctactttgg cgctgctcgc ggtactgaga ccctgcctgc 600
acaggcaatg accaagtggt ttgataccaa ctaccactac ctcgtgccgg agttgtctgc 660
ggatacacgt ttcgttttgg atgcgtccgc gctgattgag gatctccgtt gccagcaggt 720
tcgtggcgtt aatgcccgcc ctgttctggt tggtccactg actttccttt cccttgctcg 780
caccactgat ggttccaatc ctttggatca cctgcctgca ctgtttgagg tctacgagcg 840
cctcatcaag tctttcgata ctgagtgggt tcagatcgat gagcctgcgt tggtcaccga 900
tgttgctcct gaggttttgg agcaggtccg cgctggttac accactttgg ctaagcgcga 960

-continued

```
tggcgtgttt gtcaatactt acttcggctc tggcgatcag gcgctgaaca ctcttgcggg   1020
catcggcctt ggcgcgattg gcgttgactt ggtcacccat ggcgtcactg agcttgctgc   1080
gtggaagggt gaggagctgc tggttgcggg catcgttgat ggtcgtaaca tttggcgcac   1140
cgacctgtgt gctgctcttg cttccctgaa gcgcctggca gctcgcggcc caatcgcagt   1200
gtctacctct tgttcactgc tgcacgttcc ttacaccctc gaggctgaga acattgagcc   1260
tgaggtccgc gactggcttg ccttcggctc ggagaagatc accgaggtca agctgcttgc   1320
cgacgcccta gccggcaaca tcgacgcggc tgcgttcgat gcggcgtccg cagcaattgc   1380
ttctcgacgc acctccccac gcaccgcacc aatcacgcag gaactccctg gccgtagccg   1440
tggatccttc gacactcgtg ttacgctgca ggagaagtca ctggagcttc cagctctgcc   1500
aaccaccacc attggttctt tcccacagac cccatccatt cgttctgctc gcgctcgtct   1560
gcgcaaggaa tccatcactt tggagcagta cgaagaggca atgcgcgaag aaatcgatct   1620
ggtcatcgcc aagcaggaag aacttggtct tgatgtgttg gttcacggtg agccagagcg   1680
caacgacatg gttcagtact tctctgaact tctcgacggt ttcctctcaa ccgccaacgg   1740
ctgggtccaa agctacggct cccgctgtgt tcgtcctcca gtgttgttcg gaaacgtttc   1800
ccgcccagcg ccaatgactg tcaagtggtt ccagtacgca cagagcctga cccagaagca   1860
tgtcaaggga atgctcaccg gtccagtcac catccttgca tggtccttcg ttcgcgatga   1920
tcagccgctg gctaccactg ctgaccaggt tgcactggca ctgcgcgatg aaattaacga   1980
tctcatcgag gctggcgcga agatcatcca ggtggatgag cctgcgattc gtgaactgtt   2040
gccgctacga gacgtcgata agcctgccta cctgcagtgg tccgtggact ccttccgcct   2100
ggcgactgcc ggcgcacccg acgacgtcca aatccacacc cacatgtgct actccgagtt   2160
caacgaagtg atctcctcgg tcatcgcgtt ggatgccgat gtcaccacca tcgaagcagc   2220
acgttccgac atgcaggtcc tcgctgctct gaaatcttcc ggcttcgagc tcggcgtcgg   2280
acctggtgtg tgggatatcc actccccgcg cgttccttcc gcgcagaaag tggacggtct   2340
cctcgaggct gcactgcagt ccgtggatcc tcgccagctg tgggtcaacc cagactgtgg   2400
tctgaagacc cgtggatggc cagaagtgga agcttcccta aaggttctcg ttgagtccgc   2460
taagcaggct cgtgagaaaa tcggagcaac tatctaatct agagttctgt gaaaaacacc   2520
gtggggcagt ttctgcttcg cggtgttttt tatttgtggg gcactagacc cgggatttaa   2580
atcgctagcg ggctgctaaa ggaagcggaa cacgtagaaa gccagtccgc agaaacggtg   2640
ctgaccccgg atgaatgtca gctactgggc tatctggaca agggaaaacg caagcgcaaa   2700
gagaaagcag gtagcttgca gtgggcttac atggcgatag ctagactggg cggttttatg   2760
gacagcaagc gaaccggaat tgccagctgg ggcgccctct ggtaaggttg ggaagccctg   2820
caaagtaaac tggatggctt tcttgccgcc aaggatctga tggcgcaggg gatcaagatc   2880
tgatcaagag acaggatgag gatcgtttcg catgattgaa caagatggat tgcacgcagg   2940
ttctccggcc gcttgggtgg agaggctatt cggctatgac tgggcacaac agacaatcgg   3000
ctgctctgat gccgccgtgt tccggctgtc agcgcagggg cgcccggttc tttttgtcaa   3060
gaccgacctg tccggtgccc tgaatgaact gcaggacgag gcagcgcggc tatcgtggct   3120
ggccacgacg ggcgttcctt gcgcagctgt gctcgacgtt gtcactgaag cgggaaggga   3180
ctggctgcta ttgggcgaag tgccggggca ggatctcctg tcatctcacc ttgctcctgc   3240
cgagaaagta tccatcatgg ctgatgcaat gcggcggctg catacgcttg atccggctac   3300
ctgcccattc gaccaccaag cgaaacatcg catcgagcga gcacgtactc ggatggaagc   3360
```

```
cggtcttgtc gatcaggatg atctggacga agagcatcag gggctcgcgc cagccgaact   3420
gttcgccagg ctcaaggcgc gcatgcccga cggcgaggat ctcgtcgtga cccatggcga   3480
tgcctgcttg ccgaatatca tggtggaaaa tggccgcttt tctggattca tcgactgtgg   3540
ccggctgggt gtggcggacc gctatcagga catagcgttg gctacccgtg atattgctga   3600
agagcttggc ggcgaatggg ctgaccgctt cctcgtgctt tacggtatcg ccgctcccga   3660
ttcgcagcgc atcgccttct atcgccttct tgacgagttc ttctgagcgg gactctgggg   3720
ttcgaaatga ccgaccaagc gacgcccaac ctgccatcac gagatttcga ttccaccgcc   3780
gccttctatg aaaggttggg cttcggaatc gttttccggg acgccggctg gatgatcctc   3840
cagcgcgggg atctcatgct ggagttcttc gcccacgcta gcggcgcgcc ggccggcccg   3900
gtgtgaaata ccgcacagat gcgtaaggag aaaataccgc atcaggcgct cttccgcttc   3960
ctcgctcact gactcgctgc gctcggtcgt tcggctgcgg cgagcggtat cagctcactc   4020
aaaggcggta atacggttat ccacagaatc aggggataac gcaggaaaga acatgtgagc   4080
aaaaggccag caaaaggcca ggaaccgtaa aaaggccgcg ttgctggcgt ttttccatag   4140
gctccgcccc cctgacgagc atcacaaaaa tcgacgctca agtcagaggt ggcgaaaccc   4200
gacaggacta taaagatacc aggcgtttcc ccctggaagc tccctcgtgc gctctcctgt   4260
tccgaccctg ccgcttaccg gatacctgtc cgcctttctc ccttcgggaa gcgtggcgct   4320
ttctcatagc tcacgctgta ggtatctcag ttcggtgtag gtcgttcgct ccaagctggg   4380
ctgtgtgcac gaaccccccg ttcagcccga ccgctgcgcc ttatccggta actatcgtct   4440
tgagtccaac ccggtaagac acgacttatc gccactggca gcagccactg gtaacaggat   4500
tagcagagcg aggtatgtag gcggtgctac agagttcttg aagtggtggc ctaactacgg   4560
ctacactaga aggacagtat ttggtatctg cgctctgctg aagccagtta ccttcggaaa   4620
aagagttggt agctcttgat ccggcaaaca aaccaccgct ggtagcggtg gtttttttgt   4680
ttgcaagcag cagattacgc gcagaaaaaa aggatctcaa gaagatcctt tgatcttttc   4740
tacggggtct gacgctcagt ggaacgaaaa ctcacgttaa gggattttgg tcatgagatt   4800
atcaaaaagg atcttcacct agatcctttt aaaggccggc cgcggccgcg caaagtcccg   4860
cttcgtgaaa attttcgtgc cgcgtgattt tccgccaaaa actttaacga acgttcgtta   4920
taatggtgtc atgaccttca cgacgaagta ctaaaattgg cccgaatcat cagctatgga   4980
tctctctgat gtcgcgctgg agtccgacgc gctcgatgct gccgtcgatt taaaaacggt   5040
gatcggattt ttccgagctc tcgatacgac ggacgcgcca gcatcacgag actgggccag   5100
tgccgcgagc gacctagaaa ctctcgtggc ggatcttgag gagctggctg acgagctgcg   5160
tgctcggcca gcgccaggag gacgcacagt agtggaggat gcaatcagtt gcgcctactg   5220
cggtggcctg attcctcccc ggcctgaccc gcgaggacgg cgcgcaaaat attgctcaga   5280
tgcgtgtcgt gccgcagcca gccgcgagcg cgccaacaaa cgccacgccg aggagctgga   5340
ggcggctagg tcgcaaatgg cgctggaagt gcgtcccccg agcgaaattt tggccatggt   5400
cgtcacagag ctggaagcgg cagcgagaat tatcgcgatc gtggcggtgc ccgcaggcat   5460
gacaaacatc gtaaatgccg cgtttcgtgt gccgtggccg cccaggacgt gtcagcgccg   5520
ccaccacctg caccgaatcg gcagcagcgt cgcgcgtcga aaaagcgcac aggcggcaag   5580
aagcgataag ctgcacgaat acctgaaaaa tgttgaacgc cccgtgagcg gtaactcaca   5640
gggcgtcggc taacccccag tccaaacctg ggagaaagcg ctcaaaaatg actctagcgg   5700
attcacgaga cattgacaca ccggcctgga aattttccgc tgatctgttc gacacccatc   5760
```

ccgagctcgc gctgcgatca cgtggctgga cgagcgaaga ccgccgcgaa ttcctcgctc 5820
acctgggcag agaaaatttc cagggcagca agacccgcga cttcgccagc gcttggatca 5880
aagacccgga cacggagaaa cacagccgaa gttataccga gttggttcaa aatcgcttgc 5940
ccggtgccag tatgttgctc tgacgcacgc gcagcacgca gccgtgcttg tcctggacat 6000
tgatgtgccg agccaccagg ccggcgggaa aatcgagcac gtaaaccccg aggtctacgc 6060
gattttggag cgctgggcac gcctggaaaa agcgccagct tggatcggcg tgaatccact 6120
gagcgggaaa tgccagctca tctggctcat tgatccggtg tatgccgcag caggcatgag 6180
cagcccgaat atgcgcctgc tggctgcaac gaccgaggaa atgacccgcg ttttcggcgc 6240
tgaccaggct tttcacata ggctgagccg tggccactgc actctccgac gatcccagcc 6300
gtaccgctgg catgcccagc acaatcgcgt ggatcgccta gctgatctta tggaggttgc 6360
tcgcatgatc tcaggcacag aaaaacctaa aaaacgctat gagcaggagt tttctagcgg 6420
acgggcacgt atcgaagcgg caagaaaagc cactgcggaa gcaaaagcac ttgccacgct 6480
tgaagcaagc ctgccgagcg ccgctgaagc gtctggagag ctgatcgacg gcgtccgtgt 6540
cctctggact gctccagggc gtgccgcccg tgatgagacg gcttttcgcc acgctttgac 6600
tgtgggatac cagttaaaag cggctggtga gcgcctaaaa gacaccaagg gtcatcgagc 6660
ctacgagcgt gcctacaccg tcgctcaggc ggtcggagga ggccgtgagc ctgatctgcc 6720
gccggactgt gaccgccaga cggattggcc gcgacgtgtg cgcggctacg tcgctaaagg 6780
ccagccagtc gtccctgctc gtcagacaga gacgcagagc cagccgaggc gaaaagctct 6840
ggccactatg ggaagacgtg gcggtaaaaa ggccgcagaa cgctggaaag acccaaacag 6900
tgagtacgcc cgagcacagc gagaaaaact agctaagtcc agtcaacgac aagctaggaa 6960
agctaaagga aatcgcttga ccattgcagg ttggtttatg actgttgagg gagagactgg 7020
ctcgtggccg acaatcaatg aagctatgtc tgaatttagc gtgtcacgtc agaccgtgaa 7080
tagagcactt aaggtctgcg ggcattgaac ttccacgagg acgccgaaag cttcccagta 7140
aatgtgccat ctcgtaggca gaaaacggtt cccccgtagg gtctctctct tggcctcctt 7200
tctaggtcgg gctgattgct cttgaagctc tctagggggg ctcacaccat aggcagataa 7260
cgttccccac cggctcgcct cgtaagcgca caaggactgc tcccaaagat cttcaaagcc 7320
actgccgcga ctgccttcgc gaagccttgc cccgcggaaa tttcctccac cgagttcgtg 7380
cacaccccta tgccaagctt ctttcaccct aaattcgaga gattggattc ttaccgtgga 7440
aattcttcgc aaaaatcgtc ccctgatcgc ccttgcgacg ttggcgtcgg tgccgctggt 7500
tgcgcttggc ttgaccgact tgatcagcgg ccgc 7534

<210> SEQ ID NO 34
<211> LENGTH: 8877
<212> TYPE: DNA
<213> ORGANISM: artificial
<220> FEATURE:
<223> OTHER INFORMATION: Plasmid: pH170

<400> SEQUENCE: 34
tcgatttaaa tctcgagagg cctgacgtcg ggcccggtac cgggcccccc ctcgaggtcg 60
agcggcttaa agtttggctg ccatgtgaat ttttagcacc ctcaacagtt gagtgctggc 120
actctcgggg gtagagtgcc aaataggttg tttgacacac agttgttcac ccgcgacgac 180
ggctgtgctg gaaacccaca accggcacac acaaaatttt tctcatggag ggattcatca 240
tgtcgacttc agttacttca ccagcccaca acaacgcaca ttcctccgaa tttttggatg 300

-continued

```
cgttggcaaa ccatgtgttg atcggcgacg gcgccatggg cacccagctc caaggctttg    360
acctggacgt ggaaaaggat ttccttgatc tggaggggtg taatgagatt ctcaacgaca    420
cccgccctga tgtgttgagg cagattcacc gcgcctactt tgaggcggga gctgacttgg    480
ttgagaccaa tacttttggt tgcaacctgc cgaacttggc ggattatgac atcgctgatc    540
gttgccgtga gcttgcctac aagggcactg cagtggctag ggaagtggct gatgagatgg    600
ggccgggccg aaacggcatg cggcgtttcg tggttggttc cctgggacct ggaacgaagc    660
ttccatcgct gggccatgca ccgtatgcag atttgcgtgg gcactacaag gaagcagcgc    720
ttggcatcat cgacggtggt ggcgatgcct tttgattga gactgctcag gacttgcttc     780
aggtcaaggc tgcggttcac ggcgttcaag atgccatggc tgaacttgat acattcttgc    840
ccattatttg ccacgtcacc gtagagacca ccggcaccat gctcatgggt tctgagatcg    900
gtgccgcgtt gacagcgctg cagccactgg gtatcgacat gattggtctg aactgcgcca    960
ccggcccaga tgagatgagc gagcacctgc gttacctgtc caagcacgcc gatattcctg   1020
tgtcggtgat gcctaacgca ggtcttcctg tcctgggtaa aaacggtgca gaatacccac   1080
ttgaggctga ggatttggcg caggcgctgg ctggattcgt ctccgaatat ggcctgtcca   1140
tggtgggtgg ttgttgtggc accacacctg agcacatccg tgcggtccgc gatgcggtgg   1200
ttggtgttcc agagcaggaa acctccacac tgaccaagat ccctgcaggc cctgttgagc   1260
aggcctcccg cgaggtggag aaagaggact ccgtcgcgtc gctgtacacc tcggtgccat   1320
tgtcccagga aaccggcatt tccatgatcg gtgagcgcac caactccaac ggttccaagg   1380
cattccgtga ggcaatgctg tctggcgatt gggaaaagtg tgtggatatt gccaagcagc   1440
aaacccgcga tggtgcacac atgctggatc tttgtgtgga ttacgtggga cgagacggca   1500
ccgccgatat ggcgaccttg gcagcacttc ttgctaccag ctccactttg ccaatcatga   1560
ttgactccac cgagccagag gttattcgca caggccttga gcacttgggt ggacgaagca   1620
tcgttaactc cgtcaacttt gaagacggcg atggccctga gtcccgctac cagcgcatca   1680
tgaaactggt aaagcagcac ggtgcggccg tggttgcgct gaccattgat gaggaaggcc   1740
aggcacgtac cgctgagcac aaggtgcgca ttgctaaacg actgattgac gatatcaccg   1800
gcagctacgg cctggatatc aaagacatcg ttgtggactg cctgaccttc ccgatctcta   1860
ctggccagga agaaaccagg cgagatggca ttgaaaccat cgaagccatc cgcgagctga   1920
agaagctcta cccagaaatc cacaccaccc tgggtctgtc caatatttcc ttcggcctga   1980
accctgctgc acgccaggtt cttaactctg tgttcctcaa tgagtgcatt gaggctggtc   2040
tggactctgc gattgcgcac agctccaaga ttttgccgat gaaccgcatt gatgatcgcc   2100
agcgcgaagt ggcgttggat atggtctatg atcgccgcac cgaggattac gatccgctgc   2160
aggaattcat gcagctgttt gagggcgttt ctgctgccga tgccaaggat gctcgcgctg   2220
aacagctggc cgctatgcct ttgtttgagc gtttggcaca gcgcatcatc gacggcgata   2280
agaatggcct tgaggatgat ctggaagcag gcatgaagga gaagtctcct attgcgatca   2340
tcaacgagga ccttctcaac ggcatgaaga ccgtgggtga gctgtttggt tccggacaga   2400
tgcagctgcc attcgtgctg caatcggcag aaaccatgaa aactgcggtg gcctatttgg   2460
aaccgttcat ggaagaggaa gcagaagcta ccggatctgc gcaggcagag ggcaagggca   2520
aaatcgtcgt ggccaccgtc aagggtgacg tgcacgatat cggcaagaac ttggtggaca   2580
tcattttgtc caacaacggt tacgacgtgg tgaacttggg catcaagcag ccactgtccg   2640
ccatgttgga agcagcggaa gaacacaaag cagacgtcat cggcatgtcg ggacttcttg   2700
```

-continued

```
tgaagtccac cgtggtgatg aaggaaaacc ttgaggagat gaacaacgcc ggcgcatcca   2760
attacccagt cattttgggt ggcgctgcgc tgacgcgtac ctacgtggaa aacgatctca   2820
acgaggtgta caccggtgag gtgtactacg cccgtgatgc tttcgagggc ctgcgcctga   2880
tggatgaggt gatggcagaa aagcgtggtg aaggacttga tcccaactca ccagaagcta   2940
ttgagcaggc gaagaagaag gcggaacgta aggctcgtaa tgagcgttcc cgcaagattg   3000
ccgcggagcg taaagctaat gcggctcccg tgattgttcc ggagcgttct gatgtctcca   3060
ccgatactcc aaccgcggca ccaccgttct ggggaacccg cattgtcaag ggtctgccct   3120
tggcggagtt cttgggcaac cttgatgagc gcgccttgtt catggggcag tggggtctga   3180
aatccacccg cggcaacgag ggtccaagct atgaggattt ggtggaaact gaaggccgac   3240
cacgcctgcg ctactggctg gatcgcctga agtctgaggg cattttggac cacgtggcct   3300
tggtgtatgg ctacttccca gcggtcgcgg aaggcgatga cgtggtgatc ttggaatccc   3360
cggatccaca cgcagccgaa cgcatgcgct ttagcttccc acgccagcag cgcggcaggt   3420
tcttgtgcat cgcggatttc attcgcccac gcgagcaagc tgtcaaggac ggccaagtgg   3480
acgtcatgcc attccagctg gtcaccatgg gtaatcctat tgctgatttc gccaacgagt   3540
tgttcgcagc caatgaatac cgcgagtact tggaagttca cggcatcggc gtgcagctca   3600
ccgaagcatt ggccgagtac tggcactccc gagtgcgcag cgaactcaag ctgaacgacg   3660
gtggatctgt cgctgatttt gatccagaag acaagaccaa gttcttcgac ctggattacc   3720
gcggcgcccg cttctccttt ggttacggtt cttgccctga tctggaagac cgcgcaaagc   3780
tggtggaatt gctcgagcca ggccgtatcg gcgtggagtt gtccgaggaa ctccagctgc   3840
acccagagca gtccacagac gcgtttgtgc tctaccaccc agaggcaaag tactttaacg   3900
tctaatctag acccgggatt taaatcgcta gcgggctgct aaaggaagcg gaacacgtag   3960
aaagccagtc cgcagaaacg gtgctgaccc cggatgaatg tcagctactg ggctatctgg   4020
acaagggaaa acgcaagcgc aaagagaaag caggtagctt gcagtgggct tacatggcga   4080
tagctagact gggcggtttt atggacagca agcgaaccgg aattgccagc tggggcgccc   4140
tctggtaagg ttgggaagcc ctgcaaagta aactggatgg ctttcttgcc gccaaggatc   4200
tgatggcgca ggggatcaag atctgatcaa gagacaggat gaggatcgtt tcgcatgatt   4260
gaacaagatg gattgcacgc aggttctccg gccgcttggg tggagaggct attcggctat   4320
gactgggcac aacagacaat cggctgctct gatgccgccg tgttccggct gtcagcgcag   4380
gggcgcccgg ttctttttgt caagaccgac ctgtccggtg ccctgaatga actgcaggac   4440
gaggcagcgc ggctatcgtg gctggccacg acgggcgttc cttgcgcagc tgtgctcgac   4500
gttgtcactg aagcgggaag ggactggctg ctattgggcg aagtgccggg gcaggatctc   4560
ctgtcatctc accttgctcc tgccgagaaa gtatccatca tggctgatgc aatgcggcgg   4620
ctgcatacgc ttgatccggc tacctgccca ttcgaccacc aagcgaaaca tcgcatcgag   4680
cgagcacgta ctcggatgga agccggtctt gtcgatcagg atgatctgga cgaagagcat   4740
caggggctcg cgccagccga actgttcgcc aggctcaagg cgcgcatgcc cgacggcgag   4800
gatctcgtcg tgacccatgg cgatgcctgc ttgccgaata tcatggtgga aaatggccgc   4860
ttttctggat tcatcgactg tggccggctg ggtgtggcgg accgctatca ggacatagcg   4920
ttggctaccc gtgatattgc tgaagagctt ggcggcgaat gggctgaccg cttcctcgtg   4980
ctttacggta tcgccgctcc cgattcgcag cgcatcgcct tctatcgcct tcttgacgag   5040
ttcttctgag cgggactctg gggttcgaaa tgaccgacca agcgacgccc aacctgccat   5100
```

-continued

```
cacgagattt cgattccacc gccgccttct atgaaaggtt gggcttcgga atcgttttcc   5160
gggacgccgg ctggatgatc ctccagcgcg gggatctcat gctggagttc ttcgcccacg   5220
ctagcggcgc gccggccggc ccggtgtgaa ataccgcaca gatgcgtaag gagaaaatac   5280
cgcatcaggc gctcttccgc ttcctcgctc actgactcgc tgcgctcggt cgttcggctg   5340
cggcgagcgg tatcagctca ctcaaaggcg gtaatacggt tatccacaga atcaggggat   5400
aacgcaggaa agaacatgtg agcaaaaggc cagcaaaagg ccaggaaccg taaaaaggcc   5460
gcgttgctgg cgtttttcca taggctccgc ccccctgacg agcatcacaa aaatcgacgc   5520
tcaagtcaga ggtggcgaaa cccgacagga ctataaagat accaggcgtt tccccctgga   5580
agctccctcg tgcgctctcc tgttccgacc ctgccgctta ccggatacct gtccgccttt   5640
ctcccttcgg gaagcgtggc gctttctcat agctcacgct gtaggtatct cagttcggtg   5700
taggtcgttc gctccaagct gggctgtgtg cacgaacccc ccgttcagcc cgaccgctgc   5760
gccttatccg gtaactatcg tcttgagtcc aacccggtaa gacacgactt atcgccactg   5820
gcagcagcca ctggtaacag gattagcaga gcgaggtatg taggcggtgc tacagagttc   5880
ttgaagtggt ggcctaacta cggctacact agaaggacag tatttggtat ctgcgctctg   5940
ctgaagccag ttaccttcgg aaaaagagtt ggtagctctt gatccggcaa acaaaccacc   6000
gctggtagcg gtggtttttt tgtttgcaag cagcagatta cgcgcagaaa aaaaggatct   6060
caagaagatc ctttgatctt ttctacgggg tctgacgctc agtggaacga aaactcacgt   6120
taagggattt tggtcatgag attatcaaaa aggatcttca cctagatcct tttaaaggcc   6180
ggccgcggcc gcgcaaagtc ccgcttcgtg aaaattttcg tgccgcgtga ttttccgcca   6240
aaaactttaa cgaacgttcg ttataatggt gtcatgacct tcacgacgaa gtactaaaat   6300
tggcccgaat catcagctat ggatctctct gatgtcgcgc tggagtccga cgcgctcgat   6360
gctgccgtcg atttaaaaac ggtgatcgga tttttccgag ctctcgatac gacggacgcg   6420
ccagcatcac gagactgggc cagtgccgcg agcgacctag aaactctcgt ggcggatctt   6480
gaggagctgg ctgacgagct gcgtgctcgg ccagcgccag gaggacgcac agtagtggag   6540
gatgcaatca gttgcgccta ctgcggtggc ctgattcctc cccggcctga cccgcgagga   6600
cggcgcgcaa aatattgctc agatgcgtgt cgtgccgcag ccagccgcga gcgcgccaac   6660
aaacgccacg ccgaggagct ggaggcggct aggtcgcaaa tggcgctgga agtgcgtccc   6720
ccgagcgaaa ttttggccat ggtcgtcaca gagctggaag cggcagcgag aattatcgcg   6780
atcgtggcgg tgcccgcagg catgacaaac atcgtaaatg ccgcgtttcg tgtgccgtgg   6840
ccgcccagga cgtgtcagcg ccgccaccac ctgcaccgaa tcggcagcag cgtcgcgcgt   6900
cgaaaaagcg cacaggcggc aagaagcgat aagctgcacg aatacctgaa aaatgttgaa   6960
cgccccgtga gcggtaactc acagggcgtc ggctaacccc cagtccaaac ctgggagaaa   7020
gcgctcaaaa atgactctag cggattcacg agacattgac acaccggcct ggaaattttc   7080
cgctgatctg ttcgacaccc atcccgagct cgcgctgcga tcacgtggct ggacgagcga   7140
agaccgccgc gaattcctcg ctcacctggg cagagaaaat ttccagggca gcaagacccg   7200
cgacttcgcc agcgcttgga tcaaagaccc ggacacggag aaacacagcc gaagttatac   7260
cgagttggtt caaaatcgct tgcccggtgc cagtatgttg ctctgacgca cgcgcagcac   7320
gcagccgtgc ttgtcctgga cattgatgtg ccgagccacc aggccggcgg gaaaatcgag   7380
cacgtaaacc ccgaggtcta cgcgattttg gagcgctggg cacgcctgga aaaagcgcca   7440
gcttggatcg gcgtgaatcc actgagcggg aaatgccagc tcatctggct cattgatccg   7500
```

```
gtgtatgccg cagcaggcat gagcagcccg aatatgcgcc tgctggctgc aacgaccgag   7560

gaaatgaccc gcgttttcgg cgctgaccag gctttttcac ataggctgag ccgtggccac   7620

tgcactctcc gacgatccca gccgtaccgc tggcatgccc agcacaatcg cgtggatcgc   7680

ctagctgatc ttatggaggt tgctcgcatg atctcaggca cagaaaaacc taaaaaacgc   7740

tatgagcagg agttttctag cggacgggca cgtatcgaag cggcaagaaa agccactgcg   7800

gaagcaaaag cacttgccac gcttgaagca agcctgccga gcgccgctga agcgtctgga   7860

gagctgatcg acggcgtccg tgtcctctgg actgctccag ggcgtgccgc ccgtgatgag   7920

acggcttttc gccacgcttt gactgtggga taccagttaa aagcggctgg tgagcgccta   7980

aaagacacca agggtcatcg agcctacgag cgtgcctaca ccgtcgctca ggcggtcgga   8040

ggaggccgtg agcctgatct gccgccggac tgtgaccgcc agacggattg gccgcgacgt   8100

gtgcgcggct acgtcgctaa aggccagcca gtcgtccctg ctcgtcagac agagacgcag   8160

agccagccga ggcgaaaagc tctggccact atgggaagac gtggcggtaa aaaggccgca   8220

gaacgctgga aagacccaaa cagtgagtac gcccgagcac agcgagaaaa actagctaag   8280

tccagtcaac gacaagctag gaaagctaaa ggaaatcgct tgaccattgc aggttggttt   8340

atgactgttg agggagagac tggctcgtgg ccgacaatca atgaagctat gtctgaattt   8400

agcgtgtcac gtcagaccgt gaatagagca cttaaggtct gcgggcattg aacttccacg   8460

aggacgccga aagcttccca gtaaatgtgc catctcgtag gcagaaaacg gttccccccgt   8520

agggtctctc tcttggcctc ctttctaggt cgggctgatt gctcttgaag ctctctaggg   8580

gggctcacac cataggcaga taacgttccc caccggctcg cctcgtaagc gcacaaggac   8640

tgctcccaaa gatcttcaaa gccactgccg cgactgcctt cgcgaagcct tgccccgcgg   8700

aaatttcctc caccgagttc gtgcacaccc ctatgccaag cttctttcac cctaaattcg   8760

agagattgga ttcttaccgt ggaaattctt cgcaaaaatc gtcccctgat cgcccttgcg   8820

acgttggcgt cggtgccgct ggttgcgctt ggcttgaccg acttgatcag cggccgc      8877
```

```
<210> SEQ ID NO 35
<211> LENGTH: 5106
<212> TYPE: DNA
<213> ORGANISM: artificial
<220> FEATURE:
<223> OTHER INFORMATION: Plasmid: pH469

<400> SEQUENCE: 35

tcgaggtcga cggtatcgat ggtttgatgt tggttccgat gggcatcatc tctgtggtga     60

tgtcaccagt aattggacga ttggtggatc gcctggcacc aggaatgatc tccaagatcg    120

gattcggcgc gctgattttc tcgatggcgt tgatggctgt ctttatgatc gccaacctat    180

cgccgtggtg gctactcatc ccgattattt tgttcggtag ctccaacgcg atgagttttg    240

caccgaactc tgtgattgct ctgcgtgatg ttccgcagga tttagtgggc tctgcttctg    300

gtttttacaa cacctcacgc caggtgggcg ctgttttggg cgccgctacc ttgggcgctg    360

tgatgcaaat aggagtgggc acggtgtcct tcggtgttgc catgggtgcg gcaatcctgg    420

tgacactcgt gcccttaatc tttgggttcc tagcggtaac ccaatgctag ctcttctgac    480

gatgtttcaa ggttcgcgaa atcaccgggt ggcagaaagc tgccccgggg gtttcctcgc    540

ctttttgtaa tcgaggtcgt cccacttaac gcttaaaatt tccattcaga aagctttggc    600

gttcctcatc atccggggct ccagggagag gattaaaagt gaaccgattg cgttttcaac    660

caaaccctag actgctcggt ctgtcaagaa gttccgggga tttaaattca tggtgccgtt    720
```

```
ttgggctcct gttgtctgcg tcgggtgggg aagtggcgta aaggtgtgca acctcatagt   780

caagttgacg gaaaagggga gatcgcattt taccccccgca gattttgggg aacctgtttt   840

gaactggggt tttgcaaaat gcaacgcggt gacgtgtggt tacaactagt tctagacccg   900

ggatttaaat cgctagcggg ctgctaaagg aagcggaaca cgtagaaagc cagtccgcag   960

aaacggtgct gaccccggat gaatgtcagc tactgggcta tctggacaag ggaaaacgca  1020

agcgcaaaga gaaagcaggt agcttgcagt gggcttacat ggcgatagct agactgggcg  1080

gttttatgga cagcaagcga accggaattg ccagctgggg cgccctctgg taaggttggg  1140

aagccctgca aagtaaactg gatggctttc ttgccgccaa ggatctgatg gcgcagggga  1200

tcaagatctg atcaagagac aggatgagga tcgtttcgca tgattgaaca agatggattg  1260

cacgcaggtt ctccggccgc ttgggtggag aggctattcg gctatgactg ggcacaacag  1320

acaatcggct gctctgatgc cgccgtgttc cggctgtcag cgcaggggcg cccggttctt  1380

tttgtcaaga ccgacctgtc cggtgccctg aatgaactgc aggacgaggc agcgcggcta  1440

tcgtggctgg ccacgacggg cgttccttgc gcagctgtgc tcgacgttgt cactgaagcg  1500

ggaagggact ggctgctatt gggcgaagtg ccggggcagg atctcctgtc atctcacctt  1560

gctcctgccg agaaagtatc catcatggct gatgcaatgc ggcggctgca tacgcttgat  1620

ccggctacct gcccattcga ccaccaagcg aaacatcgca tcgagcgagc acgtactcgg  1680

atggaagccg gtcttgtcga tcaggatgat ctggacgaag agcatcaggg gctcgcgcca  1740

gccgaactgt tcgccaggct caaggcgcgc atgcccgacg gcgaggatct cgtcgtgacc  1800

catggcgatg cctgcttgcc gaatatcatg gtggaaaatg gccgcttttc tggattcatc  1860

gactgtggcc ggctgggtgt ggcggaccgc tatcaggaca tagcgttggc tacccgtgat  1920

attgctgaag agcttggcgg cgaatgggct gaccgcttcc tcgtgcttta cggtatcgcc  1980

gctcccgatt cgcagcgcat cgccttctat cgccttcttg acgagttctt ctgagcggga  2040

ctctggggtt cgaaatgacc gaccaagcga cgcccaacct gccatcacga gatttcgatt  2100

ccaccgccgc cttctatgaa aggttgggct tcggaatcgt tttccgggac gccggctgga  2160

tgatcctcca gcgcggggat ctcatgctgg agttcttcgc ccacgctagc ggcgcgccgg  2220

ccggcccggt gtgaaatacc gcacagatgc gtaaggagaa aataccgcat caggcgctct  2280

tccgcttcct cgctcactga ctcgctgcgc tcggtcgttc ggctgcggcg agcggtatca  2340

gctcactcaa aggcggtaat acggttatcc acagaatcag gggataacgc aggaaagaac  2400

atgtgagcaa aaggccagca aaaggccagg aaccgtaaaa aggccgcgtt gctggcgttt  2460

ttccataggc tccgcccccc tgacgagcat cacaaaaatc gacgctcaag tcagaggtgg  2520

cgaaacccga caggactata aagataccag gcgtttcccc ctggaagctc cctcgtgcgc  2580

tctcctgttc cgaccctgcc gcttaccgga tacctgtccg cctttctccc ttcgggaagc  2640

gtggcgcttt ctcatagctc acgctgtagg tatctcagtt cggtgtaggt cgttcgctcc  2700

aagctgggct gtgtgcacga accccccgtt cagcccgacc gctgcgcctt atccggtaac  2760

tatcgtcttg agtccaaccc ggtaagacac gacttatcgc cactggcagc agccactggt  2820

aacaggatta gcagagcgag gtatgtaggc ggtgctacag agttcttgaa gtggtggcct  2880

aactacggct acactagaag gacagtattt ggtatctgcg ctctgctgaa gccagttacc  2940

ttcggaaaaa gagttggtag ctcttgatcc ggcaaacaaa ccaccgctgg tagcggtggt  3000

tttttttgttt gcaagcagca gattacgcgc agaaaaaaag gatctcaaga agatcctttg  3060

atcttttcta cggggtctga cgctcagtgg aacgaaaact cacgttaagg gattttggtc  3120
```

-continued atgagattat caaaaaggat cttcacctag atccttttaa aggccggccg cggccgccat 3180
cggcattttc ttttgcgttt ttatttgtta actgttaatt gtccttgttc aaggatgctg 3240
tctttgacaa cagatgtttt cttgcctttg atgttcagca ggaagctcgg cgcaaacgtt 3300
gattgtttgt ctgcgtagaa tcctctgttt gtcatatagc ttgtaatcac gacattgttt 3360
cctttcgctt gaggtacagc gaagtgtgag taagtaaagg ttacatcgtt aggatcaaga 3420
tccattttta acacaaggcc agttttgttc agcggcttgt atgggccagt taaagaatta 3480
gaaacataac caagcatgta aatatcgtta gacgtaatgc cgtcaatcgt catttttgat 3540
ccgcgggagt cagtgaacag gtaccatttg ccgttcattt taaagacgtt cgcgcgttca 3600
atttcatctg ttactgtgtt agatgcaatc agcggtttca tcactttttt cagtgtgtaa 3660
tcatcgttta gctcaatcat accgagagcg ccgtttgcta actcagccgt gcgtttttta 3720
tcgctttgca gaagtttttg actttcttga cggaagaatg atgtgctttt gccatagtat 3780
gctttgttaa ataaagattc ttcgccttgg tagccatctt cagttccagt gtttgcttca 3840
aatactaagt atttgtggcc tttatcttct acgtagtgag gatctctcag cgtatggttg 3900
tcgcctgagc tgtagttgcc ttcatcgatg aactgctgta cattttgata cgtttttccg 3960
tcaccgtcaa agattgattt ataatcctct acaccgttga tgttcaaaga gctgtctgat 4020
gctgatacgt taacttgtgc agttgtcagt gtttgtttgc cgtaatgttt accggagaaa 4080
tcagtgtaga ataaacggat ttttccgtca gatgtaaatg tggctgaacc tgaccattct 4140
tgtgtttggt cttttaggat agaatcattt gcatcgaatt tgtcgctgtc tttaaagacg 4200
cggccagcgt tttccagct gtcaatagaa gtttcgccga ctttttgata gaacatgtaa 4260
atcgatgtgt catccgcatt tttaggatct ccggctaatg caaagacgat gtggtagccg 4320
tgatagtttg cgacagtgcc gtcagcgttt tgtaatggcc agctgtccca aacgtccagg 4380
ccttttgcag aagagatatt tttaattgtg gacgaatcaa attcagaaac ttgatatttt 4440
tcattttttt gctgttcagg gatttgcagc atatcatggc gtgtaatatg ggaaatgccg 4500
tatgtttcct tatatggctt ttggttcgtt tctttcgcaa acgcttgagt tgcgcctcct 4560
gccagcagtg cggtagtaaa ggttaatact gttgcttgtt ttgcaaactt tttgatgttc 4620
atcgttcatg tctccttttt tatgtactgt gttagcggtc tgcttcttcc agccctcctg 4680
tttgaagatg gcaagttagt tacgcacaat aaaaaaagac ctaaaatatg taaggggtga 4740
cgccaaagta tacactttgc cctttacaca ttttaggtct tgcctgcttt atcagtaaca 4800
aacccgcgcg atttactttt cgacctcatt ctattagact ctcgtttgga ttgcaactgg 4860
tctattttcc tcttttgttt gatagaaaat cataaaagga tttgcagact acgggcctaa 4920
agaactaaaa aatctatctg tttcttttca ttctctgtat tttttatagt ttctgttgca 4980
tgggcataaa gttgcctttt taatcacaat tcagaaaata tcataatatc tcatttcact 5040
aaataatagt gaacggcagg tatatgtgat gggttaaaaa ggatcggcgg ccgctcgatt 5100
taaatc 5106

<210> SEQ ID NO 36
<211> LENGTH: 5512
<212> TYPE: DNA
<213> ORGANISM: artificial
<220> FEATURE:
<223> OTHER INFORMATION: Plasmid: pH300

<400> SEQUENCE: 36
tcgagaggcc tgacgtcggg cccggtacca cgcgtcatat gactagttcg gacctaggga 60

-continued

```
tatcgtcgac atcgatgctc ttctgcgtta attaacaatt gggatctctc aactaatgca    120
gcgatgcgtt ctttccagaa tgctttcatg acagggatgc tgtcttgatc aggcaggcgt    180
ctgtgctgga tgccgaagct ggatttattg tcgcctttgg aggtgaagtt gacgctcact    240
cgagaatcat cggccaacca tttggcattg aatgttctag gttcggaggc ggaggttttc    300
tcaattagtg cgggatcgag ccactgcgcc cgcaggtcat cgtctccgaa gagcttccac    360
actttttcga ccggcaggtt aagggttttg gaggcattgg ccgcgaaccc atcgctggtc    420
atcccgggtt tgcgcatgcc acgttcgtat tcataaccaa tcgcgatgcc ttgagcccac    480
cagccactga catcaaagtt gtccacgatg tgctttgcga tgtgggtgtg agtccaagag    540
gtggctttta cgtcgtcaag caattttagc cactcttccc acggctttcc ggtgccgttg    600
aggatagctt caggggacat gcctggtgtt gagccttgcg gagtggagtc agtcatgcga    660
ccgagactag tggcgctttg gtacccttgg tgtatggcta cttcccagcg gtcgcggaag    720
gcgatgacgt ggtgatcttg gaatccccgg atccacacgc agccgaacgc atgcgcttta    780
gcttcccacg ccagcagcgc ggcaggttct tgtgcatcgc ggatttcatt cgcccacgcg    840
agcaagctgt caaggacggc caagtggacg tcatgccatt ccagctggtc accatgggta    900
atcctattgc tgatttcgcc aacgagttgt tcgcagccaa tgaataccgc gagtacttgg    960
aagttcacgg catcggcgtg cagctcaccg aagcattggc cgagtactgg cactcccgag   1020
tgcgcagcga actcaagctg aacgacggtg gatctgtcgc tgattttgat ccagaagaca   1080
agaccaagtt cttcgacctg gattaccgcg gcgcccgctt ctcctttggt tacggttctt   1140
gccctgatct ggaagaccgc gcaaagctgg tggaattgct cgagccaggc cgtatcggcg   1200
tggagttgtc cgaggaactc cagctgcacc cagagcagtc cacagacgcg tttgtgctct   1260
accacccaga ggcaaagtac tttaacgtct aatctagacc cgggatttaa atgatccgct   1320
agcgggctgc taaaggaagc ggaacacgta gaaagccagt ccgcagaaac ggtgctgacc   1380
ccggatgaat gtcagctact gggctatctg gacaagggaa aacgcaagcg caaagagaaa   1440
gcaggtagct tgcagtgggc ttacatggcg atagctagac tgggcggttt tatggacagc   1500
aagcgaaccg gaattgccag ctggggcgcc ctctggtaag gttgggaagc cctgcaaagt   1560
aaactggatg gctttcttgc cgccaaggat ctgatggcgc aggggatcaa gatctgatca   1620
agagacagga tgaggatcgt ttcgcatgat tgaacaagat ggattgcacg caggttctcc   1680
ggccgcttgg gtggagaggc tattcggcta tgactgggca caacagacaa tcggctgctc   1740
tgatgccgcc gtgttccggc tgtcagcgca ggggcgcccg gttctttttg tcaagaccga   1800
cctgtccggt gccctgaatg aactgcagga cgaggcagcg cggctatcgt ggctggccac   1860
gacgggcgtt ccttgcgcag ctgtgctcga cgttgtcact gaagcgggaa gggactggct   1920
gctattgggc gaagtgccgg ggcaggatct cctgtcatct caccttgctc ctgccgagaa   1980
agtatccatc atggctgatg caatgcggcg gctgcatacg cttgatccgg ctacctgccc   2040
attcgaccac caagcgaaac atcgcatcga gcgagcacgt actcggatgg aagccggtct   2100
tgtcgatcag gatgatctgg acgaagagca tcaggggctc gcgccagccg aactgttcgc   2160
caggctcaag gcgcgcatgc ccgacggcga ggatctcgtc gtgacccatg gcgatgcctg   2220
cttgccgaat atcatggtgg aaaatggccg cttttctgga ttcatcgact gtggccggct   2280
gggtgtggcg gaccgctatc aggacatagc gttggctacc cgtgatattg ctgaagagct   2340
tggcggcgaa tgggctgacc gcttcctcgt gctttacggt atcgccgctc ccgattcgca   2400
gcgcatcgcc ttctatcgcc ttcttgacga gttcttctga gcgggactct ggggttcgaa   2460
```

-continued

```
atgaccgacc aagcgacgcc caacctgcca tcacgagatt tcgattccac cgccgccttc   2520
tatgaaaggt tgggcttcgg aatcgttttc cgggacgccg gctggatgat cctccagcgc   2580
ggggatctca tgctggagtt cttcgcccac gctagcggcg cgccggccgg cccggtgtga   2640
aataccgcac agatgcgtaa ggagaaaata ccgcatcagg cgctcttccg cttcctcgct   2700
cactgactcg ctgcgctcgg tcgttcggct gcggcgagcg gtatcagctc actcaaaggc   2760
ggtaatacgg ttatccacag aatcagggga taacgcagga aagaacatgt gagcaaaagg   2820
ccagcaaaag gccaggaacc gtaaaaaggc cgcgttgctg gcgtttttcc ataggctccg   2880
cccccctgac gagcatcaca aaaatcgacg ctcaagtcag aggtggcgaa acccgacagg   2940
actataaaga taccaggcgt ttccccctgg aagctccctc gtgcgctctc ctgttccgac   3000
cctgccgctt accggatacc tgtccgcctt tctcccttcg ggaagcgtgg cgctttctca   3060
tagctcacgc tgtaggtatc tcagttcggt gtaggtcgtt cgctccaagc tgggctgtgt   3120
gcacgaaccc cccgttcagc ccgaccgctg cgccttatcc ggtaactatc gtcttgagtc   3180
caacccggta agacacgact tatcgccact ggcagcagcc actggtaaca ggattagcag   3240
agcgaggtat gtaggcggtg ctacagagtt cttgaagtgg tggcctaact acggctacac   3300
tagaaggaca gtatttggta tctgcgctct gctgaagcca gttaccttcg gaaaaagagt   3360
tggtagctct tgatccggca aacaaaccac cgctggtagc ggtggttttt ttgtttgcaa   3420
gcagcagatt acgcgcagaa aaaaaggatc tcaagaagat cctttgatct tttctacggg   3480
gtctgacgct cagtggaacg aaaactcacg ttaagggatt ttggtcatga gattatcaaa   3540
aaggatcttc acctagatcc ttttaaaggc cggccgcggc cgccatcggc attttctttt   3600
gcgtttttat ttgttaactg ttaattgtcc ttgttcaagg atgctgtctt tgacaacaga   3660
tgttttcttg cctttgatgt tcagcaggaa gctcggcgca aacgttgatt gtttgtctgc   3720
gtagaatcct ctgtttgtca tatagcttgt aatcacgaca ttgtttcctt tcgcttgagg   3780
tacagcgaag tgtgagtaag taaaggttac atcgttagga tcaagatcca tttttaacac   3840
aaggccagtt ttgttcagcg gcttgtatgg gccagttaaa gaattagaaa cataaccaag   3900
catgtaaata tcgttagacg taatgccgtc aatcgtcatt tttgatccgc gggagtcagt   3960
gaacaggtac catttgccgt tcattttaaa gacgttcgcg cgttcaattt catctgttac   4020
tgtgttagat gcaatcagcg gtttcatcac ttttttcagt gtgtaatcat cgtttagctc   4080
aatcataccg agagcgccgt ttgctaactc agccgtgcgt tttttatcgc tttgcagaag   4140
tttttgactt tcttgacgga agaatgatgt gcttttgcca tagtatgctt tgttaaataa   4200
agattcttcg ccttggtagc catcttcagt tccagtgttt gcttcaaata ctaagtattt   4260
gtggccttta tcttctacgt agtgaggatc tctcagcgta tggttgtcgc ctgagctgta   4320
gttgccttca tcgatgaact gctgtacatt ttgatacgtt tttccgtcac cgtcaaagat   4380
tgatttataa tcctctacac cgttgatgtt caaagagctg tctgatgctg atacgttaac   4440
ttgtgcagtt gtcagtgttt gtttgccgta atgtttaccg gagaaatcag tgtagaataa   4500
acggattttt ccgtcagatg taaatgtggc tgaacctgac cattcttgtg tttggtcttt   4560
taggatagaa tcatttgcat cgaatttgtc gctgtcttta aagacgcggc cagcgttttt   4620
ccagctgtca atagaagttt cgccgacttt ttgatagaac atgtaaatcg atgtgtcatc   4680
cgcattttta ggatctccgg ctaatgcaaa gacgatgtgg tagccgtgat agtttgcgac   4740
agtgccgtca gcgttttgta atggccagct gtcccaaacg tccaggcctt ttgcagaaga   4800
gatattttta attgtggacg aatcaaattc agaaacttga tatttttcat ttttttgctg   4860
```

ttcagggatt tgcagcatat catggcgtgt aatatgggaa atgccgtatg tttccttata 4920
tggcttttgg ttcgtttctt tcgcaaacgc ttgagttgcg cctcctgcca gcagtgcggt 4980
agtaaaggtt aatactgttg cttgttttgc aaactttttg atgttcatcg ttcatgtctc 5040 ctttttatg tactgtgtta gcggtctgct tcttccagcc ctcctgtttg aagatggcaa 5100
gttagttacg cacaataaaa aaagacctaa aatatgtaag ggtgacgcc aaagtataca 5160 ctttgccctt tacacatttt aggtcttgcc tgctttatca gtaacaaacc cgcgcgattt 5220
acttttcgac ctcattctat tagactctcg tttggattgc aactggtcta ttttcctctt 5280
ttgtttgata gaaaatcata aaaggatttg cagactacgg gcctaaagaa ctaaaaaatc 5340
tatctgtttc ttttcattct ctgtattttt tatagtttct gttgcatggg cataaagttg 5400
cctttttaat cacaattcag aaaatatcat aatatctcat ttcactaaat aatagtgaac 5460
ggcaggtata tgtgatgggt taaaaaggat cggcggccgc tcgatttaaa tc 5512

<210> SEQ ID NO 37
<211> LENGTH: 11177
<212> TYPE: DNA
<213> ORGANISM: artificial
<220> FEATURE:
<223> OTHER INFORMATION: Plasmid: pOM232

<400> SEQUENCE: 37
ggatcggcgg ccagggccct catgggccgg gcgtgcgcaa tagactcgtc accaaaaccg 60
atggagtgtt tttgacgctg gaagatggca gcaccgtgat tgacgcgatg agctcctggt 120
ggtcggcaat tcatggacac ggacaccccc gactgaaagc tgccgcccaa aaacaaatcg 180
acaccatgag tcacgtcatg tttggcggac taacccacga gcccgccatt aagctcaccc 240
acaaactcct caatctcact ggaaattcct ttgaccacgt cttttattcc gattcgggct 300
cggtctcagt ggaggtcgcc atcaaaatgg cactgcaggc ctccaaagga caaggccacc 360
cggaacgaac aaaactcctc acctggcggt ccggctacca cggagacaca ttcaccgcga 420
tgagcgtgtg cgacccagaa aatggcatgc atagcctctg gaaaggcaca ctccccgagc 480
agattttcgc cccgccccca ccagttcggg ggtcatcgcc gcaggcgatt tccgagtacc 540
tgcgcagcat ggaattgctt atcgacgaga ccgtctccgc aatcatcatc gaaccgatcg 600
tccaaggcgc tggaggcatg cgcgcggccg cttcgcgaag cttgtcgacc gaaacagcag 660
ttataaggca tgaagctgtc cggtttttgc aaaagtggct gtgactgtaa aaagaaatcg 720
aaaaagaccg ttttgtgtga aaacggtctt tttgtttcct tttaaccaac tgccataact 780
cgaggctatt gacgacagct atggttcact gtccaccaac caaaactgtg ctcagtaccg 840
ccaatatttc tcccttgagg ggtacaaaga ggtgtcccta gaagagatcc acgctgtgta 900
aaaattttac aaaaaggtat tgactttccc tacagggtgt gtaataattt aattacaggc 960
gggggcaacc ccgcctgttc tagaaggagg tgaaagtatg tcttcgaaag tggaacaact 1020
gcgtgcgcag ttaaatgaac gtattctggt gctggacggc ggtatgggca ccatgatcca 1080
gagttatcga ctgaacgaag ccgattttcg tggtgaacgc tttgccgact ggccatgcga 1140
cctcaaaggc aacaacgacc tgctggtact cagtaaaccg gaagtgatcg ccgctatcca 1200
caacgcctac tttgaagcgg gcgcggatat catcgaaacc aacaccttca actccacgac 1260
cattgcgatg gcggattacc agatggaatc cctgtcggcg gaaatcaact ttgcggcggc 1320
gaaactggcg cgagcttgtg ctgacgagtg gaccgcgcgc acgccagaga aaccgcgcta 1380
cgttgccggt gttctcggcc cgaccaaccg cacggcgtct atttctccgg acgtcaacga 1440

-continued

```
tccggcattt cgtaatatca cttttgacgg gctggtggcg gcttatcgag agtccaccaa   1500
agcgctggtg gaaggtggcg cggatctgat cctgattgaa accgttttcg acacccttaa   1560
cgccaaagcg gcggtatttg cggtgaaaac ggagtttgaa gcgctgggcg ttgagctgcc   1620
gattatgatc tccggcacca tcaccgacgc ctccgggcgc acgctctccg ggcagaccac   1680
cgaagcattt tacaactcat tgcgccacgc cgaagctctg acctttggcc tgaactgtgc   1740
gctggggccc gatgaactgc gccagtacgt gcaggagctg tcacggattg cggaatgcta   1800
cgtcaccgcg cacccgaacg ccgggctacc caacgccttt ggtgagtacg atctcgacgc   1860
cgacacgatg gcaaaacaga tacgtgaatg ggcgcaagcg ggttttctca atatcgtcgg   1920
cggctgctgt ggcaccacgc cacaacatat tgcagcgatg agtcgtgcag tagaaggatt   1980
agcgccgcgc aaactgccgg aaattcccgt agcctgccgt ttgtccggcc tggagccgct   2040
gaacattggc gaagatagcc tgtttgtgaa cgtgggtgaa cgcaccaacg tcaccggttc   2100
cgctaagttc aagcgcctga tcaaagaaga gaaatacagc gaggcgctgg atgtcgcgcg   2160
tcaacaggtg gaaaacggcg cgcagattat cgatatcaac atggatgaag ggatgctcga   2220
tgccgaagcg gcgatggtgc gttttctcaa tctgattgcc ggtgaaccgg atatcgctcg   2280
cgtgccgatt atgatcgact cctcaaaatg ggacgtcatt gaaaaaggtc tgaagtgtat   2340
ccagggcaaa ggcattgtta actctatctc gatgaaagag ggcgtcgatg cctttatcca   2400
tcacgcgaaa ttgttgcgtc gctacggtgc ggcagtggtg gtaatggcct ttgacgaaca   2460
gggacaggcc gatactcgcg cacggaaaat cgagatttgc cgtcgggcgt acaaaatcct   2520
caccgaagag gttggcttcc cgccagaaga tatcatcttc gacccaaaca tcttcgcggt   2580
cgcaactggc attgaagagc acaacaacta cgcgcaggac tttatcggcg cgtgtgaaga   2640
catcaaacgc gaactgccgc acgcgctgat ttccggcggc gtatctaacg tttctttctc   2700
gttccgtggc aacgatccgg tgcgcgaagc cattcacgca gtgttcctct actacgctat   2760
tcgcaatggc atggatatgg ggatcgtcaa cgccgggcaa ctggcgattt acgacgacct   2820
acccgctgaa ctgcgcgacg cggtggaaga tgtgattctt aatcgtcgcg acgatggcac   2880
cgagcgttta ctggagcttg ccgagaaata tcgcggcagc aaaaccgacg acaccgccaa   2940
cgcccagcag gcggagtggc gctcgtggga agtgaataaa cgtctggaat actcgctggt   3000
caaaggcatt accgagttta tcgagcagga taccgaagaa gcccgccagc aggctacgcg   3060
cccgattgaa gtgattgaag gcccgttgat ggacggcatg aatgtggtcg gcgacctgtt   3120
tggcgaaggg aaaatgttcc tgccacaggt ggtcaaatcg gcgcgcgtca tgaaacaggc   3180
ggtggcctac ctcgaaccgt ttattgaagc cagcaaagag cagggcaaaa ccaacggcaa   3240
gatggtgatc gccaccgtga agggcgacgt ccacgacatc ggtaaaaata tcgttggtgt   3300
ggtgctgcaa tgtaacaact acgaaattgt cgatctcggc gttatggtgc ctgcggaaaa   3360
aattctccgt accgctaaag aagtgaatgc tgatctgatt ggcctttcgg ggcttatcac   3420
gccgtcgctg gacgagatgg ttaacgtggc gaaagagatg gagcgtcagg gcttcactat   3480
tccgttactg attggcggcg cgacgacctc aaaagcgcac acggcggtga aaatcgagca   3540
gaactacagc ggcccgacgg tgtatgtgca gaatgcctcg cgtaccgttg gtgtggtggc   3600
ggcgctgctt tccgataccc agcgtgatga ttttgtcgct cgtacccgca aggagtacga   3660
aaccgtacgt attcagcacg ggcgcaagaa accgcgcaca ccaccggtca cgctggaagc   3720
ggcgcgcgat aacgatttcg cttttgactg gcaggcttac acgccgccgg tggcgcaccg   3780
tctcggcgtg caggaagtcg aagccagcat cgaaacgctg cgtaattaca tcgactggac   3840
```

-continued accgttcttt atgacctggt cgctggccgg gaagtatccg cgcattctgg aagatgaagt 3900
ggtgggcgtt gaggcgcagc ggctgtttaa agacgccaac gacatgctgg ataaattaag 3960
cgccgagaaa acgctgaatc cgcgtggcgt ggtgggcctg ttcccggcaa accgtgtggg 4020
cgatgacatt gaaatctacc gtgacgaaac gcgtacccat gtgatcaacg tcagccacca 4080
tctgcgtcaa cagaccgaaa aaacaggctt cgctaactac tgtctcgctg acttcgttgc 4140
gccgaagctt tctggtaaag cagattacat cggcgcattt gccgtgactg gcgggctgga 4200
agaggacgca ctggctgatg cctttgaagc gcagcacgat gattacaaca aaatcatggt 4260
gaaagcgctt gccgaccgtt tagccgaagc ctttgcggag tatctccatg agcgtgtgcg 4320
taaagtctac tggggctatg cgccgaacga gaacctcagc aacgaagagc tgatccgcga 4380
aaactaccag ggcatccgtc cggcaccggg ctatccggcc tgcccggaac atacggaaaa 4440
agccaccatc tgggagctgc tggaagtgga aaaacacact ggcatgaaac tcacagaatc 4500
tttcgccatg tggcccggtg catcggtttc gggttggtac ttcagccacc cggacagcaa 4560
gtactacgct gtagcacaaa ttcagcgcga tcaggttgaa gattatgccc gccgtaaagg 4620
tatgagcgtt accgaagttg agcgctggct ggcaccgaat ctggggtatg acgcggactg 4680
attcacaaat ctgtcacttt tccttacaac aaacagggcg ctcaatgagt gccctgtctc 4740
tttattaata tgaaacactt atactggaaa caggctggaa aaatcggatc cgccctcccg 4800
cacgctttgc gggagggcgg taccggaact ggggttggga aaaccttctc cacagccgtt 4860
ttggttcgat acttagccga tcaaggacac gatgttctgc ccgtaaagct agtccaaacc 4920
ggtgaacttc caggcgaggg agacatcttt aacattgaac gcttgactgg aattgctgga 4980
gaggaatttg ctcgtttcaa agaccctctt gcgccaaatc tggcagcccg acgagagggg 5040
gtcgagccaa tacagtttga tcagattatc tcgtggcttc gtggttttga cgacccagat 5100
cgcatcattg tggtggaggg cgctggtggc ctgctggtca gattagggga agatttcacc 5160
ctggcagatg ttgcctccgc tttgaatgca ccccttagtga ttgtgacaag caccggattg 5220
ggaagcctca acgctgctga attaagcgtt gaggcagcaa accgccgagg actcacagtg 5280
ttgggagtcc tcggcggttc gatccctcaa aatcctgatc tagctacgat gcttaatctc 5340
gaagaatttg agagagtcac cggcgtgccc ttttggggag ctttgccgga agggttgtca 5400
cgggtggagg ggttcgtcga aaagcaatct tttccggccc ttgatgcctt taagaaaccg 5460
ccggcaaggc tcccaacgcg tcccgggatt taaatcgcta gcgggctgct aaaggaagcg 5520
gaacacgtag aaagccagtc cgcagaaacg gtgctgaccc cggatgaatg tcagctactg 5580
ggctatctgg acaagggaaa acgcaagcgc aaagagaaag caggtagctt gcagtgggct 5640
tacatggcga tagctagact gggcggtttt atggacagca agcgaaccgg aattgccagc 5700
tggggcgccc tctggtaagg ttgggaagcc ctgcaaagta aactggatgg ctttcttgcc 5760
gccaaggatc tgatggcgca ggggatcaag atctgatcaa gagacaggat gaggatcgtt 5820
tcgcatgatt gaacaagatg gattgcacgc aggttctccg gccgcttggg tggagaggct 5880
attcggctat gactgggcac aacagacaat cggctgctct gatgccgccg tgttccggct 5940
gtcagcgcag gggcgcccgg ttctttttgt caagaccgac ctgtccggtg ccctgaatga 6000
actgcaggac gaggcagcgc ggctatcgtg gctggccacg acgggcgttc cttgcgcagc 6060
tgtgctcgac gttgtcactg aagcgggaag ggactggctg ctattgggcg aagtgccggg 6120
gcaggatctc ctgtcatctc accttgctcc tgccgagaaa gtatccatca tggctgatgc 6180
aatgcggcgg ctgcatacgc ttgatccggc tacctgccca ttcgaccacc aagcgaaaca 6240

-continued

```
tcgcatcgag cgagcacgta ctcggatgga agccggtctt gtcgatcagg atgatctgga   6300
cgaagagcat caggggctcg cgccagccga actgttcgcc aggctcaagg cgcgcatgcc   6360
cgacggcgag gatctcgtcg tgacccatgg cgatgcctgc ttgccgaata tcatggtgga   6420
aaatggccgc ttttctggat tcatcgactg tggccggctg ggtgtggcgg accgctatca   6480
ggacatagcg ttggctaccc gtgatattgc tgaagagctt ggcggcgaat gggctgaccg   6540
cttcctcgtg ctttacggta tcgccgctcc cgattcgcag cgcatcgcct tctatcgcct   6600
tcttgacgag ttcttctgag cgggactctg gggttcgaaa tgaccgacca agcgacgccc   6660
aacctgccat cacgagattt cgattccacc gccgccttct atgaaaggtt gggcttcgga   6720
atcgttttcc gggacgccgg ctggatgatc ctccagcgcg gggatctcat gctggagttc   6780
ttcgcccacg ctagtttaaa ctgcggatca gtgagggttt gtaactgcgg gtcaaggatc   6840
tggatttcga tcacggcacg atcatcgtgc gggagggcaa gggctccaag gatcgggcct   6900
tgatgttacc cgagagcttg gcacccagcc tgcgcgagca ggggaattga tccggtggat   6960
gaccttttga atgaccttta atagattata ttactaatta attggggacc ctagaggtcc   7020
cctttttat tttaaaaatt ttttcacaaa acggtttaca agcataacgg gttttgctgc   7080
ccgcaaacgg gctgttctgg tgttgctagt ttgttatcag aatcgcagat ccggcttcag   7140
gtttgccggc tgaaagcgct atttcttcca gaattgccat gatttttcc ccacgggagg   7200
cgtcactggc tcccgtgttg tcggcagctt tgattcgata agcagcatcg cctgtttcag   7260
gctgtctatg tgtgactgtt gagctgtaac aagttgtctc aggtgttcaa tttcatgttc   7320
tagttgcttt gttttactgg tttcacctgt tctattaggt gttacatgct gttcatctgt   7380
tacattgtcg atctgttcat ggtgaacagc tttaaatgca ccaaaaactc gtaaaagctc   7440
tgatgtatct atcttttta caccgttttc atctgtgcat atggacagtt ttccctttga   7500
tatctaacgg tgaacagttg ttctactttt gtttgttagt cttgatgctt cactgataga   7560
tacaagagcc ataagaacct cagatccttc cgtatttagc cagtatgttc tctagtgtgg   7620
ttcgttgttt ttgcgtgagc catgagaacg aaccattgag atcatgctta ctttgcatgt   7680
cactcaaaaa ttttgcctca aaactggtga gctgaatttt tgcagttaaa gcatcgtgta   7740
gtgtttttct tagtccgtta cgtaggtagg aatctgatgt aatggttgtt ggtattttgt   7800
caccattcat ttttatctgg ttgttctcaa gttcggttac gagatccatt tgtctatcta   7860
gttcaacttg gaaaatcaac gtatcagtcg ggcggcctcg cttatcaacc accaatttca   7920
tattgctgta agtgtttaaa tctttactta ttggtttcaa aacccattgg ttaagccttt   7980
taaactcatg gtagttattt tcaagcatta acatgaactt aaattcatca aggctaatct   8040
ctatatttgc cttgtgagtt ttcttttgtg ttagttcttt taataaccac tcataaatcc   8100
tcatagagta tttgttttca aaagacttaa catgttccag attatatttt atgaattttt   8160
ttaactggaa aagataaggc aatatctctt cactaaaaac taattctaat ttttcgcttg   8220
agaacttggc atagtttgtc cactggaaaa tctcaaagcc tttaaccaaa ggattcctga   8280
tttccacagt tctcgtcatc agctctctgg ttgctttagc taatacacca taagcatttt   8340
ccctactgat gttcatcatc tgagcgtatt ggttataagt gaacgatacc gtccgttctt   8400
tccttgtagg gttttcaatc gtggggttga gtagtgccac acagcataaa attagcttgg   8460
tttcatgctc cgttaagtca tagcgactaa tcgctagttc atttgctttg aaaacaacta   8520
attcagacat acatctcaat tggtctaggt gattttaatc actataccaa ttgagatggg   8580
ctagtcaatg ataattacta gtccttttcc tttgagttgt gggtatctgt aaattctgct   8640
```

-continued agacctttgc tggaaaactt gtaaattctg ctagaccctc tgtaaattcc gctagacctt 8700
tgtgtgtttt ttttgtttat attcaagtgg ttataattta tagaataaag aaagaataaa 8760
aaaagataaa aagaatagat cccagccctg tgtataactc actactttag tcagttccgc 8820
agtattacaa aaggatgtcg caaacgctgt ttgctcctct acaaaacaga ccttaaaacc 8880
ctaaaggctt aagtagcacc ctcgcaagct cgggcaaatc gctgaatatt ccttttgtct 8940
ccgaccatca ggcacctgag tcgctgtctt tttcgtgaca ttcagttcgc tgcgctcacg 9000
gctctggcag tgaatggggg taaatggcac tacaggcgcc ttttatggat tcatgcaagg 9060
aaactaccca taatacaaga aaagcccgtc acgggcttct cagggcgttt tatggcgggt 9120
ctgctatgtg gtgctatctg actttttgct gttcagcagt tcctgccctc tgattttcca 9180
gtctgaccac ttcggattat cccgtgacag gtcattcaga ctggctaatg cacccagtaa 9240
ggcagcggta tcatcaacag gcttagttta aacccatcgg cattttcttt tgcgttttta 9300
tttgttaact gttaattgtc cttgttcaag gatgctgtct ttgacaacag atgttttctt 9360
gcctttgatg ttcagcagga agctcggcgc aaacgttgat tgtttgtctg cgtagaatcc 9420
tctgtttgtc atatagcttg taatcacgac attgtttcct ttcgcttgag gtacagcgaa 9480
gtgtgagtaa gtaaaggtta catcgttagg atcaagatcc atttttaaca caaggccagt 9540
tttgttcagc ggcttgtatg ggccagttaa agaattagaa acataaccaa gcatgtaaat 9600
atcgttagac gtaatgccgt caatcgtcat ttttgatccg cgggagtcag tgaacaggta 9660
ccatttgccg ttcattttaa agacgttcgc gcgttcaatt tcatctgtta ctgtgttaga 9720
tgcaatcagc ggtttcatca cttttttcag tgtgtaatca tcgtttagct caatcatacc 9780
gagagcgccg tttgctaact cagccgtgcg ttttttatcg ctttgcagaa gtttttgact 9840
ttcttgacgg aagaatgatg tgcttttgcc atagtatgct ttgttaaata aagattcttc 9900
gccttggtag ccatcttcag ttccagtgtt tgcttcaaat actaagtatt tgtggccttt 9960
atcttctacg tagtgaggat ctctcagcgt atggttgtcg cctgagctgt agttgccttc 10020
atcgatgaac tgctgtacat tttgatacgt ttttccgtca ccgtcaaaga ttgatttata 10080
atcctctaca ccgttgatgt tcaaagagct gtctgatgct gatacgttaa cttgtgcagt 10140
tgtcagtgtt tgtttgccgt aatgtttacc ggagaaatca gtgtagaata aacggatttt 10200
tccgtcagat gtaaatgtgg ctgaacctga ccattcttgt gtttggtctt ttaggataga 10260
atcatttgca tcgaatttgt cgctgtcttt aaagacgcgg ccagcgtttt tccagctgtc 10320
aatagaagtt tcgccgactt tttgatagaa catgtaaatc gatgtgtcat ccgcattttt 10380
aggatctccg gctaatgcaa agacgatgtg gtagccgtga tagtttgcga cagtgccgtc 10440
agcgttttgt aatggccagc tgtcccaaac gtccaggcct tttgcagaag agatattttt 10500
aattgtggac gaatcaaatt cagaaacttg atatttttca tttttttgct gttcagggat 10560
ttgcagcata tcatggcgtg taatatggga aatgccgtat gtttccttat atggcttttg 10620
gttcgtttct ttcgcaaacg cttgagttgc gcctcctgcc agcagtgcgg tagtaaaggt 10680
taatactgtt gcttgttttg caaacttttt gatgttcatc gttcatgtct cctttttat 10740
gtactgtgtt agcggtctgc ttcttccagc cctcctgttt gaagatggca agttagttac 10800
gcacaataaa aaaagaccta aaatatgtaa ggggtgacgc caaagtatac actttgccct 10860
ttacacattt taggtcttgc ctgctttatc agtaacaaac ccgcgcgatt tacttttcga 10920
cctcattcta ttagactctc gtttggattg caactggtct attttcctct tttgtttgat 10980
agaaaatcat aaaaggattt gcagactacg ggcctaaaga actaaaaaat ctatctgttt 11040
cttttcattc tctgtatttt ttatagtttc tgttgcatgg gcataaagtt gcctttttaa 11100
tcacaattca gaaaatatca taatatctca tttcactaaa taatagtgaa cggcaggtat 11160
atgtgatggg ttaaaaa 11177

<210> SEQ ID NO 38
<211> LENGTH: 200
<212> TYPE: DNA
<213> ORGANISM: artificial
<220> FEATURE:
<223> OTHER INFORMATION: Promoter phage SP01 P15

<400> SEQUENCE: 38
tcgaggctat tgacgacagc tatggttcac tgtccaccaa ccaaaactgt gctcagtacc 60
gccaatattt ctcccttgag ggtacaaag aggtgtccct agaagagatc cacgctgtgt 120
aaaaatttta caaaaaggta ttgactttcc ctacagggtg tgtaataatt taattacagg 180
cgggggcaac cccgcctgtt 200

<210> SEQ ID NO 39
<211> LENGTH: 11133
<212> TYPE: DNA
<213> ORGANISM: artificial
<220> FEATURE:
<223> OTHER INFORMATION: Plasmid: pOM240

<400> SEQUENCE: 39
ggatcggcgg ccagggccct catgggccgg gcgtgcgcaa tagactcgtc accaaaaccg 60
atggagtgtt tttgacgctg gaagatggca gcaccgtgat tgacgcgatg agctcctggt 120
ggtcggcaat tcatggacac ggacaccccc gactgaaagc tgccgcccaa aaacaaatcg 180
acaccatgag tcacgtcatg tttggcggac taacccacga gcccgccatt aagctcaccc 240
acaaactcct caatctcact ggaaattcct ttgaccacgt cttttattcc gattcgggct 300
cggtctcagt ggaggtcgcc atcaaaatgg cactgcaggc ctccaaagga caaggccacc 360
cggaacgaac aaaactcctc acctggcggt ccggctacca cggagacaca ttcaccgcga 420
tgagcgtgtg cgacccagaa aatggcatgc atagcctctg gaaaggcaca ctccccgagc 480
agattttcgc ccccgcccca ccagttcggg ggtcatcgcc gcaggcgatt tccgagtacc 540
tgcgcagcat ggaattgctt atcgacgaga ccgtctccgc aatcatcatc gaaccgatcg 600
tccaaggcgc tggaggcatg cgcgcggccg cttcgcgaag cttgtcgacc gaaacagcag 660
ttataaggca tgaagctgtc cggtttttgc aaaagtggct gtgactgtaa aaagaaatcg 720
aaaaagaccg ttttgtgtga aaacggtctt tttgtttcct tttaaccaac tgccataact 780
cgaggctatt gacgacagct atggttcact gtccaccaac caaaactgtg ctcagtaccg 840
ccaatatttc tcccttgagg ggtacaaaga ggtgtcccta gaagagatcc acgctgtgta 900
aaaattttac aaaaaggtat tgactttccc tacagggtgt gtaataattt aattacaggc 960
gggggcaacc ccgcctgttc tagaaggagg agaaacaatg tctacttcag ttacttcacc 1020
agcccacaac aacgcacatt cctccgaatt tttggatgcg ttggcaaacc atgtgttgat 1080
cggcgacggc gccatgggca cccagctcca aggctttgac ctggacgtgg aaaaggattt 1140
ccttgatctg gaggggtgta atgagattct caacgacacc cgccctgatg tgttgaggca 1200
gattcaccgc gcctactttg aggcgggagc tgacttggtt gagaccaata cttttggttg 1260
caacctgccg aacttggcgg attatgacat cgctgatcgt tgccgtgagc ttgcctacaa 1320
gggcactgca gtggctaggg aagtggctga tgagatgggg ccgggccgaa acggcatgcg 1380

-continued

```
gcgtttcgtg gttggttccc tgggacctgg aacgaagctt ccatcgctgg gccatgcacc   1440
gtatgcagat ttgcgtgggc actacaagga agcagcgctt ggcatcatcg acggtggtgg   1500
cgatgccttt ttgattgaga ctgctcagga cttgcttcag gtcaaggctg cggttcacgg   1560
cgttcaagat gccatggctg aacttgatac attcttgccc attatttgcc acgtcaccgt   1620
agagaccacc ggcaccatgc tcatgggttc tgagatcggt gccgcgttga cagcgctgca   1680
gccactgggt atcgacatga ttggtctgaa ctgcgccacc ggcccagatg agatgagcga   1740
gcacctgcgt tacctgtcca agcacgccga tattcctgtg tcggtgatgc ctaacgcagg   1800
tcttcctgtc ctgggtaaaa acggtgcaga atacccactt gaggctgagg atttggcgca   1860
ggcgctggct ggattcgtct ccgaatatgg cctgtccatg gtgggtggtt gttgtggcac   1920
cacacctgag cacatccgtg cggtccgcga tgcggtggtt ggtgttccag agcaggaaac   1980
ctccacactg accaagatcc ctgcaggccc tgttgagcag gcctcccgcg aggtggagaa   2040
agaggactcc gtcgcgtcgc tgtacacctc ggtgccattg tcccaggaaa ccggcatttc   2100
catgatcggt gagcgcacca actccaacgg ttccaaggca ttccgtgagg caatgctgtc   2160
tggcgattgg gaaaagtgtg tggatattgc caagcagcaa acccgcgatg gtgcacacat   2220
gctggatctt tgtgtggatt acgtgggacg agacggcacc gccgatatgg cgaccttggc   2280
agcacttctt gctaccagct ccactttgcc aatcatgatt gactccaccg agccagaggt   2340
tattcgcaca ggccttgagc acttgggtgg acgaagcatc gttaactccg tcaactttga   2400
agacggcgat ggccctgagt cccgctacca gcgcatcatg aaactggtaa agcagcacgg   2460
tgcggccgtg gttgcgctga ccattgatga ggaaggccag gcacgtaccg ctgagcacaa   2520
ggtgcgcatt gctaaacgac tgattgacga tatcaccggc agctacggcc tggatatcaa   2580
agacatcgtt gtggactgcc tgaccttccc gatctctact ggccaggaag aaaccaggcg   2640
agatggcatt gaaaccatcg aagccatccg cgagctgaag aagctctacc cagaaatcca   2700
caccaccctg ggtctgtcca atatttcctt cggcctgaac cctgctgcac gccaggttct   2760
taactctgtg ttcctcaatg agtgcattga ggctggtctg gactctgcga ttgcgcacag   2820
ctccaagatt ttgccgatga accgcattga tgatcgccag cgcgaagtgg cgttggatat   2880
ggtctatgat cgccgcaccg aggattacga tccgctgcag gaattcatgc agctgtttga   2940
gggcgtttct gctgccgatg ccaaggatgc tcgcgctgaa cagctggccg ctatgccttt   3000
gtttgagcgt ttggcacagc gcatcatcga cggcgataag aatggccttg aggatgatct   3060
ggaagcaggc atgaaggaga agtctcctat tgcgatcatc aacgaggacc ttctcaacgg   3120
catgaagacc gtgggtgagc tgtttggttc cggacagatg cagctgccat tcgtgctgca   3180
atcggcagaa accatgaaaa ctgcggtggc ctatttggaa ccgttcatgg aagaggaagc   3240
agaagctacc ggatctgcgc aggcagaggg caagggcaaa atcgtcgtgg ccaccgtcaa   3300
gggtgacgtg cacgatatcg gcaagaactt ggtggacatc attttgtcca acaacggtta   3360
cgacgtggtg aacttgggca tcaagcagcc actgtccgcc atgttggaag cagcggaaga   3420
acacaaagca gacgtcatcg gcatgtcggg acttcttgtg aagtccaccg tggtgatgaa   3480
ggaaaacctt gaggagatga acaacgccgg cgcatccaat tacccagtca ttttgggtgg   3540
cgctgcgctg acgcgtacct acgtggaaaa cgatctcaac gaggtgtaca ccggtgaggt   3600
gtactacgcc cgtgatgctt tcgagggcct gcgcctgatg gatgaggtga tggcagaaaa   3660
gcgtggtgaa ggacttgatc ccaactcacc agaagctatt gagcaggcga agaagaaggc   3720
ggaacgtaag gctcgtaatg agcgttcccg caagattgcc gcggagcgta aagctaatgc   3780
```

-continued

```
ggctcccgtg attgttccgg agcgttctga tgtctccacc gatactccaa ccgcggcacc   3840
accgttctgg ggaacccgca ttgtcaaggg tctgcccttg gcggagttct tgggcaacct   3900
tgatgagcgc gccttgttca tggggcagtg gggtctgaaa tccacccgcg gcaacgaggg   3960
tccaagctat gaggatttgg tggaaactga aggccgacca cgcctgcgct actggctgga   4020
tcgcctgaag tctgagggca ttttggacca cgtggccttg gtgtatggct acttcccagc   4080
ggtcgcggaa ggcgatgacg tggtgatctt ggaatccccg gatccacacg cagccgaacg   4140
catgcgcttt agcttcccac gccagcagcg cggcaggttc ttgtgcatcg cggatttcat   4200
tcgcccacgc gagcaagctg tcaaggacgg ccaagtggac gtcatgccat tccagctggt   4260
caccatgggt aatcctattg ctgatttcgc caacgagttg ttcgcagcca atgaataccg   4320
cgagtacttg gaagttcacg gcatcggcgt gcagctcacc gaagcattgg ccgagtactg   4380
gcactcccga gtgcgcagcg aactcaagct gaacgacggt ggatctgtcg ctgattttga   4440
tccagaagac aagaccaagt tcttcgacct ggattaccgc ggcgcccgct tctcctttgg   4500
ttacggttct tgccctgatc tggaagaccg cgcaaagctg gtggaattgc tcgagccagg   4560
ccgtatcggc gtggagttgt ccgaggaact ccagctgcac ccagagcagt ccacagacgc   4620
gtttgtgctc taccacccag aggcaaagta ctttaacgtc taacaccttt gagagggaaa   4680
actttcccgc acattgcaga tcgtgccact ttaactaagg ttgacggcaa gatccgccct   4740
cccgcacgct ttgcgggagg gcttttcttt taccggtacc ggaactgggg ttgggaaaac   4800
cttctccaca gccgttttgg ttcgatactt agccgatcaa ggacacgatg ttctgcccgt   4860
aaagctagtc caaaccggtg aacttccagg cgagggagac atctttaaca ttgaacgctt   4920
gactggaatt gctggagagg aatttgctcg tttcaaagac cctcttgcgc caaatctggc   4980
agcccgacga gagggggtcg agccaataca gtttgatcag attatctcgt ggcttcgtgg   5040
ttttgacgac ccagatcgca tcattgtggt ggagggcgct ggtggcctgc tggtcagatt   5100
aggggaagat ttcaccctgg cagatgttgc ctccgctttg aatgcaccct tagtgattgt   5160
gacaagcacc ggattgggaa gcctcaacgc tgctgaatta agcgttgagg cagcaaaccg   5220
ccgaggactc acagtgttgg gagtcctcgg cggttcgatc cctcaaaatc ctgatctagc   5280
tacgatgctt aatctcgaag aatttgagag agtcaccggc gtgccctttt ggggagcttt   5340
gccggaaggg ttgtcacggg tggaggggtt cgtcgaaaag caatcttttc cggcccttga   5400
tgcctttaag aaaccgccgg caaggctccc aacgcgtccc gggatttaaa tcgctagcgg   5460
gctgctaaag gaagcggaac acgtagaaag ccagtccgca gaaacggtgc tgaccccgga   5520
tgaatgtcag ctactgggct atctggacaa gggaaaacgc aagcgcaaag agaaagcagg   5580
tagcttgcag tgggcttaca tggcgatagc tagactgggc ggttttatgg acagcaagcg   5640
aaccggaatt gccagctggg gcgccctctg gtaaggttgg gaagccctgc aaagtaaact   5700
ggatggcttt cttgccgcca aggatctgat ggcgcagggg atcaagatct gatcaagaga   5760
caggatgagg atcgtttcgc atgattgaac aagatggatt gcacgcaggt tctccggccg   5820
cttgggtgga gaggctattc ggctatgact gggcacaaca gacaatcggc tgctctgatg   5880
ccgccgtgtt ccggctgtca gcgcaggggc gcccggttct ttttgtcaag accgacctgt   5940
ccggtgccct gaatgaactg caggacgagg cagcgcggct atcgtggctg gccacgacgg   6000
gcgttccttg cgcagctgtg ctcgacgttg tcactgaagc gggaagggac tggctgctat   6060
tgggcgaagt gccggggcag gatctcctgt catctcacct tgctcctgcc gagaaagtat   6120
ccatcatggc tgatgcaatg cggcggctgc atacgcttga tccggctacc tgcccattcg   6180
```

-continued

```
accaccaagc gaaacatcgc atcgagcgag cacgtactcg gatggaagcc ggtcttgtcg   6240
atcaggatga tctggacgaa gagcatcagg ggctcgcgcc agccgaactg ttcgccaggc   6300
tcaaggcgcg catgcccgac ggcgaggatc tcgtcgtgac ccatggcgat gcctgcttgc   6360
cgaatatcat ggtggaaaat ggccgctttt ctggattcat cgactgtggc cggctgggtg   6420
tggcggaccg ctatcaggac atagcgttgg ctacccgtga tattgctgaa gagcttggcg   6480
gcgaatgggc tgaccgcttc ctcgtgcttt acggtatcgc cgctcccgat tcgcagcgca   6540
tcgccttcta tcgccttctt gacgagttct tctgagcggg actctggggt tcgaaatgac   6600
cgaccaagcg acgcccaacc tgccatcacg agatttcgat tccaccgccg ccttctatga   6660
aaggttgggc ttcggaatcg ttttccggga cgccggctgg atgatcctcc agcgcgggga   6720
tctcatgctg gagttcttcg cccacgctag tttaaactgc ggatcagtga gggtttgtaa   6780
ctgcgggtca aggatctgga tttcgatcac ggcacgatca tcgtgcggga gggcaagggc   6840
tccaaggatc gggccttgat gttacccgag agcttggcac ccagcctgcg cgagcagggg   6900
aattgatccg gtggatgacc ttttgaatga cctttaatag attatattac taattaattg   6960
gggaccctag aggtcccctt ttttatttta aaaatttttt cacaaaacgg tttacaagca   7020
taacgggttt tgctgcccgc aaacgggctg ttctggtgtt gctagtttgt tatcagaatc   7080
gcagatccgg cttcaggttt gccggctgaa agcgctattt cttccagaat tgccatgatt   7140
ttttccccac gggaggcgtc actggctccc gtgttgtcgg cagctttgat tcgataagca   7200
gcatcgcctg tttcaggctg tctatgtgtg actgttgagc tgtaacaagt tgtctcaggt   7260
gttcaatttc atgttctagt tgctttgttt tactggtttc acctgttcta ttaggtgtta   7320
catgctgttc atctgttaca ttgtcgatct gttcatggtg aacagcttta aatgcaccaa   7380
aaactcgtaa aagctctgat gtatctatct tttttacacc gttttcatct gtgcatatgg   7440
acagttttcc ctttgatatc taacggtgaa cagttgttct acttttgttt gttagtcttg   7500
atgcttcact gatagataca agagccataa gaacctcaga tccttccgta tttagccagt   7560
atgttctcta gtgtggttcg ttgtttttgc gtgagccatg agaacgaacc attgagatca   7620
tgcttacttt gcatgtcact caaaaatttt gcctcaaaac tggtgagctg aatttttgca   7680
gttaaagcat cgtgtagtgt ttttcttagt ccgttacgta ggtaggaatc tgatgtaatg   7740
gttgttggta ttttgtcacc attcattttt atctggttgt tctcaagttc ggttacgaga   7800
tccatttgtc tatctagttc aacttggaaa atcaacgtat cagtcgggcg gcctcgctta   7860
tcaaccacca atttcatatt gctgtaagtg tttaaatctt tacttattgg tttcaaaacc   7920
cattggttaa gccttttaaa ctcatggtag ttattttcaa gcattaacat gaacttaaat   7980
tcatcaaggc taatctctat atttgccttg tgagttttct tttgtgttag ttcttttaat   8040
aaccactcat aaatcctcat agagtatttg ttttcaaaag acttaacatg ttccagatta   8100
tattttatga atttttttaa ctggaaaaga taaggcaata tctcttcact aaaaactaat   8160
tctaattttt cgcttgagaa cttggcatag tttgtccact ggaaaatctc aaagccttta   8220
accaaaggat tcctgatttc cacagttctc gtcatcagct ctctggttgc tttagctaat   8280
acaccataag cattttccct actgatgttc atcatctgag cgtattggtt ataagtgaac   8340
gataccgtcc gttctttcct tgtagggttt tcaatcgtgg ggttgagtag tgccacacag   8400
cataaaatta gcttggtttc atgctccgtt aagtcatagc gactaatcgc tagttcattt   8460
gctttgaaaa caactaattc agacatacat ctcaattggt ctaggtgatt ttaatcacta   8520
taccaattga gatgggctag tcaatgataa ttactagtcc ttttcctttg agttgtgggt   8580
```

-continued

```
atctgtaaat tctgctagac ctttgctgga aaacttgtaa attctgctag accctctgta   8640
aattccgcta gacctttgtg tgtttttttt gtttatattc aagtggttat aatttataga   8700
ataaagaaag aataaaaaaa gataaaaaga atagatccca gccctgtgta taactcacta   8760
ctttagtcag ttccgcagta ttacaaaagg atgtcgcaaa cgctgtttgc tcctctacaa   8820
aacagacctt aaaaccctaa aggcttaagt agcaccctcg caagctcggg caaatcgctg   8880
aatattcctt ttgtctccga ccatcaggca cctgagtcgc tgtctttttc gtgacattca   8940
gttcgctgcg ctcacggctc tggcagtgaa tgggggtaaa tggcactaca ggcgcctttt   9000
atggattcat gcaaggaaac tacccataat acaagaaaag cccgtcacgg gcttctcagg   9060
gcgttttatg gcgggtctgc tatgtggtgc tatctgactt tttgctgttc agcagttcct   9120
gccctctgat tttccagtct gaccacttcg gattatcccg tgacaggtca ttcagactgg   9180
ctaatgcacc cagtaaggca gcggtatcat caacaggctt agtttaaacc catcggcatt   9240
ttcttttgcg tttttatttg ttaactgtta attgtccttg ttcaaggatg ctgtctttga   9300
caacagatgt ttcttgcct ttgatgttca gcaggaagct cggcgcaaac gttgattgtt   9360
tgtctgcgta gaatcctctg tttgtcatat agcttgtaat cacgacattg tttcctttcg   9420
cttgaggtac agcgaagtgt gagtaagtaa aggttacatc gttaggatca agatccattt   9480
ttaacacaag gccagttttg ttcagcggct tgtatgggcc agttaaagaa ttagaaacat   9540
aaccaagcat gtaaatatcg ttagacgtaa tgccgtcaat cgtcattttt gatccgcggg   9600
agtcagtgaa caggtaccat ttgccgttca ttttaaagac gttcgcgcgt tcaatttcat   9660
ctgttactgt gttagatgca atcagcggtt tcatcacttt tttcagtgtg taatcatcgt   9720
ttagctcaat cataccgaga gcgccgtttg ctaactcagc cgtgcgtttt ttatcgcttt   9780
gcagaagttt ttgactttct tgacggaaga atgatgtgct tttgccatag tatgctttgt   9840
taaataaaga ttcttcgcct tggtagccat cttcagttcc agtgtttgct tcaaatacta   9900
agtatttgtg gcctttatct tctacgtagt gaggatctct cagcgtatgg ttgtcgcctg   9960
agctgtagtt gccttcatcg atgaactgct gtacattttg atacgttttt ccgtcaccgt  10020
caaagattga tttataatcc tctacaccgt tgatgttcaa agagctgtct gatgctgata  10080
cgttaacttg tgcagttgtc agtgtttgtt tgccgtaatg tttaccggag aaatcagtgt  10140
agaataaacg gatttttccg tcagatgtaa atgtggctga acctgaccat tcttgtgttt  10200
ggtcttttag gatagaatca tttgcatcga atttgtcgct gtctttaaag acgcggccag  10260
cgtttttcca gctgtcaata gaagtttcgc cgactttttg atagaacatg taaatcgatg  10320
tgtcatccgc atttttagga tctccggcta atgcaaagac gatgtggtag ccgtgatagt  10380
ttgcgacagt gccgtcagcg ttttgtaatg gccagctgtc ccaaacgtcc aggccttttg  10440
cagaagagat atttttaatt gtggacgaat caaattcaga aacttgatat ttttcatttt  10500
tttgctgttc agggatttgc agcatatcat ggcgtgtaat atgggaaatg ccgtatgttt  10560
ccttatatgg cttttggttc gtttctttcg caaacgcttg agttgcgcct cctgccagca  10620
gtgcggtagt aaaggttaat actgttgctt gttttgcaaa ctttttgatg ttcatcgttc  10680
atgtctcctt ttttatgtac tgtgttagcg gtctgcttct tccagccctc ctgtttgaag  10740
atggcaagtt agttacgcac aataaaaaaa gacctaaaat atgtaagggg tgacgccaaa  10800
gtatacactt tgccctttac acattttagg tcttgcctgc tttatcagta acaaacccgc  10860
gcgatttact tttcgacctc attctattag actctcgttt ggattgcaac tggtctattt  10920
tcctcttttg tttgatagaa aatcataaaa ggatttgcag actacgggcc taaagaacta  10980
```

aaaaatctat ctgtttcttt tcattctctg tattttttat agtttctgtt gcatgggcat 11040
aaagttgcct ttttaatcac aattcagaaa atatcataat atctcatttc actaaataat 11100
agtgaacggc aggtatatgt gatgggttaa aaa 11133

<210> SEQ ID NO 40
<211> LENGTH: 9881
<212> TYPE: DNA
<213> ORGANISM: artificial
<220> FEATURE:
<223> OTHER INFORMATION: Plasmid: pOM324

<400> SEQUENCE: 40
ggatcggcgg ccagggccct catgagatat cgagtcagcg ctgtattgcc cgtgaagttg 60
atggtgtttc cgctgccctg ctgggtggga ttggaggtgt aatcaatgaa ccaaccagga 120
gttccggtgc cagtgagatc aaataccacg cggtcaaagc cactgtgaga gccaatccga 180
acatcggtga ccatgagctg tgcaggcgca tcaggtcgga gagtcttcat tgctacatcg 240
gcttcgccca atgcggttgg gccggtggaa gcttcgttgg acaactgtgc gccatccgca 300
gttgcggaca tagtttgggt tacagaagaa gcatcgttgg tggtggaatt ggaggttcca 360
caacccgcaa gagtcaacgc gctagcgccg acaatcgcta gagtcttcag gcgggcacga 420
tgctttgaat gagaagttgg ctgcacaatc atgcacacac cgtaaccctg ggtcaccccc 480
gaaacctaag caagacgccc aatttcgctc aatcgtgaac gaattgttgt aattcgtctt 540
aaaaacgcca ggagacgtga aaattacaga caccccagac atcagatgga ggcggcgata 600
ctagggtaga ggacatgact cttcgctgtt ctgacgtcaa tgttgaaccc ctgccgggaa 660
cggcaaaaac aggttctggg tttgttctcc ttgaacatgc tggctcgtgg agccgtgatg 720
ttttagacgg cggaacattt gatcctgagt tgactgatca attgaagagg cacctgaaag 780
cttccggaat gggtctgcaa ttaattagga agccgggaag ggagggtcga aacgtcgaaa 840
agcataatct ttttctcgtt tttgctgagg cctcaattat tgagcacctg gtggtggacg 900
cgccggctga tgttttggat cttgatttaa gcgggccggg caaaaacaat gcgcagcgca 960
tggatgatcc gatgctgctg atttgtacgc attcgaagcg cgatgtgtgc tgcgcgatca 1020
aggggcgtcc gctggcagct gccgtggagc cacaatttgg gccgctgcat gtgtgggagg 1080
cttcgcacac caagggccac cgttttgcgc catcgatgct gctcatgccg tggaattact 1140
cttatggcct acttgatgag gccgaaaccg tgcagctttt ccaaggcgcg ttggacaaca 1200
aactcttcct gccgggcaac cgtggccgag gaaccttaga tgctcgtggc caggttgcag 1260
aaattgccgt ggcggaagct ttcggcgagg cggttgctcc tgcgagtttg caggttgaat 1320
tcgaagatga ttctgttttg gttactcatc ccgatgggcg cacgtgggtt gtggagcttg 1380
aacgcatcga ggtcgacggc gtggtgtcct cgtgtggtga tcagccgaaa actggaaaag 1440
cgtgggtggc taggcaagtt acagaactga tcggataaaa gcagagttat atctgatgaa 1500
ttgctattag cagtatcgtt atcacagcac caacaaagta gttcagccac aggaaaactt 1560
tccaactgcg attagcctgt tcacaactgg catctgtaat gttccaaaat cgtgcggcat 1620
taaatacgta agttagaatc gcaatcccga tgatccacgc cggattaggc aaagtagtga 1680
ctaacacagc agctagtaaa taaagtacta ctgaaagccg aatggctcca cgcgccccaa 1740
ttacagtggc aattgagctg cggccgcttc gcgaagcttg tcgaccgaaa cagcagttat 1800
aaggcatgaa gctgtccggt ttttgcaaaa gtggctgtga ctgtaaaaag aaatcgaaaa 1860
agaccgtttt gtgtgaaaac ggtctttttg tttcctttta accaactgcc ataactcgag 1920

-continued

```
gctattgacg acagctatgg ttcactgtcc accaaccaaa actgtgctca gtaccgccaa   1980
tatttctccc ttgaggggta caaagaggtg tccctagaag agatccacgc tgtgtaaaaa   2040
ttttacaaaa aggtattgac tttccctaca gggtgtgtaa taatttaatt acaggcgggg   2100
gcaaccccgc ctgttctaga aggaggtgaa caaatggcaa tcactggcat ctttttcggc   2160
agcgacaccg gtaataccga aaatatcgca aaaatgattc aaaaacagct tggtaaagac   2220
gttgccgatg tccatgacat tgcaaaaagc agcaaagaag atctggaagc ttatgacatt   2280
ctgctgctgg gcatcccaac ctggtattac ggcgaagcgc agtgtgactg ggatgacttc   2340
ttcccgactc tcgaagagat tgatttcaac ggcaaactgg ttgcgctgtt tggttgtggt   2400
gaccaggaag attacgccga atatttctgc gacgcattgg gcaccatccg cgacatcatt   2460
gaaccgcgcg gtgcaaccat cgttggtcac tggccaactg cgggctatca tttcgaagca   2520
tcaaaaggtc tggcagatga cgaccacttt gtcggtctgg ctatcgacga agaccgtcag   2580
ccggaactga ccgctgaacg tgtagaaaaa tgggttaaac agatttctga agagttgcat   2640
ctcgacgaaa ttctcaatgc ctgatgtgat gcggcgtaga ctcatgtcta cgccgtatta   2700
atagataatg ccaatcaaaa taattgctac aaatttgtaa cttttgctgt tgtacctgta   2760
ggatcccagt gctatccaca tcgctgctga aggagatgtt ccagtgatcg ttgcaccgat   2820
taatgcaggt gaagtgaagt gagtagaaga tgttagagca tcgataaagg ggcgttcttt   2880
aaaacgcaat ttcggtgctg aataagcaat cactgctagc actgagagtg tcagccataa   2940
agacgacatc caggtgccaa atatgaaaag aataactagg aaaggaattg ttgagatagc   3000
cgaggcccat aacagtgtgc tgtgggaact tttcggtagc acggccccct cgacgccgcc   3060
tttgcgggga ttacgcatat cagattcgta atcaaaaaca tcgttgatac catacatggc   3120
gatgttatac gggataagaa aaaatacgat gcctagccaa aacagccagt caatctctcc   3180
tgcatttaat aggtaggcca gaccaaaggg gtaggcggta ttgatccagc taatggggcg   3240
agatgacaat agaattagtc ttattttttc catcatgact acggcttttc tggctcagat   3300
tgcgtggtgg tggatctagt agtgatgctt ccattggcga tggtgggtaa ggaatggtgt   3360
ggacgttttt tcctgcgttt aaacatattt ccaggcaacc atagggcagg aatcagaagt   3420
actgcgaaga gcggatagaa aagatcctct agggggatta aaccgagcca aatgccaagg   3480
tgctgggtat cgccatatcc aaagagatca gcccaaacca tgaggttatc aaatatgata   3540
gttagggaac atagggtaag ggcactgaca gcggtgattg gtaaaagttt aggtgttcca   3600
gactgcagct ttaagacaaa taggaccatg gctattgcta aaaaaggaat gcttataaaa   3660
atataagtca tggttcaacc tcgggagtgg tagttggttg gaaagtatcg cgctgtggtg   3720
tgaggggaga ctttttaccg ggtttttttag gcagtggtgc tttaagccat aatgctgctg   3780
ccgaggtaag gttgagggtg atgtagcaga ggaagaataa gaaaaaaagt tcttcaatgg   3840
gcatatgggg tgcaaggtta ataccggaca taaacgctga gtctccgcga taaaaagtgc   3900
cagtaataat gccaaatata tcccataaaa gaaatccaat atatgcagca cctaccgaaa   3960
gaattgctcg taacggatgg cggaagaacg ctagcttcca acggtggtcg cacaaagcca   4020
tgcacccaat gagaactagg agagtaccta gataaataaa ggccataaaa atatcgctat   4080
cttgctcatt ttgtgaaata tcgatgatag ggatcaaaat ttaatgatcg tatgaggtct   4140
tttgagatgg tgtcgtttta ggcggcaatg gttcggctca cgcgtcccgg gatttaaatc   4200
gctagcgggc tgctaaagga agcggaacac gtagaaagcc agtccgcaga aacggtgctg   4260
accccggatg aatgtcagct actgggctat ctggacaagg gaaaacgcaa gcgcaaagag   4320
```

-continued

```
aaagcaggta gcttgcagtg ggcttacatg gcgatagcta gactgggcgg ttttatggac   4380
agcaagcgaa ccggaattgc cagctggggc gccctctggt aaggttggga agccctgcaa   4440
agtaaactgg atggctttct tgccgccaag gatctgatgg cgcaggggat caagatctga   4500
tcaagagaca ggatgaggat cgtttcgcat gattgaacaa gatggattgc acgcaggttc   4560
tccggccgct tgggtggaga ggctattcgg ctatgactgg gcacaacaga caatcggctg   4620
ctctgatgcc gccgtgttcc ggctgtcagc gcaggggcgc ccggttcttt ttgtcaagac   4680
cgacctgtcc ggtgccctga atgaactgca ggacgaggca gcgcggctat cgtggctggc   4740
cacgacgggc gttccttgcg cagctgtgct cgacgttgtc actgaagcgg gaagggactg   4800
gctgctattg ggcgaagtgc cggggcagga tctcctgtca tctcaccttg ctcctgccga   4860
gaaagtatcc atcatggctg atgcaatgcg gcggctgcat acgcttgatc cggctacctg   4920
cccattcgac caccaagcga aacatcgcat cgagcgagca cgtactcgga tggaagccgg   4980
tcttgtcgat caggatgatc tggacgaaga gcatcagggg ctcgcgccag ccgaactgtt   5040
cgccaggctc aaggcgcgca tgcccgacgg cgaggatctc gtcgtgaccc atggcgatgc   5100
ctgcttgccg aatatcatgg tggaaaatgg ccgcttttct ggattcatcg actgtggccg   5160
gctgggtgtg gcggaccgct atcaggacat agcgttggct acccgtgata ttgctgaaga   5220
gcttggcggc gaatgggctg accgcttcct cgtgctttac ggtatcgccg ctcccgattc   5280
gcagcgcatc gccttctatc gccttcttga cgagttcttc tgagcgggac tctggggttc   5340
gaaatgaccg accaagcgac gcccaacctg ccatcacgag atttcgattc caccgccgcc   5400
ttctatgaaa ggttgggctt cggaatcgtt ttccgggacg ccggctggat gatcctccag   5460
cgcggggatc tcatgctgga gttcttcgcc cacgctagtt taaactgcgg atcagtgagg   5520
gtttgtaact gcgggtcaag gatctggatt tcgatcacgg cacgatcatc gtgcgggagg   5580
gcaagggctc caaggatcgg gccttgatgt tacccgagag cttggcaccc agcctgcgcg   5640
agcaggggaa ttgatccggt ggatgacctt ttgaatgacc tttaatagat tatattacta   5700
attaattggg gaccctagag gtccccttttttattttaaa aatttttca caaaacggtt   5760
tacaagcata acgggttttg ctgcccgcaa acgggctgtt ctggtgttgc tagtttgtta   5820
tcagaatcgc agatccggct tcaggtttgc cggctgaaag cgctatttct tccagaattg   5880
ccatgatttt ttccccacgg gaggcgtcac tggctcccgt gttgtcggca gctttgattc   5940
gataagcagc atcgcctgtt tcaggctgtc tatgtgtgac tgttgagctg taacaagttg   6000
tctcaggtgt tcaatttcat gttctagttg ctttgtttta ctggtttcac ctgttctatt   6060
aggtgttaca tgctgttcat ctgttacatt gtcgatctgt tcatggtgaa cagctttaaa   6120
tgcaccaaaa actcgtaaaa gctctgatgt atctatcttt tttacaccgt tttcatctgt   6180
gcatatggac agttttccct ttgatatcta acggtgaaca gttgttctac ttttgtttgt   6240
tagtcttgat gcttcactga tagatacaag agccataaga acctcagatc cttccgtatt   6300
tagccagtat gttctctagt gtggttcgtt gtttttgcgt gagccatgag aacgaaccat   6360
tgagatcatg cttactttgc atgtcactca aaaattttgc ctcaaaactg gtgagctgaa   6420
tttttgcagt taaagcatcg tgtagtgttt ttcttagtcc gttacgtagg taggaatctg   6480
atgtaatggt tgttggtatt ttgtcaccat tcatttttat ctggttgttc tcaagttcgg   6540
ttacgagatc catttgtcta tctagttcaa cttggaaaat caacgtatca gtcgggcggc   6600
ctcgcttatc aaccaccaat ttcatattgc tgtaagtgtt taaatcttta cttattggtt   6660
tcaaaaccca ttggttaagc cttttaaact catggtagtt attttcaagc attaacatga   6720
```

-continued

```
acttaaattc atcaaggcta atctctatat ttgccttgtg agttttcttt tgtgttagtt 6780
cttttaataa ccactcataa atcctcatag agtatttgtt ttcaaaagac ttaacatgtt 6840
ccagattata ttttatgaat ttttttaact ggaaaagata aggcaatatc tcttcactaa 6900
aaactaattc taatttttcg cttgagaact tggcatagtt tgtccactgg aaaatctcaa 6960
agcctttaac caaaggattc ctgatttcca cagttctcgt catcagctct ctggttgctt 7020
tagctaatac accataagca ttttccctac tgatgttcat catctgagcg tattggttat 7080
aagtgaacga taccgtccgt tctttccttg tagggttttc aatcgtgggg ttgagtagtg 7140
ccacacagca taaaattagc ttggtttcat gctccgttaa gtcatagcga ctaatcgcta 7200
gttcatttgc tttgaaaaca actaattcag acatacatct caattggtct aggtgatttt 7260
aatcactata ccaattgaga tgggctagtc aatgataatt actagtcctt ttcctttgag 7320
ttgtgggtat ctgtaaattc tgctagacct ttgctggaaa acttgtaaat tctgctagac 7380
cctctgtaaa ttccgctaga cctttgtgtg tttttttgt ttatattcaa gtggttataa 7440
tttatagaat aaagaaagaa taaaaaaaga taaaaagaat agatcccagc cctgtgtata 7500
actcactact ttagtcagtt ccgcagtatt acaaaaggat gtcgcaaacg ctgtttgctc 7560
ctctacaaaa cagaccttaa aaccctaaag gcttaagtag caccctcgca agctcgggca 7620
aatcgctgaa tattcctttt gtctccgacc atcaggcacc tgagtcgctg tctttttcgt 7680
gacattcagt tcgctgcgct cacggctctg gcagtgaatg gggtaaatg gcactacagg 7740
cgccttttat ggattcatgc aaggaaacta cccataatac aagaaaagcc cgtcacgggc 7800
ttctcagggc gttttatggc gggtctgcta tgtggtgcta tctgactttt tgctgttcag 7860
cagttcctgc cctctgattt tccagtctga ccacttcgga ttatcccgtg acaggtcatt 7920
cagactggct aatgcaccca gtaaggcagc ggtatcatca acaggcttag tttaaaccca 7980
tcggcatttt cttttgcgtt tttatttgtt aactgttaat tgtccttgtt caaggatgct 8040
gtctttgaca acagatgttt tcttgccttt gatgttcagc aggaagctcg gcgcaaacgt 8100
tgattgtttg tctgcgtaga atcctctgtt tgtcatatag cttgtaatca cgacattgtt 8160
tcctttcgct tgaggtacag cgaagtgtga gtaagtaaag gttacatcgt taggatcaag 8220
atccattttt aacacaaggc cagttttgtt cagcggcttg tatgggccag ttaaagaatt 8280
agaaacataa ccaagcatgt aaatatcgtt agacgtaatg ccgtcaatcg tcatttttga 8340
tccgcgggag tcagtgaaca ggtaccattt gccgttcatt ttaaagacgt tcgcgcgttc 8400
aatttcatct gttactgtgt tagatgcaat cagcggtttc atcacttttt tcagtgtgta 8460
atcatcgttt agctcaatca taccgagagc gccgtttgct aactcagccg tgcgtttttt 8520
atcgctttgc agaagttttt gactttcttg acggaagaat gatgtgcttt tgccatagta 8580
tgctttgtta aataaagatt cttcgccttg gtagccatct tcagttccag tgtttgcttc 8640
aaatactaag tatttgtggc ctttatcttc tacgtagtga ggatctctca gcgtatggtt 8700
gtcgcctgag ctgtagttgc cttcatcgat gaactgctgt acattttgat acgtttttcc 8760
gtcaccgtca aagattgatt tataatcctc tacaccgttg atgttcaaag agctgtctga 8820
tgctgatacg ttaacttgtg cagttgtcag tgtttgtttg ccgtaatgtt taccggagaa 8880
atcagtgtag aataaacgga tttttccgtc agatgtaaat gtggctgaac ctgaccattc 8940
ttgtgtttgg tcttttagga tagaatcatt tgcatcgaat ttgtcgctgt ctttaaagac 9000
gcggccagcg tttttccagc tgtcaataga agtttcgccg actttttgat agaacatgta 9060
aatcgatgtg tcatccgcat tttaggatc tccggctaat gcaaagacga tgtggtagcc 9120
```

```
gtgatagttt gcgacagtgc cgtcagcgtt ttgtaatggc cagctgtccc aaacgtccag   9180

gcctttgca gaagagatat ttttaattgt ggacgaatca aattcagaaa cttgatattt   9240

ttcatttttt tgctgttcag ggatttgcag catatcatgg cgtgtaatat gggaaatgcc   9300

gtatgtttcc ttatatggct tttggttcgt ttctttcgca aacgcttgag ttgcgcctcc   9360

tgccagcagt gcggtagtaa aggttaatac tgttgcttgt tttgcaaact ttttgatgtt   9420

catcgttcat gtctcctttt ttatgtactg tgttagcggt ctgcttcttc cagccctcct   9480

gtttgaagat ggcaagttag ttacgcacaa taaaaaaaga cctaaaatat gtaaggggtg   9540

acgccaaagt atacactttg ccctttacac attttaggtc ttgcctgctt tatcagtaac   9600

aaacccgcgc gatttacttt tcgacctcat tctattagac tctcgtttgg attgcaactg   9660

gtctattttc ctcttttgtt tgatagaaaa tcataaaagg atttgcagac tacgggccta   9720

aagaactaaa aaatctatct gtttcttttc attctctgta tttttatag tttctgttgc   9780

atgggcataa agttgccttt ttaatcacaa ttcagaaaat atcataatat ctcatttcac   9840

taaataatag tgaacggcag gtatatgtga tgggttaaaa a                        9881
```

<210> SEQ ID NO 41
<211> LENGTH: 9039
<212> TYPE: DNA
<213> ORGANISM: artificial
<220> FEATURE:
<223> OTHER INFORMATION: Plasmid: pOM154

<400> SEQUENCE: 41

```
ggatcggcgg ccagggccct catgagatat cgagtggatt tgtgcaaaac tttcaggtgt     60

gcgatgcatg agaatctgcc caataaaatt aagtttgcct cggcgataga ggtctccgtc    120

aataacatcg tcatgaacca aaagggaaaa atgcagtagt tctaaagcca ctgctacctg    180

taaaacggtg ttgagtttga cctcaatgtc atcgtctaca agcgtgttgt atagccccag    240

tagcattcga gggcggatta acttgccacc tcgcaaagct tggaaagcag catctaggca    300

ggtacggaac tctggttgat atgtgctgca ctgttgagat agcgaagcgc agatgcggtt    360

tagttcccga taaatctcat cattgaaatc aagatcagga tgagttgaat gttctgtggt    420

gattgtcatg ccattgtcca ttcgagtatc acacggccag ttatctcgca aaaattccca    480

atcgttgtat atggcgcttt attttgatga agtacagaaa gtgtgaattt gggtccataa    540

aaataatgtg cctacaagaa atttatagta tcccatgagt taatattttt aaaaataaac    600

tttatctgac tttgtagaaa aaggtgatta ctatgctgaa tatgcaggaa ccagataaaa    660

tccatccggc agaacctaca cttcgtaata tttatgacgt taaaactagt gatcccaaaa    720

gtgaattagt tgatcgttct ggcatgtcgg aagaagacat tgcgcaaatt gggcggctaa    780

tgaaatcgtt ggccagtctt cgcgatgtgg aacgtagtat tggtgaagcc tcggcacgtt    840

atatggagct aagtgcccct gatatgcgag ctttgcacta tttgattgtg gcgggcaatg    900

cgggcgaagt ggtgactcca ggaatgcttg gagctgcggc cgcttcgcga agcttgtcga    960

ccgaaacagc agttataagg catgaagctg tccggttttt gcaaaagtgg ctgtgactgt   1020

aaaaagaaat cgaaaaagac cgttttgtgt gaaaacggtc tttttgtttc cttttaacca   1080

actgccataa ctcgaggcta ttgacgacag ctatggttca ctgtccacca accaaaactg   1140

tgctcagtac cgccaatatt tctcccttga ggggtacaaa gaggtgtccc tagaagagat   1200

ccacgctgtg taaaaatttt acaaaaaggt attgactttc cctacagggt gtgtaataat   1260

ttaattacag gcgggggcaa ccccgcctgt tctagaagga ggagaaaaca tggctgattg   1320
```

-continued

```
ggtaacaggc aaagtcacta aagtgcagaa ctggaccgac gccctgttta gtctcaccgt   1380
tcacgccccc gtgcttccgt ttaccgccgg gcaatttacc aagcttggcc ttgaaatcga   1440
cggcgaacgc gtccagcgcg cctactccta tgtaaactcg cccgataatc ccgatctgga   1500
gttttacctg gtcaccgtcc ccgatggcaa attaagccca cgactggcgg cactgaaacc   1560
aggcgatgaa gtgcaggtgg ttagcgaagc ggcaggattc tttgtgctcg atgaagtgcc   1620
gcactgcgaa acgctatgga tgctggcaac cggtacagcg attggccctt atttatcgat   1680
tctgcaacta ggtaaagatt tagatcgctt caaaaatctg gtcctggtgc acgccgcacg   1740
ttatgccgcc gacttaagct atttgccact gatgcaggaa ctggaaaaac gctacgaagg   1800
aaaactgcgc attcagacgg tggtcagtcg ggaaacggca gcggggtcgc tcaccggacg   1860
gataccggca ttaattgaaa gtggggaact ggaaagcacg attggcctgc cgatgaataa   1920
agaaaccagc catgtgatgc tgtgcggcaa tccacagatg gtgcgcgata cacaacagtt   1980
gctgaaagag acccggcaga tgacgaaaca tttacgtcgc cgaccgggcc atatgacagc   2040
ggagcattac tggtaagcgg ttacttatcg ataaacggca cgatgagcaa atccgcactc   2100
atcttattga tcatcccgga tccgccctcc cgcacgcttt gcgggagggc ttttctttta   2160
ccggtaccag ctcaccttaa gctttccccg gcatctgtaa caaagacgct taataggcta   2220
gaaaaaggtg ggcatattgt tcgtaatgtg caccccgtcg accgcagggc tttcgccctc   2280
atggtcactg atgccactcg tggagaggcg atgcggacgc ttggtaagca tcaggcgcgt   2340
cgttttgatg ctgctaaacg attaactcca caagagcgtg aagtggttat ccgattcctt   2400
caggatatgg cacaggagtt atcccttaat aatgcaccat ggctcaacac ggagtagatg   2460
accatctacg ttaattaaag tgtgcagagc ggagtggcgg tgtttaagcc acctgtcgct   2520
gggactgtaa tgaatgcgca tggccaccac ccactgtcct ctgtaatgtt ccgaacgtga   2580
gaccattggt cactactgag ctgtggcgtg cgggatagta taaatcctga ggaccggctt   2640
gggctgccga cgattgctag tgaataatca tcttcgatat aggtcacgcg gtagtttgct   2700
tgattgtctt cactctgaaa tggaatacct gggaagctaa cctttaatga agcattggaa   2760
actactttag cgctgccttc aataactgaa ggcccaaaga aagtgccaca cttatttgtt   2820
acagagattg tgtccgagtc gatcacgccg taatcagcgg taacgtcatg tgagcactgt   2880
aaagagaatg gttggggaat tgctgcgact tgataccact tgcctttgta gcgttctagg   2940
tcaatgctat tttcaatttc gggcagcgct aggttttcag gaaccgaact taggttagat   3000
acctgcgagg agccacctgc aagtcgtccg ccgtcaaaaa tgtcttgggc ttgtgccgtg   3060
gatatcccga aaagtgaaat ggctgcgagt agtgctgtgg tgacaagttt gcttgaaatg   3120
cgcataaagc aaatcctttc ttcatgttta tattaactca atagttatta cttctaaaag   3180
tatagtagat agttgtggat gggtgaagaa tttcatagaa atcgcactcg attcactaaa   3240
gacccaagag taaaatccca ggatttgctt atacttgcgc tcatggataa tcaacttcgt   3300
cccactttgc attatcaagc tcaaaacccg caccctcacg cgtcccggga tttaaatcgc   3360
tagcgggctg ctaaaggaag cggaacacgt agaaagccag tccgcagaaa cggtgctgac   3420
cccggatgaa tgtcagctac tgggctatct ggacaaggga aaacgcaagc gcaaagagaa   3480
agcaggtagc ttgcagtggg cttacatggc gatagctaga ctgggcggtt ttatggacag   3540
caagcgaacc ggaattgcca gctggggcgc cctctggtaa ggttgggaag ccctgcaaag   3600
taaactggat ggctttcttg ccgccaagga tctgatggcg caggggatca agatctgatc   3660
aagagacagg atgaggatcg tttcgcatga ttgaacaaga tggattgcac gcaggttctc   3720
```

-continued cggccgcttg ggtggagagg ctattcggct atgactgggc acaacagaca atcggctgct 3780
ctgatgccgc cgtgttccgg ctgtcagcgc aggggcgccc ggttcttttt gtcaagaccg 3840
acctgtccgg tgccctgaat gaactgcagg acgaggcagc gcggctatcg tggctggcca 3900
cgacgggcgt tccttgcgca gctgtgctcg acgttgtcac tgaagcggga agggactggc 3960
tgctattggg cgaagtgccg gggcaggatc tcctgtcatc tcaccttgct cctgccgaga 4020
aagtatccat catggctgat gcaatgcggc ggctgcatac gcttgatccg gctacctgcc 4080
cattcgacca ccaagcgaaa catcgcatcg agcgagcacg tactcggatg gaagccggtc 4140
ttgtcgatca ggatgatctg gacgaagagc atcaggggct cgcgccagcc gaactgttcg 4200
ccaggctcaa ggcgcgcatg cccgacggcg aggatctcgt cgtgacccat ggcgatgcct 4260
gcttgccgaa tatcatggtg gaaaatggcc gcttttctgg attcatcgac tgtggccggc 4320
tgggtgtggc ggaccgctat caggacatag cgttggctac ccgtgatatt gctgaagagc 4380
ttggcggcga atgggctgac cgcttcctcg tgctttacgg tatcgccgct cccgattcgc 4440
agcgcatcgc cttctatcgc cttcttgacg agttcttctg agcgggactc tggggttcga 4500
aatgaccgac caagcgacgc ccaacctgcc atcacgagat ttcgattcca ccgccgcctt 4560
ctatgaaagg ttgggcttcg gaatcgtttt ccgggacgcc ggctggatga tcctccagcg 4620
cggggatctc atgctggagt tcttcgccca cgctagttta aactgcggat cagtgagggt 4680
ttgtaactgc gggtcaagga tctggatttc gatcacggca cgatcatcgt gcgggagggc 4740
aagggctcca aggatcgggc cttgatgtta cccgagagct tggcacccag cctgcgcgag 4800
caggggaatt gatccggtgg atgacctttt gaatgacctt taatagatta tattactaat 4860
taattgggga ccctagaggt cccctttttt attttaaaaa ttttttcaca aaacggttta 4920
caagcataac gggttttgct gcccgcaaac gggctgttct ggtgttgcta gtttgttatc 4980
agaatcgcag atccggcttc aggtttgccg gctgaaagcg ctatttcttc cagaattgcc 5040
atgatttttt ccccacggga ggcgtcactg gctcccgtgt tgtcggcagc tttgattcga 5100
taagcagcat cgcctgtttc aggctgtcta tgtgtgactg ttgagctgta acaagttgtc 5160
tcaggtgttc aatttcatgt tctagttgct ttgttttact ggtttcacct gttctattag 5220
gtgttacatg ctgttcatct gttacattgt cgatctgttc atggtgaaca gctttaaatg 5280
caccaaaaac tcgtaaaagc tctgatgtat ctatcttttt tacaccgttt tcatctgtgc 5340
atatggacag ttttcccttt gatatctaac ggtgaacagt tgttctactt ttgtttgtta 5400
gtcttgatgc ttcactgata gatacaagag ccataagaac ctcagatcct tccgtattta 5460
gccagtatgt tctctagtgt ggttcgttgt ttttgcgtga gccatgagaa cgaaccattg 5520
agatcatgct tactttgcat gtcactcaaa aattttgcct caaaactggt gagctgaatt 5580
tttgcagtta aagcatcgtg tagtgttttt cttagtccgt tacgtaggta ggaatctgat 5640
gtaatggttg ttggtatttt gtcaccattc atttttatct ggttgttctc aagttcggtt 5700
acgagatcca tttgtctatc tagttcaact tggaaaatca acgtatcagt cgggcggcct 5760
cgcttatcaa ccaccaattt catattgctg taagtgttta aatctttact tattggtttc 5820
aaaacccatt ggttaagcct tttaaactca tggtagttat tttcaagcat taacatgaac 5880
ttaaattcat caaggctaat ctctatattt gccttgtgag ttttcttttg tgttagttct 5940
tttaataacc actcataaat cctcatagag tatttgtttt caaaagactt aacatgttcc 6000
agattatatt ttatgaattt ttttaactgg aaaagataag gcaatatctc ttcactaaaa 6060
actaattcta atttttcgct tgagaacttg gcatagtttg tccactggaa aatctcaaag 6120

-continued

```
cctttaacca aaggattcct gatttccaca gttctcgtca tcagctctct ggttgcttta   6180
gctaatacac cataagcatt ttccctactg atgttcatca tctgagcgta ttggttataa   6240
gtgaacgata ccgtccgttc tttccttgta gggttttcaa tcgtggggtt gagtagtgcc   6300
acacagcata aaattagctt ggtttcatgc tccgttaagt catagcgact aatcgctagt   6360
tcatttgctt tgaaaacaac taattcagac atacatctca attggtctag gtgattttaa   6420
tcactatacc aattgagatg ggctagtcaa tgataattac tagtcctttt cctttgagtt   6480
gtgggtatct gtaaattctg ctagaccttt gctggaaaac ttgtaaattc tgctagaccc   6540
tctgtaaatt ccgctagacc tttgtgtgtt tttttgttt atattcaagt ggttataatt   6600
tatagaataa agaaagaata aaaaaagata aaaagaatag atcccagccc tgtgtataac   6660
tcactacttt agtcagttcc gcagtattac aaaaggatgt cgcaaacgct gtttgctcct   6720
ctacaaaaca gaccttaaaa ccctaaaggc ttaagtagca ccctcgcaag ctcgggcaaa   6780
tcgctgaata ttcctttgt ctccgaccat caggcacctg agtcgctgtc tttttcgtga   6840
cattcagttc gctgcgctca cggctctggc agtgaatggg ggtaaatggc actacaggcg   6900
ccttttatgg attcatgcaa ggaaactacc cataatacaa gaaaagcccg tcacgggctt   6960
ctcagggcgt tttatggcgg gtctgctatg tggtgctatc tgactttttg ctgttcagca   7020
gttcctgccc tctgattttc cagtctgacc acttcggatt atcccgtgac aggtcattca   7080
gactggctaa tgcacccagt aaggcagcgg tatcatcaac aggcttagtt taaacccatc   7140
ggcattttct tttgcgtttt tatttgttaa ctgttaattg tccttgttca aggatgctgt   7200
ctttgacaac agatgttttc ttgcctttga tgttcagcag gaagctcggc gcaaacgttg   7260
attgtttgtc tgcgtagaat cctctgtttg tcatatagct tgtaatcacg acattgtttc   7320
ctttcgcttg aggtacagcg aagtgtgagt aagtaaaggt tacatcgtta ggatcaagat   7380
ccatttttaa cacaaggcca gttttgttca gcggcttgta tgggccagtt aaagaattag   7440
aaacataacc aagcatgtaa atatcgttag acgtaatgcc gtcaatcgtc atttttgatc   7500
cgcgggagtc agtgaacagg taccatttgc cgttcatttt aaagacgttc gcgcgttcaa   7560
tttcatctgt tactgtgtta gatgcaatca gcggtttcat cactttttc agtgtgtaat    7620
catcgtttag ctcaatcata ccgagagcgc cgtttgctaa ctcagccgtg cgttttttat   7680
cgctttgcag aagtttttga ctttcttgac ggaagaatga tgtgcttttg ccatagtatg   7740
ctttgttaaa taaagattct tcgccttggt agccatcttc agttccagtg tttgcttcaa   7800
atactaagta tttgtggcct ttatcttcta cgtagtgagg atctctcagc gtatggttgt   7860
cgcctgagct gtagttgcct tcatcgatga actgctgtac attttgatac gtttttccgt   7920
caccgtcaaa gattgattta taatcctcta caccgttgat gttcaaagag ctgtctgatg   7980
ctgatacgtt aacttgtgca gttgtcagtg tttgtttgcc gtaatgttta ccggagaaat   8040
cagtgtagaa taaacggatt tttccgtcag atgtaaatgt ggctgaacct gaccattctt   8100
gtgtttggtc ttttaggata gaatcatttg catcgaattt gtcgctgtct ttaaagacgc   8160
ggccagcgtt tttccagctg tcaatagaag tttcgccgac tttttgatag aacatgtaaa   8220
tcgatgtgtc atccgcattt ttaggatctc cggctaatgc aaagacgatg tggtagccgt   8280
gatagtttgc gacagtgccg tcagcgtttt gtaatggcca gctgtcccaa acgtccaggc   8340
cttttgcaga agagatattt ttaattgtgg acgaatcaaa ttcagaaact tgatattttt   8400
catttttttg ctgttcaggg atttgcagca tatcatggcg tgtaatatgg gaaatgccgt   8460
atgtttcctt atatggcttt tggttcgttt ctttcgcaaa cgcttgagtt gcgcctcctg   8520
```

-continued

```
ccagcagtgc ggtagtaaag gttaatactg ttgcttgttt tgcaaacttt ttgatgttca   8580

tcgttcatgt ctcctttttt atgtactgtg ttagcggtct gcttcttcca gccctcctgt   8640

ttgaagatgg caagttagtt acgcacaata aaaaaagacc taaaatatgt aaggggtgac   8700

gccaaagtat acactttgcc ctttacacat tttaggtctt gcctgcttta tcagtaacaa   8760

acccgcgcga tttacttttc gacctcattc tattagactc tcgtttggat tgcaactggt   8820

ctattttcct cttttgtttg atagaaaatc ataaaaggat ttgcagacta cgggcctaaa   8880

gaactaaaaa atctatctgt ttcttttcat tctctgtatt ttttatagtt tctgttgcat   8940

gggcataaag ttgccttttt aatcacaatt cagaaaatat cataatatct catttcacta   9000

aataatagtg aacggcaggt atatgtgatg ggttaaaaa                          9039
```

<210> SEQ ID NO 42
<211> LENGTH: 7291
<212> TYPE: DNA
<213> ORGANISM: artificial
<220> FEATURE:
<223> OTHER INFORMATION: Plasmid: pOM413

<400> SEQUENCE: 42

```
tcgactcata cgttaaatct atcaccgcaa gggataaata tctaacaccg tgcgtgttga     60

ctattttacc tctggcggtg ataatggttg catgtactaa ggaggattaa ttaatgacaa    120

caaccaccgg aagtgcccgg ccagcacgtg ccgccaggaa gcctaagccc gaaggccaat    180

ggaaaatcga cggcaccgag ccgcttaacc atgccgagga aattaagcaa gaagaacccg    240

cttttgctgt caagcagcgg gtcattgata tttactccaa gcagggtttt tcttccattg    300

caccggatga cattgcccca cgctttaagt ggttgggcat ttacacccag cgtaagcagg    360

atctgggcgg tgaactgacc ggtcagcttc ctgatgatga gctgcaggat gagtacttca    420

tgatgcgtgt gcgttttgat ggcggactgg cttcccctga gcgcctgcgt gccgtgggtg    480

aaatttctag ggattatgct cgttccaccg cggacttcac cgaccgccag aacattcagc    540

tgcactggat tcgtattgaa gatgtgcctg cgatctggga gaagctagaa accgtcggac    600

tgtccaccat gcttggttgc ggtgacgttc cacgtgttat cttgggctcc ccagtttctg    660

gcgtagctgc tgaagagctg atcgatgcca ccccggctat cgatgcgatt cgtgagcgct    720

acctagacaa ggaagagttc cacaaccttc ctcgtaagga tcctgttttg gcggatgaga    780

gaagatttc agcctgatac agattaaatc agaacgcaga agcggtctga taaaacagaa     840

tttgcctggc ggcagtagcg cggtggtccc acctgacccc atgccgaact cagaagtgaa    900

acgccgtagc gccgatggta gtgtggggtc tccccatgcg agagtaggga actgccaggc    960

atcaaataaa acgaaaggct cagtcgaaag actgggcctt tcgttttatc tgttgtttgt   1020

cggtgaacgc tctcctgagt aggacaaatc cgccgggagc ggatttgaac gttgcgaagc   1080

aacggcccgg agggtggcgg gcaggacgcc cgccataaac tgccaggcat caaattaagc   1140

agaaggccat cctgacggat ggcctttttg cgtttctaca aactcttggt acgggattta   1200

aatgatccgc tagcgggctg ctaaaggaag cggaacacgt agaaagccag tccgcagaaa   1260

cggtgctgac cccggatgaa tgtcagctac tgggctatct ggacaaggga aaacgcaagc   1320

gcaaagagaa agcaggtagc ttgcagtggg cttacatggc gatagctaga ctgggcggtt   1380

ttatggacag caagcgaacc ggaattgcca gctggggcgc cctctggtaa ggttgggaag   1440

ccctgcaaag taaactggat ggctttcttg ccgccaagga tctgatggcg caggggatca   1500

agatctgatc aagagacagg atgaggatcg tttcgcatga ttgaacaaga tggattgcac   1560
```

-continued

```
gcaggttctc cggccgcttg ggtggagagg ctattcggct atgactgggc acaacagaca   1620
atcggctgct ctgatgccgc cgtgttccgg ctgtcagcgc aggggcgccc ggttcttttt   1680
gtcaagaccg acctgtccgg tgccctgaat gaactgcagg acgaggcagc gcggctatcg   1740
tggctggcca cgacgggcgt tccttgcgca gctgtgctcg acgttgtcac tgaagcggga   1800
agggactggc tgctattggg cgaagtgccg gggcaggatc tcctgtcatc tcaccttgct   1860
cctgccgaga aagtatccat catggctgat gcaatgcggc ggctgcatac gcttgatccg   1920
gctacctgcc cattcgacca ccaagcgaaa catcgcatcg agcgagcacg tactcggatg   1980
gaagccggtc ttgtcgatca ggatgatctg gacgaagagc atcaggggct cgcgccagcc   2040
gaactgttcg ccaggctcaa ggcgcgcatg cccgacggcg aggatctcgt cgtgacccat   2100
ggcgatgcct gcttgccgaa tatcatggtg gaaaatggcc gcttttctgg attcatcgac   2160
tgtggccggc tgggtgtggc ggaccgctat caggacatag cgttggctac ccgtgatatt   2220
gctgaagagc ttggcggcga atgggctgac cgcttcctcg tgctttacgg tatcgccgct   2280
cccgattcgc agcgcatcgc cttctatcgc cttcttgacg agttcttctg agcgggactc   2340
tggggttcga aatgaccgac caagcgacgc ccaacctgcc atcacgagat ttcgattcca   2400
ccgccgcctt ctatgaaagg ttgggcttcg gaatcgtttt ccgggacgcc ggctggatga   2460
tcctccagcg cggggatctc atgctggagt tcttcgccca cgctagcggc gcgccacggg   2520
tgcgcatgat cgtgctcctg tcgttgagga cccggctagg ctggcggggt tgccttactg   2580
gttagcagaa tgaatcaccg atacgcgagc gaacgtgaag cgactgctgc tgcaaaacgt   2640
ctgcgacctg agcaacaaca tgaatggtct tcggtttccg tgtttcgtaa agtctggaaa   2700
cgcggaagtc agcgccctgc accattatgt tccggatctg catcgcagga tgctgctggc   2760
taccctgtgg aacacctaca tctgtattaa cgaagcgctg gcattgaccc tgagtgattt   2820
ttctctggtc ccgccgcatc cataccgcca gttgtttacc ctcacaacgt tccagtaacc   2880
gggcatgttc atcatcagta acccgtatcg tgagcatcct ctctcgtttc atcggtatca   2940
ttacccccat gaacagaaat cccccttaca cggaggcatc agtgaccaaa caggaaaaaa   3000
ccgcccttaa catggcccgc tttatcagaa gccagacatt aacgcttctg gagaaactca   3060
acgagctgga cgcggatgaa caggcagaca tctgtgaatc gcttcacgac cacgctgatg   3120
agctttaccg cagctgcctc gcgcgtttcg gtgatgacgg tgaaaacctc tgacacatgc   3180
agctcccgga gacggtcaca gcttgtctgt aagcggatgc cgggagcaga caagcccgtc   3240
agggcgcgtc agcgggtgtt ggcgggtgtc ggggcgcagc catgacccag tcacgtagcg   3300
atagcggagt gtatactggc ttaactatgc ggcatcagag cagattgtac tgagagtgca   3360
ccatatgcgg tgtgaaatac cgcacagatg cgtaaggaga aaataccgca tcaggcgctc   3420
ttccgcttcc tcgctcactg actcgctgcg ctcggtcgtt cggctgcggc gagcggtatc   3480
agctcactca aaggcggtaa tacggttatc cacagaatca ggggataacg caggaaagaa   3540
catgtgagca aaaggccagc aaaaggccag gaaccgtaaa aaggccgcgt tgctggcgtt   3600
tttccatagg ctccgccccc ctgacgagca tcacaaaaat cgacgctcaa gtcagaggtg   3660
gcgaaacccg acaggactat aaagatacca ggcgtttccc cctggaagct ccctcgtgcg   3720
ctctcctgtt ccgaccctgc cgcttaccgg atacctgtcc gcctttctcc cttcgggaag   3780
cgtggcgctt tctcatagct cacgctgtag gtatctcagt tcggtgtagg tcgttcgctc   3840
caagctgggc tgtgtgcacg aaccccccgt tcagcccgac cgctgcgcct tatccggtaa   3900
ctatcgtctt gagtccaacc cggtaagaca cgacttatcg ccactggcag cagccactgg   3960
```

-continued

```
taacaggatt agcagagcga ggtatgtagg cggtgctaca gagttcttga agtggtggcc   4020
taactacggc tacactagaa ggacagtatt tggtatctgc gctctgctga agccagttac   4080
cttcggaaaa agagttggta gctcttgatc cggcaaacaa accaccgctg gtagcggtgg   4140
tttttttgtt tgcaagcagc agattacgcg cagaaaaaaa ggatctcaag aagatccttt   4200
gatcttttct acggggtctg acgctcagtg gaacgaaaac tcacgttaag ggattttggt   4260
catgagatta tcaaaaagga tcttcaccta gatcctttta aaggccggcc gcggccgcca   4320
tcggcatttt cttttgcgtt tttatttgtt aactgttaat tgtccttgtt caaggatgct   4380
gtctttgaca acagatgttt tcttgccttt gatgttcagc aggaagctcg gcgcaaacgt   4440
tgattgtttg tctgcgtaga atcctctgtt tgtcatatag cttgtaatca cgacattgtt   4500
tcctttcgct tgaggtacag cgaagtgtga gtaagtaaag gttacatcgt taggatcaag   4560
atccattttt aacacaaggc cagttttgtt cagcggcttg tatgggccag ttaaagaatt   4620
agaaacataa ccaagcatgt aaatatcgtt agacgtaatg ccgtcaatcg tcatttttga   4680
tccgcgggag tcagtgaaca ggtaccattt gccgttcatt ttaaagacgt tcgcgcgttc   4740
aatttcatct gttactgtgt tagatgcaat cagcggtttc atcacttttt tcagtgtgta   4800
atcatcgttt agctcaatca taccgagagc gccgtttgct aactcagccg tgcgtttttt   4860
atcgctttgc agaagttttt gactttcttg acggaagaat gatgtgcttt tgccatagta   4920
tgctttgtta aataaagatt cttcgccttg gtagccatct tcagttccag tgtttgcttc   4980
aaatactaag tatttgtggc ctttatcttc tacgtagtga ggatctctca gcgtatggtt   5040
gtcgcctgag ctgtagttgc cttcatcgat gaactgctgt acattttgat acgtttttcc   5100
gtcaccgtca aagattgatt tataatcctc tacaccgttg atgttcaaag agctgtctga   5160
tgctgatacg ttaacttgtg cagttgtcag tgtttgtttg ccgtaatgtt taccggagaa   5220
atcagtgtag aataaacgga tttttccgtc agatgtaaat gtggctgaac ctgaccattc   5280
ttgtgtttgg tcttttagga tagaatcatt tgcatcgaat ttgtcgctgt ctttaaagac   5340
gcggccagcg tttttccagc tgtcaataga agtttcgccg actttttgat agaacatgta   5400
aatcgatgtg tcatccgcat tttaggatc tccggctaat gcaaagacga tgtggtagcc   5460
gtgatagttt gcgacagtgc cgtcagcgtt ttgtaatggc cagctgtccc aaacgtccag   5520
gccttttgca gaagagatat ttttaattgt ggacgaatca aattcagaaa cttgatattt   5580
ttcatttttt tgctgttcag ggatttgcag catatcatgg cgtgtaatat gggaaatgcc   5640
gtatgtttcc ttatatggct tttggttcgt ttctttcgca aacgcttgag ttgcgcctcc   5700
tgccagcagt gcggtagtaa aggttaatac tgttgcttgt tttgcaaact tttgatgtt   5760
catcgttcat gtctcctttt ttatgtactg tgttagcggt ctgcttcttc cagccctcct   5820
gtttgaagat ggcaagttag ttacgcacaa taaaaaaaga cctaaaatat gtaaggggtg   5880
acgccaaagt atacactttg ccctttacac attttaggtc ttgcctgctt tatcagtaac   5940
aaacccgcgc gatttacttt tcgacctcat tctattagac tctcgtttgg attgcaactg   6000
gtctattttc ctcttttgtt tgatagaaaa tcataaaagg atttgcagac tacgggccta   6060
aagaactaaa aaatctatct gtttcttttc attctctgta ttttttatag tttctgttgc   6120
atgggcataa agttgccttt ttaatcacaa ttcagaaaat atcataatat ctcatttcac   6180
taaataatag tgaacggcag gtatatgtga tgggttaaaa aggatcggcg gccgctcgat   6240
ttaaatctcg agctctggag tgcgacaggt ttgatgataa aaaattagcg caagaagaca   6300
aaaatcacct tgcgctaatg ctctgttaca ggtcactaat accatctaag tagttgattc   6360
```

-continued atagtgactg catatgtaag tatttcctta gataacaatt gattgaatgt atgcaaataa 6420
atgcatacac cataggtgtg gtttaatttg atgccctttt tcagggctgg aatgtgtaag 6480
agcggggtta tttatgctgt tgtttttttg ttactcggga agggctttac ctcttccgca 6540
taaacgcttc catcagcgtt tatagttaaa aaaatctttc ggggggatgg ggagtaagct 6600
tgtgttatcc gctgggcccg gtaccacgcg tgagttcttt gagttcctgt ggggtgaact 6660
tgacctgtgc tgggccacga cgtccgaaaa cgtgcacttc agtggccttg ttttctttga 6720
gggagtcgta gacgttgtcg gaaatttcgg tgactttgag ctcgtcgcct gtcttagcca 6780
ggatgcgggc tacgtcgagg ccgacgttac caacgccgat aacagcgacg gactgtgcag 6840
acagatccca ggagcgctcg aagcgtgggt tgccgtcgta gaagccaacg aactcgccgg 6900
caccgaagga gccttctgct tcaattccgg ggatgttgag gtcgcggtct gcaactgcgc 6960
cggtggagaa cacgactgca tcgtagtagt cgcggagttc ttcgacggtg atgtctttgc 7020
cgatttcaat gttaccgagc aggcgcaggc gtggcttgtc caacacgttg tgcagggact 7080
taacgatgcc cttgatgcgt gggtggtctg gagcaacgcc gtaacggatg agtccgaacg 7140
gtgcaggcat ttgctcgaaa aggtcaacga acacttcgcg ctcttcattg cggatgagga 7200
ggtcggatgc gtaaatgcca gcagggccag ctccgatgac ggctacgcgc aggggagttg 7260
tcatatttaa atcacctcct ttctaatcta g 7291

<210> SEQ ID NO 43
<211> LENGTH: 8234
<212> TYPE: DNA
<213> ORGANISM: artificial
<220> FEATURE:
<223> OTHER INFORMATION: Plasmid: pOM429

<400> SEQUENCE: 43
tcgatttaaa tctcgagctc tggagtgcga caggtttgat gataaaaaat tagcgcaaga 60
agacaaaaat caccttgcgc taatgctctg ttacaggtca ctaataccat ctaagtagtt 120
gattcatagt gactgcatat gtaagtattt ccttagataa caattgattg aatgtatgca 180
aataaatgca tacaccatag gtgtggttta atttgatgcc ctttttcagg gctggaatgt 240
gtaagagcgg ggttatttat gctgttgttt ttttgttact cgggaagggc tttacctctt 300
ccgcataaac gcttccatca gcgtttatag ttaaaaaaat ctttcggggg gatggggagt 360
aagcttgtgt tatccgctcg ggcccggtac cacgcgtcat atgactagtt cggacctagg 420
gatatcgtcg actcatacgt taaatctatc accgcaaggg ataaatatct aacaccgtgc 480
gtgttgacta ttttacctct ggcggtgata atggttgcat gtactaagga ggattaatta 540
atgacaactc ccctgcgcgt agccgtcatc ggagctggcc ctgctggcat ttacgcatcc 600
gacctcctca tccgcaatga agagcgcgaa gtgttcgttg accttttcga gcaaatgcct 660
gcaccgttcg gactcatccg ttacggcgtt gctccagacc acccacgcat caagggcatc 720
gttaagtccc tgcacaacgt gttggacaag ccacgcctgc gcctgctcgg taacattgaa 780
atcggcaaag acatcaccgt cgaagaactc cgcgactact acgatgcagt cgtgttctcc 840
accggcgcag ttgcagaccg cgacctcaac atccccggaa ttgaagcaga aggctccttc 900
ggtgccggcg agttcgttgg cttctacgac ggcaacccac gcttcgagcg ctcctgggat 960
ctgtctgcac agtccgtcgc tgttatcggc gttggtaacg tcggcctcga cgtagcccgc 1020
atcctggcta agacaggcga cgagctcaaa gtcaccgaaa tttccgacaa cgtctacgac 1080
tccctcaaag aaaacaaggc cactgaagtg cacgttttcg gacgtcgtgg cccagcacag 1140

-continued

```
gtcaagttca ccccacagga actcaaagaa ctcgaccact cccccaccat caacgtggtt   1200
gttgatccag aagacatcga ctacgacggc gcctctgaag aagcccgccg cgcatccaag   1260
tcccaggacc tggtctgcca gatcctggaa cagtacgcaa tccgcgagcc aaaggacgct   1320
ccgcacaccc tgcagatcca cctctttgaa aacccagttg aggttcttca aaaggacggc   1380
aaggttgttg gcctgcgcac cgaacgcacc tcacttgatg gcaacggcgg cgtaaacgga   1440
accggcgaat tcaaggactg gccagtccag gctgtctacc gcgcagtcgg ctacaagtcc   1500
gaccccatcg acggcgtccc attcgatgag aacaagcacg tcatccctaa tgacggcgga   1560
catgtcctca ccgctccagg cgcagaacca gtaccaggcc tctatgcaac cggctggatc   1620
aagcgtggac caatcggtct aatcggcaac accaagtccg acgccaagga aaccaccgac   1680
atcctcatca aggatgccgt cgccggtgta cttgaagctc caaagcacca gggcgaagaa   1740
gccatcatcg agcttctcga ttcccgcaac atcccattca ccacctggga aggctggtac   1800
aaactcgacg cagcagagcg cgcactcggt gaagccgaag gccgcgagcg caagaagatt   1860
gttgattggg aagaaatggt ccgccaggcc cgcgaagctc cagcaattgt ctaaattgtt   1920
ttaacgcgtg aagcagtccc cgcccgattt attcgaggcg gggactttcg ctttccggga   1980
taaaaattgg atcctgtttt ggcggatgag agaagatttt cagcctgata cagattaaat   2040
cagaacgcag aagcggtctg ataaaacaga atttgcctgg cggcagtagc gcggtggtcc   2100
cacctgaccc catgccgaac tcagaagtga aacgccgtag cgccgatggt agtgtggggt   2160
ctccccatgc gagagtaggg aactgccagg catcaaataa aacgaaaggc tcagtcgaaa   2220
gactgggcct ttcgttttat ctgttgtttg tcggtgaacg ctctcctgag taggacaaat   2280
ccgccgggag cggatttgaa cgttgcgaag caacggcccg gagggtggcg ggcaggacgc   2340
ccgccataaa ctgccaggca tcaaattaag cagaaggcca tcctgacgga tggccttttt   2400
gcgtttctac aaactcttgg tacgggattt aaatgatccg ctagcgggct gctaaaggaa   2460
gcggaacacg tagaaagcca gtccgcagaa acggtgctga ccccggatga atgtcagcta   2520
ctgggctatc tggacaaggg aaaacgcaag cgcaaagaga aagcaggtag cttgcagtgg   2580
gcttacatgg cgatagctag actgggcggt tttatggaca gcaagcgaac cggaattgcc   2640
agctggggcg ccctctggta aggttgggaa gccctgcaaa gtaaactgga tggctttctt   2700
gccgccaagg atctgatggc gcaggggatc aagatctgat caagagacag gatgaggatc   2760
gtttcgcatg attgaacaag atggattgca cgcaggttct ccggccgctt gggtggagag   2820
gctattcggc tatgactggg cacaacagac aatcggctgc tctgatgccg ccgtgttccg   2880
gctgtcagcg caggggcgcc cggttctttt tgtcaagacc gacctgtccg gtgccctgaa   2940
tgaactgcag gacgaggcag cgcggctatc gtggctggcc acgacgggcg ttccttgcgc   3000
agctgtgctc gacgttgtca ctgaagcggg aagggactgg ctgctattgg gcgaagtgcc   3060
ggggcaggat ctcctgtcat ctcaccttgc tcctgccgag aaagtatcca tcatggctga   3120
tgcaatgcgg cggctgcata cgcttgatcc ggctacctgc ccattcgacc accaagcgaa   3180
acatcgcatc gagcgagcac gtactcggat ggaagccggt cttgtcgatc aggatgatct   3240
ggacgaagag catcaggggc tcgcgccagc cgaactgttc gccaggctca aggcgcgcat   3300
gcccgacggc gaggatctcg tcgtgaccca tggcgatgcc tgcttgccga atatcatggt   3360
ggaaaatggc cgcttttctg gattcatcga ctgtggccgg ctgggtgtgg cggaccgcta   3420
tcaggacata gcgttggcta cccgtgatat tgctgaagag cttggcggcg aatgggctga   3480
ccgcttcctc gtgctttacg gtatcgccgc tcccgattcg cagcgcatcg ccttctatcg   3540
```

-continued

```
ccttcttgac gagttcttct gagcgggact ctggggttcg aaatgaccga ccaagcgacg   3600
cccaacctgc catcacgaga tttcgattcc accgccgcct tctatgaaag gttgggcttc   3660
ggaatcgttt tccgggacgc cggctggatg atcctccagc gcggggatct catgctggag   3720
ttcttcgccc acgctagcgg cgcgccacgg gtgcgcatga tcgtgctcct gtcgttgagg   3780
acccggctag gctggcgggg ttgccttact ggttagcaga atgaatcacc gatacgcgag   3840
cgaacgtgaa gcgactgctg ctgcaaaacg tctgcgacct gagcaacaac atgaatggtc   3900
ttcggtttcc gtgtttcgta aagtctggaa acgcggaagt cagcgccctg caccattatg   3960
ttccggatct gcatcgcagg atgctgctgg ctaccctgtg gaacacctac atctgtatta   4020
acgaagcgct ggcattgacc ctgagtgatt tttctctggt cccgccgcat ccataccgcc   4080
agttgtttac cctcacaacg ttccagtaac cgggcatgtt catcatcagt aacccgtatc   4140
gtgagcatcc tctctcgttt catcggtatc attaccccca tgaacagaaa tcccccttac   4200
acggaggcat cagtgaccaa acaggaaaaa accgccctta acatggcccg ctttatcaga   4260
agccagacat taacgcttct ggagaaactc aacgagctgg acgcggatga acaggcagac   4320
atctgtgaat cgcttcacga ccacgctgat gagctttacc gcagctgcct cgcgcgtttc   4380
ggtgatgacg gtgaaaacct ctgacacatg cagctcccgg agacggtcac agcttgtctg   4440
taagcggatg ccgggagcag acaagcccgt cagggcgcgt cagcgggtgt tggcgggtgt   4500
cggggcgcag ccatgaccca gtcacgtagc gatagcggag tgtatactgg cttaactatg   4560
cggcatcaga gcagattgta ctgagagtgc accatatgcg gtgtgaaata ccgcacagat   4620
gcgtaaggag aaaataccgc atcaggcgct cttccgcttc ctcgctcact gactcgctgc   4680
gctcggtcgt tcggctgcgg cgagcggtat cagctcactc aaaggcggta atacggttat   4740
ccacagaatc aggggataac gcaggaaaga acatgtgagc aaaaggccag caaaaggcca   4800
ggaaccgtaa aaaggccgcg ttgctggcgt ttttccatag gctccgcccc cctgacgagc   4860
atcacaaaaa tcgacgctca agtcagaggt ggcgaaaccc gacaggacta taaagatacc   4920
aggcgtttcc ccctggaagc tccctcgtgc gctctcctgt tccgaccctg ccgcttaccg   4980
gatacctgtc cgcctttctc ccttcgggaa gcgtggcgct ttctcatagc tcacgctgta   5040
ggtatctcag ttcggtgtag gtcgttcgct ccaagctggg ctgtgtgcac gaaccccccg   5100
ttcagcccga ccgctgcgcc ttatccggta actatcgtct tgagtccaac ccggtaagac   5160
acgacttatc gccactggca gcagccactg gtaacaggat tagcagagcg aggtatgtag   5220
gcggtgctac agagttcttg aagtggtggc ctaactacgg ctacactaga aggacagtat   5280
ttggtatctg cgctctgctg aagccagtta ccttcggaaa aagagttggt agctcttgat   5340
ccggcaaaca aaccaccgct ggtagcggtg gtttttttgt ttgcaagcag cagattacgc   5400
gcagaaaaaa aggatctcaa gaagatcctt tgatcttttc tacggggtct gacgctcagt   5460
ggaacgaaaa ctcacgttaa gggattttgg tcatgagatt atcaaaaagg atcttcacct   5520
agatcctttt aaaggccggc cgcggccgcg caaagtcccg cttcgtgaaa attttcgtgc   5580
cgcgtgattt tccgccaaaa actttaacga acgttcgtta taatggtgtc atgaccttca   5640
cgacgaagta ctaaaattgg cccgaatcat cagctatgga tctctctgat gtcgcgctgg   5700
agtccgacgc gctcgatgct gccgtcgatt taaaaacggt gatcggattt ttccgagctc   5760
tcgatacgac ggacgcgcca gcatcacgag actgggccag tgccgcgagc gacctagaaa   5820
ctctcgtggc ggatcttgag gagctggctg acgagctgcg tgctcggcca gcgccaggag   5880
gacgcacagt agtggaggat gcaatcagtt gcgcctactg cggtggcctg attcctcccc   5940
```

-continued

```
ggcctgaccc gcgaggacgg cgcgcaaaat attgctcaga tgcgtgtcgt gccgcagcca   6000
gccgcgagcg cgccaacaaa cgccacgccg aggagctgga ggcggctagg tcgcaaatgg   6060
cgctggaagt gcgtcccccg agcgaaattt tggccatggt cgtcacagag ctggaagcgg   6120
cagcgagaat tatcgcgatc gtggcggtgc ccgcaggcat gacaaacatc gtaaatgccg   6180
cgtttcgtgt gccgtggccg cccaggacgt gtcagcgccg ccaccacctg caccgaatcg   6240
gcagcagcgt cgcgcgtcga aaaagcgcac aggcggcaag aagcgataag ctgcacgaat   6300
acctgaaaaa tgttgaacgc cccgtgagcg gtaactcaca gggcgtcggc taacccccag   6360
tccaaacctg ggagaaagcg ctcaaaaatg actctagcgg attcacgaga cattgacaca   6420
ccggcctgga aattttccgc tgatctgttc gacacccatc ccgagctcgc gctgcgatca   6480
cgtggctgga cgagcgaaga ccgccgcgaa ttcctcgctc acctgggcag agaaaatttc   6540
cagggcagca agacccgcga cttcgccagc gcttggatca aagacccgga cacggagaaa   6600
cacagccgaa gttataccga gttggttcaa aatcgcttgc ccggtgccag tatgttgctc   6660
tgacgcacgc gcagcacgca gccgtgcttg tcctggacat tgatgtgccg agccaccagg   6720
ccggcgggaa aatcgagcac gtaaaccccg aggtctacgc gattttggag cgctgggcac   6780
gcctggaaaa agcgccagct tggatcggcg tgaatccact gagcgggaaa tgccagctca   6840
tctggctcat tgatccggtg tatgccgcag caggcatgag cagcccgaat atgcgcctgc   6900
tggctgcaac gaccgaggaa atgacccgcg ttttcggcgc tgaccaggct ttttcacata   6960
ggctgagccg tggccactgc actctccgac gatcccagcc gtaccgctgg catgcccagc   7020
acaatcgcgt ggatcgccta gctgatctta tggaggttgc tcgcatgatc tcaggcacag   7080
aaaaacctaa aaaacgctat gagcaggagt tttctagcgg acgggcacgt atcgaagcgg   7140
caagaaaagc cactgcggaa gcaaaagcac ttgccacgct tgaagcaagc ctgccgagcg   7200
ccgctgaagc gtctggagag ctgatcgacg gcgtccgtgt cctctggact gctccagggc   7260
gtgccgcccg tgatgagacg gcttttcgcc acgctttgac tgtgggatac cagttaaaag   7320
cggctggtga gcgcctaaaa gacaccaagg gtcatcgagc ctacgagcgt gcctacaccg   7380
tcgctcaggc ggtcggagga ggccgtgagc ctgatctgcc gccggactgt gaccgccaga   7440
cggattggcc gcgacgtgtg cgcggctacg tcgctaaagg ccagccagtc gtccctgctc   7500
gtcagacaga gacgcagagc cagccgaggc gaaaagctct ggccactatg ggaagacgtg   7560
gcggtaaaaa ggccgcagaa cgctggaaag acccaaacag tgagtacgcc cgagcacagc   7620
gagaaaaact agctaagtcc agtcaacgac aagctaggaa agctaaagga aatcgcttga   7680
ccattgcagg ttggtttatg actgttgagg gagagactgg ctcgtggccg acaatcaatg   7740
aagctatgtc tgaatttagc gtgtcacgtc agaccgtgaa tagagcactt aaggtctgcg   7800
ggcattgaac ttccacgagg acgccgaaag cttcccagta aatgtgccat ctcgtaggca   7860
gaaaacggtt cccccgtagg gtctctctct tggcctcctt tctaggtcgg gctgattgct   7920
cttgaagctc tctagggggg ctcacaccat aggcagataa cgttccccac cggctcgcct   7980
cgtaagcgca caaggactgc tcccaaagat cttcaaagcc actgccgcga ctgccttcgc   8040
gaagccttgc cccgcggaaa tttcctccac cgagttcgtg cacaccccta tgccaagctt   8100
ctttcaccct aaattcgaga gattggattc ttaccgtgga aattcttcgc aaaaatcgtc   8160
ccctgatcgc ccttgcgacg ttggcgtcgg tgccgctggt tgcgcttggc ttgaccgact   8220
tgatcagcgg ccgc                                                     8234
```

<210> SEQ ID NO 44

<211> LENGTH: 7956
<212> TYPE: DNA
<213> ORGANISM: Brevibacterium linens

<400> SEQUENCE: 44
gcttcggctc tcatttctga ctccagcgac atccttgctc cagcgctgct ccatgacggc 60
gcgaaaaccc cgccattgct ggtcgacgtc gtccgcgacc gcataatctc ggcactctga 120
ccgggcgtca attttctcga ctcgcagcgt catcgtctga cttatgacgt cgtgcgtcat 180
gaaacgacat gattggacac cctaatttgt tgagcaatct atttctcttg tagcgtgact 240
caccaaaggt tcaccgcagc gtttggagac gatcgtgtcc gcacatgtag acgaaatcaa 300
gcaagttccg aggtccgggg cttccacgcg tccggcccga ccgaagaagt ccaacggtca 360
gtggaaggtc gacggtcagg aaccgttgaa caaaaacgag atcgacaagg ccgcagataa 420
cggtctcaac gtgcgcacgc gcatcgaaga ggtgtactcc aagggcggtt tcgcctcaat 480
cgatccggat gacctgcatg gtcgtttccg ctggtggggg ctgtacaccc agcgcaaacc 540
cggtatcgac ggcggccgta ccgcgaagct cgaaccccac gagctcgaag acgagtactt 600
catgatgcgc attcgcaccg acggtggagc gctcaatctc gagcagctgc gcaccatcgc 660
agagatcgcc gaggagtttg cccgtggcag tgcggacctg acagaccgtc agaacatcca 720
gctgcactgg atcgagatcg agaacgtgcc cgagatctgg cgccgcctcg aagccgtggg 780
catgcagacg acggaggcct gcggagatgt tccgcgtggc ttcctcggtt cgccggtagc 840
cggaatcgcc gcggatgagc tcatcgatcc caccccagcg atcgaagaga tcactcgccg 900
ctatatcggc gacccgagcc tgtcgaacct gccgcgcaag tacaagactg cgatcaccgg 960
tcaccccagt caggacgtcg tccacgagat caacgactgc tcgttcgtcg ccgttgatca 1020
ccccgaacac ggcatcggct acgacctgtg ggtcggcggg gcattgtcag ttgttccccg 1080
cttcgccgaa cgcctcggtg cctgggtcgc cccggaccag gtcgtcgatg tctggctcgg 1140
cgtcacggag atcttccgtg actacggcta tcgccgcctg cgcaacaaag cccgcatgaa 1200
gttcctgctg gccgactggg gccccgagaa gctgcgcgat gtcctcgaga ccgagtacct 1260
cggctaccga ctcgcagacg gtccgccccc accgaagccc atggtctccg gagaccacgt 1320
cggcgtccac cggcagaagg atggaaagta cttcatcggc accagcctcg tggctgggcg 1380
cgcctcaggc acgctgttcc accagatggc tgacctgatc gaagagtacg ggatcgatcg 1440
gatccgattg accccgatgc agaagatcct cgtgctcgat gtcgacgaga ctgatcttga 1500
tgatgtcgtc gcccgcctcg acgccctggg actgtccagc cgcaaggacc tgttccggcg 1560
ctcggtgatg gcgtgcacgg gaatcgaata ctgcaagctg gctatcgtcg agacgaagca 1620
gacagccatc gacgccgtca ctcgactcga agaacgcctc gctgacatcg acctgcccca 1680
cccgatcagt ctccatctca acggctgccc gaactcctgc gcgcgcatcc agacggctga 1740
catcggactc aaaggtcaga tcgtgaccac tgacgagggc gaacaggtcc ccgggttcca 1800
ggtccacgtc ggcggaggtc tggcatcgaa ggaccgtgac gaagcaggct tgggccgaac 1860
ggtgcgtgga ctcaaggtca ctgtcgacgg tctcgaggag tacgtcgaga agatggtccg 1920
ccgattcctc gacggacggt ccgagtctga gacattctcc gaatgggcac accgagtcga 1980
agacgaggag ctggtatgag cacgacacca tcccgaaccg cagcaccgct gcccacgccc 2040
acccgccagc gtcgcgacat tgacgagctc aagtccctcg ccgaggcggg ggctaagcag 2100
ctcgcgggcg atcccgacaa cggcgtggcc gaggccaacc cggccgacgt catccgctgg 2160
gtctcacgaa acttcgacac ctccacctgc gcggtggcct gctcgatggc cgatgcggcc 2220

-continued

```
ctgccgcact atgtcgccca gtacctgccg ggcgtcgacg tgctcttcct cgacaccggc   2280
taccacttca aggagaccta ttcgacccgc gacgaggtgg ccagcaaggt cgacgtcaac   2340
atcgtcgacg tcctcccgga gcagaccgtg gcacagcagg atgcggaatt cggtgccgaa   2400
ctgttcaacc gcgaccccgg cctctgctgt gccaggcgca aggtcgcacc tctgaagaag   2460
tcgctggccg gctacgaact ctggttcacc ggagtccgcc gggacgaagc accgacgcgg   2520
gcgaacacac cgctggtgac cttcgatgag aagaacgggc tggtcaaggt caaccccctg   2580
gccgcctggt ccttcgacga tcttctcgac tacgccggtg ccttcgacgt gccggtcaat   2640
ccactgctgt cgcaggggta cccgtccatc gggtgccagc cctgcaccaa ccccgtggcc   2700
gagggggagg acccccgtgc cggccgttgg gctggaacct cgaaaacaga atgcgggctg   2760
cacgtatgag catcgatcac acaccactgt ccacacagaa accactgtcc acacagaaac   2820
cactgtccac cctcgacgtc ctcgaatccg aagcgatcca catcatccgc gaggtcgccg   2880
ccgaattcga gaagcccgtg ctgctgttct ccggcggcaa ggactccgtc accgtcctcc   2940
acctcgcggc caaggccttc tggcccgcga agattccgtt cggtcttctc cacgtcgaca   3000
ccggtcacaa cttcccggag atcctgaagt tccgcgatga gaccgccgcc cactacggca   3060
tcgacctgaa agtggcgaag gtccaggact acatcgacga cggccgtctg cgcgagcgcg   3120
ccgatggaac ccgcaacacc ctgcagaccc agcccctcat cgacgcgatc gccgagggag   3180
gatacgacgc ggtcttcggc ggcgcccgcc gtgacgagga caaggcccga gccaaggagc   3240
gcatcttctc cctgcgcgat gaattcggcc agtgggatcc gagcaaccag cgcccccgaac  3300
tgtggaacct ctacaacggt cgccacgtca atggcgagca cgtgcgcgta ttcccgatct   3360
cgaacttcac cgaactcgac gtgtggagct acatcgcccg ggagaacatc gccctgcctc   3420
atctctacta cgcccatgag cgcgaggtct tccagcgcga cggcatgtgg tggtcgacgg   3480
gtgagttctc ggccccgcgg cccgaggagt cggtcatccg caagtcggtg cgctaccgca   3540
ccgtcggcga catgagctgc acaggtgccg tggaatccga ggccgacgac atcgcctcgg   3600
tcctcgccga ggtggctgtg accactgtga cagaacgcgg agcgacccgc gccgacgacc   3660
ggatctcggc cgcggcgatg gaagaccgca agaaggacgg atacttctga tgaccacaac   3720
accagacacc accgctgcca cacagacgaa gacacttctg cgcttcgcca cggccggttc   3780
cgtcgacgac ggcaaatcga cgctcgtggg ccgcctcctc cacgatgcga aggcgatcct   3840
cgccgatcag ctcgaggccg tgacgcgcac cagcgaggaa cgcggcttcg tcggcggcga   3900
attcgacttc gcactgctca ccgacggtct gcgggccgaa cgggaacagg gcatcacgat   3960
cgacgtcgcc taccgctact tcgccaccga caagcgctca ttcatcctcg ccgactgccc   4020
cggacacgtg cagtacacgc gaaacatggt taccggagcc acgaccgccg atgccgtcgt   4080
cgtcctcatc gacgcacgca ccggtgcgac cgagcagacc cgtcgccacc tcacggtcgt   4140
tcaccgtctg ggcatcaggc acgtcatcct cgcgatcaac aagatcgacc tcctcgacta   4200
cgatcaggca gcgtatgcga aggtggaggc cgagatcgaa gcgctgacgg cagagatcgg   4260
cctcgactcg gcccatctga tccccgtctc ggcactggcc ggggacaatg tggccgaggc   4320
ttcggcgaac acaccctggt accagggccc cgcactgctg gagctgctcg agaacctgcc   4380
cagcaaggaa gaggacacgg ccgacctcga gcccttccgc ctcgacgtgc agtcggtgct   4440
gcgcccgcag ggcggactgg caccgggact cgaccccgat gagttccgcg actaccgggc   4500
ggtgaccgga caggtcacgt cagggcggat ccgcctcggc gatgagatcg acgtgcatcc   4560
ggccggtctg cggaccactg tggtcggcat cgacacggca gatggcccgc tggagaccgc   4620
```

-continued

```
gggtgccccg ctgtccgtgg cgctgcgcct ggccgatgac atcgacaccg cgcgcggcag   4680
cgtccttgcc gcggccggaa gcctgcctga accgcgcaag gctctgcggg ccgaggtctt   4740
ccccttcacc tcgcagggac tgcgctccgg tgaccgggtg ctcgtcaaag ccggcacctc   4800
gacggtcaag gcgatcgtga cgatcgaatc gaagcacaac ctgctgaccg ccggatccga   4860
acccgccgag gtgctcgccg gcaacgacat cggcaccgcc gaggtgaagt tggcgaccgc   4920
tctgccgctc gcggacttcc gtgagcacgg acgcgcaggt ggattcctca tcatcgatcc   4980
gcagactggg tccaccgtgg ccgcgggaat ccacactccc gaagacgctc acactcctga   5040
gggcgaacag tcatgagcct cttcactctt caggcaccgg gcagcgtgct gctcatcggt   5100
gccggacccg gtgatctcgg cctgctgacc gtcaaaggtc tgcgcgcatt ggaatctgcc   5160
gaggtcatcg ttgccgaccg cctcggcgcg cgttcggtca tcgaccagct cgagaccgag   5220
cgcggggagt cactcgacgc cgagatcatc gacgtcggca agaccccggg acaccacccg   5280
gttccgcagc agcgcatcaa tgagatcctc gtcgaacagg ctcgcgccgg gcgacgtgtg   5340
gtccgactca agggcggaga cccgttcgtc ttcggccgtg gcggcgaaga gctcgcccac   5400
tgccacgaag ccggcgtcga cgtgcaggtg gtgccgggag tcacgagtgc gaactcggtt   5460
cccgccgttg ccggaatccc gctgacgcac aggggactgg ccaccgcgta cacggtcatc   5520
accggccacg atcagctctc cgagctcggc ggaggacgcg accacacggt cgtcgtgctc   5580
atgggcatcg gcacgctggc acattcggcg atgatcctgg cccgcggtgg acgcgggga   5640
gactgccccg tcgcgatcat cgaagacggg ttcggagaca accagcgggt caccgtgggc   5700
acactcgata cgatcgcctt ccaggccgcc cgccgaggtg tccgctcacc ggccgtcgtc   5760
atcgccggtg acgtcgtgac cctgagcccg tatgccgtcg gagccttcgc cgcagcgcag   5820
gtgcccgagc cagaactcat gaggaaccca tgacctacat catcgcccag ccctgcgtcg   5880
acttgaagga ccgggcctgc atcgacgaat gccccgtcga ctgcatctac gagggcagcc   5940
gctcgctcta catccatccc gaggaatgcg tcgactgcgg cgcctgcgaa ccagtctgcc   6000
ccgtcgaagc gatcttctac gaagacgacg tcccagacga atgggaagcc tactactcgg   6060
cgaacgtcga cttcttcgac accatcggat ccccgggagg cgccgccgcg cacggaatca   6120
tcgacggcga ccaccccttc atcgcggcac tgccgcccca gaacactgac gactgactct   6180
cctgaggaga accatgacga cgaatccctt ccgcgtggcc atcgtgggcg caggccccgc   6240
aggcatctac gctgccgacc tgctgaccaa agccgatcgt gacttcgaga tcagcatcga   6300
cctcttcgac cggctgccga ccccgttcgg gctggtccgc tacggagtcg cccctgatca   6360
cccacgcatc aagggcatca tcaatgccct catcaaggtc ctcgaccgcg gcgacatccg   6420
cctgttctcc aacgtcgagt acggtgccga catcgccttg ggtgagctga cagatcgcta   6480
cgatgcggtg atcttctcca ccggctgctt catcgatgcc tccttggatc tgcccggagt   6540
agatctcccc ggctcctacg gtgccgccga tttcgtcaac tggtacgact cgcacccgga   6600
cgtggctcag acgtggccgc tggatgctga gaaggttgcc gtcatcggca acggcaacgt   6660
agccctcgac gtggcacgcg tgctggccaa gcaggccgat gacatgcaca cgactgagat   6720
ccccgaccat gtctacgagg gtctgaaatc gtcaaaggtc acggacgttc acgtgttcgg   6780
ccggcgtggt ccggcgcagg cgaagttcac cccccttggag ctgcgcgagc tgggccaggt   6840
caaggatgtc gatgtcatcg tctatcccga ggacttcgag ttcgatgagg gttcgctggc   6900
cgcgatcgag gcgagcaacc agaccaagca ggtcgcgaag actctgaccg acttcacgat   6960
gagggagccg gtgggagcca aacgccgcct gcacctgcac ttcctccacg caccggtggc   7020
```

catcctcggc gaggatgcag tcacaggact gcgcacggag cgccaggaat tggacggcac 7080
cgggggagtc aagggcacgg gagagttcat cgactgggac gtcacagccg tctatcgcgc 7140
cgtcggctac gcaggcactc cgctgccgca gctgcccttc gacgagacca agcgcgtgat 7200
cccgaatcac gagggacgcg tcgtcgatac agggcagcag gcttcggcgg ccgaagccga 7260
tgtggtccag ggcgtgtacg cgaccgggtg gatcaaacgc ggaccggtcg gcctgatcgg 7320
tcacacgaag ggtgatgcgc tggagacgat cgggcacatc ctcgttgacc gcgccgccgg 7380
tgtactcacc gaaccgctgt tccccgacga ggactcgatc gtcgagctgc ttgagtccaa 7440
gggcgtcgac ttcggggact gggagggcta ccaccgactg gaggccgcgg agaaggcatt 7500
gggcgaagcc gaaggccgag agcgcgtgaa gctcgcgacc cgcgaggcca tgctgcgtga 7560
ggcccgtgat catgtcagaa gcgaatccca ctccggcgcc tgagccgaat cagccgctga 7620
gccgaatcgc catctgagcc gaaccgccat cacgccccgt cagtcactat tcctcccgtt 7680
gcacgtgtag gaacagtcac cggcggggcg tgatgtgttt ttgacggttg tgtatggcac 7740
gggcgggagg tatcggcact agcgggaggg cgtaggctcg aggtgttcaa cagccaccgt 7800
ccaaggtgcg cactcgtcag aatttaaggt tcgcactcgt caaaggagac gcactgccgt 7860
gatcgataca tcagctcggg ttgccgtcat cggcggtgga atcgcaggcg cctgcgttgc 7920
cttcggcctg gcgtcacgag acgtcaacgt caccat 7956

<210> SEQ ID NO 45
<211> LENGTH: 8635
<212> TYPE: DNA
<213> ORGANISM: artificial
<220> FEATURE:
<223> OTHER INFORMATION: Plasmid: pOM327

<400> SEQUENCE: 45
ccatcgaatg gccagatgat taattcctaa tttttgttga cactctatca ttgatagagt 60
tattttacca ctccctatca gtgatagaga aaagtgaaat gaatagttcg acaaaaatct 120
agattagaaa ggaggtttaa ttaatgacaa ctcccctgcg cgtagccgtc atcggagctg 180
gccctgctgg catttacgca tccgacctcc tcatccgcaa tgaagagcgc gaagtgttcg 240
ttgacctttt cgagcaaatg cctgcaccgt tcggactcat ccgttacggc gttgctccag 300
accacccacg catcaagggc atcgttaagt ccctgcacaa cgtgttggac aagccacgcc 360
tgcgcctgct cggtaacatt gaaatcggca aagacatcac cgtcgaagaa ctccgcgact 420
actacgatgc agtcgtgttc tccaccggcg cagttgcaga ccgcgacctc aacatccccg 480
gaattgaagc agaaggctcc ttcggtgccg gcgagttcgt tggcttctac gacggcaacc 540
cacgcttcga gcgctcctgg gatctgtctg cacagtccgt cgctgttatc ggcgttggta 600
acgtcggcct cgacgtagcc cgcatcctgg ctaagacagg cgacgagctc aaagtcaccg 660
aaatttccga caacgtctac gactccctca aagaaaacaa ggccactgaa gtgcacgttt 720
tcggacgtcg tggcccagca caggtcaagt tcaccccaca ggaactcaaa gaactcgacc 780
actcccccac catcaacgtg gttgttgatc cagaagacat cgactacgac ggcgcctctg 840
aagaagcccg ccgcgcatcc aagtcccagg acctggtctg ccagatcctg gaacagtacg 900
caatccgcga gccaaaggac gctccgcaca ccctgcagat ccacctcttt gaaaacccag 960
ttgaggttct tcaaaaggac ggcaaggttg ttggcctgcg caccgaacgc acctcacttg 1020
atggcaacgg cggcgtaaac ggaaccggcg aattcaagga ctggccagtc caggctgtct 1080
accgcgcagt cggctacaag tccgacccca tcgacggcgt cccattcgat gagaacaagc 1140
acgtcatccc taatgacggc ggacatgtcc tcaccgctcc aggcgcagaa ccagtaccag 1200
gcctctatgc aaccggctgg atcaagcgtg gaccaatcgg tctaatcggc aacaccaagt 1260
ccgacgccaa ggaaaccacc gacatcctca tcaaggatgc cgtcgccggt gtacttgaag 1320
ctccaaagca ccagggcgaa gaagccatca tcgagcttct cgattcccgc aacatcccat 1380
tcaccacctg ggaaggctgg tacaaactcg acgcagcaga gcgcgcactc ggtgaagccg 1440
aaggccgcga gcgcaagaag attgttgatt gggaagaaat ggtccgccag gcccgcgaag 1500
ctccagcaat tgtctaaatt gttttaacgc gtgaagcagt ccccgcccga tttattcgag 1560
gcggggactt tcgctttccg ggataaaaat tggatccctc gaggtcgacc tgcaggggga 1620
ccaaaatctc gagaggcctg acgtcgggcc cggtaccggg ccccccctcg aggtcgagcg 1680
gcttaaagtt tggctgccat gtgaattttt agcaccctca acagttgagt gctggcactc 1740
tcgggggtag agtgccaaat aggttgtttg acacacagtt gttcacccgc gacgacggct 1800
gtgctggaaa cccacaaccg gcacacacaa aatttttctc atggagggat tcatcatgtc 1860
gacttcagtt acttcaccag cccacaacaa cgcacattcc tccgaatttt tggatgcgtt 1920
ggcaaaccat gtgttgatcg gcgacggcgc catgggcacc cagctccaag gctttgacct 1980
ggacgtggaa aaggatttcc ttgatctgga ggggtgtaat gagattctca acgacacccg 2040
ccctgatgtg ttgaggcaga ttcaccgcgc ctactttgag gcgggagctg acttggttga 2100
gaccaatact tttggttgca acctgccgaa cttggcggat tatgacatcg ctgatcgttg 2160
ccgtgagctt gcctacaagg gcactgcagt ggctagggaa gtggctgatg agatggggcc 2220
gggccgaaac ggcatgcggc gtttcgtggt tggttccctg ggacctggaa cgaagcttcc 2280
atcgctgggc catgcaccgt atgcagattt gcgtgggcac tacaaggaag cagcgcttgg 2340
catcatcgac ggtggtggcg atgccttttt gattgagact gctcaggact tgcttcaggt 2400
caaggctgcg gttcacggcg ttcaagatgc catggctgaa cttgatacat tcttgcccat 2460
tatttgccac gtcaccgtag agaccaccgg caccatgctc atgggttctg agatcggtgc 2520
cgcgttgaca gcgctgcagc cactgggtat cgacatgatt ggtctgaact gcgccaccgg 2580
cccagatgag atgagcgagc acctgcgtta cctgtccaag cacgccgata ttcctgtgtc 2640
ggtgatgcct aacgcaggtc ttcctgtcct gggtaaaaac ggtgcagaat acccacttga 2700
ggctgaggat ttggcgcagg cgctggctgg attcgtctcc gaatatggcc tgtccatggt 2760
gggtggttgt tgtggcacca cacctgagca catccgtgcg gtccgcgatg cggtggttgg 2820
tgttccagag caggaaacct ccacactgac caagatccct gcaggccctg ttgagcaggc 2880
ctcccgcgag gtggagaaag aggactccgt cgcgtcgctg tacacctcgg tgccattgtc 2940
ccaggaaacc ggcatttcca tgatcggtga gcgcaccaac tccaacggtt ccaaggcatt 3000
ccgtgaggca atgctgtctg gcgattggga aaagtgtgtg gatattgcca agcagcaaac 3060
ccgcgatggt gcacacatgc tggatctttg tgtggattac gtgggacgag acggcaccgc 3120
cgatatggcg accttggcag cacttcttgc taccagctcc actttgccaa tcatgattga 3180
ctccaccgag ccagaggtta ttcgcacagg ccttgagcac ttgggtggac gaagcatcgt 3240
taactccgtc aactttgaag acggcgatgg ccctgagtcc cgctaccagc gcatcatgaa 3300
actggtaaag cagcacggtg cggccgtggt tgcgctgacc attgatgagg aaggccaggc 3360
acgtaccgct gagcacaagg tgcgcattgc taaacgactg attgacgata tcaccggcag 3420
ctacggcctg gatatcaaag acatcgttgt ggactgcctg accttcccga tctctactgg 3480
ccaggaagaa accaggcgag atggcattga aaccatcgaa gccatccgcg agctgaagaa 3540

-continued

```
gctctaccca gaaatccaca ccaccctggg tctgtccaat atttccttcg gcctgaaccc   3600
tgctgcacgc caggttctta actctgtgtt cctcaatgag tgcattgagg ctggtctgga   3660
ctctgcgatt gcgcacagct ccaagatttt gccgatgaac cgcattgatg atcgccagcg   3720
cgaagtggcg ttggatatgg tctatgatcg ccgcaccgag gattacgatc cgctgcagga   3780
attcatgcag ctgtttgagg gcgtttctgc tgccgatgcc aaggatgctc gcgctgaaca   3840
gctggccgct atgcctttgt ttgagcgttt ggcacagcgc atcatcgacg gcgataagaa   3900
tggccttgag gatgatctgg aagcaggcat gaaggagaag tctcctattg cgatcatcaa   3960
cgaggacctt ctcaacggca tgaagaccgt gggtgagctg tttggttccg gacagatgca   4020
gctgccattc gtgctgcaat cggcagaaac catgaaaact gcggtggcct atttggaacc   4080
gttcatggaa gaggaagcag aagctaccgg atctgcgcag gcagagggca agggcaaaat   4140
cgtcgtggcc accgtcaagg gtgacgtgca cgatatcggc aagaacttgg tggacatcat   4200
tttgtccaac aacggttacg acgtggtgaa cttgggcatc aagcagccac tgtccgccat   4260
gttggaagca gcggaagaac acaaagcaga cgtcatcggc atgtcgggac ttcttgtgaa   4320
gtccaccgtg gtgatgaagg aaaaccttga ggagatgaac aacgccggcg catccaatta   4380
cccagtcatt ttgggtggcg ctgcgctgac gcgtacctac gtggaaaacg atctcaacga   4440
ggtgtacacc ggtgaggtgt actacgcccg tgatgctttc gagggcctgc gcctgatgga   4500
tgaggtgatg gcagaaaagc gtggtgaagg acttgatccc aactcaccag aagctattga   4560
gcaggcgaag aagaaggcgg aacgtaaggc tcgtaatgag cgttcccgca agattgccgc   4620
ggagcgtaaa gctaatgcgg ctcccgtgat tgttccggag cgttctgatg tctccaccga   4680
tactccaacc gcggcaccac cgttctgggg aacccgcatt gtcaagggtc tgcccttggc   4740
ggagttcttg ggcaaccttg atgagcgcgc cttgttcatg gggcagtggg gtctgaaatc   4800
cacccgcggc aacgagggtc caagctatga ggatttggtg gaaactgaag gccgaccacg   4860
cctgcgctac tggctggatc gcctgaagtc tgagggcatt ttggaccacg tggccttggt   4920
gtatggctac ttcccagcgg tcgcggaagg cgatgacgtg gtgatcttgg aatccccgga   4980
tccacacgca gccgaacgca tgcgctttag cttcccacgc cagcagcgcg gcaggttctt   5040
gtgcatcgcg gatttcattc gcccacgcga gcaagctgtc aaggacggcc aagtggacgt   5100
catgccattc cagctggtca ccatgggtaa tcctattgct gatttcgcca acgagttgtt   5160
cgcagccaat gaataccgcg agtacttgga agttcacggc atcggcgtgc agctcaccga   5220
agcattggcc gagtactggc actcccgagt gcgcagcgaa ctcaagctga acgacggtgg   5280
atctgtcgct gattttgatc cagaagacaa gaccaagttc ttcgacctgg attaccgcgg   5340
cgcccgcttc tcctttggtt acggttcttg ccctgatctg gaagaccgcg caaagctggt   5400
ggaattgctc gagccaggcc gtatcggcgt ggagttgtcc gaggaactcc agctgcaccc   5460
agagcagtcc acagacgcgt ttgtgctcta ccacccagag gcaaagtact ttaacgtcta   5520
atctagaccc gggattttgg tctcagcgct tggagccacc cgcagttcga aaaataataa   5580
gcttgacctg tgaagtgaaa aatggcgcac attgtgcgac attttttttg tctgccgttt   5640
accgctactg cgtcacggat ctccacgcgc cctgtagcgg cgcattaagc gcggcgggtg   5700
tggtggttac gcgcagcgtg accgctacac ttgccagcgc cctagcgccc gctcctttcg   5760
ctttcttccc ttcctttctc gccacgttcg ccggctttcc ccgtcaagct ctaaatcggg   5820
ggctcccttt agggttccga tttagtgctt tacggcacct cgaccccaaa aaacttgatt   5880
agggtgatgg ttcacgtagt gggccatcgc cctgatagac ggtttttcgc cctttgacgt   5940
```

-continued

```
tggagtccac gttctttaat agtggactct tgttccaaac tggaacaaca ctcaacccta   6000
tctcggtcta ttcttttgat ttataaggga ttttgccgat ttcggcctat tggttaaaaa   6060
atgagctgat ttaacaaaaa tttaacgcga attttaacaa aatattaacg cttacaattt   6120
caggtggcac ttttcgggga aatgtgcgcg gaacccctat ttgtttattt ttctaaatac   6180
attcaaatat gtatccgctc atgagacaat aaccctgata aatgcttcaa taatattgaa   6240
aaaggaagag tatgagtatt caacatttcc gtgtcgccct tattcccttt tttgcggcat   6300
tttgccttcc tgtttttgct cacccagaaa cgctggtgaa agtaaaagat gctgaagatc   6360
agttgggtgc acgagtgggt tacatcgaac tggatctcaa cagcggtaag atccttgaga   6420
gttttcgccc cgaagaacgt tttccaatga tgagcacttt taaagttctg ctatgtggcg   6480
cggtattatc ccgtattgac gccgggcaag agcaactcgg tcgccgcata cactattctc   6540
agaatgactt ggttgagtac tcaccagtca cagaaaagca tcttacggat ggcatgacag   6600
taagagaatt atgcagtgct gccataacca tgagtgataa cactgcggcc aacttacttc   6660
tgacaacgat cggaggaccg aaggagctaa ccgctttttt gcacaacatg ggggatcatg   6720
taactcgcct tgatcgttgg gaaccggagc tgaatgaagc cataccaaac gacgagcgtg   6780
acaccacgat gcctgtagca atggcaacaa cgttgcgcaa actattaact ggcgaactac   6840
ttactctagc ttcccggcaa caattgatag actggatgga ggcggataaa gttgcaggac   6900
cacttctgcg ctcggccctt ccggctggct ggtttattgc tgataaatct ggagccggtg   6960
agcgtggctc tcgcggtatc attgcagcac tggggccaga tggtaagccc tcccgtatcg   7020
tagttatcta cacgacgggg agtcaggcaa ctatggatga acgaaataga cagatcgctg   7080
agataggtgc ctcactgatt aagcattggt aggaattaat gatgtctcgt ttagataaaa   7140
gtaaagtgat taacagcgca ttagagctgc ttaatgaggt cggaatcgaa ggtttaacaa   7200
cccgtaaact cgcccagaag ctaggtgtag agcagcctac attgtattgg catgtaaaaa   7260
ataagcgggc tttgctcgac gccttagcca ttgagatgtt agataggcac catactcact   7320
tttgcccttt agaaggggaa agctggcaag atttttacg taataacgct aaaagtttta   7380
gatgtgcttt actaagtcat cgcgatggag caaaagtaca tttaggtaca cggcctacag   7440
aaaaacagta tgaaactctc gaaaatcaat tagccttttt atgccaacaa ggtttttcac   7500
tagagaatgc attatatgca ctcagcgcag tggggcattt tactttaggt tgcgtattgg   7560
aagatcaaga gcatcaagtc gctaaagaag aaagggaaac acctactact gatagtatgc   7620
cgccattatt acgacaagct atcgaattat ttgatcacca aggtgcagag ccagccttct   7680
tattcggcct tgaattgatc atatgcggat tagaaaaaca acttaaatgt gaaagtgggt   7740
cttaaaagca gcataacctt tttccgtgat ggtaacttca ctagtccact gagcgtcaga   7800
ccccttaata agatgatctt cttgagatcg ttttggtctg cgcgtaatct cttgctctga   7860
aaacgaaaaa accgccttgc agggcggttt ttcgaaggtt ctctgagcta ccaactcttt   7920
gaaccgaggt aactggcttg gaggagcgca gtcaccaaaa cttgtccttt cagtttagcc   7980
ttaaccggcg catgacttca agactaactc ctctaaatca attaccagtg gctgctgcca   8040
gtggtgcttt tgcatgtctt tccgggttgg actcaagacg atagttaccg gataaggcgc   8100
agcggtcgga ctgaacgggg ggttcgtgca tacagtccag cttggagcga actgcctacc   8160
cggaactgag tgtcaggcgt ggaatgagac aaacgcggcc ataacagcgg aatgacaccg   8220
gtaaaccgaa aggcaggaac aggagagcgc acgagggagc cgccaggggg aaacgcctgg   8280
tatctttata gtcctgtcgg gtttcgccac cactgatttg agcgtcagat ttcgtgatgc   8340
```

ttgtcagggg ggcggagcct atggaaaaac ggctttgccg cggccctctc acttccctgt 8400
taagtatctt cctggcatct tccaggaaat ctccgccccg ttcgtaagcc atttccgctc 8460
gccgcagtcg aacgaccgag cgtagcgagt cagtgagcga ggaagcggaa tatatcctgt 8520
atcacatatt ctgctgacgc accggtgcag ccttttttct cctgccacat gaagcacttc 8580
actgacaccc tcatcagtgc caacatagta agccagtata cactccgcta gcgct 8635

<210> SEQ ID NO 46
<211> LENGTH: 11768
<212> TYPE: DNA
<213> ORGANISM: artificial
<220> FEATURE:
<223> OTHER INFORMATION: Plasmid: pH382

<400> SEQUENCE: 46
gtaccacgcg tcatatgcgg cttaaagttt ggctgccatg tgaattttta gcaccctcaa 60
cagttgagtg ctggcactct cgggggtaga gtgccaaata ggttgtttga cacacagttg 120
ttcacccgcg acgacggctg tgctggaaac ccacaaccgg cacacacaaa atttttctca 180
tggagggatt catcatgcca aagtacgaca attccaatgc tgaccagtgg ggctttgaaa 240
cccgctccat tcacgcaggc cagtcagtag acgcacagac cagcgcacga aaccttccga 300
tctaccaatc caccgctttc gtgttcgact ccgctgagca cgccaagcag cgtttcgcac 360
ttgaggatct aggccctgtt tactcccgcc tcaccaaccc aaccgttgag gctttggaaa 420
accgcatcgc ttccctcgaa ggtggcgtcc acgctgtagc gttctcctcc ggacaggccg 480
caaccaccaa cgccatttg aacctggcag gagcgggcga ccacatcgtc acctccccac 540
gcctctacgg tggcaccgag actctattcc ttatcactct taaccgcctg ggtatcgatg 600
tttccttcgt ggaaaacccc gacgaccctg agtcctggca ggcagccgtt cagccaaaca 660
ccaaagcatt cttcggcgag actttcgcca acccacaggc agacgtcctg gatattcctg 720
cggtggctga agttgcgcac cgcaacagcg ttccactgat catcgacaac accatcgcta 780
ccgcagcgct cgtgcgcccg ctcgagctcg gcgcagacgt tgtcgtcgct tccctcacca 840
agttctacac cggcaacggc tccggactgg gcggcgtgct tatcgacggc ggaaagttcg 900
attggactgt cgaaaaggat ggaaagccag tattccccta cttcgtcact ccagatgctg 960
cttaccacgg attgaagtac gcagaccttg gtgcaccagc cttcggcctc aaggttcgcg 1020
ttggccttct acgcgacacc ggctccaccc tctccgcatt caacgcatgg gctgcagtcc 1080
agggcatcga caccctttcc ctgcgcctgg agcgccacaa cgaaaacgcc atcaaggttg 1140
cagaattcct caacaaccac gagaaggtgg aaaaggttaa cttcgcaggc ctgaaggatt 1200
ccccttggta cgcaaccaag gaaaagcttg gcctgaagta caccggctcc gttctcacct 1260
tcgagatcaa gggcggcaag gatgaggctt gggcatttat cgacgccctg aagctacact 1320
ccaaccttgc aaacatcggc gatgttcgct ccctcgttgt tcacccagca accaccaccc 1380
attcacagtc cgacgaagct ggcctggcac gcgcgggcgt tacccagtcc accgtccgcc 1440
tgtccgttgg catcgagacc attgatgata tcatcgctga cctcgaaggc ggctttgctg 1500
caatctagca ctagtagctg ccaattattc cgggcttgtg acccgctacc cgataaatag 1560
gtcggctgaa aaatttcgtt gcaatatcaa caaaaaggcc tatcattggg aggtgtcgca 1620
ccaagtactt ttgcgaagcg ccatctgacg gattttcaaa agatgtatat gctcggtgcg 1680
gaaacctacg aaaggatttt ttacccatgc ccaccctcgc gccttcaggt caacttgaaa 1740
tccaagcgat cggtgatgtc tccaccgaag ccggagcaat cattacaaac gctgaaatcg 1800

-continued

```
cctatcaccg ctggggtgaa taccgcgtag ataaagaagg acgcagcaat gtcgttctca   1860
tcgaacacgc cctcactgga gattccaacg cagccgattg gtgggctgac ttgctcggtc   1920
ccggcaaagc catcaacact gatatttact gcgtgatctg taccaacgtc atcggtggtt   1980
gcaacggttc caccggacct ggctccatgc atccagatgg aaatttctgg ggtaatcgct   2040
tccccgccac gtccattcgt gatcaggtaa acgccgaaaa acaattcctc gacgcactcg   2100
gcatcaccac ggtcgccgca gtacttggtg gttccatggg tggtgcccgc accctagagt   2160
gggccgcaat gtacccagaa actgttggcg cagctgctgt tcttgcagtt tctgcacgcg   2220
ccagcgcctg gcaaatcggc attcaatccg cccaaattaa ggcgattgaa aacgaccacc   2280
actggcacga aggcaactac tacgaatccg gctgcaaccc agccaccgga ctcggcgccg   2340
cccgacgcat cgcccacctc acctaccgtg gcgaactaga aatcgacgaa cgcttcggca   2400
ccaaagccca aaagaacgaa aacccactcg gtccctaccg caagcccgac cagcgcttcg   2460
ccgtggaatc ctacttggac taccaagcag acaagctagt acagcgtttc gacgccggct   2520
cctacgtctt gctcaccgac gccctcaacc gccacgacat tggtcgcgac cgcggaggcc   2580
tcaacaaggc actcgaatcc atcaaagttc cagtccttgt cgcaggcgta gataccgata   2640
ttttgtaccc ctaccaccag caagaacacc tctccagaaa cctgggaaat ctactggcaa   2700
tggcaaaaat cgtatcccct gtcggccacg atgctttcct caccgaaagc cgccaaatgg   2760
atcgcatcgt gaggaacttc ttcagcctca tctccccaga cgaagacaac ccttcgacct   2820
acatcgagtt ctacatctaa gtcgaggtcg agcggcttaa agtttggctg ccatgtgaat   2880
ttttagcacc ctcaacagtt gagtgctggc actctcgggg gtagagtgcc aaataggttg   2940
tttgacacac agttgttcac ccgcgacgac ggctgtgctg gaaacccaca accggcacac   3000
acaaaatttt tctcatggag ggattcatca tgtcgacttc agttacttca ccagcccaca   3060
acaacgcaca ttcctccgaa tttttggatg cgttggcaaa ccatgtgttg atcggcgacg   3120
gcgccatggg cacccagctc caaggctttg acctggacgt ggaaaaggat ttccttgatc   3180
tggaggggtg taatgagatt ctcaacgaca cccgccctga tgtgttgagg cagattcacc   3240
gcgcctactt tgaggcggga gctgacttgg ttgagaccaa tacttttggt tgcaacctgc   3300
cgaacttggc ggattatgac atcgctgatc gttgccgtga gcttgcctac aagggcactg   3360
cagtggctag ggaagtggct gatgagatgg ggccgggccg aaacggcatg cggcgtttcg   3420
tggttggttc cctgggacct ggaacgaagc ttccatcgct gggccatgca ccgtatgcag   3480
atttgcgtgg gcactacaag gaagcagcgc ttggcatcat cgacggtggt ggcgatgcct   3540
ttttgattga gactgctcag gacttgcttc aggtcaaggc tgcggttcac ggcgttcaag   3600
atgccatggc tgaacttgat acattcttgc ccattatttg ccacgtcacc gtagagacca   3660
ccggcaccat gctcatgggt tctgagatcg gtgccgcgtt gacagcgctg cagccactgg   3720
gtatcgacat gattggtctg aactgcgcca ccggcccaga tgagatgagc gagcacctgc   3780
gttacctgtc caagcacgcc gatattcctg tgtcggtgat gcctaacgca ggtcttcctg   3840
tcctgggtaa aaacggtgca gaatacccac ttgaggctga ggatttggcg caggcgctgg   3900
ctggattcgt ctccgaatat ggcctgtcca tggtgggtgg ttgttgtggc accacacctg   3960
agcacatccg tgcggtccgc gatgcggtgg ttggtgttcc agagcaggaa acctccacac   4020
tgaccaagat ccctgcaggc cctgttgagc aggcctcccg cgaggtggag aaagaggact   4080
ccgtcgcgtc gctgtacacc tcggtgccat tgtcccagga aaccggcatt tccatgatcg   4140
gtgagcgcac caactccaac ggttccaagg cattccgtga ggcaatgctg tctggcgatt   4200
```

-continued

```
gggaaaagtg tgtggatatt gccaagcagc aaacccgcga tggtgcacac atgctggatc   4260
tttgtgtgga ttacgtggga cgagacggca ccgccgatat ggcgaccttg gcagcacttc   4320
ttgctaccag ctccactttg ccaatcatga ttgactccac cgagccagag gttattcgca   4380
caggccttga gcacttgggt ggacgaagca tcgttaactc cgtcaacttt gaagacggcg   4440
atggccctga gtcccgctac cagcgcatca tgaaactggt aaagcagcac ggtgcggccg   4500
tggttgcgct gaccattgat gaggaaggcc aggcacgtac cgctgagcac aaggtgcgca   4560
ttgctaaacg actgattgac gatatcaccg gcagctacgg cctggatatc aaagacatcg   4620
ttgtggactg cctgaccttc ccgatctcta ctggccagga agaaaccagg cgagatggca   4680
ttgaaaccat cgaagccatc cgcgagctga agaagctcta cccagaaatc cacaccaccc   4740
tgggtctgtc caatatttcc ttcggcctga accctgctgc acgccaggtt cttaactctg   4800
tgttcctcaa tgagtgcatt gaggctggtc tggactctgc gattgcgcac agctccaaga   4860
ttttgccgat gaaccgcatt gatgatcgcc agcgcgaagt ggcgttggat atggtctatg   4920
atcgccgcac cgaggattac gatccgctgc aggaattcat gcagctgttt gagggcgttt   4980
ctgctgccga tgccaaggat gctcgcgctg aacagctggc cgctatgcct ttgtttgagc   5040
gtttggcaca gcgcatcatc gacggcgata agaatggcct tgaggatgat ctggaagcag   5100
gcatgaagga gaagtctcct attgcgatca tcaacgagga ccttctcaac ggcatgaaga   5160
ccgtgggtga gctgtttggt tccggacaga tgcagctgcc attcgtgctg caatcggcag   5220
aaaccatgaa aactgcggtg gcctatttgg aaccgttcat ggaagaggaa gcagaagcta   5280
ccggatctgc gcaggcagag ggcaagggca aaatcgtcgt ggccaccgtc aagggtgacg   5340
tgcacgatat cggcaagaac ttggtggaca tcattttgtc caacaacggt tacgacgtgg   5400
tgaacttggg catcaagcag ccactgtccg ccatgttgga agcagcggaa gaacacaaag   5460
cagacgtcat cggcatgtcg ggacttcttg tgaagtccac cgtggtgatg aaggaaaacc   5520
ttgaggagat gaacaacgcc ggcgcatcca attacccagt cattttgggt ggcgctgcgc   5580
tgacgcgtac ctacgtggaa aacgatctca acgaggtgta caccggtgag gtgtactacg   5640
cccgtgatgc tttcgagggc ctgcgcctga tggatgaggt gatggcagaa aagcgtggtg   5700
aaggacttga tcccaactca ccagaagcta ttgagcaggc gaagaagaag gcggaacgta   5760
aggctcgtaa tgagcgttcc cgcaagattg ccgcggagcg taaagctaat gcggctcccg   5820
tgattgttcc ggagcgttct gatgtctcca ccgatactcc aaccgcggca ccaccgttct   5880
ggggaacccg cattgtcaag ggtctgccct tggcggagtt cttgggcaac cttgatgagc   5940
gcgccttgtt catggggcag tggggtctga aatccacccg cggcaacgag ggtccaagct   6000
atgaggattt ggtggaaact gaaggccgac cacgcctgcg ctactggctg gatcgcctga   6060
agtctgaggg cattttggac cacgtggcct tggtgtatgg ctacttccca gcggtcgcgg   6120
aaggcgatga cgtggtgatc ttggaatccc cggatccaca cgcagccgaa cgcatgcgct   6180
ttagcttccc acgccagcag cgcggcaggt tcttgtgcat cgcggatttc attcgcccac   6240
gcgagcaagc tgtcaaggac ggccaagtgg acgtcatgcc attccagctg gtcaccatgg   6300
gtaatcctat tgctgatttc gccaacgagt tgttcgcagc caatgaatac cgcgagtact   6360
tggaagttca cggcatcggc gtgcagctca ccgaagcatt ggccgagtac tggcactccc   6420
gagtgcgcag cgaactcaag ctgaacgacg gtggatctgt cgctgatttt gatccagaag   6480
acaagaccaa gttcttcgac ctggattacc gcggcgcccg cttctccttt ggttacggtt   6540
cttgccctga tctggaagac cgcgcaaagc tggtggaatt gctcgagcca ggccgtatcg   6600
```

-continued gcgtggagtt gtccgaggaa ctccagctgc acccagagca gtccacagac gcgtttgtgc 6660
tctaccaccc agaggcaaag tactttaacg tctaatctag agttctgtga aaaacaccgt 6720
ggggcagttt ctgcttcgcg gtgtttttta tttgtggggc actagacccg ggatttaaat 6780
cgctagcggg ctgctaaagg aagcggaaca cgtagaaagc cagtccgcag aaacggtgct 6840
gaccccggat gaatgtcagc tactgggcta tctggacaag ggaaaacgca agcgcaaaga 6900
gaaagcaggt agcttgcagt gggcttacat ggcgatagct agactgggcg gttttatgga 6960
cagcaagcga accggaattg ccagctgggg cgccctctgg taaggttggg aagccctgca 7020
aagtaaactg gatggctttc ttgccgccaa ggatctgatg gcgcagggga tcaagatctg 7080
atcaagagac aggatgagga tcgtttcgca tgattgaaca agatggattg cacgcaggtt 7140
ctccggccgc ttgggtggag aggctattcg gctatgactg ggcacaacag acaatcggct 7200
gctctgatgc cgccgtgttc cggctgtcag cgcaggggcg cccggttctt tttgtcaaga 7260
ccgacctgtc cggtgccctg aatgaactgc aggacgaggc agcgcggcta tcgtggctgg 7320
ccacgacggg cgttccttgc gcagctgtgc tcgacgttgt cactgaagcg ggaagggact 7380
ggctgctatt gggcgaagtg ccggggcagg atctcctgtc atctcacctt gctcctgccg 7440
agaaagtatc catcatggct gatgcaatgc ggcggctgca tacgcttgat ccggctacct 7500
gcccattcga ccaccaagcg aaacatcgca tcgagcgagc acgtactcgg atggaagccg 7560
gtcttgtcga tcaggatgat ctggacgaag agcatcaggg gctcgcgcca gccgaactgt 7620
tcgccaggct caaggcgcgc atgcccgacg gcgaggatct cgtcgtgacc catggcgatg 7680
cctgcttgcc gaatatcatg gtggaaaatg gccgcttttc tggattcatc gactgtggcc 7740
ggctgggtgt ggcggaccgc tatcaggaca tagcgttggc tacccgtgat attgctgaag 7800
agcttggcgg cgaatgggct gaccgcttcc tcgtgcttta cggtatcgcc gctcccgatt 7860
cgcagcgcat cgccttctat cgccttcttg acgagttctt ctgagcggga ctctggggtt 7920
cgaaatgacc gaccaagcga cgcccaacct gccatcacga gatttcgatt ccaccgccgc 7980
cttctatgaa aggttgggct tcggaatcgt tttccgggac gccggctgga tgatcctcca 8040
gcgcggggat ctcatgctgg agttcttcgc ccacgctagc ggcgcgccgg ccggcccggt 8100
gtgaaatacc gcacagatgc gtaaggagaa aataccgcat caggcgctct tccgcttcct 8160
cgctcactga ctcgctgcgc tcggtcgttc ggctgcggcg agcggtatca gctcactcaa 8220
aggcggtaat acggttatcc acagaatcag gggataacgc aggaaagaac atgtgagcaa 8280
aaggccagca aaaggccagg aaccgtaaaa aggccgcgtt gctggcgttt ttccataggc 8340
tccgcccccc tgacgagcat cacaaaaatc gacgctcaag tcagaggtgg cgaaacccga 8400
caggactata aagataccag gcgtttcccc ctggaagctc cctcgtgcgc tctcctgttc 8460
cgaccctgcc gcttaccgga tacctgtccg cctttctccc ttcgggaagc gtggcgcttt 8520
ctcatagctc acgctgtagg tatctcagtt cggtgtaggt cgttcgctcc aagctgggct 8580
gtgtgcacga accccccgtt cagcccgacc gctgcgcctt atccggtaac tatcgtcttg 8640
agtccaaccc ggtaagacac gacttatcgc cactggcagc agccactggt aacaggatta 8700
gcagagcgag gtatgtaggc ggtgctacag agttcttgaa gtggtggcct aactacggct 8760
acactagaag gacagtattt ggtatctgcg ctctgctgaa gccagttacc ttcggaaaaa 8820
gagttggtag ctcttgatcc ggcaaacaaa ccaccgctgg tagcggtggt ttttttgttt 8880
gcaagcagca gattacgcgc agaaaaaaag gatctcaaga agatcctttg atcttttcta 8940
cggggtctga cgctcagtgg aacgaaaact cacgttaagg gattttggtc atgagattat 9000

-continued

```
caaaaaggat cttcacctag atccttttaa aggccggccg cggccgcgca aagtcccgct   9060
tcgtgaaaat tttcgtgccg cgtgattttc cgccaaaaac tttaacgaac gttcgttata   9120
atggtgtcat gaccttcacg acgaagtact aaaattggcc cgaatcatca gctatggatc   9180
tctctgatgt cgcgctggag tccgacgcgc tcgatgctgc cgtcgattta aaaacggtga   9240
tcggattttt ccgagctctc gatacgacgg acgcgccagc atcacgagac tgggccagtg   9300
ccgcgagcga cctagaaact ctcgtggcgg atcttgagga gctggctgac gagctgcgtg   9360
ctcggccagc gccaggagga cgcacagtag tggaggatgc aatcagttgc gcctactgcg   9420
gtggcctgat tcctccccgg cctgacccgc gaggacggcg cgcaaaatat tgctcagatg   9480
cgtgtcgtgc cgcagccagc cgcgagcgcg ccaacaaacg ccacgccgag gagctggagg   9540
cggctaggtc gcaaatggcg ctggaagtgc gtcccccgag cgaaattttg gccatggtcg   9600
tcacagagct ggaagcggca gcgagaatta tcgcgatcgt ggcggtgccc gcaggcatga   9660
caaacatcgt aaatgccgcg tttcgtgtgc cgtggccgcc caggacgtgt cagcgccgcc   9720
accacctgca ccgaatcggc agcagcgtcg cgcgtcgaaa aagcgcacag gcggcaagaa   9780
gcgataagct gcacgaatac ctgaaaaatg ttgaacgccc cgtgagcggt aactcacagg   9840
gcgtcggcta acccccagtc caaacctggg agaaagcgct caaaaatgac tctagcggat   9900
tcacgagaca ttgacacacc ggcctggaaa ttttccgctg atctgttcga cacccatccc   9960
gagctcgcgc tgcgatcacg tggctggacg agcgaagacc gccgcgaatt cctcgctcac  10020
ctgggcagag aaaatttcca gggcagcaag acccgcgact tcgccagcgc ttggatcaaa  10080
gacccggaca cggagaaaca cagccgaagt tataccgagt tggttcaaaa tcgcttgccc  10140
ggtgccagta tgttgctctg acgcacgcgc agcacgcagc cgtgcttgtc ctggacattg  10200
atgtgccgag ccaccaggcc ggcgggaaaa tcgagcacgt aaaccccgag gtctacgcga  10260
ttttggagcg ctgggcacgc ctggaaaaag cgccagcttg gatcggcgtg aatccactga  10320
gcgggaaatg ccagctcatc tggctcattg atccggtgta tgccgcagca ggcatgagca  10380
gcccgaatat gcgcctgctg gctgcaacga ccgaggaaat gacccgcgtt ttcggcgctg  10440
accaggcttt ttcacatagg ctgagccgtg gccactgcac tctccgacga tcccagccgt  10500
accgctggca tgcccagcac aatcgcgtgg atcgcctagc tgatcttatg gaggttgctc  10560
gcatgatctc aggcacagaa aaacctaaaa aacgctatga gcaggagttt tctagcggac  10620
gggcacgtat cgaagcggca agaaaagcca ctgcggaagc aaaagcactt gccacgcttg  10680
aagcaagcct gccgagcgcc gctgaagcgt ctggagagct gatcgacggc gtccgtgtcc  10740
tctggactgc tccagggcgt gccgcccgtg atgagacggc ttttcgccac gctttgactg  10800
tgggatacca gttaaaagcg gctggtgagc gcctaaaaga caccaagggt catcgagcct  10860
acgagcgtgc ctacaccgtc gctcaggcgg tcggaggagg ccgtgagcct gatctgccgc  10920
cggactgtga ccgccagacg gattggccgc gacgtgtgcg cggctacgtc gctaaaggcc  10980
agccagtcgt ccctgctcgt cagacagaga cgcagagcca gccgaggcga aaagctctgg  11040
ccactatggg aagacgtggc ggtaaaaagg ccgcagaacg ctggaaagac ccaaacagtg  11100
agtacgcccg agcacagcga gaaaaactag ctaagtccag tcaacgacaa gctaggaaag  11160
ctaaaggaaa tcgcttgacc attgcaggtt ggtttatgac tgttgaggga gagactggct  11220
cgtggccgac aatcaatgaa gctatgtctg aatttagcgt gtcacgtcag accgtgaata  11280
gagcacttaa ggtctgcggg cattgaactt ccacgaggac gccgaaagct tcccagtaaa  11340
tgtgccatct cgtaggcaga aaacggttcc cccgtagggt ctctctcttg gcctcctttc  11400
```

-continued taggtcgggc tgattgctct tgaagctctc tagggggct cacaccatag gcagataacg 11460
ttccccaccg gctcgcctcg taagcgcaca aggactgctc ccaaagatct tcaaagccac 11520
tgccgcgact gccttcgcga agccttgccc cgcggaaatt tcctccaccg agttcgtgca 11580
cacccctatg ccaagcttct ttcaccctaa attcgagaga ttggattctt accgtggaaa 11640
ttcttcgcaa aaatcgtccc ctgatcgccc ttgcgacgtt ggcgtcggtg ccgctggttg 11700
cgcttggctt gaccgacttg atcagcggcc gctcgattta aatctcgaga ggcctgacgt 11760
cgggcccg 11768

<210> SEQ ID NO 47
<211> LENGTH: 13512
<212> TYPE: DNA
<213> ORGANISM: artificial
<220> FEATURE:
<223> OTHER INFORMATION: Plasmid: pOM160

<400> SEQUENCE: 47
gcggccgctc gatttaaatc tcgagaggcc tgacgtcggg cccggtacca cgcgtcatat 60
gcggcttaaa gtttggctgc catgtgaatt tttagcaccc tcaacagttg agtgctggca 120
ctctcggggg tagagtgcca aataggttgt ttgacacaca gttgttcacc cgcgacgacg 180
gctgtgctgg aaacccacaa ccggcacaca caaaattttt ctcatggagg gattcatcat 240
gccaaagtac gacaattcca atgctgacca gtggggcttt gaaacccgct ccattcacgc 300
aggccagtca gtagacgcac agaccagcgc acgaaacctt ccgatctacc aatccaccgc 360
tttcgtgttc gactccgctg agcacgccaa gcagcgtttc gcacttgagg atctaggccc 420
tgtttactcc cgcctcacca acccaaccgt tgaggctttg gaaaaccgca tcgcttccct 480
cgaaggtggc gtccacgctg tagcgttctc ctccggacag gccgcaacca ccaacgccat 540
tttgaacctg gcaggagcgg gcgaccacat cgtcacctcc ccacgcctct acggtggcac 600
cgagactcta ttccttatca ctcttaaccg cctgggtatc gatgtttcct tcgtggaaaa 660
ccccgacgac cctgagtcct ggcaggcagc cgttcagcca aacaccaaag cattcttcgg 720
cgagactttc gccaacccac aggcagacgt cctggatatt cctgcggtgg ctgaagttgc 780
gcaccgcaac agcgttccac tgatcatcga caacaccatc gctaccgcag cgctcgtgcg 840
cccgctcgag ctcggcgcag acgttgtcgt cgcttccctc accaagttct acaccggcaa 900
cggctccgga ctgggcggcg tgcttatcga cggcggaaag ttcgattgga ctgtcgaaaa 960
ggatggaaag ccagtattcc cctacttcgt cactccagat gctgcttacc acggattgaa 1020
gtacgcagac cttggtgcac cagccttcgg cctcaaggtt cgcgttggcc ttctacgcga 1080
caccggctcc accctctccg cattcaacgc atgggctgca gtccagggca tcgacaccct 1140
ttccctgcgc ctggagcgcc acaacgaaaa cgccatcaag gttgcagaat tcctcaacaa 1200
ccacgagaag gtggaaaagg ttaacttcgc aggcctgaag gattcccctt ggtacgcaac 1260
caaggaaaag cttggcctga agtacaccgg ctccgttctc accttcgaga tcaagggcgg 1320
caaggatgag gcttgggcat ttatcgacgc cctgaagcta cactccaacc ttgcaaacat 1380
cggcgatgtt cgctccctcg ttgttcaccc agcaaccacc acccattcac agtccgacga 1440
agctggcctg gcacgcgcgg gcgttaccca gtccaccgtc cgcctgtccg ttggcatcga 1500
gaccattgat gatatcatcg ctgacctcga aggcggcttt gctgcaatct agcactagta 1560
gctgccaatt attccgggct tgtgacccgc tacccgataa ataggtcggc tgaaaaattt 1620
cgttgcaata tcaacaaaaa ggcctatcat tgggaggtgt cgcaccaagt acttttgcga 1680

-continued

```
agcgccatct gacggatttt caaaagatgt atatgctcgg tgcggaaacc tacgaaagga   1740
tttttaccc atgcccaccc tcgcgccttc aggtcaactt gaaatccaag cgatcggtga   1800
tgtctccacc gaagccggag caatcattac aaacgctgaa atcgcctatc accgctgggg   1860
tgaataccgc gtagataaag aaggacgcag caatgtcgtt ctcatcgaac acgccctcac   1920
tggagattcc aacgcagccg attggtgggc tgacttgctc ggtcccggca aagccatcaa   1980
cactgatatt tactgcgtga tctgtaccaa cgtcatcggt ggttgcaacg gttccaccgg   2040
acctggctcc atgcatccag atggaaattt ctggggtaat cgcttccccg ccacgtccat   2100
tcgtgatcag gtaaacgccg aaaaacaatt cctcgacgca ctcggcatca ccacggtcgc   2160
cgcagtactt ggtggttcca tgggtggtgc ccgcacccta gagtgggccg caatgtaccc   2220
agaaactgtt ggcgcagctg ctgttcttgc agtttctgca cgcgccagcg cctggcaaat   2280
cggcattcaa tccgcccaaa ttaaggcgat tgaaaacgac caccactggc acgaaggcaa   2340
ctactacgaa tccggctgca acccagccac cggactcggc gccgcccgac gcatcgccca   2400
cctcacctac cgtggcgaac tagaaatcga cgaacgcttc ggcaccaaag cccaaaagaa   2460
cgaaaaccca ctcggtccct accgcaagcc cgaccagcgc ttcgccgtgg aatcctactt   2520
ggactaccaa gcagacaagc tagtacagcg tttcgacgcc ggctcctacg tcttgctcac   2580
cgacgccctc aaccgccacg acattggtcg cgaccgcgga ggcctcaaca aggcactcga   2640
atccatcaaa gttccagtcc ttgtcgcagg cgtagatacc gatattttgt accccctacca   2700
ccagcaagaa cacctctcca gaaacctggg aaatctactg gcaatggcaa aaatcgtatc   2760
ccctgtcggc cacgatgctt tcctcaccga aagccgccaa atggatcgca tcgtgaggaa   2820
cttcttcagc ctcatctccc cagacgaaga caacccttcg acctacatcg agttctacat   2880
ctaagtcgag gtcgagcggc ttaaagtttg gctgccatgt gaatttttag caccctcaac   2940
agttgagtgc tggcactctc gggggtagag tgccaaatag gttgtttgac acacagttgt   3000
tcacccgcga cgacggctgt gctggaaacc cacaaccggc acacacaaaa tttttctcat   3060
ggagggattc atcatgtcga cttcagttac ttcaccagcc cacaacaacg cacattcctc   3120
cgaatttttg gatgcgttgg caaaccatgt gttgatcggc gacggcgcca tgggcaccca   3180
gctccaaggc tttgacctgg acgtggaaaa ggatttcctt gatctggagg ggtgtaatga   3240
gattctcaac gacacccgcc ctgatgtgtt gaggcagatt caccgcgcct actttgaggc   3300
gggagctgac ttggttgaga ccaatacttt tggttgcaac ctgccgaact tggcggatta   3360
tgacatcgct gatcgttgcc gtgagcttgc ctacaagggc actgcagtgg ctagggaagt   3420
ggctgatgag atggggccgg gccgaaacgg catgcggcgt ttcgtggttg gttccctggg   3480
acctggaacg aagcttccat cgctgggcca tgcaccgtat gcagatttgc gtgggcacta   3540
caaggaagca gcgcttggca tcatcgacgg tggtggcgat gcctttttga ttgagactgc   3600
tcaggacttg cttcaggtca aggctgcggt tcacggcgtt caagatgcca tggctgaact   3660
tgatacattc ttgcccatta tttgccacgt caccgtagag accaccggca ccatgctcat   3720
gggttctgag atcggtgccg cgttgacagc gctgcagcca ctgggtatcg acatgattgg   3780
tctgaactgc gccaccggcc cagatgagat gagcgagcac ctgcgttacc tgtccaagca   3840
cgccgatatt cctgtgtcgg tgatgcctaa cgcaggtctt cctgtcctgg gtaaaaacgg   3900
tgcagaatac ccacttgagg ctgaggattt ggcgcaggcg ctggctggat tcgtctccga   3960
atatggcctg tccatggtgg gtggttgttg tggcaccaca cctgagcaca tccgtgcggt   4020
ccgcgatgcg gtggttggtg ttccagagca ggaaacctcc acactgacca agatccctgc   4080
```

-continued

```
aggccctgtt gagcaggcct cccgcgaggt ggagaaagag gactccgtcg cgtcgctgta   4140
cacctcggtg ccattgtccc aggaaaccgg catttccatg atcggtgagc gcaccaactc   4200
caacggttcc aaggcattcc gtgaggcaat gctgtctggc gattgggaaa agtgtgtgga   4260
tattgccaag cagcaaaccc gcgatggtgc acacatgctg gatctttgtg tggattacgt   4320
gggacgagac ggcaccgccg atatggcgac cttggcagca cttcttgcta ccagctccac   4380
tttgccaatc atgattgact ccaccgagcc agaggttatt cgcacaggcc ttgagcactt   4440
gggtggacga agcatcgtta actccgtcaa ctttgaagac ggcgatggcc ctgagtcccg   4500
ctaccagcgc atcatgaaac tggtaaagca gcacggtgcg gccgtggttg cgctgaccat   4560
tgatgaggaa ggccaggcac gtaccgctga gcacaaggtg cgcattgcta aacgactgat   4620
tgacgatatc accggcagct acggcctgga tatcaaagac atcgttgtgg actgcctgac   4680
cttcccgatc tctactggcc aggaagaaac caggcgagat ggcattgaaa ccatcgaagc   4740
catccgcgag ctgaagaagc tctacccaga aatccacacc accctgggtc tgtccaatat   4800
ttccttcggc ctgaaccctg ctgcacgcca ggttcttaac tctgtgttcc tcaatgagtg   4860
cattgaggct ggtctggact ctgcgattgc gcacagctcc aagattttgc cgatgaaccg   4920
cattgatgat cgccagcgcg aagtggcgtt ggatatggtc tatgatcgcc gcaccgagga   4980
ttacgatccg ctgcaggaat tcatgcagct gtttgagggc gtttctgctg ccgatgccaa   5040
ggatgctcgc gctgaacagc tggccgctat gcctttgttt gagcgtttgg cacagcgcat   5100
catcgacggc gataagaatg gccttgagga tgatctggaa gcaggcatga aggagaagtc   5160
tcctattgcg atcatcaacg aggaccttct caacggcatg aagaccgtgg gtgagctgtt   5220
tggttccgga cagatgcagc tgccattcgt gctgcaatcg gcagaaacca tgaaaactgc   5280
ggtggcctat ttggaaccgt tcatggaaga ggaagcagaa gctaccggat ctgcgcaggc   5340
agagggcaag ggcaaaatcg tcgtggccac cgtcaagggt gacgtgcacg atatcggcaa   5400
gaacttggtg gacatcattt tgtccaacaa cggttacgac gtggtgaact tgggcatcaa   5460
gcagccactg tccgccatgt tggaagcagc ggaagaacac aaagcagacg tcatcggcat   5520
gtcgggactt cttgtgaagt ccaccgtggt gatgaaggaa aaccttgagg agatgaacaa   5580
cgccggcgca tccaattacc cagtcatttt gggtggcgct gcgctgacgc gtacctacgt   5640
ggaaaacgat ctcaacgagg tgtacaccgg tgaggtgtac tacgcccgtg atgctttcga   5700
gggcctgcgc ctgatggatg aggtgatggc agaaaagcgt ggtgaaggac ttgatcccaa   5760
ctcaccagaa gctattgagc aggcgaagaa gaaggcggaa cgtaaggctc gtaatgagcg   5820
ttcccgcaag attgccgcgg agcgtaaagc taatgcggct cccgtgattg ttccggagcg   5880
ttctgatgtc tccaccgata ctccaaccgc ggcaccaccg ttctggggaa cccgcattgt   5940
caagggtctg cccttggcgg agttcttggg caaccttgat gagcgcgcct tgttcatggg   6000
gcagtggggt ctgaaatcca cccgcggcaa cgagggtcca agctatgagg atttggtgga   6060
aactgaaggc cgaccacgcc tgcgctactg gctggatcgc ctgaagtctg agggcatttt   6120
ggaccacgtg gccttggtgt atggctactt cccagcggtc gcggaaggcg atgacgtggt   6180
gatcttggaa tccccggatc cacacgcagc cgaacgcatg cgctttagct tcccacgcca   6240
gcagcgcggc aggttcttgt gcatcgcgga tttcattcgc ccacgcgagc aagctgtcaa   6300
ggacggccaa gtggacgtca tgccattcca gctggtcacc atgggtaatc ctattgctga   6360
tttcgccaac gagttgttcg cagccaatga ataccgcgag tacttggaag ttcacggcat   6420
cggcgtgcag ctcaccgaag cattggccga gtactggcac tcccgagtgc gcagcgaact   6480
```

-continued

```
caagctgaac gacggtggat ctgtcgctga ttttgatcca gaagacaaga ccaagttctt   6540
cgacctggat taccgcggcg cccgcttctc ctttggttac ggttcttgcc ctgatctgga   6600
agaccgcgca aagctggtgg aattgctcga gccaggccgt atcggcgtgg agttgtccga   6660
ggaactccag ctgcacccag agcagtccac agacgcgttt gtgctctacc acccagaggc   6720
aaagtacttt aacgtctaat ctagagttct gtgaaaaaca ccgtggggca gtttctgctt   6780
cgcggtgttt tttatttgtg gggcactaga cccattcgca cagtgctgct actttttgct   6840
ggtttttccg gtggaatttg gcctgcggtc aaggggaagt agcataataa gcctaaagct   6900
ttcccatatt tattagcctc ttagagttct caggagaaaa cgaaatccca tgacatacac   6960
aatcgcacag ccctgcgttg acgtcttgga tcgtgcctgc gttgaagaat gcccagtaga   7020
ttgcatctac gaaggtaagc gcatgctgta catccacccg gatgagtgcg ttgactgtgg   7080
tgcatgtgag cctgcttgcc cagttgaggc aatcttctac gaggacgatg tcccagacga   7140
atggcttgac tacaacgatg ccaacgctgc attcttcgat gatctgggct ccccaggtgg   7200
tgcggctaag cttggaccac aagattttga tcacccaatg atcgctgcgc tgccgcctca   7260
ggcataatct aacgcatgac ctctcgcacc ccgcttgttt ctgttcttcc tgattttccg   7320
tgggattcgc tcgcttccgc aaaagccaaa gctgcgtctc acccggatgg gatcgtgaat   7380
ctttctgttg gcactccggt tgatccggtc gcgcccagca ttcagatcgc gttggcagaa   7440
gcagcggggt tttcgggtta ccctcaaacc atcggcaccc cggaactccg cgcagccatc   7500
aggggcgcgc ttgagcggcg ctacaacatg acaaagcttg tcgacgcctc cctcctcccc   7560
gtcgtgggta ccaaggaggc aattgccctt cttccattcg cgttgggtat ttccggcacc   7620
gttgtcatcc cagagattgc gtacccaacc tacgaagtcg ctgtcgtggc cgcaggatgc   7680
accgtgttgc gttctgattc gctgtttaag ctcggcccgc agatcccgtc gatgatgttt   7740
atcaactcac catccaaccc cacaggcaag gttctgggca tcccacactt gcgcaaggtt   7800
gtgaagtggg cgcaggaaaa caacgtgatc ctcgcagctg atgaatgcta cttgggtctt   7860
ggctgggacg atgaaaaccc accgatctca attttggatc cacgtgtctg cgatggcgac   7920
cacaccaact tgatcgccat tcactcgctg tctaaaacct caaacctcgc ttcttaccgc   7980
gcaggttacc tcgttggcga tccagcgctg attggtgaac tcacggaagt ccgtaagaac   8040
ttgggtctca tggttccttt cccaatccag caggccatga tcgcagccct caacgacgat   8100
gaccaagagg cagggcagaa gctcacctac gcgattcgtc gagcaaaact catgcgcgcc   8160
ctgttggaat ccggctttca ggtagataat tctgaagcgg gtctgtacct ctgggcgacg   8220
cgtgaagaac cttgccgtga cactgtcgat tggttcgctg agcgtggcat tctcgttgcc   8280
ccaggagact tctatggccc tcgcggagcg cagcatgtgc gtgtggcgat gaccgaaacc   8340
gacgagcgcg tcgacgcctt tgtttctcgc ctgagctaaa cacgactaag cttattttgt   8400
ttaattgagt ttgaagtttt ccgtcgaaag aggccatttg agttccgagt ccagtcctga   8460
gtcgagtacc gagcaaaaaa cctggggtag tcgatttctt cgcgcttccc ggcagttcat   8520
caagttcgga atcgttggag gctctggcac tttggttggg atttaaatcg ctagcgggct   8580
gctaaaggaa gcggaacacg tagaaagcca gtccgcagaa acggtgctga ccccggatga   8640
atgtcagcta ctgggctatc tggacaaggg aaaacgcaag cgcaaagaga aagcaggtag   8700
cttgcagtgg gcttacatgg cgatagctag actgggcggt tttatggaca gcaagcgaac   8760
cggaattgcc agctggggcg ccctctggta aggttgggaa gccctgcaaa gtaaactgga   8820
tggctttctt gccgccaagg atctgatggc gcaggggatc aagatctgat caagagacag   8880
```

-continued

```
gatgaggatc gtttcgcatg attgaacaag atggattgca cgcaggttct ccggccgctt   8940
gggtggagag gctattcggc tatgactggg cacaacagac aatcggctgc tctgatgccg   9000
ccgtgttccg gctgtcagcg caggggcgcc cggttctttt tgtcaagacc gacctgtccg   9060
gtgccctgaa tgaactgcag gacgaggcag cgcggctatc gtggctggcc acgacgggcg   9120
ttccttgcgc agctgtgctc gacgttgtca ctgaagcggg aagggactgg ctgctattgg   9180
gcgaagtgcc ggggcaggat ctcctgtcat ctcaccttgc tcctgccgag aaagtatcca   9240
tcatggctga tgcaatgcgg cggctgcata cgcttgatcc ggctacctgc ccattcgacc   9300
accaagcgaa acatcgcatc gagcgagcac gtactcggat ggaagccggt cttgtcgatc   9360
aggatgatct ggacgaagag catcaggggc tcgcgccagc cgaactgttc gccaggctca   9420
aggcgcgcat gcccgacggc gaggatctcg tcgtgaccca tggcgatgcc tgcttgccga   9480
atatcatggt ggaaaatggc cgcttttctg gattcatcga ctgtggccgg ctgggtgtgg   9540
cggaccgcta tcaggacata gcgttggcta cccgtgatat tgctgaagag cttggcggcg   9600
aatgggctga ccgcttcctc gtgctttacg gtatcgccgc tcccgattcg cagcgcatcg   9660
ccttctatcg ccttcttgac gagttcttct gagcgggact ctggggttcg aaatgaccga   9720
ccaagcgacg cccaacctgc catcacgaga tttcgattcc accgccgcct tctatgaaag   9780
gttgggcttc ggaatcgttt tccgggacgc cggctggatg atcctccagc gcggggatct   9840
catgctggag ttcttcgccc acgctagcgg cgcgccggcc ggcccggtgt gaaataccgc   9900
acagatgcgt aaggagaaaa taccgcatca ggcgctcttc cgcttcctcg ctcactgact   9960
cgctgcgctc ggtcgttcgg ctgcggcgag cggtatcagc tcactcaaag gcggtaatac  10020
ggttatccac agaatcaggg gataacgcag gaaagaacat gtgagcaaaa ggccagcaaa  10080
aggccaggaa ccgtaaaaag gccgcgttgc tggcgttttt ccataggctc cgcccccctg  10140
acgagcatca caaaaatcga cgctcaagtc agaggtggcg aaacccgaca ggactataaa  10200
gataccaggc gtttccccct ggaagctccc tcgtgcgctc tcctgttccg accctgccgc  10260
ttaccggata cctgtccgcc tttctccctt cgggaagcgt ggcgctttct catagctcac  10320
gctgtaggta tctcagttcg gtgtaggtcg ttcgctccaa gctgggctgt gtgcacgaac  10380
cccccgttca gcccgaccgc tgcgccttat ccggtaacta tcgtcttgag tccaacccgg  10440
taagacacga cttatcgcca ctggcagcag ccactggtaa caggattagc agagcgaggt  10500
atgtaggcgg tgctacagag ttcttgaagt ggtggcctaa ctacggctac actagaagga  10560
cagtatttgg tatctgcgct ctgctgaagc cagttacctt cggaaaaaga gttggtagct  10620
cttgatccgg caaacaaacc accgctggta gcggtggttt ttttgtttgc aagcagcaga  10680
ttacgcgcag aaaaaaagga tctcaagaag atcctttgat cttttctacg gggtctgacg  10740
ctcagtggaa cgaaaactca cgttaaggga ttttggtcat gagattatca aaaaggatct  10800
tcacctagat ccttttaaag gccggccgcg gccgcgcaaa gtcccgcttc gtgaaaattt  10860
tcgtgccgcg tgattttccg ccaaaaactt taacgaacgt tcgttataat ggtgtcatga  10920
ccttcacgac gaagtactaa aattggcccg aatcatcagc tatggatctc tctgatgtcg  10980
cgctggagtc cgacgcgctc gatgctgccg tcgatttaaa aacggtgatc ggatttttcc  11040
gagctctcga tacgacggac gcgccagcat cacgagactg ggccagtgcc gcgagcgacc  11100
tagaaactct cgtggcggat cttgaggagc tggctgacga gctgcgtgct cggccagcgc  11160
caggaggacg cacagtagtg gaggatgcaa tcagttgcgc ctactgcggt ggcctgattc  11220
ctccccggcc tgacccgcga ggacggcgcg caaaatattg ctcagatgcg tgtcgtgccg  11280
```

-continued

```
cagccagccg cgagcgcgcc aacaaacgcc acgccgagga gctggaggcg gctaggtcgc  11340

aaatggcgct ggaagtgcgt cccccgagcg aaattttggc catggtcgtc acagagctgg  11400

aagcggcagc gagaattatc gcgatcgtgg cggtgcccgc aggcatgaca aacatcgtaa  11460

atgccgcgtt tcgtgtgccg tggccgccca ggacgtgtca gcgccgccac cacctgcacc  11520

gaatcggcag cagcgtcgcg cgtcgaaaaa gcgcacaggc ggcaagaagc gataagctgc  11580

acgaatacct gaaaaatgtt gaacgccccg tgagcggtaa ctcacagggc gtcggctaac  11640

ccccagtcca aacctgggag aaagcgctca aaaatgactc tagcggattc acgagacatt  11700

gacacaccgg cctggaaatt ttccgctgat ctgttcgaca cccatcccga gctcgcgctg  11760

cgatcacgtg gctggacgag cgaagaccgc cgcgaattcc tcgctcacct gggcagagaa  11820

aatttccagg gcagcaagac ccgcgacttc gccagcgctt ggatcaaaga cccggacacg  11880

gagaaacaca gccgaagtta taccgagttg gttcaaaatc gcttgcccgg tgccagtatg  11940

ttgctctgac gcacgcgcag cacgcagccg tgcttgtcct ggacattgat gtgccgagcc  12000

accaggccgg cgggaaaatc gagcacgtaa accccgaggt ctacgcgatt ttggagcgct  12060

gggcacgcct ggaaaaagcg ccagcttgga tcggcgtgaa tccactgagc gggaaatgcc  12120

agctcatctg gctcattgat ccggtgtatg ccgcagcagg catgagcagc ccgaatatgc  12180

gcctgctggc tgcaacgacc gaggaaatga cccgcgtttt cggcgctgac caggcttttt  12240

cacataggct gagccgtggc cactgcactc tccgacgatc ccagccgtac cgctggcatg  12300

cccagcacaa tcgcgtggat cgcctagctg atcttatgga ggttgctcgc atgatctcag  12360

gcacagaaaa acctaaaaaa cgctatgagc aggagttttc tagcggacgg gcacgtatcg  12420

aagcggcaag aaaagccact gcggaagcaa aagcacttgc cacgcttgaa gcaagcctgc  12480

cgagcgccgc tgaagcgtct ggagagctga tcgacggcgt ccgtgtcctc tggactgctc  12540

cagggcgtgc cgcccgtgat gagacggctt ttcgccacgc tttgactgtg ggataccagt  12600

taaaagcggc tggtgagcgc ctaaaagaca ccaagggtca tcgagcctac gagcgtgcct  12660

acaccgtcgc tcaggcggtc ggaggaggcc gtgagcctga tctgccgccg gactgtgacc  12720

gccagacgga ttggccgcga cgtgtgcgcg gctacgtcgc taaaggccag ccagtcgtcc  12780

ctgctcgtca gacagagacg cagagccagc cgaggcgaaa agctctggcc actatgggaa  12840

gacgtggcgg taaaaaggcc gcagaacgct ggaaagaccc aaacagtgag tacgcccgag  12900

cacagcgaga aaaactagct aagtccagtc aacgacaagc taggaaagct aaaggaaatc  12960

gcttgaccat tgcaggttgg tttatgactg ttgagggaga gactggctcg tggccgacaa  13020

tcaatgaagc tatgtctgaa tttagcgtgt cacgtcagac cgtgaataga gcacttaagg  13080

tctgcgggca ttgaacttcc acgaggacgc cgaaagcttc ccagtaaatg tgccatctcg  13140

taggcagaaa acggttcccc cgtagggtct ctctcttggc ctcctttcta ggtcgggctg  13200

attgctcttg aagctctcta gggggggctca caccataggc agataacgtt ccccaccggc  13260

tcgcctcgta agcgcacaag gactgctccc aaagatcttc aaagccactg ccgcgactgc  13320

cttcgcgaag ccttgccccg cggaaatttc ctccaccgag ttcgtgcaca cccctatgcc  13380

aagcttcttt caccctaaat tcgagagatt ggattcttac cgtggaaatt cttcgcaaaa  13440

atcgtcccct gatcgccctt gcgacgttgg cgtcggtgcc gctggttgcg cttggcttga  13500

ccgacttgat ca                                                      13512
```

<210> SEQ ID NO 48
<211> LENGTH: 10621
<212> TYPE: DNA

<213> ORGANISM: artificial
<220> FEATURE:
<223> OTHER INFORMATION: Plasmid: pOM161

<400> SEQUENCE: 48
gcggccgctc gatttaaatc tcgagaggcc tgacgtcggg cccggtaccg ggccccccct 60
cgaggtcgag cggcttaaag tttggctgcc atgtgaattt ttagcaccct caacagttga 120
gtgctggcac tctcgggggt agagtgccaa ataggttgtt tgacacacag ttgttcaccc 180
gcgacgacgg ctgtgctgga aacccacaac cggcacacac aaaatttttc tcatggaggg 240
attcatcatg tcgacttcag ttacttcacc agcccacaac aacgcacatt cctccgaatt 300
tttggatgcg ttggcaaacc atgtgttgat cggcgacggc gccatgggca cccagctcca 360
aggctttgac ctggacgtgg aaaaggattt ccttgatctg gaggggtgta atgagattct 420
caacgacacc cgccctgatg tgttgaggca gattcaccgc gcctactttg aggcgggagc 480
tgacttggtt gagaccaata cttttggttg caacctgccg aacttggcgg attatgacat 540
cgctgatcgt tgccgtgagc ttgcctacaa gggcactgca gtggctaggg aagtggctga 600
tgagatgggg ccgggccgaa acggcatgcg gcgtttcgtg gttggttccc tgggacctgg 660
aacgaagctt ccatcgctgg gccatgcacc gtatgcagat ttgcgtgggc actacaagga 720
agcagcgctt ggcatcatcg acggtggtgg cgatgccttt ttgattgaga ctgctcagga 780
cttgcttcag gtcaaggctg cggttcacgg cgttcaagat gccatggctg aacttgatac 840
attcttgccc attatttgcc acgtcaccgt agagaccacc ggcaccatgc tcatgggttc 900
tgagatcggt gccgcgttga cagcgctgca gccactgggt atcgacatga ttggtctgaa 960
ctgcgccacc ggcccagatg agatgagcga gcacctgcgt tacctgtcca agcacgccga 1020
tattcctgtg tcggtgatgc ctaacgcagg tcttcctgtc ctgggtaaaa acggtgcaga 1080
atacccactt gaggctgagg atttggcgca ggcgctggct ggattcgtct ccgaatatgg 1140
cctgtccatg gtgggtggtt gttgtggcac cacacctgag cacatccgtg cggtccgcga 1200
tgcggtggtt ggtgttccag agcaggaaac ctccacactg accaagatcc ctgcaggccc 1260
tgttgagcag gcctcccgcg aggtggagaa agaggactcc gtcgcgtcgc tgtacacctc 1320
ggtgccattg tcccaggaaa ccggcatttc catgatcggt gagcgcacca actccaacgg 1380
ttccaaggca ttccgtgagg caatgctgtc tggcgattgg gaaaagtgtg tggatattgc 1440
caagcagcaa acccgcgatg gtgcacacat gctggatctt tgtgtggatt acgtgggacg 1500
agacggcacc gccgatatgg cgaccttggc agcacttctt gctaccagct ccactttgcc 1560
aatcatgatt gactccaccg agccagaggt tattcgcaca ggccttgagc acttgggtgg 1620
acgaagcatc gttaactccg tcaactttga agacggcgat ggccctgagt cccgctacca 1680
gcgcatcatg aaactggtaa agcagcacgg tgcggccgtg gttgcgctga ccattgatga 1740
ggaaggccag gcacgtaccg ctgagcacaa ggtgcgcatt gctaaacgac tgattgacga 1800
tatcaccggc agctacggcc tggatatcaa agacatcgtt gtggactgcc tgaccttccc 1860
gatctctact ggccaggaag aaaccaggcg agatggcatt gaaaccatcg aagccatccg 1920
cgagctgaag aagctctacc cagaaatcca caccaccctg ggtctgtcca atatttcctt 1980
cggcctgaac cctgctgcac gccaggttct taactctgtg ttcctcaatg agtgcattga 2040
ggctggtctg gactctgcga ttgcgcacag ctccaagatt ttgccgatga accgcattga 2100
tgatcgccag cgcgaagtgg cgttggatat ggtctatgat cgccgcaccg aggattacga 2160
tccgctgcag gaattcatgc agctgtttga gggcgtttct gctgccgatg ccaaggatgc 2220

```
tcgcgctgaa cagctggccg ctatgccttt gtttgagcgt ttggcacagc gcatcatcga   2280
cggcgataag aatggccttg aggatgatct ggaagcaggc atgaaggaga agtctcctat   2340
tgcgatcatc aacgaggacc ttctcaacgg catgaagacc gtgggtgagc tgtttggttc   2400
cggacagatg cagctgccat tcgtgctgca atcggcagaa accatgaaaa ctgcggtggc   2460
ctatttggaa ccgttcatgg aagaggaagc agaagctacc ggatctgcgc aggcagaggg   2520
caagggcaaa atcgtcgtgg ccaccgtcaa gggtgacgtg cacgatatcg gcaagaactt   2580
ggtggacatc attttgtcca acaacggtta cgacgtggtg aacttgggca tcaagcagcc   2640
actgtccgcc atgttggaag cagcggaaga acacaaagca gacgtcatcg gcatgtcggg   2700
acttcttgtg aagtccaccg tggtgatgaa ggaaaacctt gaggagatga acaacgccgg   2760
cgcatccaat tacccagtca ttttgggtgg cgctgcgctg acgcgtacct acgtggaaaa   2820
cgatctcaac gaggtgtaca ccggtgaggt gtactacgcc cgtgatgctt tcgagggcct   2880
gcgcctgatg gatgaggtga tggcagaaaa gcgtggtgaa ggacttgatc ccaactcacc   2940
agaagctatt gagcaggcga agaagaaggc ggaacgtaag gctcgtaatg agcgttcccg   3000
caagattgcc gcggagcgta aagctaatgc ggctcccgtg attgttccgg agcgttctga   3060
tgtctccacc gatactccaa ccgcggcacc accgttctgg ggaacccgca ttgtcaaggg   3120
tctgcccttg gcggagttct tgggcaacct tgatgagcgc gccttgttca tggggcagtg   3180
gggtctgaaa tccacccgcg gcaacgaggg tccaagctat gaggatttgg tggaaactga   3240
aggccgacca cgcctgcgct actggctgga tcgcctgaag tctgagggca ttttggacca   3300
cgtggccttg gtgtatggct acttcccagc ggtcgcggaa ggcgatgacg tggtgatctt   3360
ggaatccccg gatccacacg cagccgaacg catgcgcttt agcttcccac gccagcagcg   3420
cggcaggttc ttgtgcatcg cggatttcat tcgcccacgc gagcaagctg tcaaggacgg   3480
ccaagtggac gtcatgccat tccagctggt caccatgggt aatcctattg ctgatttcgc   3540
caacgagttg ttcgcagcca atgaataccg cgagtacttg gaagttcacg gcatcggcgt   3600
gcagctcacc gaagcattgg ccgagtactg gcactcccga gtgcgcagcg aactcaagct   3660
gaacgacggt ggatctgtcg ctgattttga tccagaagac aagaccaagt tcttcgacct   3720
ggattaccgc ggcgcccgct tctcctttgg ttacggttct tgccctgatc tggaagaccg   3780
cgcaaagctg gtggaattgc tcgagccagg ccgtatcggc gtggagttgt ccgaggaact   3840
ccagctgcac ccagagcagt ccacagacgc gtttgtgctc taccacccag aggcaaagta   3900
ctttaacgtc taatctagac ccattcgcac agtgctgcta ctttttgctg gtttttccgg   3960
tggaatttgg cctgcggtca aggggaagta gcataataag cctaaagctt tcccatattt   4020
attagcctct tagagttctc aggagaaaac gaaatcccat gacatacaca atcgcacagc   4080
cctgcgttga cgtcttggat cgtgcctgcg ttgaagaatg cccagtagat tgcatctacg   4140
aaggtaagcg catgctgtac atccacccgg atgagtgcgt tgactgtggt gcatgtgagc   4200
ctgcttgccc agttgaggca atcttctacg aggacgatgt cccagacgaa tggcttgact   4260
acaacgatgc caacgctgca ttcttcgatg atctgggctc cccaggtggt gcggctaagc   4320
ttggaccaca agattttgat cacccaatga tcgctgcgct gccgcctcag gcataatcta   4380
acgcatgacc tctcgcaccc cgcttgtttc tgttcttcct gattttccgt gggattcgct   4440
cgcttccgca aaagccaaag ctgcgtctca cccggatggg atcgtgaatc tttctgttgg   4500
cactccggtt gatccggtcg cgcccagcat tcagatcgcg ttggcagaag cagcggggtt   4560
ttcgggttac cctcaaacca tcggcacccc ggaactccgc gcagccatca ggggcgcgct   4620
```

-continued

```
tgagcggcgc tacaacatga caaagcttgt cgacgcctcc ctcctccccg tcgtgggtac   4680
caaggaggca attgcccttc ttccattcgc gttgggtatt tccggcaccg ttgtcatccc   4740
agagattgcg tacccaacct acgaagtcgc tgtcgtggcc gcaggatgca ccgtgttgcg   4800
ttctgattcg ctgtttaagc tcggcccgca gatcccgtcg atgatgttta tcaactcacc   4860
atccaacccc acaggcaagg ttctgggcat cccacacttg cgcaaggttg tgaagtgggc   4920
gcaggaaaac aacgtgatcc tcgcagctga tgaatgctac ttgggtcttg gctgggacga   4980
tgaaaaccca ccgatctcaa ttttggatcc acgtgtctgc gatggcgacc acaccaactt   5040
gatcgccatt cactcgctgt ctaaaacctc aaacctcgct tcttaccgcg caggttacct   5100
cgttggcgat ccagcgctga ttggtgaact cacggaagtc cgtaagaact tgggtctcat   5160
ggttcctttc ccaatccagc aggccatgat cgcagccctc aacgacgatg accaagaggc   5220
agggcagaag ctcacctacg cgattcgtcg agcaaaactc atgcgcgccc tgttggaatc   5280
cggctttcag gtagataatt ctgaagcggg tctgtacctc tgggcgacgc gtgaagaacc   5340
ttgccgtgac actgtcgatt ggttcgctga gcgtggcatt ctcgttgccc caggagactt   5400
ctatggccct cgcggagcgc agcatgtgcg tgtggcgatg accgaaaccg acgagcgcgt   5460
cgacgccttt gtttctcgcc tgagctaaac acgactaagc ttattttgtt taattgagtt   5520
tgaagttttc cgtcgaaaga ggccatttga gttccgagtc cagtcctgag tcgagtaccg   5580
agcaaaaaac ctggggtagt cgatttcttc gcgcttcccg gcagttcatc aagttcggaa   5640
tcgttggagg ctctggcact ttggttggga tttaaatcgc tagcgggctg ctaaaggaag   5700
cggaacacgt agaaagccag tccgcagaaa cggtgctgac cccggatgaa tgtcagctac   5760
tgggctatct ggacaaggga aaacgcaagc gcaaagagaa agcaggtagc ttgcagtggg   5820
cttacatggc gatagctaga ctgggcggtt ttatggacag caagcgaacc ggaattgcca   5880
gctggggcgc cctctggtaa ggttgggaag ccctgcaaag taaactggat ggctttcttg   5940
ccgccaagga tctgatggcg caggggatca agatctgatc aagagacagg atgaggatcg   6000
tttcgcatga ttgaacaaga tggattgcac gcaggttctc cggccgcttg ggtggagagg   6060
ctattcggct atgactgggc acaacagaca atcggctgct ctgatgccgc cgtgttccgg   6120
ctgtcagcgc aggggcgccc ggttcttttt gtcaagaccg acctgtccgg tgccctgaat   6180
gaactgcagg acgaggcagc gcggctatcg tggctggcca cgacgggcgt tccttgcgca   6240
gctgtgctcg acgttgtcac tgaagcggga agggactggc tgctattggg cgaagtgccg   6300
gggcaggatc tcctgtcatc tcaccttgct cctgccgaga aagtatccat catggctgat   6360
gcaatgcggc ggctgcatac gcttgatccg gctacctgcc cattcgacca ccaagcgaaa   6420
catcgcatcg agcgagcacg tactcggatg gaagccggtc ttgtcgatca ggatgatctg   6480
gacgaagagc atcaggggct cgcgccagcc gaactgttcg ccaggctcaa ggcgcgcatg   6540
cccgacggcg aggatctcgt cgtgacccat ggcgatgcct gcttgccgaa tatcatggtg   6600
gaaaatggcc gcttttctgg attcatcgac tgtggccggc tgggtgtggc ggaccgctat   6660
caggacatag cgttggctac ccgtgatatt gctgaagagc ttggcggcga atgggctgac   6720
cgcttcctcg tgctttacgg tatcgccgct cccgattcgc agcgcatcgc cttctatcgc   6780
cttcttgacg agttcttctg agcgggactc tggggttcga aatgaccgac caagcgacgc   6840
ccaacctgcc atcacgagat ttcgattcca ccgccgcctt ctatgaaagg ttgggcttcg   6900
gaatcgtttt ccgggacgcc ggctggatga tcctccagcg cggggatctc atgctggagt   6960
tcttcgccca cgctagcggc gcgccggccg gcccggtgtg aaataccgca cagatgcgta   7020
```

-continued

```
aggagaaaat accgcatcag gcgctcttcc gcttcctcgc tcactgactc gctgcgctcg   7080
gtcgttcggc tgcggcgagc ggtatcagct cactcaaagg cggtaatacg gttatccaca   7140
gaatcagggg ataacgcagg aaagaacatg tgagcaaaag gccagcaaaa ggccaggaac   7200
cgtaaaaagg ccgcgttgct ggcgtttttc cataggctcc gcccccctga cgagcatcac   7260
aaaaatcgac gctcaagtca gaggtggcga aacccgacag gactataaag ataccaggcg   7320
tttccccctg gaagctccct cgtgcgctct cctgttccga ccctgccgct taccggatac   7380
ctgtccgcct ttctcccttc gggaagcgtg gcgctttctc atagctcacg ctgtaggtat   7440
ctcagttcgg tgtaggtcgt tcgctccaag ctgggctgtg tgcacgaacc ccccgttcag   7500
cccgaccgct gcgccttatc cggtaactat cgtcttgagt ccaacccggt aagacacgac   7560
ttatcgccac tggcagcagc cactggtaac aggattagca gagcgaggta tgtaggcggt   7620
gctacagagt tcttgaagtg gtggcctaac tacggctaca ctagaaggac agtatttggt   7680
atctgcgctc tgctgaagcc agttaccttc ggaaaaagag ttggtagctc ttgatccggc   7740
aaacaaacca ccgctggtag cggtggtttt tttgtttgca agcagcagat tacgcgcaga   7800
aaaaaaggat ctcaagaaga tcctttgatc ttttctacgg ggtctgacgc tcagtggaac   7860
gaaaactcac gttaagggat tttggtcatg agattatcaa aaaggatctt cacctagatc   7920
cttttaaagg ccggccgcgg ccgcgcaaag tcccgcttcg tgaaaatttt cgtgccgcgt   7980
gattttccgc caaaaacttt aacgaacgtt cgttataatg gtgtcatgac cttcacgacg   8040
aagtactaaa attggcccga atcatcagct atggatctct ctgatgtcgc gctggagtcc   8100
gacgcgctcg atgctgccgt cgatttaaaa acggtgatcg gatttttccg agctctcgat   8160
acgacggacg cgccagcatc acgagactgg gccagtgccg cgagcgacct agaaactctc   8220
gtggcggatc ttgaggagct ggctgacgag ctgcgtgctc ggccagcgcc aggaggacgc   8280
acagtagtgg aggatgcaat cagttgcgcc tactgcggtg gcctgattcc tccccggcct   8340
gacccgcgag gacggcgcgc aaaatattgc tcagatgcgt gtcgtgccgc agccagccgc   8400
gagcgcgcca acaaacgcca cgccgaggag ctggaggcgg ctaggtcgca aatggcgctg   8460
gaagtgcgtc ccccgagcga aattttggcc atggtcgtca cagagctgga agcggcagcg   8520
agaattatcg cgatcgtggc ggtgcccgca ggcatgacaa acatcgtaaa tgccgcgttt   8580
cgtgtgccgt ggccgcccag gacgtgtcag cgccgccacc acctgcaccg aatcggcagc   8640
agcgtcgcgc gtcgaaaaag cgcacaggcg gcaagaagcg ataagctgca cgaatacctg   8700
aaaaatgttg aacgccccgt gagcggtaac tcacagggcg tcggctaacc cccagtccaa   8760
acctgggaga aagcgctcaa aaatgactct agcggattca cgagacattg acacaccggc   8820
ctggaaattt tccgctgatc tgttcgacac ccatcccgag ctcgcgctgc gatcacgtgg   8880
ctggacgagc gaagaccgcc gcgaattcct cgctcacctg ggcagagaaa atttccaggg   8940
cagcaagacc cgcgacttcg ccagcgcttg gatcaaagac ccggacacgg agaaacacag   9000
ccgaagttat accgagttgg ttcaaaatcg cttgcccggt gccagtatgt tgctctgacg   9060
cacgcgcagc acgcagccgt gcttgtcctg gacattgatg tgccgagcca ccaggccggc   9120
gggaaaatcg agcacgtaaa ccccgaggtc tacgcgattt tggagcgctg ggcacgcctg   9180
gaaaaagcgc cagcttggat cggcgtgaat ccactgagcg ggaaatgcca gctcatctgg   9240
ctcattgatc cggtgtatgc cgcagcaggc atgagcagcc cgaatatgcg cctgctggct   9300
gcaacgaccg aggaaatgac ccgcgttttc ggcgctgacc aggctttttc acataggctg   9360
agccgtggcc actgcactct ccgacgatcc cagccgtacc gctggcatgc ccagcacaat   9420
```

-continued

```
cgcgtggatc gcctagctga tcttatggag gttgctcgca tgatctcagg cacagaaaaa   9480

cctaaaaaac gctatgagca ggagttttct agcggacggg cacgtatcga agcggcaaga   9540

aaagccactg cggaagcaaa agcacttgcc acgcttgaag caagcctgcc gagcgccgct   9600

gaagcgtctg gagagctgat cgacggcgtc cgtgtcctct ggactgctcc agggcgtgcc   9660

gcccgtgatg agacggcttt tcgccacgct ttgactgtgg gataccagtt aaaagcggct   9720

ggtgagcgcc taaaagacac caagggtcat cgagcctacg agcgtgccta caccgtcgct   9780

caggcggtcg gaggaggccg tgagcctgat ctgccgccgg actgtgaccg ccagacggat   9840

tggccgcgac gtgtgcgcgg ctacgtcgct aaaggccagc cagtcgtccc tgctcgtcag   9900

acagagacgc agagccagcc gaggcgaaaa gctctggcca ctatgggaag acgtggcggt   9960

aaaaaggccg cagaacgctg gaaagaccca aacagtgagt acgcccgagc acagcgagaa  10020

aaactagcta agtccagtca acgacaagct aggaaagcta aaggaaatcg cttgaccatt  10080

gcaggttggt ttatgactgt tgagggagag actggctcgt ggccgacaat caatgaagct  10140

atgtctgaat ttagcgtgtc acgtcagacc gtgaatagag cacttaaggt ctgcgggcat  10200

tgaacttcca cgaggacgcc gaaagcttcc cagtaaatgt gccatctcgt aggcagaaaa  10260

cggttccccc gtagggtctc tctcttggcc tcctttctag gtcgggctga ttgctcttga  10320

agctctctag gggggctcac accataggca gataacgttc cccaccggct cgcctcgtaa  10380

gcgcacaagg actgctccca aagatcttca aagccactgc cgcgactgcc ttcgcgaagc  10440

cttgccccgc ggaaatttcc tccaccgagt tcgtgcacac ccctatgcca agcttctttc  10500

accctaaatt cgagagattg gattcttacc gtggaaattc ttcgcaaaaa tcgtcccctg  10560

atcgcccttg cgacgttggc gtcggtgccg ctggttgcgc ttggcttgac cgacttgatc  10620

a                                                                  10621
```

<210> SEQ ID NO 49
<211> LENGTH: 24
<212> TYPE: DNA
<213> ORGANISM: artificial
<220> FEATURE:
<223> OTHER INFORMATION: Primer: RY842

<400> SEQUENCE: 49

```
gataggtcgc agcggtgatc tgtt                                            24
```

<210> SEQ ID NO 50
<211> LENGTH: 40
<212> TYPE: DNA
<213> ORGANISM: artificial
<220> FEATURE:
<223> OTHER INFORMATION: Primer: RY841

<400> SEQUENCE: 50

```
agtggatcct cgcactcttg gtggtgattt ggtcaatgat                            40
```

<210> SEQ ID NO 51
<211> LENGTH: 12621
<212> TYPE: DNA
<213> ORGANISM: artificial
<220> FEATURE:
<223> OTHER INFORMATION: Plasmid: pOM352

<400> SEQUENCE: 51

```
gtaccacgcg tcatatgcgg cttaaagttt ggctgccatg tgaattttta gcaccctcaa     60

cagttgagtg ctggcactct cgggggtaga gtgccaaata ggttgtttga cacacagttg    120
```

-continued

```
ttcacccgcg acgacggctg tgctggaaac ccacaaccgg cacacacaaa atttttctca    180
tggagggatt catcatgcca aagtacgaca attccaatgc tgaccagtgg ggctttgaaa    240
cccgctccat tcacgcaggc cagtcagtag acgcacagac cagcgcacga aaccttccga    300
tctaccaatc caccgctttc gtgttcgact ccgctgagca cgccaagcag cgtttcgcac    360
ttgaggatct aggccctgtt tactcccgcc tcaccaaccc aaccgttgag gctttggaaa    420
accgcatcgc ttccctcgaa ggtggcgtcc acgctgtagc gttctcctcc ggacaggccg    480
caaccaccaa cgccatttg aacctggcag gagcgggcga ccacatcgtc acctccccac    540
gcctctacgg tggcaccgag actctattcc ttatcactct taaccgcctg ggtatcgatg    600
tttccttcgt ggaaaacccc gacgaccctg agtcctggca ggcagccgtt cagccaaaca    660
ccaaagcatt cttcggcgag actttcgcca acccacaggc agacgtcctg gatattcctg    720
cggtggctga agttgcgcac cgcaacagcg ttccactgat catcgacaac accatcgcta    780
ccgcagcgct cgtgcgcccg ctcgagctcg gcgcagacgt tgtcgtcgct tccctcacca    840
agttctacac cggcaacggc tccggactgg gcggcgtgct tatcgacggc ggaaagttcg    900
attggactgt cgaaaaggat ggaaagccag tattccccta cttcgtcact ccagatgctg    960
cttaccacgg attgaagtac gcagaccttg gtgcaccagc cttcggcctc aaggttcgcg   1020
ttggccttct acgcgacacc ggctccaccc tctccgcatt caacgcatgg gctgcagtcc   1080
agggcatcga caccctttcc ctgcgcctgg agcgccacaa cgaaaacgcc atcaaggttg   1140
cagaattcct caacaaccac gagaaggtgg aaaaggttaa cttcgcaggc ctgaaggatt   1200
ccccttggta cgcaaccaag gaaaagcttg gcctgaagta caccggctcc gttctcacct   1260
tcgagatcaa gggcggcaag gatgaggctt gggcatttat cgacgccctg aagctacact   1320
ccaaccttgc aaacatcggc gatgttcgct ccctcgttgt tcacccagca accaccaccc   1380
attcacagtc cgacgaagct ggcctggcac gcgcgggcgt tacccagtcc accgtccgcc   1440
tgtccgttgg catcgagacc attgatgata tcatcgctga cctcgaaggc ggctttgctg   1500
caatctagca ctagtagctg ccaattattc cgggcttgtg acccgctacc cgataaatag   1560
gtcggctgaa aaatttcgtt gcaatatcaa caaaaaggcc tatcattggg aggtgtcgca   1620
ccaagtactt ttgcgaagcg ccatctgacg gattttcaaa agatgtatat gctcggtgcg   1680
gaaacctacg aaaggatttt ttacccatgc ccaccctcgc gccttcaggt caacttgaaa   1740
tccaagcgat cggtgatgtc tccaccgaag ccggagcaat cattacaaac gctgaaatcg   1800
cctatcaccg ctggggtgaa taccgcgtag ataaagaagg acgcagcaat gtcgttctca   1860
tcgaacacgc cctcactgga gattccaacg cagccgattg gtgggctgac ttgctcggtc   1920
ccggcaaagc catcaacact gatatttact gcgtgatctg taccaacgtc atcggtggtt   1980
gcaacggttc caccggacct ggctccatgc atccagatgg aaatttctgg ggtaatcgct   2040
tccccgccac gtccattcgt gatcaggtaa acgccgaaaa acaattcctc gacgcactcg   2100
gcatcaccac ggtcgccgca gtacttggtg gttccatggg tggtgcccgc accctagagt   2160
gggccgcaat gtacccagaa actgttggcg cagctgctgt tcttgcagtt tctgcacgcg   2220
ccagcgcctg gcaaatcggc attcaatccg cccaaattaa ggcgattgaa aacgaccacc   2280
actggcacga aggcaactac tacgaatccg gctgcaaccc agccaccgga ctcggcgccg   2340
cccgacgcat cgcccacctc acctaccgtg gcgaactaga aatcgacgaa cgcttcggca   2400
ccaaagccca aaagaacgaa aacccactcg gtccctaccg caagcccgac cagcgcttcg   2460
ccgtggaatc ctacttggac taccaagcag acaagctagt acagcgtttc gacgccggct   2520
```

-continued

```
cctacgtctt gctcaccgac gccctcaacc gccacgacat tggtcgcgac cgcggaggcc   2580
tcaacaaggc actcgaatcc atcaaagttc cagtccttgt cgcaggcgta gataccgata   2640
ttttgtaccc ctaccaccag caagaacacc tctccagaaa cctgggaaat ctactggcaa   2700
tggcaaaaat cgtatcccct gtcggccacg atgctttcct caccgaaagc cgccaaatgg   2760
atcgcatcgt gaggaacttc ttcagcctca tctccccaga cgaagacaac ccttcgacct   2820
acatcgagtt ctacatctaa gtcgaggtcg agcggcttaa agtttggctg ccatgtgaat   2880
ttttagcacc ctcaacagtt gagtgctggc actctcgggg gtagagtgcc aaataggttg   2940
tttgacacac agttgttcac ccgcgacgac ggctgtgctg gaaacccaca accggcacac   3000
acaaaatttt tctcatggag ggattcatca tgtcgacttc agttacttca ccagcccaca   3060
acaacgcaca ttcctccgaa tttttggatg cgttggcaaa ccatgtgttg atcggcgacg   3120
gcgccatggg cacccagctc caaggctttg acctggacgt ggaaaaggat ttccttgatc   3180
tggaggggtg taatgagatt ctcaacgaca cccgccctga tgtgttgagg cagattcacc   3240
gcgcctactt tgaggcggga gctgacttgg ttgagaccaa tacttttggt tgcaacctgc   3300
cgaacttggc ggattatgac atcgctgatc gttgccgtga gcttgcctac aagggcactg   3360
cagtggctag ggaagtggct gatgagatgg ggccgggccg aaacggcatg cggcgtttcg   3420
tggttggttc cctgggacct ggaacgaagc ttccatcgct gggccatgca ccgtatgcag   3480
atttgcgtgg gcactacaag gaagcagcgc ttggcatcat cgacggtggt ggcgatgcct   3540
ttttgattga gactgctcag gacttgcttc aggtcaaggc tgcggttcac ggcgttcaag   3600
atgccatggc tgaacttgat acattcttgc ccattatttg ccacgtcacc gtagagacca   3660
ccggcaccat gctcatgggt tctgagatcg gtgccgcgtt gacagcgctg cagccactgg   3720
gtatcgacat gattggtctg aactgcgcca ccggcccaga tgagatgagc gagcacctgc   3780
gttacctgtc caagcacgcc gatattcctg tgtcggtgat gcctaacgca ggtcttcctg   3840
tcctgggtaa aaacggtgca gaatacccac ttgaggctga ggatttggcg caggcgctgg   3900
ctggattcgt ctccgaatat ggcctgtcca tggtgggtgg ttgttgtggc accacacctg   3960
agcacatccg tgcggtccgc gatgcggtgg ttggtgttcc agagcaggaa acctccacac   4020
tgaccaagat ccctgcaggc cctgttgagc aggcctcccg cgaggtggag aaagaggact   4080
ccgtcgcgtc gctgtacacc tcggtgccat tgtcccagga aaccggcatt tccatgatcg   4140
gtgagcgcac caactccaac ggttccaagg cattccgtga ggcaatgctg tctggcgatt   4200
gggaaaagtg tgtggatatt gccaagcagc aaacccgcga tggtgcacac atgctggatc   4260
tttgtgtgga ttacgtggga cgagacggca ccgccgatat ggcgaccttg gcagcacttc   4320
ttgctaccag ctccactttg ccaatcatga ttgactccac cgagccagag gttattcgca   4380
caggccttga gcacttgggt ggacgaagca tcgttaactc cgtcaacttt gaagacggcg   4440
atggccctga gtcccgctac cagcgcatca tgaaactggt aaagcagcac ggtgcggccg   4500
tggttgcgct gaccattgat gaggaaggcc aggcacgtac cgctgagcac aaggtgcgca   4560
ttgctaaacg actgattgac gatatcaccg gcagctacgg cctggatatc aaagacatcg   4620
ttgtggactg cctgaccttc ccgatctcta ctggccagga agaaaccagg cgagatggca   4680
ttgaaaccat cgaagccatc cgcgagctga agaagctcta cccagaaatc cacaccaccc   4740
tgggtctgtc caatatttcc ttcggcctga accctgctgc acgccaggtt cttaactctg   4800
tgttcctcaa tgagtgcatt gaggctggtc tggactctgc gattgcgcac agctccaaga   4860
ttttgccgat gaaccgcatt gatgatcgcc agcgcgaagt ggcgttggat atggtctatg   4920
```

-continued

```
atcgccgcac cgaggattac gatccgctgc aggaattcat gcagctgttt gagggcgttt   4980
ctgctgccga tgccaaggat gctcgcgctg aacagctggc cgctatgcct ttgtttgagc   5040
gtttggcaca gcgcatcatc gacggcgata agaatggcct tgaggatgat ctggaagcag   5100
gcatgaagga gaagtctcct attgcgatca tcaacgagga ccttctcaac ggcatgaaga   5160
ccgtgggtga gctgtttggt tccggacaga tgcagctgcc attcgtgctg caatcggcag   5220
aaaccatgaa aactgcggtg gcctatttgg aaccgttcat ggaagaggaa gcagaagcta   5280
ccggatctgc gcaggcagag ggcaagggca aaatcgtcgt ggccaccgtc aagggtgacg   5340
tgcacgatat cggcaagaac ttggtggaca tcattttgtc caacaacggt tacgacgtgg   5400
tgaacttggg catcaagcag ccactgtccg ccatgttgga agcagcggaa gaacacaaag   5460
cagacgtcat cggcatgtcg ggacttcttg tgaagtccac cgtggtgatg aaggaaaacc   5520
ttgaggagat gaacaacgcc ggcgcatcca attacccagt cattttgggt ggcgctgcgc   5580
tgacgcgtac ctacgtggaa aacgatctca acgaggtgta caccggtgag gtgtactacg   5640
cccgtgatgc tttcgagggc ctgcgcctga tggatgaggt gatggcagaa aagcgtggtg   5700
aaggacttga tcccaactca ccagaagcta ttgagcaggc gaagaagaag gcggaacgta   5760
aggctcgtaa tgagcgttcc cgcaagattg ccgcggagcg taaagctaat gcggctcccg   5820
tgattgttcc ggagcgttct gatgtctcca ccgatactcc aaccgcggca ccaccgttct   5880
ggggaacccg cattgtcaag ggtctgccct tggcggagtt cttgggcaac cttgatgagc   5940
gcgccttgtt catggggcag tggggtctga aatccacccg cggcaacgag ggtccaagct   6000
atgaggattt ggtggaaact gaaggccgac cacgcctgcg ctactggctg gatcgcctga   6060
agtctgaggg cattttggac cacgtggcct tggtgtatgg ctacttccca gcggtcgcgg   6120
aaggcgatga cgtggtgatc ttggaatccc cggatccaca cgcagccgaa cgcatgcgct   6180
ttagcttccc acgccagcag cgcggcaggt tcttgtgcat cgcggatttc attcgcccac   6240
gcgagcaagc tgtcaaggac ggccaagtgg acgtcatgcc attccagctg gtcaccatgg   6300
gtaatcctat tgctgatttc gccaacgagt tgttcgcagc caatgaatac cgcgagtact   6360
tggaagttca cggcatcggc gtgcagctca ccgaagcatt ggccgagtac tggcactccc   6420
gagtgcgcag cgaactcaag ctgaacgacg gtggatctgt cgctgatttt gatccagaag   6480
acaagaccaa gttcttcgac ctggattacc gcggcgcccg cttctccttt ggttacggtt   6540
cttgccctga tctggaagac cgcgcaaagc tggtggaatt gctcgagcca ggccgtatcg   6600
gcgtggagtt gtccgaggaa ctccagctgc acccagagca gtccacagac gcgtttgtgc   6660
tctaccaccc agaggcaaag tactttaacg tctaatctag agttctgtga aaaacaccgt   6720
ggggcagttt ctgcttcgcg gtgtttttta tttgtggggc actagacccg ataggtcgca   6780
gcggtgatct gttgatcgtg ccgcgatctc ggcacagcct cgaagcaatc gaggactccg   6840
ctgttttgat caccattgcc aaactgacgc aataagaaag atagggactt cccctggggt   6900
gtttgagccc gccgagggtc cgtcttccgc ggcgagacca tggaccggca ccgttcgatc   6960
accggcctcc tgcccctgat gtttgtacca gcatgcgacg gtgaccagct gaccggttcc   7020
actatcctta ccgctactgg tggcggggat aatcgaaaat atgtgcccct tggtgaaggg   7080
tcggggagct aataggatga cagtgaacct attttccacg tctttatccg tagtattgga   7140
gatccgatga cctacacaat cgcccagccc tgcgttgatg tcctggatcg agcctgcgtc   7200
gaggaatgtc ccgtggactg catctacgag ggcaaacgga tgctctacat ccaccccgat   7260
gagtgcgtcg actgcggtgc ctgcgagccc gtctgcccgg ttgaagccat cttctacgaa   7320
```

-continued

```
gatgatgttc cccacgaatg gtgggactac accggcgcta acgccgcctt tttcgacgac   7380
ctcggttcgc caggcggtgc cgccagcctg ggtccgcagg acttcgacgc ccagctcgtc   7440
gcggtgctgc cgccacagaa ccagaactag gacctgatat cggccctaaa caaggagaac   7500
ctgactgcga tgtttcatgt ccctcgtacc aatagttgtt cctggcctgt cattgtgatg   7560
gtcgaaggtc gacctgcaga agatcattga ccaaatcacc accaagagtg cgaggatcca   7620
ctgggattta aatcgctagc gggctgctaa aggaagcgga acacgtagaa agccagtccg   7680
cagaaacggt gctgaccccg gatgaatgtc agctactggg ctatctggac aagggaaaac   7740
gcaagcgcaa agagaaagca ggtagcttgc agtgggctta catggcgata gctagactgg   7800
gcggttttat ggacagcaag cgaaccggaa ttgccagctg gggcgccctc tggtaaggtt   7860
gggaagccct gcaaagtaaa ctggatggct ttcttgccgc caaggatctg atggcgcagg   7920
ggatcaagat ctgatcaaga gacaggatga ggatcgtttc gcatgattga acaagatgga   7980
ttgcacgcag gttctccggc cgcttgggtg gagaggctat tcggctatga ctgggcacaa   8040
cagacaatcg gctgctctga tgccgccgtg ttccggctgt cagcgcaggg gcgcccggtt   8100
ctttttgtca agaccgacct gtccggtgcc ctgaatgaac tgcaggacga ggcagcgcgg   8160
ctatcgtggc tggccacgac gggcgttcct tgcgcagctg tgctcgacgt tgtcactgaa   8220
gcgggaaggg actggctgct attgggcgaa gtgccggggc aggatctcct gtcatctcac   8280
cttgctcctg ccgagaaagt atccatcatg gctgatgcaa tgcggcggct gcatacgctt   8340
gatccggcta cctgcccatt cgaccaccaa gcgaaacatc gcatcgagcg agcacgtact   8400
cggatggaag ccggtcttgt cgatcaggat gatctggacg aagagcatca ggggctcgcg   8460
ccagccgaac tgttcgccag gctcaaggcg cgcatgcccg acggcgagga tctcgtcgtg   8520
acccatggcg atgcctgctt gccgaatatc atggtggaaa atggccgctt ttctggattc   8580
atcgactgtg gccggctggg tgtggcggac cgctatcagg acatagcgtt ggctacccgt   8640
gatattgctg aagagcttgg cggcgaatgg gctgaccgct tcctcgtgct ttacggtatc   8700
gccgctcccg attcgcagcg catcgccttc tatcgccttc ttgacgagtt cttctgagcg   8760
ggactctggg gttcgaaatg accgaccaag cgacgcccaa cctgccatca cgagatttcg   8820
attccaccgc cgccttctat gaaaggttgg gcttcggaat cgttttccgg gacgccggct   8880
ggatgatcct ccagcgcggg gatctcatgc tggagttctt cgcccacgct agcggcgcgc   8940
cggccggccc ggtgtgaaat accgcacaga tgcgtaagga gaaaataccg catcaggcgc   9000
tcttccgctt cctcgctcac tgactcgctg cgctcggtcg ttcggctgcg gcgagcggta   9060
tcagctcact caaaggcggt aatacggtta tccacagaat caggggataa cgcaggaaag   9120
aacatgtgag caaaaggcca gcaaaaggcc aggaaccgta aaaaggccgc gttgctggcg   9180
tttttccata ggctccgccc ccctgacgag catcacaaaa atcgacgctc aagtcagagg   9240
tggcgaaacc cgacaggact ataaagatac caggcgtttc cccctggaag ctccctcgtg   9300
cgctctcctg ttccgaccct gccgcttacc ggatacctgt ccgcctttct cccttcggga   9360
agcgtggcgc tttctcatag ctcacgctgt aggtatctca gttcggtgta ggtcgttcgc   9420
tccaagctgg gctgtgtgca cgaacccccc gttcagcccg accgctgcgc cttatccggt   9480
aactatcgtc ttgagtccaa cccggtaaga cacgacttat cgccactggc agcagccact   9540
ggtaacagga ttagcagagc gaggtatgta ggcggtgcta cagagttctt gaagtggtgg   9600
cctaactacg gctacactag aaggacagta tttggtatct gcgctctgct gaagccagtt   9660
accttcggaa aaagagttgg tagctcttga tccggcaaac aaaccaccgc tggtagcggt   9720
```

-continued

```
ggttttttg tttgcaagca gcagattacg cgcagaaaaa aaggatctca agaagatcct   9780
ttgatctttt ctacggggtc tgacgctcag tggaacgaaa actcacgtta agggattttg   9840
gtcatgagat tatcaaaaag gatcttcacc tagatccttt taaaggccgg ccgcggccgc   9900
gcaaagtccc gcttcgtgaa aattttcgtg ccgcgtgatt ttccgccaaa aactttaacg   9960
aacgttcgtt ataatggtgt catgaccttc acgacgaagt actaaaattg gcccgaatca  10020
tcagctatgg atctctctga tgtcgcgctg gagtccgacg cgctcgatgc tgccgtcgat  10080
ttaaaaacgg tgatcggatt tttccgagct ctcgatacga cggacgcgcc agcatcacga  10140
gactgggcca gtgccgcgag cgacctagaa actctcgtgg cggatcttga ggagctggct  10200
gacgagctgc gtgctcggcc agcgccagga ggacgcacag tagtggagga tgcaatcagt  10260
tgcgcctact gcggtggcct gattcctccc cggcctgacc cgcgaggacg gcgcgcaaaa  10320
tattgctcag atgcgtgtcg tgccgcagcc agccgcgagc gcgccaacaa acgccacgcc  10380
gaggagctgg aggcggctag gtcgcaaatg gcgctggaag tgcgtccccc gagcgaaatt  10440
ttggccatgg tcgtcacaga gctggaagcg gcagcgagaa ttatcgcgat cgtggcggtg  10500
cccgcaggca tgacaaacat cgtaaatgcc gcgtttcgtg tgccgtggcc gcccaggacg  10560
tgtcagcgcc gccaccacct gcaccgaatc ggcagcagcg tcgcgcgtcg aaaaagcgca  10620
caggcggcaa gaagcgataa gctgcacgaa tacctgaaaa atgttgaacg ccccgtgagc  10680
ggtaactcac agggcgtcgg ctaaccccca gtccaaacct gggagaaagc gctcaaaaat  10740
gactctagcg gattcacgag acattgacac accggcctgg aaattttccg ctgatctgtt  10800
cgacacccat cccgagctcg cgctgcgatc acgtggctgg acgagcgaag accgccgcga  10860
attcctcgct cacctgggca gagaaaattt ccagggcagc aagacccgcg acttcgccag  10920
cgcttggatc aaagacccgg acacggagaa acacagccga agttataccg agttggttca  10980
aaatcgcttg cccggtgcca gtatgttgct ctgacgcacg cgcagcacgc agccgtgctt  11040
gtcctggaca ttgatgtgcc gagccaccag gccggcggga aaatcgagca cgtaaacccc  11100
gaggtctacg cgattttgga gcgctgggca cgcctggaaa aagcgccagc ttggatcggc  11160
gtgaatccac tgagcgggaa atgccagctc atctggctca ttgatccggt gtatgccgca  11220
gcaggcatga gcagcccgaa tatgcgcctg ctggctgcaa cgaccgagga aatgacccgc  11280
gttttcggcg ctgaccaggc tttttcacat aggctgagcc gtggccactg cactctccga  11340
cgatcccagc cgtaccgctg gcatgcccag cacaatcgcg tggatcgcct agctgatctt  11400
atggaggttg ctcgcatgat ctcaggcaca gaaaaaccta aaaaacgcta tgagcaggag  11460
ttttctagcg gacgggcacg tatcgaagcg gcaagaaaag ccactgcgga agcaaaagca  11520
cttgccacgc ttgaagcaag cctgccgagc gccgctgaag cgtctggaga gctgatcgac  11580
ggcgtccgtg tcctctggac tgctccaggg cgtgccgccc gtgatgagac ggcttttcgc  11640
cacgctttga ctgtgggata ccagttaaaa gcggctggtg agcgcctaaa agacaccaag  11700
ggtcatcgag cctacgagcg tgcctacacc gtcgctcagg cggtcggagg aggccgtgag  11760
cctgatctgc cgccggactg tgaccgccag acggattggc cgcgacgtgt gcgcggctac  11820
gtcgctaaag gccagccagt cgtccctgct cgtcagacag agacgcagag ccagccgagg  11880
cgaaaagctc tggccactat gggaagacgt ggcggtaaaa aggccgcaga acgctggaaa  11940
gacccaaaca gtgagtacgc ccgagcacag cgagaaaaac tagctaagtc cagtcaacga  12000
caagctagga aagctaaagg aaatcgcttg accattgcag gttggtttat gactgttgag  12060
ggagagactg gctcgtggcc gacaatcaat gaagctatgt ctgaatttag cgtgtcacgt  12120
```

```
cagaccgtga atagagcact taaggtctgc gggcattgaa cttccacgag gacgccgaaa  12180

gcttcccagt aaatgtgcca tctcgtaggc agaaaacggt tcccccgtag ggtctctctc  12240

ttggcctcct ttctaggtcg ggctgattgc tcttgaagct ctctaggggg gctcacacca  12300

taggcagata acgttcccca ccggctcgcc tcgtaagcgc acaaggactg ctcccaaaga  12360

tcttcaaagc cactgccgcg actgccttcg cgaagccttg ccccgcggaa atttcctcca  12420

ccgagttcgt gcacacccct atgccaagct tctttcaccc taaattcgag agattggatt  12480

cttaccgtgg aaattcttcg caaaaatcgt cccctgatcg cccttgcgac gttggcgtcg  12540

gtgccgctgg ttgcgcttgg cttgaccgac ttgatcagcg gccgctcgat ttaaatctcg  12600

agaggcctga cgtcgggccc g                                            12621
```

<210> SEQ ID NO 52
<211> LENGTH: 48
<212> TYPE: DNA
<213> ORGANISM: artificial
<220> FEATURE:
<223> OTHER INFORMATION: Primer: RY843

<400> SEQUENCE: 52

```
ttattctaga aggaggagaa aacatgacct acacaatcgc ccagccct                  48
```

<210> SEQ ID NO 53
<211> LENGTH: 39
<212> TYPE: DNA
<213> ORGANISM: artificial
<220> FEATURE:
<223> OTHER INFORMATION: Primer: RY847

<400> SEQUENCE: 53

```
ccatcactat gaggatccag gaacaactat tggtacgag                            39
```

<210> SEQ ID NO 54
<211> LENGTH: 9503
<212> TYPE: DNA
<213> ORGANISM: artificial
<220> FEATURE:
<223> OTHER INFORMATION: Plasmid: pOM355

<400> SEQUENCE: 54

```
ggatcggcgg ccagggccct catgagatat cgagtcagcg ctgtattgcc cgtgaagttg     60

atggtgtttc cgctgccctg ctgggtggga ttggaggtgt aatcaatgaa ccaaccagga    120

gttccggtgc cagtgagatc aaataccacg cggtcaaagc cactgtgaga gccaatccga    180

acatcggtga ccatgagctg tgcaggcgca tcaggtcgga gagtcttcat tgctacatcg    240

gcttcgccca atgcggttgg gccggtggaa gcttcgttgg acaactgtgc gccatccgca    300

gttgcggaca tagtttgggt tacagaagaa gcatcgttgg tggtggaatt ggaggttcca    360

caacccgcaa gagtcaacgc gctagcgccg acaatcgcta gagtcttcag gcgggcacga    420

tgctttgaat gagaagttgg ctgcacaatc atgcacacac cgtaaccctg ggtcaccccc    480

gaaacctaag caagacgccc aatttcgctc aatcgtgaac gaattgttgt aattcgtctt    540

aaaaacgcca ggagacgtga aaattacaga caccccagac atcagatgga ggcggcgata    600

ctagggtaga ggacatgact cttcgctgtt ctgacgtcaa tgttgaaccc ctgccgggaa    660

cggcaaaaac aggttctggg tttgttctcc ttgaacatgc tggctcgtgg agccgtgatg    720

ttttagacgg cggaacattt gatcctgagt tgactgatca attgaagagg cacctgaaag    780

cttccggaat gggtctgcaa ttaattagga agccgggaag ggagggtcga aacgtcgaaa    840
```

-continued

```
agcataatct ttttctcgtt tttgctgagg cctcaattat tgagcacctg gtggtggacg    900
cgccggctga tgttttggat cttgatttaa gcgggccggg caaaaacaat gcgcagcgca    960
tggatgatcc gatgctgctg atttgtacgc attcgaagcg cgatgtgtgc tgcgcgatca   1020
aggggcgtcc gctggcagct gccgtggagc cacaatttgg gccgctgcat gtgtgggagg   1080
cttcgcacac caagggccac cgttttgcgc catcgatgct gctcatgccg tggaattact   1140
cttatggcct acttgatgag gccgaaaccg tgcagctttt ccaaggcgcg ttggacaaca   1200
aactcttcct gccgggcaac cgtggccgag gaaccttaga tgctcgtggc caggttgcag   1260
aaattgccgt ggcggaagct ttcggcgagg cggttgctcc tgcgagtttg caggttgaat   1320
tcgaagatga ttctgttttg gttactcatc ccgatgggcg cacgtgggtt gtggagcttg   1380
aacgcatcga ggtcgacggc gtggtgtcct cgtgtggtga tcagccgaaa actggaaaag   1440
cgtgggtggc taggcaagtt acagaactga tcggataaaa gcagagttat atctgatgaa   1500
ttgctattag cagtatcgtt atcacagcac caacaaagta gttcagccac aggaaaactt   1560
tccaactgcg attagcctgt tcacaactgg catctgtaat gttccaaaat cgtgcggcat   1620
taaatacgta agttagaatc gcaatcccga tgatccacgc cggattaggc aaagtagtga   1680
ctaacacagc agctagtaaa taaagtacta ctgaaagccg aatggctcca cgcgccccaa   1740
ttacagtggc aattgagctg cggccgcaca gcgatcccag aggaaatatc ctctggggtc   1800
gctgtgtcga ccttaaagtt tggctgccat gtgaattttt agcaccctca acagttgagt   1860
gctggcactc tcgggggtag agtgccaaat aggttgtttg acacacagtt gttcacccgc   1920
gacgacggct gtgctggaaa cccacaaccg gcacacacaa aatttttcta gaaggaggag   1980
aaaacatgac ctacacaatc gcccagccct gcgttgatgt cctggatcga gcctgcgtcg   2040
aggaatgtcc cgtggactgc atctacgagg gcaaacggat gctctacatc caccccgatg   2100
agtgcgtcga ctgcggtgcc tgcgagcccg tctgcccggt tgaagccatc ttctacgaag   2160
atgatgttcc ccacgaatgg tgggactaca ccggcgctaa cgccgccttt ttcgacgacc   2220
tcggttcgcc aggcggtgcc gccagcctgg gtccgcagga cttcgacgcc cagctcgtcg   2280
cggtgctgcc gccacagaac cagaactagg acctgatatc ggccctaaac aaggagaacc   2340
tgactgcgat gtttcatgtc cctcgtacca atagttgttc ctggatccca gtgctatcca   2400
catcgctgct gaaggagatg ttccagtgat cgttgcaccg attaatgcag gtgaagtgaa   2460
gtgagtagaa gatgttagag catcgataaa ggggcgttct ttaaaacgca atttcggtgc   2520
tgaataagca atcactgcta gcactgagag tgtcagccat aaagacgaca tccaggtgcc   2580
aaatatgaaa agaataacta ggaaaggaat tgttgagata gccgaggccc ataacagtgt   2640
gctgtgggaa cttttcggta gcacggcccc ctcgacgccg cctttgcggg gattacgcat   2700
atcagattcg taatcaaaaa catcgttgat accatacatg gcgatgttat acgggataag   2760
aaaaaatacg atgcctagcc aaaacagcca gtcaatctct cctgcattta ataggtaggc   2820
cagaccaaag ggtaggcgg tattgatcca gctaatgggg cgagatgaca atagaattag   2880
tcttattttt tccatcatga ctacggcttt tctggctcag attgcgtggt ggtggatcta   2940
gtagtgatgc ttccattggc gatggtgggt aaggaatggt gtggacgttt tttcctgcgt   3000
ttaaacatat ttccaggcaa ccatagggca ggaatcagaa gtactgcgaa gagcggatag   3060
aaaagatcct ctagggggat taaaccgagc caaatgccaa ggtgctgggt atcgccatat   3120
ccaaagagat cagcccaaac catgaggtta tcaaatatga tagttaggga acatagggta   3180
agggcactga cagcggtgat tggtaaaagt ttaggtgttc cagactgcag ctttaagaca   3240
```

-continued

```
aataggacca tggctattgc taaaaaagga atgcttataa aaatataagt catggttcaa   3300
cctcgggagt ggtagttggt tggaaagtat cgcgctgtgg tgtgagggga gactttttac   3360
cgggtttttt aggcagtggt gctttaagcc ataatgctgc tgccgaggta aggttgaggg   3420
tgatgtagca gaggaagaat aagaaaaaaa gttcttcaat gggcatatgg ggtgcaaggt   3480
taataccgga cataaacgct gagtctccgc gataaaaagt gccagtaata atgccaaata   3540
tatcccataa aagaaatcca atatatgcag cacctaccga aagaattgct cgtaacggat   3600
ggcggaagaa cgctagcttc caacggtggt cgcacaaagc catgcaccca atgagaacta   3660
ggagagtacc tagataaata aaggccataa aaatatcgct atcttgctca ttttgtgaaa   3720
tatcgatgat agggatcaaa atttaatgat cgtatgaggt cttttgagat ggtgtcgttt   3780
taggcggcaa tggttcggct cacgcgtccc gggatttaaa tcgctagcgg gctgctaaag   3840
gaagcggaac acgtagaaag ccagtccgca gaaacggtgc tgaccccgga tgaatgtcag   3900
ctactgggct atctggacaa gggaaaacgc aagcgcaaag agaaagcagg tagcttgcag   3960
tgggcttaca tggcgatagc tagactgggc ggttttatgg acagcaagcg aaccggaatt   4020
gccagctggg gcgccctctg gtaaggttgg gaagccctgc aaagtaaact ggatggcttt   4080
cttgccgcca aggatctgat ggcgcagggg atcaagatct gatcaagaga caggatgagg   4140
atcgtttcgc atgattgaac aagatggatt gcacgcaggt tctccggccg cttgggtgga   4200
gaggctattc ggctatgact gggcacaaca gacaatcggc tgctctgatg ccgccgtgtt   4260
ccggctgtca gcgcaggggc gcccggttct ttttgtcaag accgacctgt ccggtgccct   4320
gaatgaactg caggacgagg cagcgcggct atcgtggctg gccacgacgg gcgttccttg   4380
cgcagctgtg ctcgacgttg tcactgaagc gggaagggac tggctgctat tgggcgaagt   4440
gccggggcag gatctcctgt catctcacct tgctcctgcc gagaaagtat ccatcatggc   4500
tgatgcaatg cggcggctgc atacgcttga tccggctacc tgcccattcg accaccaagc   4560
gaaacatcgc atcgagcgag cacgtactcg gatggaagcc ggtcttgtcg atcaggatga   4620
tctggacgaa gagcatcagg ggctcgcgcc agccgaactg ttcgccaggc tcaaggcgcg   4680
catgcccgac ggcgaggatc tcgtcgtgac ccatggcgat gcctgcttgc cgaatatcat   4740
ggtggaaaat ggccgctttt ctggattcat cgactgtggc cggctgggtg tggcggaccg   4800
ctatcaggac atagcgttgg ctacccgtga tattgctgaa gagcttggcg gcgaatgggc   4860
tgaccgcttc ctcgtgcttt acggtatcgc cgctcccgat tcgcagcgca tcgccttcta   4920
tcgccttctt gacgagttct tctgagcggg actctggggt tcgaaatgac cgaccaagcg   4980
acgcccaacc tgccatcacg agatttcgat tccaccgccg ccttctatga aaggttgggc   5040
ttcggaatcg ttttccggga cgccggctgg atgatcctcc agcgcgggga tctcatgctg   5100
gagttcttcg cccacgctag tttaaactgc ggatcagtga gggtttgtaa ctgcgggtca   5160
aggatctgga tttcgatcac ggcacgatca tcgtgcggga gggcaagggc tccaaggatc   5220
gggccttgat gttacccgag agcttggcac ccagcctgcg cgagcagggg aattgatccg   5280
gtggatgacc ttttgaatga cctttaatag attatattac taattaattg gggaccctag   5340
aggtcccctt ttttatttta aaaatttttt cacaaaacgg tttacaagca taacgggttt   5400
tgctgcccgc aaacgggctg ttctggtgtt gctagtttgt tatcagaatc gcagatccgg   5460
cttcaggttt gccggctgaa agcgctattt cttccagaat tgccatgatt ttttccccac   5520
gggaggcgtc actggctccc gtgttgtcgg cagctttgat tcgataagca gcatcgcctg   5580
tttcaggctg tctatgtgtg actgttgagc tgtaacaagt tgtctcaggt gttcaatttc   5640
```

-continued

```
atgttctagt tgctttgttt tactggtttc acctgttcta ttaggtgtta catgctgttc   5700
atctgttaca ttgtcgatct gttcatggtg aacagcttta aatgcaccaa aaactcgtaa   5760
aagctctgat gtatctatct tttttacacc gttttcatct gtgcatatgg acagttttcc   5820
ctttgatatc taacggtgaa cagttgttct acttttgttt gttagtcttg atgcttcact   5880
gatagataca agagccataa gaacctcaga tccttccgta tttagccagt atgttctcta   5940
gtgtggttcg ttgtttttgc gtgagccatg agaacgaacc attgagatca tgcttacttt   6000
gcatgtcact caaaaatttt gcctcaaaac tggtgagctg aatttttgca gttaaagcat   6060
cgtgtagtgt ttttcttagt ccgttacgta ggtaggaatc tgatgtaatg gttgttggta   6120
ttttgtcacc attcattttt atctggttgt tctcaagttc ggttacgaga tccatttgtc   6180
tatctagttc aacttggaaa atcaacgtat cagtcgggcg gcctcgctta tcaaccacca   6240
atttcatatt gctgtaagtg tttaaatctt tacttattgg tttcaaaacc cattggttaa   6300
gccttttaaa ctcatggtag ttattttcaa gcattaacat gaacttaaat tcatcaaggc   6360
taatctctat atttgccttg tgagttttct tttgtgttag ttcttttaat aaccactcat   6420
aaatcctcat agagtatttg ttttcaaaag acttaacatg ttccagatta tattttatga   6480
attttttaa ctggaaaaga taaggcaata tctcttcact aaaaactaat tctaattttt   6540
cgcttgagaa cttggcatag tttgtccact ggaaaatctc aaagccttta accaaaggat   6600
tcctgatttc cacagttctc gtcatcagct ctctggttgc tttagctaat acaccataag   6660
cattttccct actgatgttc atcatctgag cgtattggtt ataagtgaac gataccgtcc   6720
gttctttcct tgtagggttt tcaatcgtgg ggttgagtag tgccacacag cataaaatta   6780
gcttggtttc atgctccgtt aagtcatagc gactaatcgc tagttcattt gctttgaaaa   6840
caactaattc agacatacat ctcaattggt ctaggtgatt ttaatcacta taccaattga   6900
gatgggctag tcaatgataa ttactagtcc ttttcctttg agttgtgggt atctgtaaat   6960
tctgctagac ctttgctgga aaacttgtaa attctgctag accctctgta aattccgcta   7020
gacctttgtg tgttttttt gtttatattc aagtggttat aatttataga ataaagaaag   7080
aataaaaaaa gataaaaaga atagatccca gccctgtgta taactcacta ctttagtcag   7140
ttccgcagta ttacaaaagg atgtcgcaaa cgctgtttgc tcctctacaa aacagacctt   7200
aaaaccctaa aggcttaagt agcaccctcg caagctcggg caaatcgctg aatattcctt   7260
ttgtctccga ccatcaggca cctgagtcgc tgtctttttc gtgacattca gttcgctgcg   7320
ctcacggctc tggcagtgaa tgggggtaaa tggcactaca ggcgcctttt atggattcat   7380
gcaaggaaac tacccataat acaagaaaag cccgtcacgg gcttctcagg gcgttttatg   7440
gcgggtctgc tatgtggtgc tatctgactt tttgctgttc agcagttcct gccctctgat   7500
tttccagtct gaccacttcg gattatcccg tgacaggtca ttcagactgg ctaatgcacc   7560
cagtaaggca gcggtatcat caacaggctt agtttaaacc catcggcatt ttcttttgcg   7620
tttttatttg ttaactgtta attgtccttg ttcaaggatg ctgtctttga caacagatgt   7680
tttcttgcct ttgatgttca gcaggaagct cggcgcaaac gttgattgtt tgtctgcgta   7740
gaatcctctg tttgtcatat agcttgtaat cacgacattg tttcctttcg cttgaggtac   7800
agcgaagtgt gagtaagtaa aggttacatc gttaggatca agatccattt ttaacacaag   7860
gccagttttg ttcagcggct tgtatgggcc agttaaagaa ttagaaacat aaccaagcat   7920
gtaaatatcg ttagacgtaa tgccgtcaat cgtcattttt gatccgcggg agtcagtgaa   7980
caggtaccat ttgccgttca ttttaaagac gttcgcgcgt tcaatttcat ctgttactgt   8040
```

-continued

```
gttagatgca atcagcggtt tcatcacttt tttcagtgtg taatcatcgt ttagctcaat   8100

cataccgaga gcgccgtttg ctaactcagc cgtgcgtttt ttatcgcttt gcagaagttt   8160

ttgactttct tgacggaaga atgatgtgct tttgccatag tatgctttgt taaataaaga   8220

ttcttcgcct tggtagccat cttcagttcc agtgtttgct tcaaatacta agtatttgtg   8280

gcctttatct tctacgtagt gaggatctct cagcgtatgg ttgtcgcctg agctgtagtt   8340

gccttcatcg atgaactgct gtacattttg atacgttttt ccgtcaccgt caaagattga   8400

tttataatcc tctacaccgt tgatgttcaa agagctgtct gatgctgata cgttaacttg   8460

tgcagttgtc agtgtttgtt tgccgtaatg tttaccggag aaatcagtgt agaataaacg   8520

gatttttccg tcagatgtaa atgtggctga acctgaccat tcttgtgttt ggtcttttag   8580

gatagaatca tttgcatcga atttgtcgct gtctttaaag acgcggccag cgtttttcca   8640

gctgtcaata gaagtttcgc cgactttttg atagaacatg taaatcgatg tgtcatccgc   8700

atttttagga tctccggcta atgcaaagac gatgtggtag ccgtgatagt ttgcgacagt   8760

gccgtcagcg ttttgtaatg gccagctgtc ccaaacgtcc aggccttttg cagaagagat   8820

atttttaatt gtggacgaat caaattcaga aacttgatat ttttcatttt tttgctgttc   8880

agggatttgc agcatatcat ggcgtgtaat atgggaaatg ccgtatgttt ccttatatgg   8940

cttttggttc gtttctttcg caaacgcttg agttgcgcct cctgccagca gtgcggtagt   9000

aaaggttaat actgttgctt gttttgcaaa ctttttgatg ttcatcgttc atgtctcctt   9060

ttttatgtac tgtgttagcg gtctgcttct tccagccctc ctgtttgaag atggcaagtt   9120

agttacgcac aataaaaaaa gacctaaaat atgtaagggg tgacgccaaa gtatacactt   9180

tgccctttac acattttagg tcttgcctgc tttatcagta acaaacccgc gcgatttact   9240

tttcgacctc attctattag actctcgttt ggattgcaac tggtctattt tcctcttttg   9300

tttgatagaa aatcataaaa ggatttgcag actacgggcc taaagaacta aaaaatctat   9360

ctgtttcttt tcattctctg tatttttat agtttctgtt gcatgggcat aaagttgcct   9420

ttttaatcac aattcagaaa atatcataat atctcatttc actaaataat agtgaacggc   9480

aggtatatgt gatgggttaa aaa                                           9503
```

<210> SEQ ID NO 55
<211> LENGTH: 9651
<212> TYPE: DNA
<213> ORGANISM: artificial
<220> FEATURE:
<223> OTHER INFORMATION: Plasmid: pOM356

<400> SEQUENCE: 55

```
ggatcggcgg ccagggccct catgagatat cgagtcagcg ctgtattgcc cgtgaagttg     60

atggtgtttc cgctgccctg ctgggtggga ttggaggtgt aatcaatgaa ccaaccagga    120

gttccggtgc cagtgagatc aaataccacg cggtcaaagc cactgtgaga gccaatccga    180

acatcggtga ccatgagctg tgcaggcgca tcaggtcgga gagtcttcat tgctacatcg    240

gcttcgccca atgcggttgg gccggtggaa gcttcgttgg acaactgtgc gccatccgca    300

gttgcggaca tagtttgggt tacagaagaa gcatcgttgg tggtggaatt ggaggttcca    360

caacccgcaa gagtcaacgc gctagcgccg acaatcgcta gagtcttcag gcgggcacga    420

tgctttgaat gagaagttgg ctgcacaatc atgcacacac cgtaaccctg ggtcaccccc    480

gaaacctaag caagacgccc aatttcgctc aatcgtgaac gaattgttgt aattcgtctt    540

aaaaacgcca ggagacgtga aaattacaga caccccagac atcagatgga ggcggcgata    600
```

-continued

```
ctagggtaga ggacatgact cttcgctgtt ctgacgtcaa tgttgaaccc ctgccgggaa    660
cggcaaaaac aggttctggg tttgttctcc ttgaacatgc tggctcgtgg agccgtgatg    720
ttttagacgg cggaacattt gatcctgagt tgactgatca attgaagagg cacctgaaag    780
cttccggaat gggtctgcaa ttaattagga agccgggaag ggagggtcga aacgtcgaaa    840
agcataatct ttttctcgtt tttgctgagg cctcaattat tgagcacctg gtggtggacg    900
cgccggctga tgttttggat cttgatttaa gcgggccggg caaaaacaat gcgcagcgca    960
tggatgatcc gatgctgctg atttgtacgc attcgaagcg cgatgtgtgc tgcgcgatca   1020
aggggcgtcc gctggcagct gccgtggagc cacaatttgg gccgctgcat gtgtgggagg   1080
cttcgcacac caagggccac cgttttgcgc catcgatgct gctcatgccg tggaattact   1140
cttatggcct acttgatgag gccgaaaccg tgcagctttt ccaaggcgcg ttggacaaca   1200
aactcttcct gccgggcaac cgtggccgag gaaccttaga tgctcgtggc caggttgcag   1260
aaattgccgt ggcggaagct ttcggcgagg cggttgctcc tgcgagtttg caggttgaat   1320
tcgaagatga ttctgttttg gttactcatc ccgatgggcg cacgtgggtt gtggagcttg   1380
aacgcatcga ggtcgacggc gtggtgtcct cgtgtggtga tcagccgaaa actggaaaag   1440
cgtgggtggc taggcaagtt acagaactga tcggataaaa gcagagttat atctgatgaa   1500
ttgctattag cagtatcgtt atcacagcac caacaaagta gttcagccac aggaaaactt   1560
tccaactgcg attagcctgt tcacaactgg catctgtaat gttccaaaat cgtgcggcat   1620
taaatacgta agttagaatc gcaatcccga tgatccacgc cggattaggc aaagtagtga   1680
ctaacacagc agctagtaaa taaagtacta ctgaaagccg aatggctcca cgcgccccaa   1740
ttacagtggc aattgagctg cggccgcttc gcgaagcttg tcgaccgaaa cagcagttat   1800
aaggcatgaa gctgtccggt ttttgcaaaa gtggctgtga ctgtaaaaag aaatcgaaaa   1860
agaccgtttt gtgtgaaaac ggtctttttg tttcctttta accaactgcc ataactcgag   1920
gctattgacg acagctatgg ttcactgtcc accaaccaaa actgtgctca gtaccgccaa   1980
tatttctccc ttgaggggta caaagaggtg tccctagaag agatccacgc tgtgtaaaaa   2040
ttttacaaaa aggtattgac tttccctaca gggtgtgtaa taatttaatt acaggcgggg   2100
gcaaccccgc ctgttctaga aggaggagaa aacatgacct acacaatcgc ccagccctgc   2160
gttgatgtcc tggatcgagc ctgcgtcgag gaatgtcccg tggactgcat ctacgagggc   2220
aaacggatgc tctacatcca ccccgatgag tgcgtcgact gcggtgcctg cgagcccgtc   2280
tgcccggttg aagccatctt ctacgaagat gatgttcccc acgaatggtg ggactacacc   2340
ggcgctaacg ccgccttttt cgacgacctc ggttcgccag gcggtgccgc cagcctgggt   2400
ccgcaggact tcgacgccca gctcgtcgcg gtgctgccgc cacagaacca gaactaggac   2460
ctgatatcgg ccctaaacaa ggagaacctg actgcgatgt ttcatgtccc tcgtaccaat   2520
agttgttcct ggatcccagt gctatccaca tcgctgctga aggagatgtt ccagtgatcg   2580
ttgcaccgat taatgcaggt gaagtgaagt gagtagaaga tgttagagca tcgataaagg   2640
ggcgttcttt aaaacgcaat ttcggtgctg aataagcaat cactgctagc actgagagtg   2700
tcagccataa agacgacatc caggtgccaa atatgaaaag aataactagg aaaggaattg   2760
ttgagatagc cgaggcccat aacagtgtgc tgtgggaact tttcggtagc acggcccccct  2820
cgacgccgcc tttgcgggga ttacgcatat cagattcgta atcaaaaaca tcgttgatac   2880
catacatggc gatgttatac gggataagaa aaaatacgat gcctagccaa aacagccagt   2940
caatctctcc tgcatttaat aggtaggcca gaccaaaggg gtaggcggta ttgatccagc   3000
```

-continued

```
taatggggcg agatgacaat agaattagtc ttattttttc catcatgact acggcttttc   3060
tggctcagat tgcgtggtgg tggatctagt agtgatgctt ccattggcga tggtgggtaa   3120
ggaatggtgt ggacgttttt tcctgcgttt aaacatattt ccaggcaacc atagggcagg   3180
aatcagaagt actgcgaaga gcggatagaa aagatcctct agggggatta aaccgagcca   3240
aatgccaagg tgctgggtat cgccatatcc aaagagatca gcccaaacca tgaggttatc   3300
aaatatgata gttagggaac atagggtaag ggcactgaca gcggtgattg gtaaaagttt   3360
aggtgttcca gactgcagct ttaagacaaa taggaccatg gctattgcta aaaaaggaat   3420
gcttataaaa atataagtca tggttcaacc tcgggagtgg tagttggttg gaaagtatcg   3480
cgctgtggtg tgaggggaga ctttttaccg ggtttttag gcagtggtgc tttaagccat   3540
aatgctgctg ccgaggtaag gttgagggtg atgtagcaga ggaagaataa gaaaaaaagt   3600
tcttcaatgg gcatatgggg tgcaaggtta ataccggaca taaacgctga gtctccgcga   3660
taaaaagtgc cagtaataat gccaaatata tcccataaaa gaaatccaat atatgcagca   3720
cctaccgaaa gaattgctcg taacggatgg cggaagaacg ctagcttcca acggtggtcg   3780
cacaaagcca tgcacccaat gagaactagg agagtaccta gataaataaa ggccataaaa   3840
atatcgctat cttgctcatt ttgtgaaata tcgatgatag ggatcaaaat ttaatgatcg   3900
tatgaggtct tttgagatgg tgtcgtttta ggcggcaatg gttcggctca cgcgtcccgg   3960
gatttaaatc gctagcgggc tgctaaagga agcggaacac gtagaaagcc agtccgcaga   4020
aacggtgctg accccggatg aatgtcagct actgggctat ctggacaagg gaaaacgcaa   4080
gcgcaaagag aaagcaggta gcttgcagtg ggcttacatg gcgatagcta gactgggcgg   4140
ttttatggac agcaagcgaa ccggaattgc cagctggggc gccctctggt aaggttggga   4200
agccctgcaa agtaaactgg atggctttct tgccgccaag gatctgatgg cgcaggggat   4260
caagatctga tcaagagaca ggatgaggat cgtttcgcat gattgaacaa gatggattgc   4320
acgcaggttc tccggccgct tgggtggaga ggctattcgg ctatgactgg gcacaacaga   4380
caatcggctg ctctgatgcc gccgtgttcc ggctgtcagc gcaggggcgc ccggttcttt   4440
ttgtcaagac cgacctgtcc ggtgccctga atgaactgca ggacgaggca gcgcggctat   4500
cgtggctggc cacgacgggc gttccttgcg cagctgtgct cgacgttgtc actgaagcgg   4560
gaagggactg gctgctattg ggcgaagtgc cggggcagga tctcctgtca tctcaccttg   4620
ctcctgccga gaaagtatcc atcatggctg atgcaatgcg gcggctgcat acgcttgatc   4680
cggctacctg cccattcgac caccaagcga aacatcgcat cgagcgagca cgtactcgga   4740
tggaagccgg tcttgtcgat caggatgatc tggacgaaga gcatcagggg ctcgcgccag   4800
ccgaactgtt cgccaggctc aaggcgcgca tgcccgacgg cgaggatctc gtcgtgaccc   4860
atggcgatgc ctgcttgccg aatatcatgg tggaaaatgg ccgcttttct ggattcatcg   4920
actgtggccg gctgggtgtg gcggaccgct atcaggacat agcgttggct acccgtgata   4980
ttgctgaaga gcttggcggc gaatgggctg accgcttcct cgtgctttac ggtatcgccg   5040
ctcccgattc gcagcgcatc gccttctatc gccttcttga cgagttcttc tgagcgggac   5100
tctggggttc gaaatgaccg accaagcgac gcccaacctg ccatcacgag atttcgattc   5160
caccgccgcc ttctatgaaa ggttgggctt cggaatcgtt ttccgggacg ccggctggat   5220
gatcctccag cgcggggatc tcatgctgga gttcttcgcc cacgctagtt taaactgcgg   5280
atcagtgagg gtttgtaact gcgggtcaag gatctggatt tcgatcacgg cacgatcatc   5340
gtgcgggagg gcaagggctc caaggatcgg gccttgatgt tacccgagag cttggcaccc   5400
```

-continued agcctgcgcg agcaggggaa ttgatccggt ggatgacctt ttgaatgacc tttaatagat 5460
tatattacta attaattggg gaccctagag gtcccctttt ttattttaaa aatttttca 5520
caaaacggtt tacaagcata acgggttttg ctgcccgcaa acgggctgtt ctggtgttgc 5580
tagtttgtta tcagaatcgc agatccggct tcaggtttgc cggctgaaag cgctatttct 5640
tccagaattg ccatgatttt ttccccacgg gaggcgtcac tggctcccgt gttgtcggca 5700
gctttgattc gataagcagc atcgcctgtt tcaggctgtc tatgtgtgac tgttgagctg 5760
taacaagttg tctcaggtgt tcaatttcat gttctagttg ctttgtttta ctggtttcac 5820
ctgttctatt aggtgttaca tgctgttcat ctgttacatt gtcgatctgt tcatggtgaa 5880
cagctttaaa tgcaccaaaa actcgtaaaa gctctgatgt atctatcttt tttacaccgt 5940
tttcatctgt gcatatggac agttttccct ttgatatcta acggtgaaca gttgttctac 6000
ttttgtttgt tagtcttgat gcttcactga tagatacaag agccataaga acctcagatc 6060
cttccgtatt tagccagtat gttctctagt gtggttcgtt gtttttgcgt gagccatgag 6120
aacgaaccat tgagatcatg cttactttgc atgtcactca aaaattttgc ctcaaaactg 6180
gtgagctgaa tttttgcagt taaagcatcg tgtagtgttt ttcttagtcc gttacgtagg 6240
taggaatctg atgtaatggt tgttggtatt ttgtcaccat tcatttttat ctggttgttc 6300
tcaagttcgg ttacgagatc catttgtcta tctagttcaa cttggaaaat caacgtatca 6360
gtcgggcggc ctcgcttatc aaccaccaat ttcatattgc tgtaagtgtt taaatcttta 6420
cttattggtt tcaaaaccca ttggttaagc cttttaaact catggtagtt attttcaagc 6480
attaacatga acttaaattc atcaaggcta atctctatat ttgccttgtg agttttcttt 6540
tgtgttagtt cttttaataa ccactcataa atcctcatag agtatttgtt ttcaaaagac 6600
ttaacatgtt ccagattata ttttatgaat ttttttaact ggaaaagata aggcaatatc 6660
tcttcactaa aaactaattc taatttttcg cttgagaact tggcatagtt tgtccactgg 6720
aaaatctcaa agcctttaac caaaggattc ctgatttcca cagttctcgt catcagctct 6780
ctggttgctt tagctaatac accataagca ttttccctac tgatgttcat catctgagcg 6840
tattggttat aagtgaacga taccgtccgt tctttccttg tagggttttc aatcgtgggg 6900
ttgagtagtg ccacacagca taaaattagc ttggtttcat gctccgttaa gtcatagcga 6960
ctaatcgcta gttcatttgc tttgaaaaca actaattcag acatacatct caattggtct 7020
aggtgatttt aatcactata ccaattgaga tgggctagtc aatgataatt actagtcctt 7080
ttcctttgag ttgtgggtat ctgtaaattc tgctagacct ttgctggaaa acttgtaaat 7140
tctgctagac cctctgtaaa ttccgctaga cctttgtgtg ttttttttgt ttatattcaa 7200
gtggttataa tttatagaat aaagaaagaa taaaaaaaga taaaaagaat agatcccagc 7260
cctgtgtata actcactact ttagtcagtt ccgcagtatt acaaaaggat gtcgcaaacg 7320
ctgtttgctc ctctacaaaa cagaccttaa aaccctaaag gcttaagtag caccctcgca 7380
agctcgggca aatcgctgaa tattcctttt gtctccgacc atcaggcacc tgagtcgctg 7440
tctttttcgt gacattcagt tcgctgcgct cacggctctg gcagtgaatg ggggtaaatg 7500
gcactacagg cgccttttat ggattcatgc aaggaaacta cccataatac aagaaaagcc 7560
cgtcacgggc ttctcagggc gttttatggc gggtctgcta tgtggtgcta tctgactttt 7620
tgctgttcag cagttcctgc cctctgattt tccagtctga ccacttcgga ttatcccgtg 7680
acaggtcatt cagactggct aatgcaccca gtaaggcagc ggtatcatca acaggcttag 7740
tttaaaccca tcggcatttt cttttgcgtt tttatttgtt aactgttaat tgtccttgtt 7800

```
caaggatgct gtctttgaca acagatgttt tcttgccttt gatgttcagc aggaagctcg   7860

gcgcaaacgt tgattgtttg tctgcgtaga atcctctgtt tgtcatatag cttgtaatca   7920

cgacattgtt tcctttcgct tgaggtacag cgaagtgtga gtaagtaaag gttacatcgt   7980

taggatcaag atccattttt aacacaaggc cagttttgtt cagcggcttg tatgggccag   8040

ttaaagaatt agaaacataa ccaagcatgt aaatatcgtt agacgtaatg ccgtcaatcg   8100

tcatttttga tccgcgggag tcagtgaaca ggtaccattt gccgttcatt ttaaagacgt   8160

tcgcgcgttc aatttcatct gttactgtgt tagatgcaat cagcggtttc atcacttttt   8220

tcagtgtgta atcatcgttt agctcaatca taccgagagc gccgtttgct aactcagccg   8280

tgcgtttttt atcgctttgc agaagttttt gactttcttg acggaagaat gatgtgcttt   8340

tgccatagta tgctttgtta aataaagatt cttcgccttg gtagccatct tcagttccag   8400

tgtttgcttc aaatactaag tatttgtggc ctttatcttc tacgtagtga ggatctctca   8460

gcgtatggtt gtcgcctgag ctgtagttgc cttcatcgat gaactgctgt acattttgat   8520

acgtttttcc gtcaccgtca aagattgatt tataatcctc tacaccgttg atgttcaaag   8580

agctgtctga tgctgatacg ttaacttgtg cagttgtcag tgtttgtttg ccgtaatgtt   8640

taccggagaa atcagtgtag aataaacgga tttttccgtc agatgtaaat gtggctgaac   8700

ctgaccattc ttgtgtttgg tcttttagga tagaatcatt tgcatcgaat ttgtcgctgt   8760

ctttaaagac gcggccagcg tttttccagc tgtcaataga agtttcgccg actttttgat   8820

agaacatgta aatcgatgtg tcatccgcat ttttaggatc tccggctaat gcaaagacga   8880

tgtggtagcc gtgatagttt gcgacagtgc cgtcagcgtt ttgtaatggc cagctgtccc   8940

aaacgtccag gccttttgca gaagagatat ttttaattgt ggacgaatca aattcagaaa   9000

cttgatattt ttcatttttt tgctgttcag ggatttgcag catatcatgg cgtgtaatat   9060

gggaaatgcc gtatgtttcc ttatatggct tttggttcgt ttctttcgca aacgcttgag   9120

ttgcgcctcc tgccagcagt gcggtagtaa aggttaatac tgttgcttgt tttgcaaact   9180

ttttgatgtt catcgttcat gtctcctttt ttatgtactg tgttagcggt ctgcttcttc   9240

cagccctcct gtttgaagat ggcaagttag ttacgcacaa taaaaaaaga cctaaaatat   9300

gtaaggggtg acgccaaagt atacactttg ccctttacac attttaggtc ttgcctgctt   9360

tatcagtaac aaacccgcgc gatttacttt tcgacctcat tctattagac tctcgtttgg   9420

attgcaactg gtctattttc ctcttttgtt tgatagaaaa tcataaaagg atttgcagac   9480

tacgggccta aagaactaaa aaatctatct gtttcttttc attctctgta tttttttatag   9540

tttctgttgc atgggcataa agttgccttt ttaatcacaa ttcagaaaat atcataatat   9600

ctcatttcac taaataatag tgaacggcag gtatatgtga tgggttaaaa a             9651
```

<210> SEQ ID NO 56
<211> LENGTH: 5697
<212> TYPE: DNA
<213> ORGANISM: artificial
<220> FEATURE:
<223> OTHER INFORMATION: Plasmid: pH449

<400> SEQUENCE: 56

```
tcgaggcgtc ttccggtgtc atggttgaac cgaattccag cacaatattt tccggtttaa     60

agcaatcgat cacatagtcg attttgtcca accactgaaa acctgcaagg accacccaat    120

cccctgcagc atgttcagca accattggca gcggcggata gcgaacttcc cccttttctc    180

ccgttgccat tttcgcgtca ctgatcaggt gactgagctt tttgtagcct tccggatttt    240
```

-continued

```
tacacaagac tgtcaacacg ccttcttgca gactcagctc cgcaccataa acggtatgca    300
ttccagcttc cgcggcagct tccgcaaatc tcactgcacc ataaaaacca tccctatcca    360
tgactgatag agcaacaagt cctaactttt tggcctgcac aaccacatca gacggatccg    420
atgcgccagt gagaaagtta taactgctgg tggcatgcag ctcggcaaaa ggaaccgacg    480
cttccccctg catggcagat gaaggcgcct gcgcatccgg ctcatgcagc accggacgca    540
gagattcgac ctttttacct gagaggattc tttccaattt ggaccacgat aatggcctgc    600
cgttaaagct tcccccgcca ttccattcca taatgatagg atacattttt agaacaaatt    660
ttccaataag ttttccacgc cagccggaga aggaaataga ccaagctgta cagatcgacg    720
cgtcctggct gagtacaacg tcggctccgg cgcagacctc accccagttg gctccagcga    780
aatcgtgcca ctggcactat tctggaagga ccacgactcc atcgacggca ttgacggcga    840
gtccgttgcc atccctaacg atccttccaa ccagggccgc gccatcaacg ttctcgttca    900
ggcaggtctg gtcaccctga agaccccagg tctggtcacc ccagctccag tcgatatcga    960
cgaggcagct tccaaggttt ccgtcatccc agtcgacgca gctcaggcac caaccgctta   1020
ccaggagggt cgcccagcga tcatcaacaa ctccttcctt gaccgcgcag gcatcgatcc   1080
aaacctcgcg gtcttcgaag atgatcctga gtctgaagaa gcagagccat acatcaacgt   1140
cttcgtcacc aaggctgagg acaaggacga tgccaacatc gcccgcctcg ttgagctgtg   1200
gcacgaccca gaggttctgg ctgcagtaga ccgcgactct gagggcacct ccgtcccagt   1260
tgatcgtcca ggagctgacc ttcaggaaat ccttgatcgc cttgaggctg atcaggaaaa   1320
cgcataatct cttttgagtt ctttgcatac ccatgtgcag atttctttgc acaatcacag   1380
cctgaaaatc agactgtgaa cttcaaacgc atatgactag ttcggaccta gggatatcgt   1440
cgacatcgat gctcttctgc gttaattaac aattgggatc ctctagaccc gggatttaaa   1500
tcgctagcgg gctgctaaag gaagcggaac acgtagaaag ccagtccgca gaaacggtgc   1560
tgaccccgga tgaatgtcag ctactgggct atctggacaa gggaaaacgc aagcgcaaag   1620
agaaagcagg tagcttgcag tgggcttaca tggcgatagc tagactgggc ggttttatgg   1680
acagcaagcg aaccggaatt gccagctggg gcgccctctg gtaaggttgg gaagccctgc   1740
aaagtaaact ggatggcttt cttgccgcca aggatctgat ggcgcagggg atcaagatct   1800
gatcaagaga caggatgagg atcgtttcgc atgattgaac aagatggatt gcacgcaggt   1860
tctccggccg cttgggtgga gaggctattc ggctatgact gggcacaaca gacaatcggc   1920
tgctctgatg ccgccgtgtt ccggctgtca gcgcaggggc gcccggttct ttttgtcaag   1980
accgacctgt ccggtgccct gaatgaactg caggacgagg cagcgcggct atcgtggctg   2040
gccacgacgg gcgttccttg cgcagctgtg ctcgacgttg tcactgaagc gggaagggac   2100
tggctgctat tgggcgaagt gccggggcag gatctcctgt catctcacct tgctcctgcc   2160
gagaaagtat ccatcatggc tgatgcaatg cggcggctgc atacgcttga tccggctacc   2220
tgcccattcg accaccaagc gaaacatcgc atcgagcgag cacgtactcg gatggaagcc   2280
ggtcttgtcg atcaggatga tctggacgaa gagcatcagg ggctcgcgcc agccgaactg   2340
ttcgccaggc tcaaggcgcg catgcccgac ggcgaggatc tcgtcgtgac ccatggcgat   2400
gcctgcttgc cgaatatcat ggtggaaaat ggccgctttt ctggattcat cgactgtggc   2460
cggctgggtg tggcggaccg ctatcaggac atagcgttgg ctacccgtga tattgctgaa   2520
gagcttggcg gcgaatgggc tgaccgcttc ctcgtgcttt acggtatcgc cgctcccgat   2580
tcgcagcgca tcgccttcta tcgccttctt gacgagttct tctgagcggg actctggggt   2640
```

-continued

```
tcgaaatgac cgaccaagcg acgcccaacc tgccatcacg agatttcgat tccaccgccg   2700
ccttctatga aaggttgggc ttcggaatcg ttttccggga cgccggctgg atgatcctcc   2760
agcgcgggga tctcatgctg gagttcttcg cccacgctag cggcgcgccg gccggcccgg   2820
tgtgaaatac cgcacagatg cgtaaggaga aaataccgca tcaggcgctc ttccgcttcc   2880
tcgctcactg actcgctgcg ctcggtcgtt cggctgcggc gagcggtatc agctcactca   2940
aaggcggtaa tacggttatc cacagaatca ggggataacg caggaaagaa catgtgagca   3000
aaaggccagc aaaaggccag gaaccgtaaa aaggccgcgt tgctggcgtt tttccatagg   3060
ctccgccccc ctgacgagca tcacaaaaat cgacgctcaa gtcagaggtg gcgaaacccg   3120
acaggactat aaagatacca ggcgtttccc cctggaagct ccctcgtgcg ctctcctgtt   3180
ccgaccctgc cgcttaccgg atacctgtcc gcctttctcc cttcgggaag cgtggcgctt   3240
tctcatagct cacgctgtag gtatctcagt tcggtgtagg tcgttcgctc caagctgggc   3300
tgtgtgcacg aaccccccgt tcagcccgac cgctgcgcct tatccggtaa ctatcgtctt   3360
gagtccaacc cggtaagaca cgacttatcg ccactggcag cagccactgg taacaggatt   3420
agcagagcga ggtatgtagg cggtgctaca gagttcttga agtggtggcc taactacggc   3480
tacactagaa ggacagtatt tggtatctgc gctctgctga agccagttac cttcggaaaa   3540
agagttggta gctcttgatc cggcaaacaa accaccgctg gtagcggtgg tttttttgtt   3600
tgcaagcagc agattacgcg cagaaaaaaa ggatctcaag aagatccttt gatcttttct   3660
acggggtctg acgctcagtg gaacgaaaac tcacgttaag ggattttggt catgagatta   3720
tcaaaaagga tcttcaccta gatcctttta aaggccggcc gcggccgcca tcggcatttt   3780
cttttgcgtt tttatttgtt aactgttaat tgtccttgtt caaggatgct gtctttgaca   3840
acagatgttt tcttgccttt gatgttcagc aggaagctcg gcgcaaacgt tgattgtttg   3900
tctgcgtaga atcctctgtt tgtcatatag cttgtaatca cgacattgtt tcctttcgct   3960
tgaggtacag cgaagtgtga gtaagtaaag gttacatcgt taggatcaag atccattttt   4020
aacacaaggc cagttttgtt cagcggcttg tatgggccag ttaaagaatt agaaacataa   4080
ccaagcatgt aaatatcgtt agacgtaatg ccgtcaatcg tcatttttga tccgcgggag   4140
tcagtgaaca ggtaccattt gccgttcatt ttaaagacgt tcgcgcgttc aatttcatct   4200
gttactgtgt tagatgcaat cagcggtttc atcacttttt tcagtgtgta atcatcgttt   4260
agctcaatca taccgagagc gccgtttgct aactcagccg tgcgtttttt atcgctttgc   4320
agaagttttt gactttcttg acggaagaat gatgtgcttt tgccatagta tgctttgtta   4380
aataaagatt cttcgccttg gtagccatct tcagttccag tgtttgcttc aaatactaag   4440
tatttgtggc ctttatcttc tacgtagtga ggatctctca gcgtatggtt gtcgcctgag   4500
ctgtagttgc cttcatcgat gaactgctgt acattttgat acgtttttcc gtcaccgtca   4560
aagattgatt tataatcctc tacaccgttg atgttcaaag agctgtctga tgctgatacg   4620
ttaacttgtg cagttgtcag tgtttgtttg ccgtaatgtt taccggagaa atcagtgtag   4680
aataaacgga tttttccgtc agatgtaaat gtggctgaac ctgaccattc ttgtgtttgg   4740
tcttttagga tagaatcatt tgcatcgaat ttgtcgctgt ctttaaagac gcggccagcg   4800
tttttccagc tgtcaataga agtttcgccg actttttgat agaacatgta aatcgatgtg   4860
tcatccgcat ttttaggatc tccggctaat gcaaagacga tgtggtagcc gtgatagttt   4920
gcgacagtgc cgtcagcgtt ttgtaatggc cagctgtccc aaacgtccag gccttttgca   4980
gaagagatat ttttaattgt ggacgaatca aattcagaaa cttgatattt ttcatttttt   5040
```

-continued

```
tgctgttcag ggatttgcag catatcatgg cgtgtaatat gggaaatgcc gtatgtttcc   5100

ttatatggct tttggttcgt ttctttcgca aacgcttgag ttgcgcctcc tgccagcagt   5160

gcggtagtaa aggttaatac tgttgcttgt tttgcaaact ttttgatgtt catcgttcat   5220

gtctcctttt ttatgtactg tgttagcggt ctgcttcttc cagccctcct gtttgaagat   5280

ggcaagttag ttacgcacaa taaaaaaaga cctaaaatat gtaaggggtg acgccaaagt   5340

atacactttg ccctttacac attttaggtc ttgcctgctt tatcagtaac aaacccgcgc   5400

gatttacttt tcgacctcat tctattagac tctcgtttgg attgcaactg gtctattttc   5460

ctcttttgtt tgatagaaaa tcataaaagg atttgcagac tacgggccta aagaactaaa   5520

aaatctatct gtttcttttc attctctgta ttttttatag tttctgttgc atgggcataa   5580

agttgccttt ttaatcacaa ttcagaaaat atcataaatat ctcatttcac taaataatag   5640

tgaacggcag gtatatgtga tgggttaaaa aggatcggcg gccgctcgat ttaaatc      5697
```

<210> SEQ ID NO 57
<211> LENGTH: 7318
<212> TYPE: DNA
<213> ORGANISM: artificial
<220> FEATURE:
<223> OTHER INFORMATION: Plasmid: pOM427

<400> SEQUENCE: 57

```
ggccgctcga tttaaatctc gagctctgga gtgcgacagg tttgatgata aaaaattagc     60

gcaagaagac aaaaatcacc ttgcgctaat gctctgttac aggtcactaa taccatctaa    120

gtagttgatt catagtgact gcatatgtaa gtatttcctt agataacaat tgattgaatg    180

tatgcaaata aatgcataca ccataggtgt ggtttaattt gatgcccttt ttcagggctg    240

gaatgtgtaa gagcggggtt atttatgctg ttgttttttt gttactcggg aagggcttta    300

cctcttccgc ataaacgctt ccatcagcgt ttatagttaa aaaaatcttt cggggggatg    360

gggagtaagc ttgtgttatc cgctcgggcc caatccgcaa gctccaccga ctcgttggcg    420

tgcgactcta gataaatatc aagcagctgg ccgccaataa cctcagtacg catgccacgc    480

caagcatccc tcgtgcgggc caatgcctct gcactcaaac cggaatcctg cagcatgtct    540

tctgcccaca ccaatgccat atcgccagcc aaaatcgaga ctgaaacgcc aaagtgctcg    600

ggatcgcctt cgaaattatt ggcgcggtga tcagcttcca cagcccggtg aactgtgggg    660

gctccgcgcc gggtatcaga agaatcgata atatcgtcat gaatcaaggc acaagcctgg    720

atgaattcga gactcgctgc ggcgtcaagg acggactcaa gtttttcaga agaattctta    780

tggccttgcg ccgccaggaa accagcccac gcataaagag gacggattcg ctttcctcca    840

ttgagcacga aactgcgaag atgggccaca gcatctgtga caggagcgcc gatatcagca    900

attgttagct cttgagcatc gaggaactgc gtcaaacgat ctcgcacgac ctccggaaat    960

ttgtcgaggt caaggtcatg ggcatcgaaa ctgctcaagg agacgtcctt caatcgaata   1020

gggggatgcg ggctgaattt tggtggaggt gaataaatgc cagaggcagt cccaacaaaa   1080

cactctcatc acactaagat acccgtcgac tcatacgtta aatctatcac cgcaagggat   1140

aaatatctaa caccgtgcgt gttgactatt ttacctctgg cggtgataat ggttgcatgt   1200

actaaggagg attaattaat gtccctaacg aacatcccag cctcatctca atgggcaatt   1260

agcgacgttt tgaagcgtcc ttcacccggc cgagtacctt tttctgtcga gtttatgcca   1320

ccccgcgacg atgcagctga agagcgtctt taccgcgcag cagaggtctt ccatgacctc   1380

ggtgcatcgt ttgtctccgt gacttatggt gctggcggat caacccgtga gagaacctca   1440
```

-continued

```
cgtattgctc gacgattagc gaaacaaccg ttgaccactc tggtgcacct gaccctggtt   1500
aaccacactc gcgaagagat gaaggcaatt cttcgggaat acctagagct gggattaaca   1560
aacctgttgg cgcttcgagg agatccgcct ggagacccat taggcgattg ggtgagcacc   1620
gatggaggac tgaactatgc ctctgagctc atcgatctta ttaagtccac tcctgagttc   1680
cgggaattcg acctcggtat cgcctccttc cccgaagggc atttccgggc gaaaactcta   1740
gaagaagaca ccaaatacac tctggcgaag ctgcgtggag gggcagagta ctccatcacg   1800
cagatgttct ttgatgtgga agactacctg cgacttcgtg atcgccggat cctgttttgg   1860
cggatgagag aagattttca gcctgataca gattaaatca gaacgcagaa gcggtctgat   1920
aaaacagaat ttgcctggcg gcagtagcgc ggtggtccca cctgacccca tgccgaactc   1980
agaagtgaaa cgccgtagcg ccgatggtag tgtggggtct ccccatgcga gagtagggaa   2040
ctgccaggca tcaaataaaa cgaaaggctc agtcgaaaga ctgggccttt cgttttatct   2100
gttgtttgtc ggtgaacgct ctcctgagta ggacaaatcc gccgggagcg gatttgaacg   2160
ttgcgaagca acggcccgga gggtggcggg caggacgccc gccataaact gccaggcatc   2220
aaattaagca gaaggccatc ctgacggatg gcctttttgc gtttctacaa actcttggta   2280
cgggatttaa atgatccgct agcgggctgc taaaggaagc ggaacacgta gaaagccagt   2340
ccgcagaaac ggtgctgacc ccggatgaat gtcagctact gggctatctg gacaagggaa   2400
aacgcaagcg caaagagaaa gcaggtagct tgcagtgggc ttacatggcg atagctagac   2460
tgggcggttt tatggacagc aagcgaaccg gaattgccag ctggggcgcc ctctggtaag   2520
gttgggaagc cctgcaaagt aaactggatg gctttcttgc cgccaaggat ctgatggcgc   2580
aggggatcaa gatctgatca agagacagga tgaggatcgt ttcgcatgat tgaacaagat   2640
ggattgcacg caggttctcc ggccgcttgg gtggagaggc tattcggcta tgactgggca   2700
caacagacaa tcggctgctc tgatgccgcc gtgttccggc tgtcagcgca ggggcgcccg   2760
gttctttttg tcaagaccga cctgtccggt gccctgaatg aactgcagga cgaggcagcg   2820
cggctatcgt ggctggccac gacgggcgtt ccttgcgcag ctgtgctcga cgttgtcact   2880
gaagcgggaa gggactggct gctattgggc gaagtgccgg ggcaggatct cctgtcatct   2940
caccttgctc ctgccgagaa agtatccatc atggctgatg caatgcggcg gctgcatacg   3000
cttgatccgg ctacctgccc attcgaccac caagcgaaac atcgcatcga gcgagcacgt   3060
actcggatgg aagccggtct tgtcgatcag gatgatctgg acgaagagca tcaggggctc   3120
gcgccagccg aactgttcgc caggctcaag gcgcgcatgc ccgacggcga ggatctcgtc   3180
gtgacccatg gcgatgcctg cttgccgaat atcatggtgg aaaatggccg cttttctgga   3240
ttcatcgact gtggccggct gggtgtggcg gaccgctatc aggacatagc gttggctacc   3300
cgtgatattg ctgaagagct tggcggcgaa tgggctgacc gcttcctcgt gctttacggt   3360
atcgccgctc ccgattcgca gcgcatcgcc ttctatcgcc ttcttgacga gttcttctga   3420
gcgggactct ggggttcgaa atgaccgacc aagcgacgcc caacctgcca tcacgagatt   3480
tcgattccac cgccgccttc tatgaaaggt tgggcttcgg aatcgttttc cgggacgccg   3540
gctggatgat cctccagcgc ggggatctca tgctggagtt cttcgcccac gctagcggcg   3600
cgccacgggt gcgcatgatc gtgctcctgt cgttgaggac ccggctaggc tggcggggtt   3660
gccttactgg ttagcagaat gaatcaccga tacgcgagcg aacgtgaagc gactgctgct   3720
gcaaaacgtc tgcgacctga gcaacaacat gaatggtctt cggtttccgt gtttcgtaaa   3780
gtctggaaac gcggaagtca gcgccctgca ccattatgtt ccggatctgc atcgcaggat   3840
```

-continued

```
gctgctggct accctgtgga acacctacat ctgtattaac gaagcgctgg cattgaccct   3900
gagtgatttt tctctggtcc cgccgcatcc ataccgccag ttgtttaccc tcacaacgtt   3960
ccagtaaccg ggcatgttca tcatcagtaa cccgtatcgt gagcatcctc tctcgtttca   4020
tcggtatcat tacccccatg aacagaaatc ccccttacac ggaggcatca gtgaccaaac   4080
aggaaaaaac cgcccttaac atggcccgct ttatcagaag ccagacatta acgcttctgg   4140
agaaactcaa cgagctggac gcggatgaac aggcagacat ctgtgaatcg cttcacgacc   4200
acgctgatga gctttaccgc agctgcctcg cgcgtttcgg tgatgacggt gaaaacctct   4260
gacacatgca gctcccggag acggtcacag cttgtctgta agcggatgcc gggagcagac   4320
aagcccgtca gggcgcgtca gcgggtgttg gcgggtgtcg gggcgcagcc atgacccagt   4380
cacgtagcga tagcggagtg tatactggct taactatgcg gcatcagagc agattgtact   4440
gagagtgcac catatgcggt gtgaaatacc gcacagatgc gtaaggagaa aataccgcat   4500
caggcgctct tccgcttcct cgctcactga ctcgctgcgc tcggtcgttc ggctgcggcg   4560
agcggtatca gctcactcaa aggcggtaat acggttatcc acagaatcag gggataacgc   4620
aggaaagaac atgtgagcaa aaggccagca aaaggccagg aaccgtaaaa aggccgcgtt   4680
gctggcgttt ttccataggc tccgcccccc tgacgagcat cacaaaaatc gacgctcaag   4740
tcagaggtgg cgaaacccga caggactata aagataccag gcgtttcccc ctggaagctc   4800
cctcgtgcgc tctcctgttc cgaccctgcc gcttaccgga tacctgtccg cctttctccc   4860
ttcgggaagc gtggcgcttt ctcatagctc acgctgtagg tatctcagtt cggtgtaggt   4920
cgttcgctcc aagctgggct gtgtgcacga accccccgtt cagcccgacc gctgcgcctt   4980
atccggtaac tatcgtcttg agtccaaccc ggtaagacac gacttatcgc cactggcagc   5040
agccactggt aacaggatta gcagagcgag gtatgtaggc ggtgctacag agttcttgaa   5100
gtggtggcct aactacggct acactagaag gacagtattt ggtatctgcg ctctgctgaa   5160
gccagttacc ttcggaaaaa gagttggtag ctcttgatcc ggcaaacaaa ccaccgctgg   5220
tagcggtggt ttttttgttt gcaagcagca gattacgcgc agaaaaaaag gatctcaaga   5280
agatcctttg atcttttcta cggggtctga cgctcagtgg aacgaaaact cacgttaagg   5340
gattttggtc atgagattat caaaaaggat cttcacctag atccttttaa aggccggccg   5400
cggccgccat cggcattttc ttttgcgttt ttatttgtta actgttaatt gtccttgttc   5460
aaggatgctg tctttgacaa cagatgtttt cttgcctttg atgttcagca ggaagctcgg   5520
cgcaaacgtt gattgtttgt ctgcgtagaa tcctctgttt gtcatatagc ttgtaatcac   5580
gacattgttt cctttcgctt gaggtacagc gaagtgtgag taagtaaagg ttacatcgtt   5640
aggatcaaga tccattttta acacaaggcc agttttgttc agcggcttgt atgggccagt   5700
taaagaatta gaaacataac caagcatgta aatatcgtta gacgtaatgc cgtcaatcgt   5760
catttttgat ccgcgggagt cagtgaacag gtaccatttg ccgttcattt taaagacgtt   5820
cgcgcgttca atttcatctg ttactgtgtt agatgcaatc agcggtttca tcactttttt   5880
cagtgtgtaa tcatcgttta gctcaatcat accgagagcg ccgtttgcta actcagccgt   5940
gcgtttttta tcgctttgca gaagtttttg actttcttga cggaagaatg atgtgctttt   6000
gccatagtat gctttgttaa ataaagattc ttcgccttgg tagccatctt cagttccagt   6060
gtttgcttca aatactaagt atttgtggcc tttatcttct acgtagtgag gatctctcag   6120
cgtatggttg tcgcctgagc tgtagttgcc ttcatcgatg aactgctgta cattttgata   6180
cgtttttccg tcaccgtcaa agattgattt ataatcctct acaccgttga tgttcaaaga   6240
```

gctgtctgat gctgatacgt taacttgtgc agttgtcagt gtttgtttgc cgtaatgttt 6300
accggagaaa tcagtgtaga ataaacggat ttttccgtca gatgtaaatg tggctgaacc 6360
tgaccattct tgtgtttggt cttttaggat agaatcattt gcatcgaatt tgtcgctgtc 6420
tttaaagacg cggccagcgt ttttccagct gtcaatagaa gtttcgccga ctttttgata 6480
gaacatgtaa atcgatgtgt catccgcatt tttaggatct ccggctaatg caaagacgat 6540
gtggtagccg tgatagtttg cgacagtgcc gtcagcgttt tgtaatggcc agctgtccca 6600
aacgtccagg ccttttgcag aagagatatt tttaattgtg gacgaatcaa attcagaaac 6660
ttgatatttt tcattttttt gctgttcagg gatttgcagc atatcatggc gtgtaatatg 6720
ggaaatgccg tatgtttcct tatatggctt ttggttcgtt tctttcgcaa acgcttgagt 6780
tgcgcctcct gccagcagtg cggtagtaaa ggttaatact gttgcttgtt ttgcaaactt 6840
tttgatgttc atcgttcatg tctccttttt tatgtactgt gttagcggtc tgcttcttcc 6900
agccctcctg tttgaagatg gcaagttagt tacgcacaat aaaaaaagac ctaaaatatg 6960
taaggggtga cgccaaagta tacactttgc cctttacaca ttttaggtct tgcctgcttt 7020
atcagtaaca aacccgcgcg atttactttt cgacctcatt ctattagact ctcgtttgga 7080
ttgcaactgg tctattttcc tcttttgttt gatagaaaat cataaaagga tttgcagact 7140
acgggcctaa agaactaaaa aatctatctg tttcttttca ttctctgtat tttttatagt 7200
ttctgttgca tgggcataaa gttgcctttt taatcacaat tcagaaaata tcataatatc 7260
tcatttcact aaataatagt gaacggcagg tatatgtgat gggttaaaaa ggatcggc 7318

<210> SEQ ID NO 58
<211> LENGTH: 5715
<212> TYPE: DNA
<213> ORGANISM: artificial
<220> FEATURE:
<223> OTHER INFORMATION: Plasmid: pCLIK5A PSOD TKT

<400> SEQUENCE: 58
cgcgtcggca aattagtcga atgaagttaa ttaaaagttc ccgaatcaat ctttttaatg 60
ttttcaaacc atttgaaggt gtgctgaccc aggtggacgc caacctttaa aaagcttcag 120
acttttattt ccacttcata aaaactgcct gtgacgattc cgttaaagat tgtgccaaat 180
cactgcgcaa aactcgcgcg gaaccagacc ttgccatgct atcgcctatt cacactattt 240
gagtaatcgg aaatagatgg gtgtagacgc ttgattggcg gacggttcac agcggacgat 300
ttcaggccct cgtagctcga gagtttgaag ggtccgattt cgttccgttc gtgacgcttt 360
gtgaggtttt ttgacgttgc accgtattgc ttgccgaaca tttttctttt cctttcggtt 420
tttcgagaat tttcacctac aaaagcccac gtcacagctc ccagacttaa gattgatcac 480
acctttgaca catttgaacc acagttggtt ataaaatggg ttcaacatca ctatggttag 540
aggtgttgac gggtcagatt aagcaaagac tactttcggg gtagatcacc tttgccaaat 600
ttgaaccaat taacctaagt cgtagatctg atcatcggat ctaacgaaaa cgaaccaaaa 660
ctttggtccc ggtttaaccc aggaaggata gctgccaatt attccgggct tgtgacccgc 720
tacccgataa ataggtcggc tgaaaaattt cgttgcaata tcaacaaaaa ggcctatcat 780
tgggaggtgt cgcaccaagt acttttgcga agcgccatct gacggatttt caaaagatgt 840
atatgctcgg tgcggaaacc tacgaaagga ttttttaccc ttgaccacct tgacgctgtc 900
acctgaactt caggcgctca ctgtacgcaa ttacccctct gattggtccg atgtggacac 960
caaggctgta gacactgttc gtgtcctcgc tgcagacgct gtagaaaact gtggctccgg 1020

-continued

```
ccacccaggc accgcaatga gcctggctcc ccttgcatac accttgtacc agcgggttat   1080
gaacgtagat ccacaggaca ccaactgggc aggccgtgac cgcttcgttc tttcttgtgg   1140
ccactcctct ttgacccagt acatccagct ttacttgggt ggattcggcc ttgagatgga   1200
tgacctgaag gctctgcgca cctgggattc cttgacccca ggacaccctg agtaccgcca   1260
caccaagggc gttgagatca ccactggccc tcttggccag ggtcttgcat ctgcagttgg   1320
tatggccatg gctgctcgtc gtgagcgtgg cctattcgac ccaaccgctg ctgagggcga   1380
atccccattc gaccaccaca tctacgtcat tgcttctgat gggtcgacat cgatgctctt   1440
ctgcgttaat taacaattgg gatcctctag acccgggatt taaatgatcc gctagcgggc   1500
tgctaaagga agcggaacac gtagaaagcc agtccgcaga aacggtgctg accccggatg   1560
aatgtcagct actgggctat ctggacaagg gaaaacgcaa gcgcaaagag aaagcaggta   1620
gcttgcagtg ggcttacatg gcgatagcta gactgggcgg ttttatggac agcaagcgaa   1680
ccggaattgc cagctggggc gccctctggt aaggttggga agccctgcaa agtaaactgg   1740
atggctttct tgccgccaag gatctgatgg cgcaggggat caagatctga tcaagagaca   1800
ggatgaggat cgtttcgcat gattgaacaa gatggattgc acgcaggttc tccggccgct   1860
tgggtggaga ggctattcgg ctatgactgg gcacaacaga caatcggctg ctctgatgcc   1920
gccgtgttcc ggctgtcagc gcaggggcgc ccggttcttt ttgtcaagac cgacctgtcc   1980
ggtgccctga atgaactgca ggacgaggca gcgcggctat cgtggctggc cacgacgggc   2040
gttccttgcg cagctgtgct cgacgttgtc actgaagcgg gaagggactg gctgctattg   2100
ggcgaagtgc cggggcagga tctcctgtca tctcaccttg ctcctgccga gaaagtatcc   2160
atcatggctg atgcaatgcg gcggctgcat acgcttgatc cggctacctg cccattcgac   2220
caccaagcga aacatcgcat cgagcgagca cgtactcgga tggaagccgg tcttgtcgat   2280
caggatgatc tggacgaaga gcatcagggg ctcgcgccag ccgaactgtt cgccaggctc   2340
aaggcgcgca tgcccgacgg cgaggatctc gtcgtgaccc atggcgatgc ctgcttgccg   2400
aatatcatgg tggaaaatgg ccgcttttct ggattcatcg actgtggccg gctgggtgtg   2460
gcggaccgct atcaggacat agcgttggct acccgtgata ttgctgaaga gcttggcggc   2520
gaatgggctg accgcttcct cgtgctttac ggtatcgccg ctcccgattc gcagcgcatc   2580
gccttctatc gccttcttga cgagttcttc tgagcgggac tctggggttc gaaatgaccg   2640
accaagcgac gcccaacctg ccatcacgag atttcgattc caccgccgcc ttctatgaaa   2700
ggttgggctt cggaatcgtt ttccgggacg ccggctggat gatcctccag cgcggggatc   2760
tcatgctgga gttcttcgcc cacgctagcg gcgcgccggc cggcccggtg tgaaataccg   2820
cacagatgcg taaggagaaa ataccgcatc aggcgctctt ccgcttcctc gctcactgac   2880
tcgctgcgct cggtcgttcg gctgcggcga gcggtatcag ctcactcaaa ggcggtaata   2940
cggttatcca cagaatcagg ggataacgca ggaaagaaca tgtgagcaaa aggccagcaa   3000
aaggccagga accgtaaaaa ggccgcgttg ctggcgtttt tccataggct ccgcccccct   3060
gacgagcatc acaaaaatcg acgctcaagt cagaggtggc gaaacccgac aggactataa   3120
agataccagg cgtttccccc tggaagctcc ctcgtgcgct ctcctgttcc gaccctgccg   3180
cttaccggat acctgtccgc ctttctccct tcgggaagcg tggcgctttc tcatagctca   3240
cgctgtaggt atctcagttc ggtgtaggtc gttcgctcca agctgggctg tgtgcacgaa   3300
ccccccgttc agcccgaccg ctgcgcctta tccggtaact atcgtcttga gtccaacccg   3360
gtaagacacg acttatcgcc actggcagca gccactggta acaggattag cagagcgagg   3420
```

-continued

```
tatgtaggcg gtgctacaga gttcttgaag tggtggccta actacggcta cactagaagg   3480

acagtatttg gtatctgcgc tctgctgaag ccagttacct tcggaaaaag agttggtagc   3540

tcttgatccg gcaaacaaac caccgctggt agcggtggtt tttttgtttg caagcagcag   3600

attacgcgca gaaaaaaagg atctcaagaa gatcctttga tcttttctac ggggtctgac   3660

gctcagtgga acgaaaactc acgttaaggg attttggtca tgagattatc aaaaaggatc   3720

ttcacctaga tccttttaaa ggccggccgc ggccgccatc ggcattttct tttgcgtttt   3780

tatttgttaa ctgttaattg tccttgttca aggatgctgt ctttgacaac agatgttttc   3840

ttgcctttga tgttcagcag gaagctcggc gcaaacgttg attgtttgtc tgcgtagaat   3900

cctctgtttg tcatatagct tgtaatcacg acattgtttc ctttcgcttg aggtacagcg   3960

aagtgtgagt aagtaaaggt tacatcgtta ggatcaagat ccatttttaa cacaaggcca   4020

gttttgttca gcggcttgta tgggccagtt aaagaattag aaacataacc aagcatgtaa   4080

atatcgttag acgtaatgcc gtcaatcgtc atttttgatc cgcgggagtc agtgaacagg   4140

taccatttgc cgttcatttt aaagacgttc gcgcgttcaa tttcatctgt tactgtgtta   4200

gatgcaatca gcggtttcat cacttttttc agtgtgtaat catcgtttag ctcaatcata   4260

ccgagagcgc cgtttgctaa ctcagccgtg cgttttttat cgctttgcag aagtttttga   4320

ctttcttgac ggaagaatga tgtgcttttg ccatagtatg ctttgttaaa taaagattct   4380

tcgccttggt agccatcttc agttccagtg tttgcttcaa atactaagta tttgtggcct   4440

ttatcttcta cgtagtgagg atctctcagc gtatggttgt cgcctgagct gtagttgcct   4500

tcatcgatga actgctgtac attttgatac gtttttccgt caccgtcaaa gattgattta   4560

taatcctcta caccgttgat gttcaaagag ctgtctgatg ctgatacgtt aacttgtgca   4620

gttgtcagtg tttgtttgcc gtaatgttta ccggagaaat cagtgtagaa taaacggatt   4680

tttccgtcag atgtaaatgt ggctgaacct gaccattctt gtgtttggtc ttttaggata   4740

gaatcatttg catcgaattt gtcgctgtct ttaaagacgc ggccagcgtt tttccagctg   4800

tcaatagaag tttcgccgac tttttgatag aacatgtaaa tcgatgtgtc atccgcattt   4860

ttaggatctc cggctaatgc aaagacgatg tggtagccgt gatagtttgc gacagtgccg   4920

tcagcgtttt gtaatggcca gctgtcccaa acgtccaggc cttttgcaga agagatattt   4980

ttaattgtgg acgaatcaaa ttcagaaact tgatattttt catttttttg ctgttcaggg   5040

atttgcagca tatcatggcg tgtaatatgg gaaatgccgt atgtttcctt atatggcttt   5100

tggttcgttt ctttcgcaaa cgcttgagtt gcgcctcctg ccagcagtgc ggtagtaaag   5160

gttaatactg ttgcttgttt tgcaaacttt ttgatgttca tcgttcatgt ctcctttttt   5220

atgtactgtg ttagcggtct gcttcttcca gccctcctgt ttgaagatgg caagttagtt   5280

acgcacaata aaaaaagacc taaaatatgt aaggggtgac gccaaagtat acactttgcc   5340

ctttacacat tttaggtctt gcctgcttta tcagtaacaa acccgcgcga tttacttttc   5400

gacctcattc tattagactc tcgtttggat tgcaactggt ctattttcct cttttgtttg   5460

atagaaaatc ataaaaggat ttgcagacta cgggcctaaa gaactaaaaa atctatctgt   5520

ttcttttcat tctctgtatt ttttatagtt tctgttgcat gggcataaag ttgccttttt   5580

aatcacaatt cagaaaatat cataatatct catttcacta aataatagtg aacggcaggt   5640

atatgtgatg ggttaaaaag gatcggcggc cgctcgattt aaatctcgag aggcctgacg   5700

tcgggcccgg tacca                                                    5715
```

<210> SEQ ID NO 59

<211> LENGTH: 5083
<212> TYPE: DNA
<213> ORGANISM: artificial
<220> FEATURE:
<223> OTHER INFORMATION: Plasmid: pH626 int SacB delta sdaA

<400> SEQUENCE: 59
ctagacccgg gatttaaatc gctagcgggc tgctaaagga agcggaacac gtagaaagcc 60
agtccgcaga aacggtgctg accccggatg aatgtcagct actgggctat ctggacaagg 120
gaaaacgcaa gcgcaaagag aaagcaggta gcttgcagtg ggcttacatg gcgatagcta 180
gactgggcgg ttttatggac agcaagcgaa ccggaattgc cagctggggc gccctctggt 240
aaggttggga agccctgcaa agtaaactgg atggctttct tgccgccaag gatctgatgg 300
cgcaggggat caagatctga tcaagagaca ggatgaggat cgtttcgcat gattgaacaa 360
gatggattgc acgcaggttc tccggccgct tgggtggaga ggctattcgg ctatgactgg 420
gcacaacaga caatcggctg ctctgatgcc gccgtgttcc ggctgtcagc gcaggggcgc 480
ccggttcttt ttgtcaagac cgacctgtcc ggtgccctga atgaactgca ggacgaggca 540
gcgcggctat cgtggctggc cacgacgggc gttccttgcg cagctgtgct cgacgttgtc 600
actgaagcgg gaagggactg gctgctattg ggcgaagtgc cggggcagga tctcctgtca 660
tctcaccttg ctcctgccga gaaagtatcc atcatggctg atgcaatgcg gcggctgcat 720
acgcttgatc cggctacctg cccattcgac caccaagcga aacatcgcat cgagcgagca 780
cgtactcgga tggaagccgg tcttgtcgat caggatgatc tggacgaaga gcatcagggg 840
ctcgcgccag ccgaactgtt cgccaggctc aaggcgcgca tgcccgacgg cgaggatctc 900
gtcgtgaccc atggcgatgc ctgcttgccg aatatcatgg tggaaaatgg ccgcttttct 960
ggattcatcg actgtggccg gctgggtgtg gcggaccgct atcaggacat agcgttggct 1020
acccgtgata ttgctgaaga gcttggcggc gaatgggctg accgcttcct cgtgctttac 1080
ggtatcgccg ctcccgattc gcagcgcatc gccttctatc gccttcttga cgagttcttc 1140
tgagcgggac tctggggttc gaaatgaccg accaagcgac gcccaacctg ccatcacgag 1200
atttcgattc caccgccgcc ttctatgaaa ggttgggctt cggaatcgtt ttccgggacg 1260
ccggctggat gatcctccag cgcggggatc tcatgctgga gttcttcgcc cacgctagcg 1320
gcgcgccggc cggcccggtg tgaaataccg cacagatgcg taaggagaaa ataccgcatc 1380
aggcgctctt ccgcttcctc gctcactgac tcgctgcgct cggtcgttcg gctgcggcga 1440
gcggtatcag ctcactcaaa ggcggtaata cggttatcca cagaatcagg ggataacgca 1500
ggaaagaaca tgtgagcaaa aggccagcaa aaggccagga accgtaaaaa ggccgcgttg 1560
ctggcgtttt tccataggct ccgcccccct gacgagcatc acaaaaatcg acgctcaagt 1620
cagaggtggc gaaacccgac aggactataa agataccagg cgtttccccc tggaagctcc 1680
ctcgtgcgct ctcctgttcc gaccctgccg cttaccggat acctgtccgc ctttctccct 1740
tcgggaagcg tggcgctttc tcatagctca cgctgtaggt atctcagttc ggtgtaggtc 1800
gttcgctcca agctgggctg tgtgcacgaa ccccccgttc agcccgaccg ctgcgcctta 1860
tccggtaact atcgtcttga gtccaacccg gtaagacacg acttatcgcc actggcagca 1920
gccactggta acaggattag cagagcgagg tatgtaggcg gtgctacaga gttcttgaag 1980
tggtggccta actacggcta cactagaagg acagtatttg gtatctgcgc tctgctgaag 2040
ccagttacct tcggaaaaag agttggtagc tcttgatccg gcaaacaaac caccgctggt 2100
agcggtggtt tttttgtttg caagcagcag attacgcgca gaaaaaaagg atctcaagaa 2160

-continued gatcctttga tcttttctac ggggtctgac gctcagtgga acgaaaactc acgttaaggg 2220
attttggtca tgagattatc aaaaaggatc ttcacctaga tccttttaaa ggccggccgc 2280
ggccgccatc ggcatttttct tttgcgtttt tatttgttaa ctgttaattg tccttgttca 2340
aggatgctgt ctttgacaac agatgttttc ttgcctttga tgttcagcag gaagctcggc 2400
gcaaacgttg attgtttgtc tgcgtagaat cctctgtttg tcatatagct tgtaatcacg 2460
acattgtttc ctttcgcttg aggtacagcg aagtgtgagt aagtaaaggt tacatcgtta 2520
ggatcaagat ccatttttaa cacaaggcca gttttgttca gcggcttgta tgggccagtt 2580
aaagaattag aaacataacc aagcatgtaa atatcgttag acgtaatgcc gtcaatcgtc 2640
atttttgatc cgcgggagtc agtgaacagg taccatttgc cgttcatttt aaagacgttc 2700
gcgcgttcaa tttcatctgt tactgtgtta gatgcaatca gcggtttcat cactttttc 2760 agtgtgtaat catcgtttag ctcaatcata ccgagagcgc cgtttgctaa ctcagccgtg 2820
cgttttttat cgctttgcag aagtttttga ctttcttgac ggaagaatga tgtgcttttg 2880
ccatagtatg ctttgttaaa taaagattct tcgccttggt agccatcttc agttccagtg 2940
tttgcttcaa atactaagta tttgtggcct ttatcttcta cgtagtgagg atctctcagc 3000
gtatggttgt cgcctgagct gtagttgcct tcatcgatga actgctgtac attttgatac 3060
gtttttccgt caccgtcaaa gattgattta taatcctcta caccgttgat gttcaaagag 3120
ctgtctgatg ctgatacgtt aacttgtgca gttgtcagtg tttgtttgcc gtaatgttta 3180
ccggagaaat cagtgtagaa taaacggatt tttccgtcag atgtaaatgt ggctgaacct 3240
gaccattctt gtgtttggtc ttttaggata gaatcatttg catcgaattt gtcgctgtct 3300
ttaaagacgc ggccagcgtt tttccagctg tcaatagaag tttcgccgac tttttgatag 3360
aacatgtaaa tcgatgtgtc atccgcattt ttaggatctc cggctaatgc aaagacgatg 3420
tggtagccgt gatagtttgc gacagtgccg tcagcgtttt gtaatggcca gctgtcccaa 3480
acgtccaggc cttttgcaga agagatattt ttaattgtgg acgaatcaaa ttcagaaact 3540
tgatattttt cattttttg ctgttcaggg atttgcagca tatcatggcg tgtaatatgg 3600
gaaatgccgt atgtttcctt atatggcttt tggttcgttt ctttcgcaaa cgcttgagtt 3660
gcgcctcctg ccagcagtgc ggtagtaaag gttaatactg ttgcttgttt tgcaaacttt 3720
ttgatgttca tcgttcatgt ctcctttttt atgtactgtg ttagcggtct gcttcttcca 3780
gccctcctgt ttgaagatgg caagttagtt acgcacaata aaaaaagacc taaaatatgt 3840
aaggggtgac gccaaagtat acactttgcc ctttacacat tttaggtctt gcctgcttta 3900
tcagtaacaa acccgcgcga tttacttttc gacctcattc tattagactc tcgtttggat 3960
tgcaactggt ctattttcct cttttgtttg atagaaaatc ataaaaggat ttgcagacta 4020
cgggcctaaa gaactaaaaa atctatctgt ttcttttcat tctctgtatt ttttatagtt 4080
tctgttgcat gggcataaag ttgccttttt aatcacaatt cagaaaatat cataatatct 4140
catttcacta aataatagtg aacggcaggt atatgtgatg ggttaaaaag gatcggcggc 4200
cgctcgattt aaatctcgag aggcctgacg tcgggcccgg taccacgcgt gccgatcttc 4260
tcaaaggaca cgacggaaac ggctaaattc gcggatctcc gtttaaggca ttgaagcatt 4320
tggaggcccc aagacatgac ccagaccctg taaagcgctt aaacggcgtt ttagagggtc 4380
atagttttgg gacaagtggg acaagtgtga atcctgaaag cttccagggc aaggatccac 4440
cacaaaccgg ccatcgccct ttggaatcgg tccgaaaatt gcaggtacag agccttttac 4500
cgagaaaatc caccacagat tgctgaaatt tcgtgatctg tggtggattc gtgcaacttc 4560
agactcttac ggaggcgatg gaccaaaaac aactacaatc aagcagatca ccttgtacac 4620
caccatagaa aaggcccacc ctcagcccgg tacggcttta acacggcttg gattttgtct 4680
tgcttggcga ggtaggactg gcactgggcg tcgataagct cagctgacca cccggtgacc 4740
tgcgccattg cttcggccgt cgcacgcacg gcagccggtt gcacataacc cagcgtgccg 4800
agcacgatgc gacgatccag cacgtccgcc aggtcgacgg ccgcctcctc ggcgacagca 4860
aaaacggcct gcgccgcgat atcaaggttg tctgggtcaa gtcggcgccc caggtcgggt 4920
tgctttgcga cgagatccag cactttttca tgctcagttc catacagtct ggccagatgc 4980
acgcggattt catcatccac atccagctcg ggtggctgc gaagcgctga ctcaaaggaa 5040
tcagccacgg actcatacgc gccaaaagaa gtactcaacg gct 5083

<210> SEQ ID NO 60
<211> LENGTH: 9730
<212> TYPE: DNA
<213> ORGANISM: artificial
<220> FEATURE:
<223> OTHER INFORMATION: Plasmid: pOM350

<400> SEQUENCE: 60
tcgatttaaa tctcgagagg cctgacgtcg ggcccggtac cgggcccccc ctcgaggtcg 60
agcggcttaa agtttggctg ccatgtgaat ttttagcacc ctcaacagtt gagtgctggc 120
actctcgggg gtagagtgcc aaataggttg tttgacacac agttgttcac ccgcgacgac 180
ggctgtgctg gaaacccaca accggcacac acaaaatttt tctcatggag ggattcatca 240
tgtcgacttc agttacttca ccagcccaca acaacgcaca ttcctccgaa tttttggatg 300
cgttggcaaa ccatgtgttg atcggcgacg gcgccatggg cacccagctc caaggctttg 360
acctggacgt ggaaaaggat ttccttgatc tggaggggtg taatgagatt ctcaacgaca 420
cccgccctga tgtgttgagg cagattcacc gcgcctactt tgaggcggga gctgacttgg 480
ttgagaccaa tacttttggt tgcaacctgc cgaacttggc ggattatgac atcgctgatc 540
gttgccgtga gcttgcctac aagggcactg cagtggctag ggaagtggct gatgagatgg 600
ggccgggccg aaacggcatg cggcgtttcg tggttggttc cctgggacct ggaacgaagc 660
ttccatcgct gggccatgca ccgtatgcag atttgcgtgg gcactacaag gaagcagcgc 720
ttggcatcat cgacggtggt ggcgatgcct ttttgattga gactgctcag gacttgcttc 780
aggtcaaggc tgcggttcac ggcgttcaag atgccatggc tgaacttgat acattcttgc 840
ccattatttg ccacgtcacc gtagagacca ccggcaccat gctcatgggt tctgagatcg 900
gtgccgcgtt gacagcgctg cagccactgg gtatcgacat gattggtctg aactgcgcca 960
ccggcccaga tgagatgagc gagcacctgc gttacctgtc caagcacgcc gatattcctg 1020
tgtcggtgat gcctaacgca ggtcttcctg tcctgggtaa aaacggtgca gaatacccac 1080
ttgaggctga ggatttggcg caggcgctgg ctggattcgt ctccgaatat ggcctgtcca 1140
tggtgggtgg ttgttgtggc accacacctg agcacatccg tgcggtccgc gatgcggtgg 1200
ttggtgttcc agagcaggaa acctccacac tgaccaagat ccctgcaggc cctgttgagc 1260
aggcctcccg cgaggtggag aaagaggact ccgtcgcgtc gctgtacacc tcggtgccat 1320
tgtcccagga aaccggcatt tccatgatcg gtgagcgcac caactccaac ggttccaagg 1380
cattccgtga ggcaatgctg tctggcgatt gggaaaagtg tgtggatatt gccaagcagc 1440
aaacccgcga tggtgcacac atgctggatc tttgtgtgga ttacgtggga cgagacggca 1500
ccgccgatat ggcgaccttg gcagcacttc ttgctaccag ctccactttg ccaatcatga 1560

-continued

```
ttgactccac cgagccagag gttattcgca caggccttga gcacttgggt ggacgaagca   1620
tcgttaactc cgtcaacttt gaagacggcg atggccctga gtcccgctac cagcgcatca   1680
tgaaactggt aaagcagcac ggtgcggccg tggttgcgct gaccattgat gaggaaggcc   1740
aggcacgtac cgctgagcac aaggtgcgca ttgctaaacg actgattgac gatatcaccg   1800
gcagctacgg cctggatatc aaagacatcg ttgtggactg cctgaccttc ccgatctcta   1860
ctggccagga agaaaccagg cgagatggca ttgaaaccat cgaagccatc cgcgagctga   1920
agaagctcta cccagaaatc cacaccaccc tgggtctgtc caatatttcc ttcggcctga   1980
accctgctgc acgccaggtt cttaactctg tgttcctcaa tgagtgcatt gaggctggtc   2040
tggactctgc gattgcgcac agctccaaga ttttgccgat gaaccgcatt gatgatcgcc   2100
agcgcgaagt ggcgttggat atggtctatg atcgccgcac cgaggattac gatccgctgc   2160
aggaattcat gcagctgttt gagggcgttt ctgctgccga tgccaaggat gctcgcgctg   2220
aacagctggc cgctatgcct ttgtttgagc gtttggcaca gcgcatcatc gacggcgata   2280
agaatggcct tgaggatgat ctggaagcag gcatgaagga gaagtctcct attgcgatca   2340
tcaacgagga ccttctcaac ggcatgaaga ccgtgggtga gctgtttggt tccggacaga   2400
tgcagctgcc attcgtgctg caatcggcag aaaccatgaa aactgcggtg gcctatttgg   2460
aaccgttcat ggaagaggaa gcagaagcta ccggatctgc gcaggcagag ggcaagggca   2520
aaatcgtcgt ggccaccgtc aagggtgacg tgcacgatat cggcaagaac ttggtggaca   2580
tcattttgtc caacaacggt tacgacgtgg tgaacttggg catcaagcag ccactgtccg   2640
ccatgttgga agcagcggaa gaacacaaag cagacgtcat cggcatgtcg ggacttcttg   2700
tgaagtccac cgtggtgatg aaggaaaacc ttgaggagat gaacaacgcc ggcgcatcca   2760
attacccagt cattttgggt ggcgctgcgc tgacgcgtac ctacgtggaa aacgatctca   2820
acgaggtgta caccggtgag gtgtactacg cccgtgatgc tttcgagggc ctgcgcctga   2880
tggatgaggt gatggcagaa aagcgtggtg aaggacttga tcccaactca ccagaagcta   2940
ttgagcaggc gaagaagaag gcggaacgta aggctcgtaa tgagcgttcc cgcaagattg   3000
ccgcggagcg taaagctaat gcggctcccg tgattgttcc ggagcgttct gatgtctcca   3060
ccgatactcc aaccgcggca ccaccgttct ggggaacccg cattgtcaag ggtctgccct   3120
tggcggagtt cttgggcaac cttgatgagc gcgccttgtt catggggcag tggggtctga   3180
aatccacccg cggcaacgag ggtccaagct atgaggattt ggtggaaact gaaggccgac   3240
cacgcctgcg ctactggctg gatcgcctga agtctgaggg cattttggac cacgtggcct   3300
tggtgtatgg ctacttccca gcggtcgcgg aaggcgatga cgtggtgatc ttggaatccc   3360
cggatccaca cgcagccgaa cgcatgcgct ttagcttccc acgccagcag cgcggcaggt   3420
tcttgtgcat cgcggatttc attcgcccac gcgagcaagc tgtcaaggac ggccaagtgg   3480
acgtcatgcc attccagctg gtcaccatgg gtaatcctat tgctgatttc gccaacgagt   3540
tgttcgcagc caatgaatac cgcgagtact tggaagttca cggcatcggc gtgcagctca   3600
ccgaagcatt ggccgagtac tggcactccc gagtgcgcag cgaactcaag ctgaacgacg   3660
gtggatctgt cgctgatttt gatccagaag acaagaccaa gttcttcgac ctggattacc   3720
gcggcgcccg cttctccttt ggttacggtt cttgccctga tctggaagac cgcgcaaagc   3780
tggtggaatt gctcgagcca ggccgtatcg gcgtggagtt gtccgaggaa ctccagctgc   3840
acccagagca gtccacagac gcgtttgtgc tctaccaccc agaggcaaag tactttaacg   3900
tctaatctag acccgatagg tcgcagcggt gatctgttga tcgtgccgcg atctcggcac   3960
```

-continued

```
agcctcgaag caatcgagga ctccgctgtt ttgatcacca ttgccaaact gacgcaataa   4020
gaaagatagg gacttcccct ggggtgtttg agcccgccga gggtccgtct tccgcggcga   4080
gaccatggac cggcaccgtt cgatcaccgg cctcctgccc ctgatgtttg taccagcatg   4140
cgacggtgac cagctgaccg gttccactat ccttaccgct actggtggcg gggataatcg   4200
aaaatatgtg ccccttggtg aagggtcggg gagctaatag gatgacagtg aacctatttt   4260
ccacgtcttt atccgtagta ttggagatcc gatgacctac acaatcgccc agccctgcgt   4320
tgatgtcctg gatcgagcct gcgtcgagga atgtcccgtg gactgcatct acgagggcaa   4380
acggatgctc tacatccacc ccgatgagtg cgtcgactgc ggtgcctgcg agcccgtctg   4440
cccggttgaa gccatcttct acgaagatga tgttccccac gaatggtggg actacaccgg   4500
cgctaacgcc gcctttttcg acgacctcgg ttcgccaggc ggtgccgcca gcctgggtcc   4560
gcaggacttc gacgcccagc tcgtcgcggt gctgccgcca cagaaccaga actaggacct   4620
gatatcggcc ctaaacaagg agaacctgac tgcgatgttt catgtccctc gtaccaatag   4680
ttgttcctgg cctgtcattg tgatggtcga aggtcgacct gcagaagatc attgaccaaa   4740
tcaccaccaa gagtgcgagg atccactggg atttaaatcg ctagcgggct gctaaaggaa   4800
gcggaacacg tagaaagcca gtccgcagaa acggtgctga ccccggatga atgtcagcta   4860
ctgggctatc tggacaaggg aaaacgcaag cgcaaagaga aagcaggtag cttgcagtgg   4920
gcttacatgg cgatagctag actgggcggt tttatggaca gcaagcgaac cggaattgcc   4980
agctggggcg ccctctggta aggttgggaa gccctgcaaa gtaaactgga tggctttctt   5040
gccgccaagg atctgatggc gcaggggatc aagatctgat caagagacag gatgaggatc   5100
gtttcgcatg attgaacaag atggattgca cgcaggttct ccggccgctt gggtggagag   5160
gctattcggc tatgactggg cacaacagac aatcggctgc tctgatgccg ccgtgttccg   5220
gctgtcagcg caggggcgcc cggttctttt tgtcaagacc gacctgtccg gtgccctgaa   5280
tgaactgcag gacgaggcag cgcggctatc gtggctggcc acgacgggcg ttccttgcgc   5340
agctgtgctc gacgttgtca ctgaagcggg aagggactgg ctgctattgg gcgaagtgcc   5400
ggggcaggat ctcctgtcat ctcaccttgc tcctgccgag aaagtatcca tcatggctga   5460
tgcaatgcgg cggctgcata cgcttgatcc ggctacctgc ccattcgacc accaagcgaa   5520
acatcgcatc gagcgagcac gtactcggat ggaagccggt cttgtcgatc aggatgatct   5580
ggacgaagag catcaggggc tcgcgccagc cgaactgttc gccaggctca aggcgcgcat   5640
gcccgacggc gaggatctcg tcgtgaccca tggcgatgcc tgcttgccga atatcatggt   5700
ggaaaatggc cgcttttctg gattcatcga ctgtggccgg ctgggtgtgg cggaccgcta   5760
tcaggacata gcgttggcta cccgtgatat tgctgaagag cttggcggcg aatgggctga   5820
ccgcttcctc gtgctttacg gtatcgccgc tcccgattcg cagcgcatcg ccttctatcg   5880
ccttcttgac gagttcttct gagcgggact ctggggttcg aaatgaccga ccaagcgacg   5940
cccaacctgc catcacgaga tttcgattcc accgccgcct tctatgaaag gttgggcttc   6000
ggaatcgttt tccgggacgc cggctggatg atcctccagc gcggggatct catgctggag   6060
ttcttcgccc acgctagcgg cgcgccggcc ggcccggtgt gaaataccgc acagatgcgt   6120
aaggagaaaa taccgcatca ggcgctcttc cgcttcctcg ctcactgact cgctgcgctc   6180
ggtcgttcgg ctgcggcgag cggtatcagc tcactcaaag gcggtaatac ggttatccac   6240
agaatcaggg gataacgcag gaaagaacat gtgagcaaaa ggccagcaaa aggccaggaa   6300
ccgtaaaaag gccgcgttgc tggcgttttt ccataggctc cgcccccctg acgagcatca   6360
```

-continued

```
caaaaatcga cgctcaagtc agaggtggcg aaacccgaca ggactataaa gataccaggc   6420
gtttccccct ggaagctccc tcgtgcgctc tcctgttccg accctgccgc ttaccggata   6480
cctgtccgcc tttctccctt cgggaagcgt ggcgctttct catagctcac gctgtaggta   6540
tctcagttcg gtgtaggtcg ttcgctccaa gctgggctgt gtgcacgaac cccccgttca   6600
gcccgaccgc tgcgccttat ccggtaacta tcgtcttgag tccaacccgg taagacacga   6660
cttatcgcca ctggcagcag ccactggtaa caggattagc agagcgaggt atgtaggcgg   6720
tgctacagag ttcttgaagt ggtggcctaa ctacggctac actagaagga cagtatttgg   6780
tatctgcgct ctgctgaagc cagttacctt cggaaaaaga gttggtagct cttgatccgg   6840
caaacaaacc accgctggta gcggtggttt ttttgtttgc aagcagcaga ttacgcgcag   6900
aaaaaaagga tctcaagaag atcctttgat cttttctacg gggtctgacg ctcagtggaa   6960
cgaaaactca cgttaaggga ttttggtcat gagattatca aaaaggatct tcacctagat   7020
ccttttaaag gccggccgcg gccgcgcaaa gtcccgcttc gtgaaaattt tcgtgccgcg   7080
tgattttccg ccaaaaactt taacgaacgt tcgttataat ggtgtcatga ccttcacgac   7140
gaagtactaa aattggcccg aatcatcagc tatggatctc tctgatgtcg cgctggagtc   7200
cgacgcgctc gatgctgccg tcgatttaaa aacggtgatc ggatttttcc gagctctcga   7260
tacgacggac gcgccagcat cacgagactg ggccagtgcc gcgagcgacc tagaaactct   7320
cgtggcggat cttgaggagc tggctgacga gctgcgtgct cggccagcgc caggaggacg   7380
cacagtagtg gaggatgcaa tcagttgcgc ctactgcggt ggcctgattc ctccccggcc   7440
tgacccgcga ggacggcgcg caaaatattg ctcagatgcg tgtcgtgccg cagccagccg   7500
cgagcgcgcc aacaaacgcc acgccgagga gctggaggcg gctaggtcgc aaatggcgct   7560
ggaagtgcgt cccccgagcg aaattttggc catggtcgtc acagagctgg aagcggcagc   7620
gagaattatc gcgatcgtgg cggtgcccgc aggcatgaca aacatcgtaa atgccgcgtt   7680
tcgtgtgccg tggccgccca ggacgtgtca gcgccgccac cacctgcacc gaatcggcag   7740
cagcgtcgcg cgtcgaaaaa gcgcacaggc ggcaagaagc gataagctgc acgaatacct   7800
gaaaaatgtt gaacgccccg tgagcggtaa ctcacagggc gtcggctaac cccagtcca    7860
aacctgggag aaagcgctca aaaatgactc tagcggattc acgagacatt gacacaccgg   7920
cctggaaatt ttccgctgat ctgttcgaca cccatcccga gctcgcgctg cgatcacgtg   7980
gctggacgag cgaagaccgc cgcgaattcc tcgctcacct gggcagagaa aatttccagg   8040
gcagcaagac ccgcgacttc gccagcgctt ggatcaaaga cccggacacg gagaaacaca   8100
gccgaagtta taccgagttg gttcaaaatc gcttgcccgg tgccagtatg ttgctctgac   8160
gcacgcgcag cacgcagccg tgcttgtcct ggacattgat gtgccgagcc accaggccgg   8220
cgggaaaatc gagcacgtaa accccgaggt ctacgcgatt ttggagcgct gggcacgcct   8280
ggaaaaagcg ccagcttgga tcggcgtgaa tccactgagc gggaaatgcc agctcatctg   8340
gctcattgat ccggtgtatg ccgcagcagg catgagcagc ccgaatatgc gcctgctggc   8400
tgcaacgacc gaggaaatga cccgcgtttt cggcgctgac caggcttttt cacataggct   8460
gagccgtggc cactgcactc tccgacgatc ccagccgtac cgctggcatg cccagcacaa   8520
tcgcgtggat cgcctagctg atcttatgga ggttgctcgc atgatctcag gcacagaaaa   8580
acctaaaaaa cgctatgagc aggagttttc tagcggacgg gcacgtatcg aagcggcaag   8640
aaaagccact gcggaagcaa aagcacttgc cacgcttgaa gcaagcctgc cgagcgccgc   8700
tgaagcgtct ggagagctga tcgacggcgt ccgtgtcctc tggactgctc cagggcgtgc   8760
```

-continued

```
cgcccgtgat gagacggctt ttcgccacgc tttgactgtg ggataccagt taaaagcggc   8820

tggtgagcgc ctaaaagaca ccaagggtca tcgagcctac gagcgtgcct acaccgtcgc   8880

tcaggcggtc ggaggaggcc gtgagcctga tctgccgccg gactgtgacc gccagacgga   8940

ttggccgcga cgtgtgcgcg gctacgtcgc taaaggccag ccagtcgtcc ctgctcgtca   9000

gacagagacg cagagccagc cgaggcgaaa agctctggcc actatgggaa gacgtggcgg   9060

taaaaaggcc gcagaacgct ggaaagaccc aaacagtgag tacgcccgag cacagcgaga   9120

aaaactagct aagtccagtc aacgacaagc taggaaagct aaaggaaatc gcttgaccat   9180

tgcaggttgg tttatgactg ttgagggaga gactggctcg tggccgacaa tcaatgaagc   9240

tatgtctgaa tttagcgtgt cacgtcagac cgtgaataga gcacttaagg tctgcgggca   9300

ttgaacttcc acgaggacgc cgaaagcttc ccagtaaatg tgccatctcg taggcagaaa   9360

acggttcccc cgtagggtct ctctcttggc ctcctttcta ggtcgggctg attgctcttg   9420

aagctctcta ggggggctca caccataggc agataacgtt ccccaccggc tcgcctcgta   9480

agcgcacaag gactgctccc aaagatcttc aaagccactg ccgcgactgc cttcgcgaag   9540

ccttgccccg cggaaatttc ctccaccgag ttcgtgcaca cccctatgcc aagcttcttt   9600

caccctaaat tcgagagatt ggattcttac cgtggaaatt cttcgcaaaa atcgtcccct   9660

gatcgccctt gcgacgttgg cgtcggtgcc gctggttgcg cttggcttga ccgacttgat   9720

cagcggccgc                                                          9730
```